(12) United States Patent
Bunk et al.

(10) Patent No.: US 12,162,940 B2
(45) Date of Patent: Dec. 10, 2024

(54) BMA031 ANTIGEN BINDING POLYPEPTIDES

(71) Applicant: Immatics Biotechnologies GmbH, Tuebingen (DE)

(72) Inventors: Sebastian Bunk, Tuebingen (DE); Felix Unverdorben, Tuebingen (DE); Martin Hofmann, Tuebingen (DE)

(73) Assignee: Immatics Biotechnologies GmbH, Tübingen (DE)

( * ) Notice: Subject to any disclaimer, the term of this patent is extended or adjusted under 35 U.S.C. 154(b) by 0 days.

(21) Appl. No.: 17/736,699

(22) Filed: May 4, 2022

(65) Prior Publication Data

US 2022/0356252 A1 Nov. 10, 2022

Related U.S. Application Data

(60) Provisional application No. 63/184,698, filed on May 5, 2021.

(30) Foreign Application Priority Data

May 5, 2021 (EP) ..................................... 21172352

(51) Int. Cl.
| | | |
|---|---|---|
| *C07K 16/28* | (2006.01) | |
| *C07K 14/725* | (2006.01) | |
| *C07K 16/30* | (2006.01) | |
| *C12N 5/0783* | (2010.01) | |

(52) U.S. Cl.
CPC ...... *C07K 16/2809* (2013.01); *C07K 14/7051* (2013.01); *C07K 16/2833* (2013.01); *C07K 16/30* (2013.01); *C12N 5/0636* (2013.01); *C07K 2317/55* (2013.01); *C07K 2317/565* (2013.01); *C07K 2317/92* (2013.01); *C07K 2319/03* (2013.01); *C12N 2510/00* (2013.01)

(58) Field of Classification Search
CPC ............ C07K 16/2809; C07K 14/7051; C07K 16/2833; C07K 16/30; C07K 2317/55; C07K 2317/565; C07K 2317/92; C07K 2319/03; C07K 2317/31; C07K 2317/33; C07K 2317/622; C07K 2317/73; C07K 2317/94; C12N 5/0636; C12N 2510/00
See application file for complete search history.

(56) References Cited

U.S. PATENT DOCUMENTS

| | | |
|---|---|---|
| 6,534,633 B1 | 5/2003 | Weidanz et al. |
| 8,105,830 B2 | 1/2012 | Weidanz et al. |
| 9,056,911 B2 | 6/2015 | Yang et al. |
| 9,096,664 B2 | 8/2015 | Winston, Jr. et al. |
| 9,580,511 B2 | 2/2017 | Pan et al. |
| 9,701,753 B2 | 7/2017 | Pan et al. |
| 9,765,156 B2 | 9/2017 | June et al. |
| 9,790,268 B2 | 10/2017 | Pan et al. |
| 10,017,573 B2 | 7/2018 | Snell et al. |
| 10,098,951 B2 | 10/2018 | Lu et al. |
| 10,130,721 B2 | 11/2018 | Jakobsen et al. |
| 10,196,444 B2 | 2/2019 | Jarjour et al. |
| 10,214,589 B2 | 2/2019 | Pan et al. |
| 10,420,846 B2 | 9/2019 | Jakobsen et al. |
| 10,428,142 B2 | 10/2019 | Jarjour et al. |
| 10,457,731 B2 | 10/2019 | Jarjour et al. |
| 10,464,988 B2 | 11/2019 | Lu et al. |
| 10,494,439 B2 | 12/2019 | Pan et al. |
| 10,517,960 B2 | 12/2019 | Jakobsen et al. |
| 10,576,162 B2 | 3/2020 | Jakobsen et al. |
| 10,696,749 B2 | 6/2020 | June et al. |
| 10,822,389 B2 | 11/2020 | Lu et al. |
| 10,835,577 B2 | 11/2020 | Powlesland et al. |
| 10,836,813 B2 | 11/2020 | Pan et al. |
| 10,851,366 B2 | 12/2020 | Powlesland et al. |
| 10,927,186 B2 | 2/2021 | Roobrouck et al. |

(Continued)

FOREIGN PATENT DOCUMENTS

| | | |
|---|---|---|
| EP | 0403156 A1 | 12/1990 |
| WO | 2006/037960 | 4/2006 |

(Continued)

OTHER PUBLICATIONS

Mariuzza (Annu. Rev. Biophys. Biophys. Chem., 16: 139-159, 1987).*

(Continued)

*Primary Examiner* — Nelson B Moseley, II
(74) *Attorney, Agent, or Firm* — McBee, Moore & Vanik IP, LLC

(57) ABSTRACT

Antigen binding polypeptide specifically binding to α/β T cell receptor (TCR)/cluster of differentiation 3 (CD3) complex. Nucleic acid containing a sequence encoding for the antigen binding polypeptide or a vector containing the nucleic acid. Recombinant host cells containing the antigen binding polypeptide, and pharmaceutical compositions containing the antigen binding polypeptide, the nucleic acid, the vector, and/or the host cell. Use of the antigen binding polypeptide, the nucleic acid, the vector, the host cell, or the pharmaceutical composition in medicine, in particular for use in the diagnosis, prevention, and/or treatment of a proliferative disease. Methods for improving or maintaining the binding and/or improving the stability of the antigen binding polypeptides. Methods for detecting, determining or enriching T cells expressing the α/β TCR/CD3 complex.

15 Claims, 8 Drawing Sheets

Figure 1:
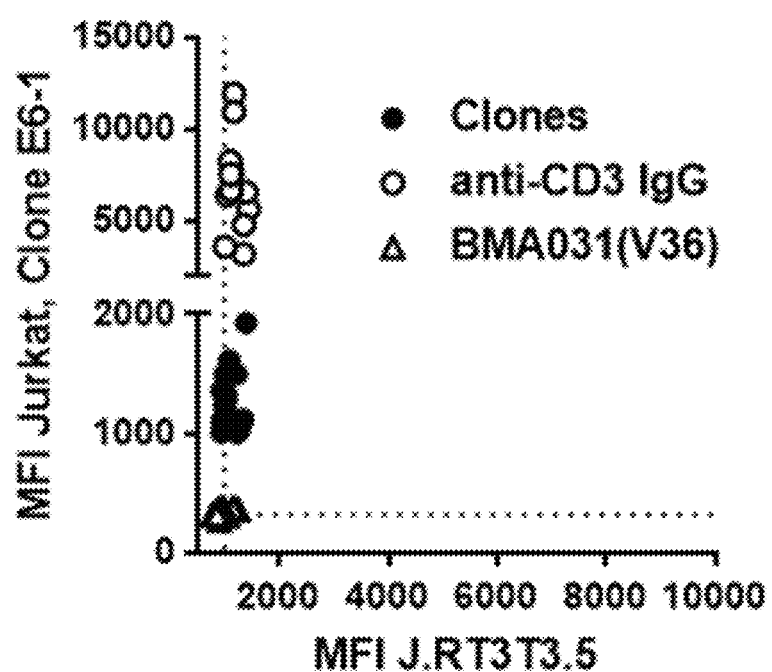

Specification includes a Sequence Listing.

(56) References Cited

U.S. PATENT DOCUMENTS

| | | |
|---|---|---|
| 10,975,169 B1 | 4/2021 | Kolesnick et al. |
| 11,000,601 B2 | 5/2021 | Chang et al. |
| 11,046,767 B2 | 6/2021 | Roobrouck et al. |
| 11,066,483 B2 | 7/2021 | Nezu et al. |
| 11,142,575 B2 | 10/2021 | Blank et al. |
| 11,186,638 B2 | 11/2021 | Snell et al. |
| 11,421,013 B2 | 8/2022 | Lu et al. |
| 2003/0144474 A1 | 7/2003 | Weidanz et al. |
| 2012/0034221 A1 | 2/2012 | Bonvini et al. |
| 2012/0230995 A1 | 9/2012 | Weidanz et al. |
| 2013/0115191 A1 | 5/2013 | Weidanz et al. |
| 2017/0319674 A1 | 11/2017 | Kuball |
| 2018/0086810 A1 | 3/2018 | Weidanz et al. |
| 2019/0054170 A1 | 2/2019 | Lindhofer et al. |
| 2019/0233531 A1 | 8/2019 | Pan et al. |
| 2019/0247512 A1 | 8/2019 | Jakobsen et al. |
| 2019/0375852 A1 | 12/2019 | Lindhofer et al. |
| 2020/0071399 A1 | 3/2020 | Jarjour et al. |
| 2020/0071401 A1 | 3/2020 | Jarjour et al. |
| 2020/0071425 A1 | 3/2020 | Yan et al. |
| 2020/0140564 A1 | 5/2020 | Pan et al. |
| 2020/0157216 A1 | 5/2020 | Van Hoorick et al. |
| 2020/0172905 A1 | 6/2020 | Rossi et al. |
| 2020/0181264 A1 | 6/2020 | Rossi et al. |
| 2021/0041435 A1 | 2/2021 | Ogasawara |
| 2021/0077632 A1 | 3/2021 | Smith et al. |
| 2021/0121526 A1 | 4/2021 | Powlesland et al. |
| 2021/0121547 A1 | 4/2021 | Powlesland et al. |
| 2021/0121551 A1 | 4/2021 | Powlesland et al. |
| 2021/0122784 A1 | 4/2021 | Powlesland et al. |
| 2021/0122794 A1 | 4/2021 | Powlesland et al. |
| 2021/0123037 A1 | 4/2021 | Powlesland et al. |
| 2021/0139585 A1 | 5/2021 | Granda et al. |
| 2021/0147524 A1 | 5/2021 | Pan et al. |
| 2021/0198375 A1 | 7/2021 | Mo et al. |
| 2021/0246222 A1 | 8/2021 | Karow et al. |
| 2021/0355209 A1 | 11/2021 | Willemsen et al. |
| 2021/0363251 A1 | 11/2021 | Roobrouck et al. |
| 2021/0371533 A1 | 12/2021 | Sun et al. |
| 2021/0380696 A1 | 12/2021 | Blair et al. |
| 2021/0386866 A1 | 12/2021 | Chuang et al. |
| 2021/0388105 A1 | 12/2021 | Qiu et al. |
| 2021/0395398 A1 | 12/2021 | Roobrouck et al. |
| 2022/0017630 A1 | 1/2022 | Zhao et al. |
| 2022/0041756 A1 | 2/2022 | Nezu et al. |
| 2022/0080030 A1 | 3/2022 | Johnson et al. |
| 2022/0098299 A1 | 3/2022 | Blank et al. |
| 2022/0098306 A1 | 3/2022 | Desjarlais et al. |
| 2022/0119472 A1 | 4/2022 | Kley et al. |
| 2022/0119479 A1 | 4/2022 | Conroy et al. |
| 2022/0119530 A1 | 4/2022 | Desjarlais et al. |
| 2022/0119824 A1 | 4/2022 | Glickman et al. |
| 2022/0135673 A1 | 5/2022 | Youngblood et al. |
| 2022/0135680 A1 | 5/2022 | Tran et al. |
| 2022/0153841 A1 | 5/2022 | Snell et al. |
| 2022/0154136 A1 | 5/2022 | Thanos et al. |
| 2022/0185910 A1 | 6/2022 | Liu et al. |
| 2022/0235142 A1 | 7/2022 | Mo et al. |
| 2022/0242968 A1 | 8/2022 | Mo et al. |
| 2022/0380463 A1 | 12/2022 | Geoghegan et al. |
| 2023/0046744 A1 | 2/2023 | Renes et al. |

FOREIGN PATENT DOCUMENTS

| | | |
|---|---|---|
| WO | 2019/129850 | 7/2019 |
| WO | 2020/142672 | 7/2020 |
| WO | 2020/150364 | 7/2020 |
| WO | 2020/193745 | 10/2020 |
| WO | 2020193745 A1 | 10/2020 |
| WO | 2020237173 | 11/2020 |
| WO | 2020238926 | 12/2020 |
| WO | 2020247873 | 12/2020 |
| WO | 2020247932 | 12/2020 |
| WO | 2020257407 | 12/2020 |
| WO | 2021026021 | 2/2021 |
| WO | 2021027674 | 2/2021 |
| WO | 2021027687 | 2/2021 |
| WO | 2021043961 | 3/2021 |
| WO | 2021044008 | 3/2021 |
| WO | 2021046289 | 3/2021 |
| WO | 2021046293 | 3/2021 |
| WO | 2021062323 | 4/2021 |
| WO | 2021064152 | 4/2021 |
| WO | 2021064153 | 4/2021 |
| WO | 2021072264 | 4/2021 |
| WO | 2021073624 | 4/2021 |
| WO | 2021076554 | 4/2021 |
| WO | 2021076564 | 4/2021 |
| WO | 2021077250 | 4/2021 |
| WO | 2021078774 | 4/2021 |
| WO | 2021081303 | 4/2021 |
| WO | 2021087016 | 5/2021 |
| WO | 2021088904 | 5/2021 |
| WO | 2021099347 | 5/2021 |
| WO | 2021101991 | 5/2021 |
| WO | 2021102197 | 5/2021 |
| WO | 2021110935 | 6/2021 |
| WO | 2021110995 | 6/2021 |
| WO | 2021112676 | 6/2021 |
| WO | 2021113831 | 6/2021 |
| WO | 2021119551 | 6/2021 |
| WO | 2021133723 | 7/2021 |
| WO | 2021136176 | 7/2021 |
| WO | 2021136415 | 7/2021 |
| WO | 2021139755 | 7/2021 |
| WO | 2021142302 | 7/2021 |
| WO | 2021144315 | 7/2021 |
| WO | 2021146218 | 7/2021 |
| WO | 2021147937 | 7/2021 |
| WO | 2021151180 | 8/2021 |
| WO | 2021155028 | 8/2021 |
| WO | 2021163346 | 8/2021 |
| WO | 2021163366 | 8/2021 |
| WO | 2021170684 | 9/2021 |
| WO | 2021173783 | 9/2021 |
| WO | 2021173985 | 9/2021 |
| WO | 2021188631 | 9/2021 |
| WO | 2021195598 | 9/2021 |
| WO | 2021204781 | 10/2021 |
| WO | 2021205172 | 10/2021 |
| WO | 2021205173 | 10/2021 |
| WO | 2021209356 | 10/2021 |
| WO | 2021209357 | 10/2021 |
| WO | 2021209358 | 10/2021 |
| WO | 2021216913 | 10/2021 |
| WO | 2021222783 | 11/2021 |
| WO | 2021222861 | 11/2021 |
| WO | 2021224261 | 11/2021 |
| WO | 2021224913 | 11/2021 |
| WO | 2021228091 | 11/2021 |
| WO | 2021237717 | 12/2021 |
| WO | 2021244590 | 12/2021 |
| WO | 2021250419 | 12/2021 |
| WO | 2021259304 | 12/2021 |
| WO | 2022001020 | 1/2022 |
| WO | 2022002249 | 1/2022 |
| WO | 2022002801 | 1/2022 |
| WO | 2022002802 | 1/2022 |
| WO | 2022005678 | 1/2022 |
| WO | 2022008418 | 1/2022 |
| WO | 2022026915 | 2/2022 |
| WO | 2022031137 | 2/2022 |
| WO | 2022035200 | 2/2022 |
| WO | 2022035201 | 2/2022 |
| WO | 2022037002 | 2/2022 |
| WO | 2022038261 | 2/2022 |
| WO | 2022040454 | 2/2022 |
| WO | 2022045126 | 3/2022 |
| WO | 2022045247 | 3/2022 |
| WO | 2022046920 | 3/2022 |
| WO | 2022046941 | 3/2022 |
| WO | 2022053036 | 3/2022 |
| WO | 2022055243 | 3/2022 |

WO 2021027590 10/2021

(56) References Cited

FOREIGN PATENT DOCUMENTS

| WO | 2022057941 | 3/2022 |
|----|------------|--------|
| WO | 2022061032 | 3/2022 |
| WO | 2022063272 | 3/2022 |
| WO | 2022067224 | 3/2022 |
| WO | 2022068895 | 4/2022 |
| WO | 2022072538 | 4/2022 |
| WO | 2022082068 | 4/2022 |
| WO | 2022087610 | 4/2022 |
| WO | 2022094174 | 5/2022 |
| WO | 2022103603 | 5/2022 |
| WO | 2022111576 | 6/2022 |
| WO | 2022126687 | 6/2022 |
| WO | 2022130013 | 6/2022 |
| WO | 2022147108 | 7/2022 |
| WO | 2022148736 | 7/2022 |
| WO | 2022150637 | 7/2022 |
| WO | 2022157352 | 7/2022 |
| WO | 2020/157210 | 8/2022 |
| WO | 2022167689 | 8/2022 |
| WO | 2022178367 | 8/2022 |
| WO | 2020/188348 | 9/2022 |

OTHER PUBLICATIONS

McCarthy et al. (J. Immunol. Methods, 251(1-2): 137-149, 2001).*
Lin et al. (African Journal of Biotechnology, 10(79):18294-18302, 2011).*
Brinkmann, Ulrich, and Roland E. Kontermann. "The making of bispecific antibodies." In MAbs, vol. 9, No. 2, pp. 182-212. Taylor & Francis, 2017.

* cited by examiner

BMA031 ANTIGEN BINDING POLYPEPTIDES

The present invention relates to an antigen binding polypeptide specifically binding to an α/β T cell receptor (TCR)/cluster of differentiation 3 (CD3) complex. The present invention further provides a nucleic acid comprising a sequence encoding the antigen binding polypeptide or a vector comprising said nucleic acid. The invention further relates to recombinant host cells comprising the antigen binding polypeptide, pharmaceutical compositions comprising the antigen binding polypeptide, the nucleic acid, the vector and/or the host cell. The present invention further relates to the antigen binding polypeptide, the nucleic acid, the vector, the host cell or the pharmaceutical composition for use in medicine, in particular for use in the diagnosis, prevention, and/or treatment of a proliferative disease. The invention also relates to a method for improving or maintaining the binding and/or improving the stability of the antigen binding polypeptides. The invention also relates to a method for detecting, determining or enriching T cells expressing the α/β TCR/CD3 complex.

Two types of T lymphocytes can be distinguished based on the expression of two types of respective TCRs: either the α/β TCRs or γ/δ TCRs. α/β TCRs are expressed on the majority of human T lymphocytes (about >80%) whereas γ/δ TCRs are expressed to the extent of <20% on human T cells in peripheral lymphoid organs and blood, as well as in most epithelial tissues. α/β TCRs recognize foreign antigens bound to molecules of the major histocompatibility complex (M H C; Borst et al.; Human Immunology, 29, 175-188, 1990). The murine antibody BMA031 is directed against the human α/β TCR/CD3 complex (Borst et al., 1990). Humanized antibodies with specificity for α/β TCRs have been produced based on the murine monoclonal antibody BMA031; Shearman et al., The Journal of Immunology; vol. 147, 4366-4373, no: 12; 1991, or EP 0403156A1). However, humanized versions of BMA031, such as EUCIV3, showed a lower binding compared to murine BMA031; Shearman et al., 1991. Further humanized BMA031 variants have also been disclosed in the prior art and were shown to induce cell-mediated cytolysis (Shearman et al.; 1990). Therefore, humanized BMA031 molecules may provide a considerable medical potential to improve immunotherapies of diseases and disorders, e.g. proliferative diseases. However, so far, humanized BMA031 variants suffered either from low binding and/or poor stability.

Accordingly, there is a need in the art for humanized BMA031 variants that effectively bind and have a favourable stability.

The present invention provides antigen binding polypeptides which are derived from BMA031 and which specifically bind to an α/β TCR/CD3 complex. The antigen binding polypeptides comprise the herein provided substitutions. In particular, the antigen binding polypeptides comprise the inventive substitution(s) by a positively charged amino acid (i) at one or more of the following positions of the heavy chain: 30, 31, 53 and 54; and/or
(ii) at one or more of the following positions of the light chain: 31 and 56, and wherein the positions are according to Kabat numbering. Further, the herein provided antigen binding polypeptides comprise the inventive substitution at position 90 according to Kabat numbering (e.g. of histidine (H) at position 90) by tyrosine (Y).

The antigen binding polypeptides of the present invention are suitable for the use in various different antibody formats by utilizing antibody engineering methods such as inter alia described in Brinkmann et al.; MABS2017, Vol. 9, No. 2, 182-212. The antigen binding polypeptides of the invention provide inter alia the following advantages over the art: (i) increased binding to cells expressing the α/β TCR/CD3 complex; and/or (ii) increased stability, in particular thermal stability, compared to an antigen binding polypeptide not comprising the herein provided substitutions. Furthermore, it was unexpectedly demonstrated that combinations of the herein provided substitutions provide synergistic effects leading to an improved binding to cells expressing the α/β TCR/CD3 complex. Moreover, the antigen binding polypeptides of the invention improve the effector function of recruited T cells, for example, improved medical effects, compared to an antigen binding polypeptide not comprising the inventive substitutions. The antigen binding polypeptides of the invention comprising an effector molecule, for example, if the antigen binding polypeptide is a bispecific molecule and comprises inter alia a TCR (e.g. TCER® molecule), may lead to an increased potency of an effector function of recruited T cells, for example killing of tumor cells, compared to an antigen binding polypeptide not comprising the inventive substitutions. Accordingly, the herein provided substitutions in the antigen binding polypeptide may lead to improved medical properties of the antigen binding polypeptide.

A first aspect of the invention relates to an antigen binding polypeptide comprising a heavy chain variable domain (VH) and a light chain variable domain (VL), wherein
  (1) the VH comprises
    (a) a heavy chain complementarity determining region 1 (HCDR1) comprising the amino acid sequence of SEQ ID NO: 52,
    (b) a HCDR2 comprising the amino acid sequence of YINPYNDVTKYX$_1$X$_2$KFX$_3$G (SEQ ID NO: 53), wherein
      X$_1$ is A or N;
      X$_2$ is E or Q; and/or
      X$_3$ is Q or K
    (c) a HCDR3, and
    (d) heavy chain framework regions (HFR) 1-4;
  (2) the VL comprises
    (a) a light chain complementarity determining region 1 (LCDR1) comprising the amino acid sequence of SEQ ID NO: 54,
    (b) a LCDR2 comprising the amino acid sequence of SEQ ID NO: 55,
    (c) a LCDR3, and
    (d) light chain framework regions (LFR) 1-4;
wherein
  (i) at least one amino acid of HCDR1 comprising the amino acid sequence of SEQ ID NO: 52 and/or at least one amino acid of HCDR2 comprising the amino acid sequence of SEQ ID NO: 53 that is not positively charged is substituted with a positively charged amino acid; and/or
  (ii) at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid; and/or
  (iii) position 30 in HFR1 according to Kabat numbering is substituted with a positively charged amino acid, and/or (iv) position 90 in HFR3 according to Kabat numbering is substituted with a tyrosine (Y) residue, and wherein the antigen binding polypeptide specifically binds to an α/β T cell receptor (TCR)/CD3 complex.

A second aspect of the invention relates to an isolated nucleic acid comprising a sequence encoding an antigen binding polypeptide of the first aspect of the invention, or a nucleic acid vector comprising said nucleic acid.

A third aspect of the invention relates to a recombinant host cell comprising an antigen binding polypeptide of the first aspect of the invention, or a nucleic acid or a vector of the second aspect of the invention.

A fourth aspect of the invention relates to a pharmaceutical composition comprising the antigen binding polypeptide of the first aspect of the invention, the nucleic acid or vector of the second aspect of the invention or the host cell of the third aspect of the invention and a pharmaceutically acceptable carrier.

A fifth aspect of the invention relates to the antigen binding polypeptide of the first aspect of the invention, the nucleic acid or vector of the second aspect of the invention or the host cell of the third aspect of the invention or the pharmaceutical composition of the fourth aspect of the invention for use in medicine.

A sixth aspect of the invention relates to the antigen binding polypeptide of the first aspect of the invention, the nucleic acid or vector of the second aspect of the invention or the host cell of the third aspect of the invention or the pharmaceutical composition of the fourth aspect of the invention for use in the diagnosis, prevention, and/or treatment of a proliferative disease, preferably cancer.

A seventh aspect of the invention relates to a method for improving or maintaining the binding and/or improving the stability of the antigen binding polypeptide of the first aspect of the invention.

An eighth aspect of the invention relates to a method for detecting, determining or enriching T cells expressing the α/β TCR/CD3 complex.

Further aspects, inter alia relate to methods of producing the antigen binding polypeptides and/or kits comprising the antigen binding polypeptides and are also described herein below.

LIST OF FIGURES

In the following, the content of the figures comprised in this specification is described. In this context reference is made to the detailed description of the invention above and/or below.

FIG. 1: Binding and specificity screening of selected scFv clones after phage display selection. Flow cytometric binding analysis was performed with Jurkat, Clone E6-1 cell line (y-axis) and J.RT3T3.5 cells (x-axis). ScFv BMA031 (V36) (open triangles) served as reference and the anti-CD3 antibody (open circles) served as positive control for target binding. The selected clones (closed circles) with improved staining of the target positive cells were advanced to further analysis. The dotted lines represent background staining of the respective cell lines without the scFvs, but including the detection antibody.

Figure 2:
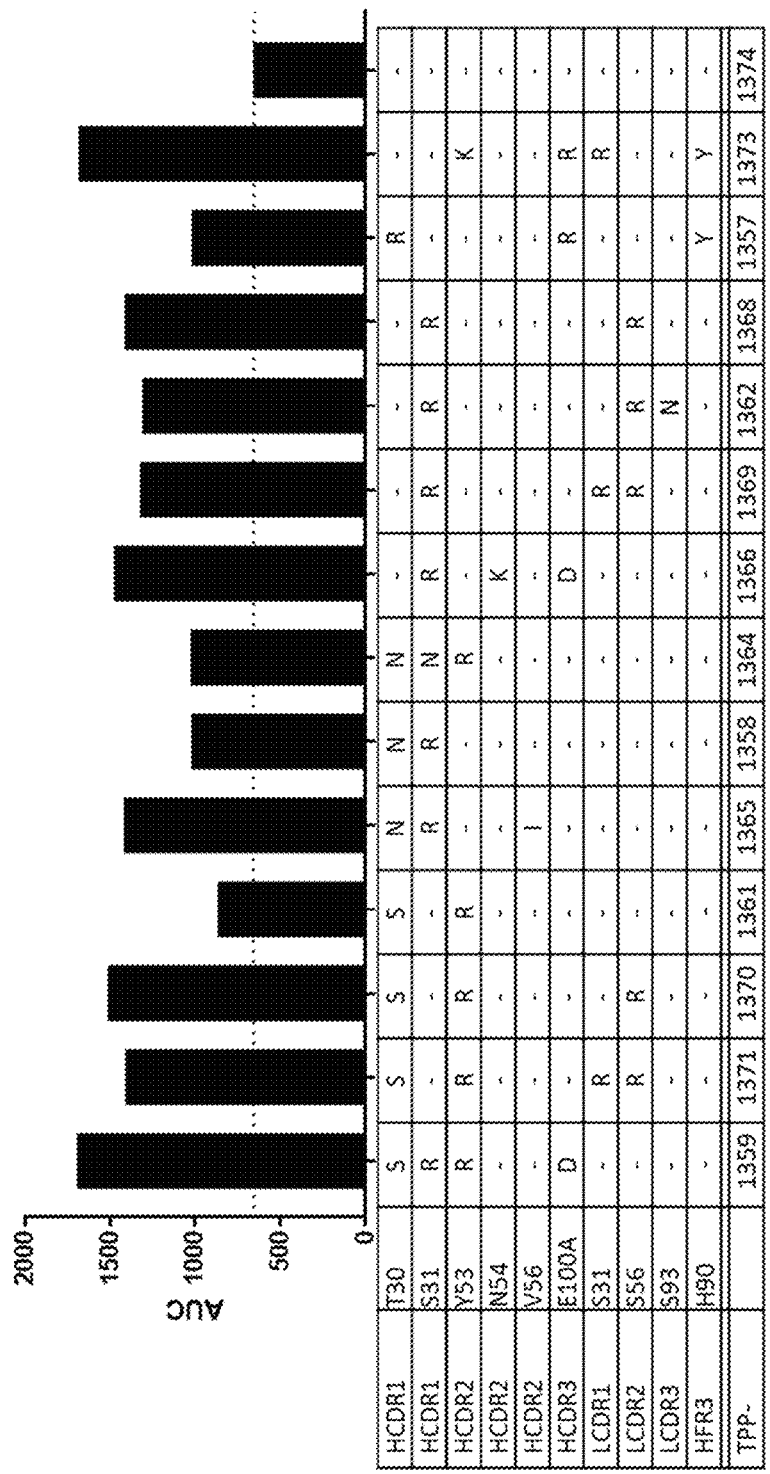

FIG. 2: Binding of selected Fab variants after phage display. Purified Fabs were applied to Jurkat, Clone E6-1 cell line as a titration series with concentrations ranging from 10 µg/ml to 10 ng/ml and staining was detected via anti-His tag antibody. Binding under the curve (AUC) was calculated from median fluorescence intensity (MFI) and logarithmized concentrations. The dashed line represents binding AUC of the exemplary parental antibody TPP-1374.

Figure 3:
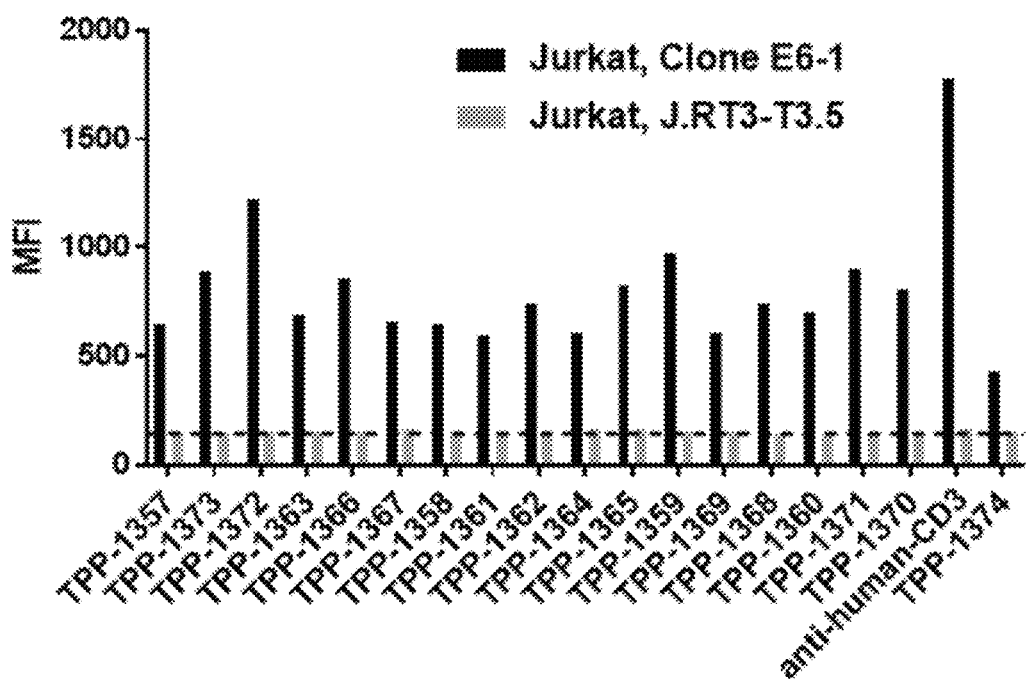

FIG. 3: Binding and specificity screening of selected Fab variants after phage display. Purified Fabs were applied to Jurkat, Clone E6-1 cell line and J.RT3T3.5 cells at a concentration of 1 µg/ml and staining was detected via anti-His tag antibody. The dashed line represents background signal without any Fab being present.

Figure 4:
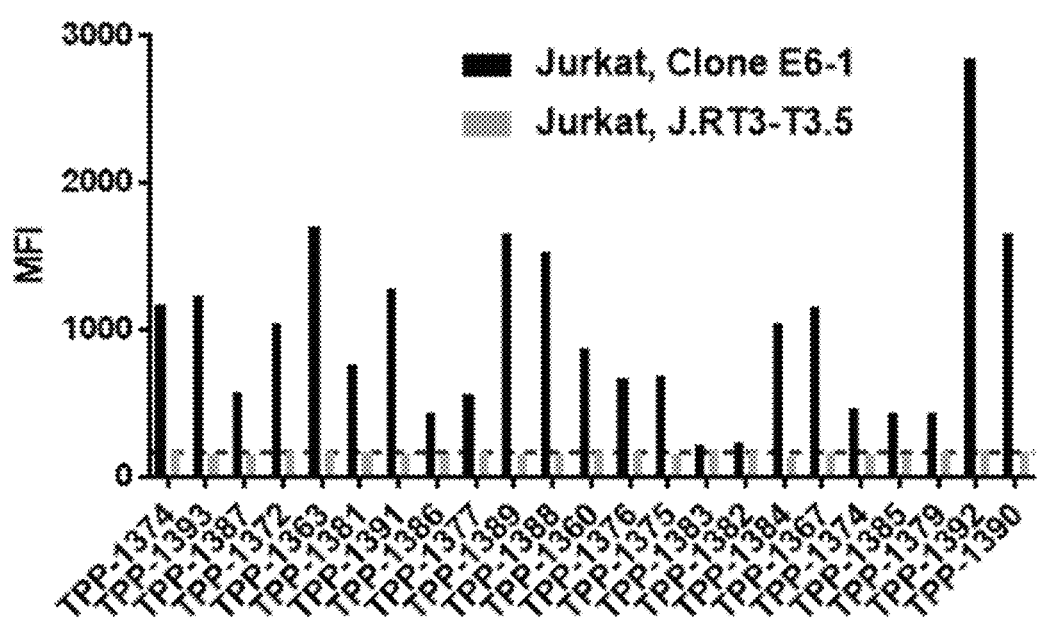

FIG. 4: Binding and specificity screening of designed Fab variants. Purified Fabs were applied to Jurkat, Clone E6-1 cell line and J.RT3T3.5 cells at a concentration of 1 µg/ml and staining was detected via anti-His tag antibody. The dashed line represents background signal without any Fab being present.

Figure 5:
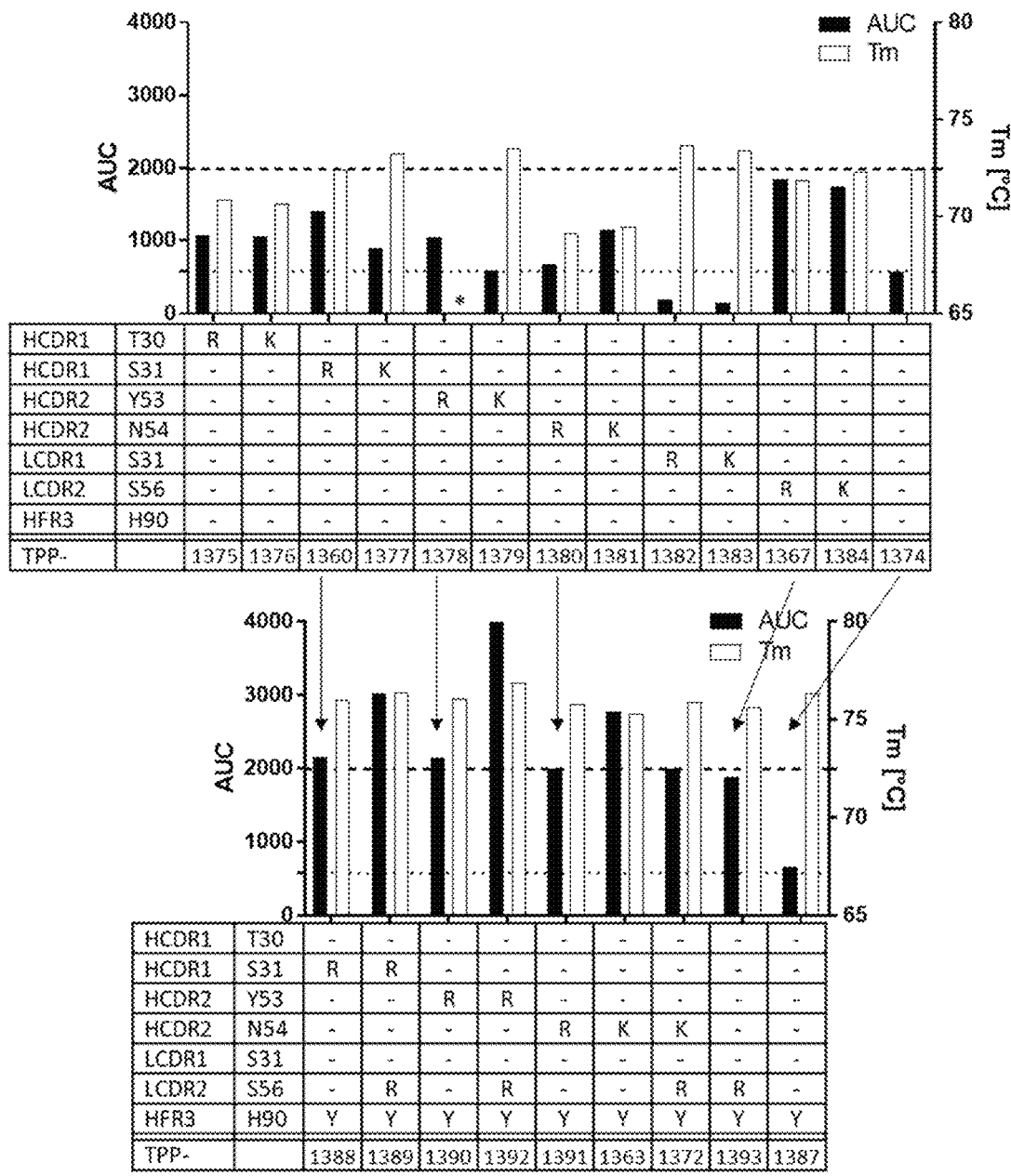

FIG. 5: Binding area under the curve and melting temperature of designed Fab variants. Purified Fabs were applied to Jurkat, Clone E6-1 cell line in a titration series of concentrations ranging from 10 µg/ml to and 10 ng/ml and binding AUC was calculated based on the resulting binding curves (left Y-axis). Melting temperatures (Tm) were calculated from nanoDSF measurements (right Y-axis). The upper panel represents variants with mutated CDRs only, the lower panel further includes the variants carrying heavy chain framework mutation H90Y. Arrows indicate the relationship of variants with and without the heavy chain framework region 3 (HFR3) mutation H90Y. *: melting point for VH_Y53R_VL_VL_wt (TPP-1378) was not determined. Bold dashed line indicates the Tm of VH_wt_VL_wt (TPP-1374, an exemplary parental antibody). Dotted line indicates the binding AUC of VH_wt_VL_wt (TPP-1374).

Figure 6:
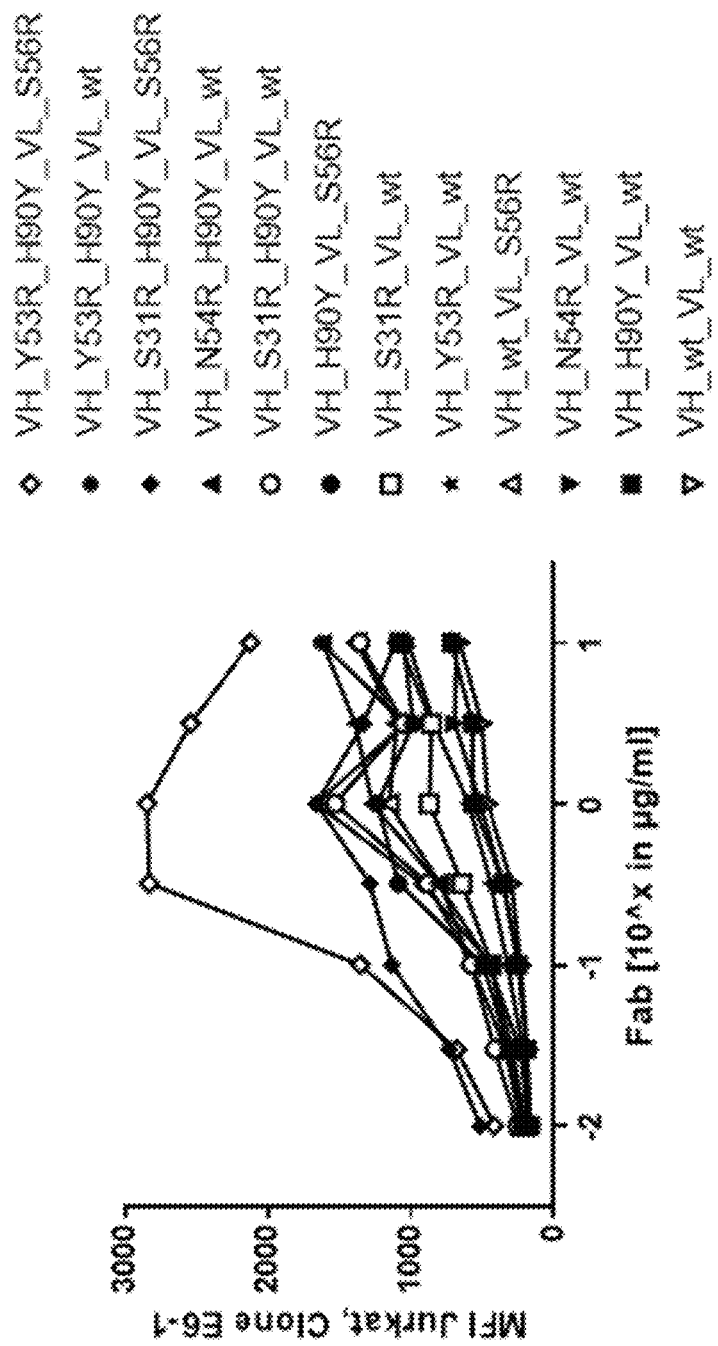

FIG. 6: Target cell binding of designed Fab variants. Purified Fabs were applied to Jurkat, Clone E6-1 cell line in a titration series of concentrations ranging from 10 µg/ml to and 10 ng/ml and staining was detected via anti-His tag antibody.

Figure 7:
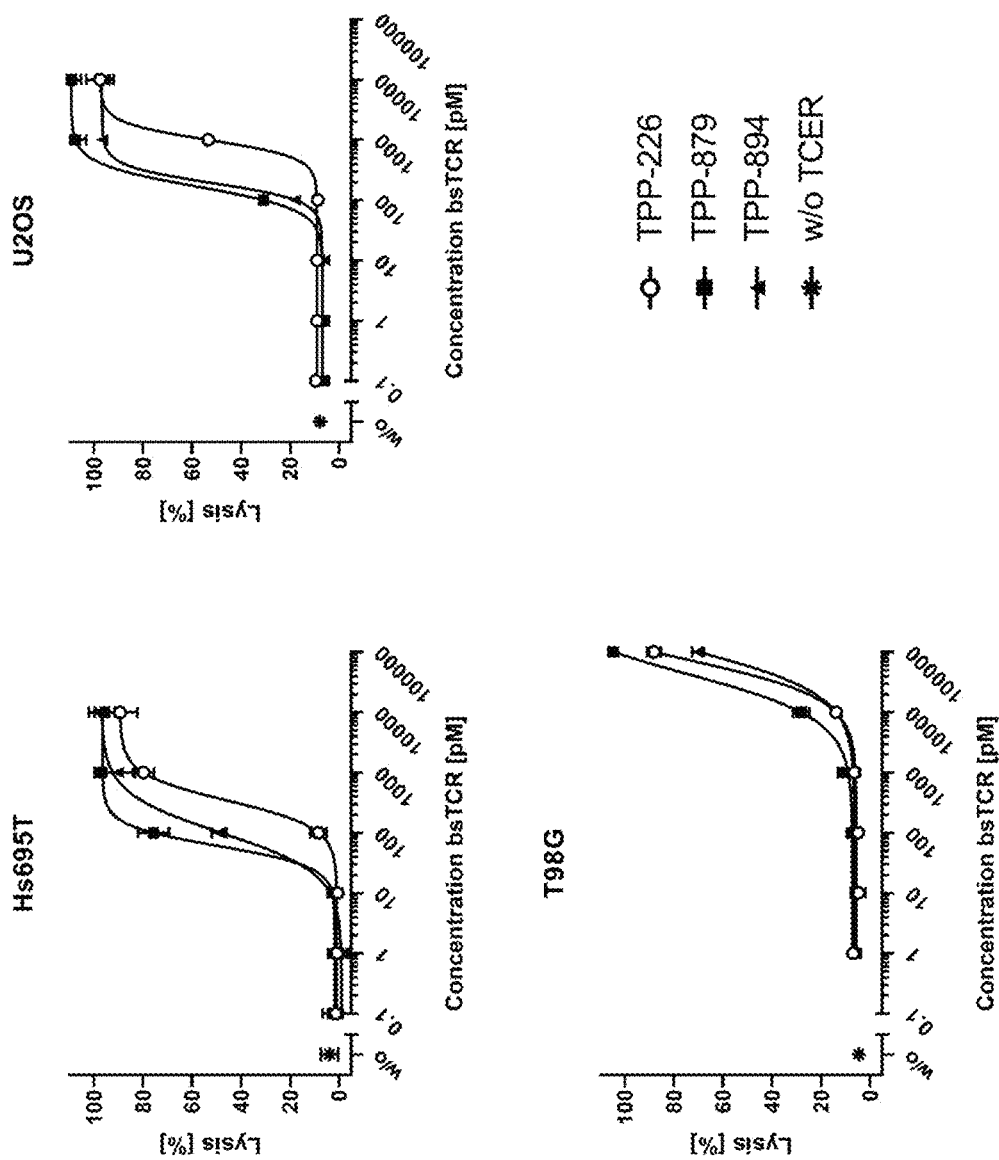

FIG. 7: Potency of modified BMA031 molecules in context of the TCER® format. Potency of purified T cell engaging receptor (TCER®) molecules was assessed in lactate dehydrogenase (LDH)-release assays. Tumor cell lines presenting various levels of target peptide HLA (pHLA) on their cell surface (Hs695T, U2OS) as well as a target peptide-human leukocyte antigen (pHLA)-negative tumor cell line (T98G) were used as targets for peripheral blood mononuclear cells (PBMCs) derived from healthy HLA-A*02-positive donor HBC-1005 (E:T=10:1) in presence of raising concentrations of TCER® molecules. TCER®-induced cytolysis was quantified after 48 hours by measurement of released LDH. EC50 values of dose-response curves were calculated utilizing non-linear 4-point curve fitting.

Figure 8:
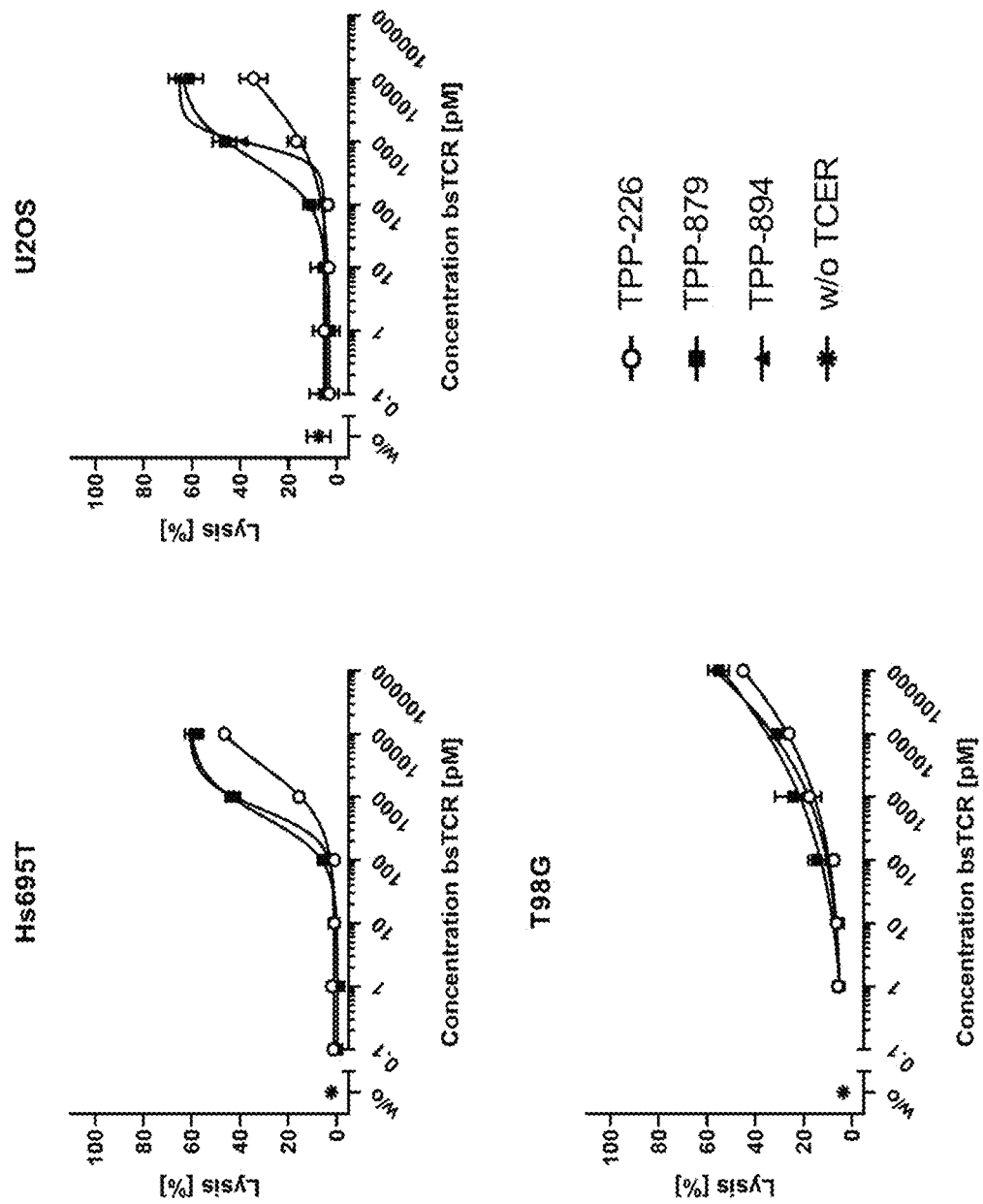

FIG. 8: Potency of modified BMA031 molecules in context of the TCER® format. Potency of purified TCER® molecules was assessed in LDH-release assays. Tumor cell lines presenting various levels of target pHLA on their cell surface (Hs695T, U2OS) as well as a target pHLA-negative tumor cell line (T98G) were used as targets for PBMC derived from healthy HLA-A*02-positive donor HBC-1039 (E:T=10:1) in presence of raising concentrations of TCER® molecules. TCER®-induced cytolysis was quantified after 48 hours by measurement of released LDH. EC50 values of dose-response curves were calculated utilizing non-linear 4-point curve fitting.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

To practice the present invention, unless otherwise indicated, conventional methods of chemistry, biochemistry, and recombinant DNA techniques are employed which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term "antigen binding polypeptide" refers in the context of this invention to polypeptides or binding proteins that are able to specifically bind to at least one antigen, in particular, an epitope of said antigen. The antigen binding polypeptide of the present invention comprise complementary determining regions (CDR) 1 to CDR3 which are part of a variable domain.

Preferably, the antigen binding polypeptide of the invention comprises a heavy chain variable domain (VH) and a light chain variable domain (VL) which may be comprised on the same or different polypeptide chains. The VH and VL comprise complementary determining regions (CDRs) and framework regions (FR) of an antibody or a fragment thereof as defined herein below. Preferably, the antigen binding polypeptide comprises a VH and VL as defined herein below wherein specific positions in the VH and/or specific positions in the VL have positively charged amino acids compared to an antigen binding polypeptide or fragment thereof that has no positively charged amino acids at the respective positions. In other words, said specific amino acid positions are substituted with positively charged amino acids in the antigen binding polypeptide of the present invention. Preferably, the antigen binding polypeptide or functional fragments thereof comprise CDRs wherein at least one amino acid of the amino acids that are not positively charged is substituted with a positively charged amino acid. Position 30 in FR1 of the heavy chain may be substituted with a positively charged amino acid. Furthermore, position 90 in FR3 of the heavy chain is substituted with a tyrosine according to Kabat numbering in the antigen binding polypeptide.

The antigen binding polypeptide refers in the context of this invention to a polypeptide that comprises a paratope (alternatively referred to as "antigen binding site") that specifically binds to an antigen. Examples of antigen binding polypeptides are inter alia antibodies or fragments thereof or single chain antibodies. The antigen binding polypeptide of the invention or the functional fragment thereof specifically binds to cells expressing an $\alpha/\beta$ TCR/CD3 complex or to an $\alpha/\beta$ TCR/CD3 complex. In certain aspects, the antigen binding polypeptide of the invention or the functional fragment thereof does not specifically bind to the cynomolgus $\alpha/\beta$ TCR/CD3 complex. In further aspects, the antigen binding polypeptide of the invention does not specifically bind to cells expressing the $\gamma/\delta$ T cell receptor (TCR). In further aspects, the antigen binding polypeptide of the invention binds to the extracellular domain of CD3.

In certain further aspects, the antigen binding polypeptide of the invention or the functional fragment thereof specifically binds to the human $\alpha/\beta$ TCR/CD3 complex. In other words, the antigen binding polypeptide of the invention or the functional fragment thereof does not specifically bind to the $\alpha/\beta$ TCR/CD3 complex of any other species than human.

It is preferred that the antigen binding polypeptide comprises CDR sequences as defined in the appended claims and herein below wherein at least one amino acid that is not positively charged is substituted with a positively charged amino acid as defined herein below. It is preferred that not more than four amino acid positions are substituted with a positively charged amino acid in the CDRs of the antigen binding polypeptide. Preferably, the antigen binding polypeptides of the invention comprise at least the VH and VL variable domains that are derived from the antibody sequences of BMA031 or the antibody sequences of BMA031(V36) as defined herein below, which are designated as reference antibody, parental antigen binding polypeptide or parental antibody and will be defined further below. The antigen binding polypeptides of the invention comprise VH and VL domains comprising consensus sequences which are based on antibodies targeting the $\alpha/\beta$ TCR/CD3 complex, and comprise the herein provided inventive substitutions. Exemplary sequences of such antibodies are disclosed herein below. As shown in the appended examples, the introduction of particular substitutions, with positively charged amino acids and/or a substitution at position 90 in HFR3 in the variable domains of the parental antigen binding polypeptide, for example, BMA031(V36), provided the herein demonstrated advantageous effects, for example increased binding and/or increased stability compared to the parental antigen binding polypeptide not comprising the herein provided substitutions. In certain further aspects, the antigen binding polypeptide of the invention may also have an increased stability while essentially maintaining or maintaining binding compared to an antigen binding polypeptide not comprising the herein provided substitutions. In certain further aspects, the herein provided antigen binding polypeptide may also have an increased binding while essentially maintaining or maintaining the stability of the antigen binding polypeptide compared to an antigen binding polypeptide not comprising the herein provided substitutions. The term "essentially" in context of "essentially maintaining the binding" means that the binding (e.g. expressed in "% gain binding AUC) is not substantially altered, i.e. not more altered than a decrease of about 25%, preferably about 15%, more preferably about 10%, and even more preferably about 5%, if compared to the parental antigen binding polypeptide. The term "essentially" in context of "essentially maintaining the stability" means that the stability is not substantially altered, i.e. not more altered than a decrease of about 25%, more preferably about 15%, more preferably about 10%, and even more preferably about 5% compared to the parental antigen binding polypeptide.

The term "variable domain" refers in the context of this invention to a region of an immunoglobulin, which is defined on the basis of sequence homologies as known to the skilled person. Typically, two variable domains form an antigen binding site. Non-exhausting examples of such domains are the variable light chain domain comprised in the antibody light chain (VL), the variable heavy chain domain comprised in the antibody heavy chain (VH), the alpha variable domain comprised in the alpha chain of a TCR molecule (Vα) or the beta variable domain comprised in the beta chain of a TCR (Vβ).

The term "complementary determining region" (CDR) refers in the context of this invention to the non-contiguous antigen combining sites found within the variable domains of immunoglobulins, e.g. in VH, VL, Vα and Vβ. CDRs have been described by Lefranc et al. (2003) *Developmental and Comparative Immunology* 27:55; Kabat et al., J. Biol. Chem. 252:6609-6616 (1977); Kabat et al., U.S. Dept. of Health and Human Services, "Sequences of proteins of immunological interest", 1991; Chothia et al., *J. Mol. Biol.* I96:90I-917, 1987; and Contact annotation (MacCallum et al., *J. Mol. Biol.* 262:732-745 (1996) for the Contact annotation); Abhinandan and Martin, Mol. Immunol. (2008), 45(14):3832-9. for AbM annotation; IMGT (Lefranc MP. Unique database numbering system for immunogenetic analysis; Immunol. Today (1997) 18:509), where the definitions include overlapping or subsets of amino acid residues when compared against each other. Nevertheless, application of either definition to refer to a CDR of an antibody or grafted antibodies or variants or fragments thereof, is intended to be within the scope of the term as defined and used herein. The amino acid residues, which encompass the CDRs, as defined by each of the above cited references are exemplarily set forth below in Table 1 as a comparison.

TABLE 1

CDR numbering according to different annotations of antibody BMA031(V36).

| | Kabat[1] | Chothia[2] | AbM[3] | Contact[4] |
|---|---|---|---|---|
| HCDR1 | 31-35 | 26-32 | 26-35 | 30-35 |
| HCDR2 | 50-65 | 52-56 | 50-58 | 47-58 |
| HCDR3 | 95-102 | 95-102 | 95-102 | 93-101 |
| LCDR1 | 24-34 | 24-34 | 24-34 | 31-36 |
| LCDR2 | 50-56 | 50-56 | 50-56 | 46-55 |
| LCDR3 | 89-97 | 89-97 | 89-97 | 89-96 |

[1]Residue numbering follows the nomenclature of Kabat et al., supra
[2]Residue numbering follows the nomenclature of Chothia et al., supra
[3]Residue numbering according to AbM, Abhinandan and Martin, supra;
[4]Residue according to Contact Numbering, MacCallum et al., supra.

The terms "HCDR1", HCDR2", and "HCDR3" refer in the context of the present invention to the first, second, and third CDR in a heavy chain variable domain of an antigen binding polypeptide, for example an antibody or functional fragment thereof. As used herein, the terms "LCDR1", "LCDR2", and "LCDR3" refer, respectively, to the first, second, and third CDR in a light chain variable domain of an antigen binding polypeptide, for example an antibody or a fragment thereof. As used herein, the terms "CDR1", "CDR2", and "CDR3" refer, respectively, to the first, second and third CDRs of either chain's variable region of an antigen binding polypeptide, for example an antibody or functional fragment thereof. The antigen binding polypeptides of the present invention are substituted with positively charged amino acids, for example in the CDRs, compared to a parental antigen binding polypeptide that has no positively charged residues at the respective positions. Positions of the amino acids within the CDRs, and similarly positions of the amino acids within a VH or VL, are assigned according to Kabat, Chothia, AbM or Contact annotations as described above, in particular according to Kabat numbering.

The term "framework region" (FR) refers in the context of the present invention to all amino acid residues outside the CDR regions within the variable domain of an antigen binding polypeptide, for example an antibody or a fragment thereof. A framework region is generally a discontinuous amino acid sequence between about 100-120 amino acids in length but is intended to reference only those amino acids outside of the CDRs. As used herein, the term "framework region" is intended to mean each domain of the framework that is separated by the CDRs. FR1 to FR4 refers to framework region 1 which is the first N-terminal amino acid sequence of a variable domain, followed by FR2, FR3 and FR4 which are interspersed with CDR1, 2 and 3, respectively. In some embodiments, the antigen binding polypeptides of the present invention comprises substitution(s) in the framework region, for example in heavy chain framework region 3 (HFR3).

The term "polypeptide" refers in the context of the present invention, to a single linear chain of amino acids bonded together by peptide bonds and typically comprises at least about 50, at least about 60, at least about 70, at least about 80, at least about 90, or at least about 100 amino acids. It is also envisaged herein that the antigen binding polypeptide provided herein has a length lower than the indicated range as long as the antigen binding polypeptide comprises the inventive substitutions and specifically binds to cells expressing the α/β TCR/CD3 complex. A polypeptide can be one chain of a protein that is composed of more than one chain or it can be the protein itself if the protein is composed of one chain.

The term "protein" refers to a functional unit that may comprise one or more polypeptide chains. If the protein comprises two or more polypeptide chains these may be non-covalently and/or covalently bound to each other.

The term "antigen-binding site" refers in the context of the present invention to at least one binding site which is responsible for specifically and/or selectively binding to a target antigen of interest, in particular to the epitope of the target antigen. The term "antigen binding site" is interchangeably used with the term "paratope" in the context of the present invention and refers to the part of the antigen binding polypeptide that binds to the antigen. Exemplary binding sites include an antibody variable domain, such as a heavy chain variable domain or light chain variable domain, a TCR variable domain, such as an alpha or beta variable domain or a gamma or delta variable domain. In particular aspects, the antigen binding polypeptides described herein comprise multiple (e.g., two, three, four, or more) binding sites.

The term "antigen" or "target antigen" refers in the context of the present invention to a molecule or a portion of a molecule or complex that is capable of being bound by at least one antigen binding site, wherein said one antigen binding site is, for example, comprised in an antibody, a TCR and/or in the antigen binding polypeptides of the present invention.

The term "epitope" refers in the context of the present invention to the functional epitope of an antigen. The functional epitope comprises the residues, typically amino acids or polysaccharides, that contribute to the non-covalent interaction between the paratope of the antigen binding polypeptide and the antigen. The non-covalent interaction comprises electrostatic forces, van der Walls forces, hydrogen bonds, and hydrophobic interaction, respectively. The functional epitope is a subgroup of the residues that constitute the structural epitope of an antigen binding polypeptide. The structural epitope comprises all residues that are covered by an antigen binding polypeptide, i.e. the footprint of an antigen binding polypeptide. Typically, the functional epitope of an antigen bound by an antibody comprises 4 to 10 amino acids. Similarly, the functional epitope of a peptide that is MHC presented typically comprises 4 to 8 amino acids. Competition between two antibodies occurs, if the structural epitopes of the antibodies are identical or overlap.

The term "α/β TCR/CD3 complex" refers in the context of the present invention to a T cell receptor complex as present on the surface of T cells. Most T cells express α/β TCRs, composed of disulfide bonded α and β chains which typically bind composite surfaces of antigenic peptides presented by MHC. TCRs do not signal on its own but are constitutively associated with CD3, a protein complex which is designated as T cell co-receptor and contains intracellular signaling motifs (Birnbaum et al.; PNAS vol. 11, no. 49; 17576-17581, 2014). The α/β TCR is noncovalently coupled to this conserved multi-subunit signaling apparatus that comprises the CD3εγ, CD3εδ, and CD3ζζ dimers, which collectively form the α/β TCR/CD3 complex. The α/β TCR/CD3 complex comprises the epitope which is specifically bound by the antigen binding polypeptides of the present invention. The specific amino acid sequence of the target epitope of the BMA031 antibody (Shearman et al., 1991) or the antigen binding polypeptides herein provided is not known. However, the antigen binding polypeptides of the present invention bind to the same or similar functional epitope as BMA031 or BMA031 (V36) and thus compete with each other. Accordingly, the epitope specificity of the antigen binding polypeptides of the invention is characterized by their ability to compete with a "reference antibody" for binding to cells expressing the α/β TCR/CD3 complex, preferably T cells, in particular for binding to the α/β TCR/CD3 complex present on the surface of T cells. Thus, the herein provided antigen binding polypeptides may compete with a reference antibody that specifically binds to the α/β TCR/CD3 complex, preferably BMA031, or even more preferably BMA031 (V36), for binding to T cells, in particular for binding to T cells expressing the α/β TCR/CD3 complex, more preferably for binding to the α/β TCR/CD3 complex present on the surface of T cells. T cells are preferably T lymphocytes, more preferably Jurkat cells, for example Clone E6-1 cells. It is noted that the antigen binding polypeptides of the invention were developed based on the sequences of the above-mentioned reference antibodies, i.e. BMA031 or BMA031 (V36). The competition between the reference antibody and the antigen binding polypeptide can be tested by known assay methods. For example, a binding assay as described in the appended examples herein can be used. Specifically, the competition between the reference antibody and the antigen binding polypeptide can be tested by a flow cytometer assay as herein further disclosed below, e.g. FACS, wherein the binding of the reference antibody to α/β TCR/CD3-positive cells is determined in presence of the antigen binding polypeptide and compared to the binding of the reference antibody alone. An example for α/β TCR/CD3-positive cells are T cells, preferably Jurkat cells. In the competition assay, it is preferred to use an antigen binding polypeptide of the invention that comprises an Fc part, e.g. the antigen binding polypeptide of the invention comprises elements of an antibody. For example, the reference antibody can exhibit constant domains derived from mouse IgG1, whereas the antigen binding polypeptide can exhibit constant domains derived from human IgG 1. In such an experiment the reference antibody, is used at a concentration of about the EC50 of the binding determined before, is incubated in presence or absence of equimolar concentration of the antigen binding polypeptide on the α/β TCR/CD3-positive cells. Binding of the reference antibody can then be determined using mouse-specific secondary reagents, e.g. goat F(ab')2 anti-mouse IgG1 (Fc)-RPE (Dianova, SBA-1072-09) in a second staining step. Competition of reference antibody and antigen binding polypeptide is indicated by reduced binding of the reference antibody in presence of the antigen binding polypeptide compared to binding of the reference antibody alone. Preferably, the reference antibody reduces the binding of the antigen binding polypeptide to the α/β TCR/CD3 complex, in particular α/β TCR/CD3-positive cells by at least 10%, more preferably by at least 20%, more preferably by at least 30%.

The "reference antibody" as used herein in context of the competition assay is defined by its heavy and light chain variable domain, and preferably further comprises an IgG1 constant domain and a Cκ light chain. Preferably, the reference antibody comprises a human IgG1 constant domain. More preferably the reference antibody comprises a hinge-CH2-CH3 region according to SEQ ID NO: 61. Preferably, the reference antibody comprises a VH according to SEQ ID NO: 1 and a VL according to SEQ ID NO: 2, more preferably BMA031 (V36) consisting of a heavy chain (HC) according to SEQ NO: 60 and a light chain (LC) according to SEQ ID NO. 6 The reference antibody does not comprise the inventive substitutions as defined herein above and below. In particular, the reference antibody does not comprise the positively charged amino acid substitution(s). Preferably, the reference antibody does not comprise the positively charged amino acid substitution(s) and/or the substitution with tyrosine at position 90 of the heavy chain.

A "parental antigen binding polypeptide" generally refers to an antigen binding polypeptide to which the antigen binding polypeptide of the invention is compared to, e.g. when assessing properties like Tm, EC50 or % gain in binding AUC. The "parental antigen binding polypeptide" does not comprise the inventive substitutions as defined herein above and below. In particular, the parental antigen binding polypeptide does not comprise the positively charged amino acid substitution(s). Preferably, the parental antigen binding polypeptide does not comprise the positively charged amino acid(s) and/or the substitution with tyrosine at position 90 of the heavy chain. The effect of the inventive substitutions should preferably be compared between two similar molecules, i.e. molecules that only differ in the inventive substitutions according to the first aspect of the invention. The "parental antigen binding polypeptide" thus may refer in certain aspects to a molecule that comprises a VH according to SEQ ID NO: 1 (BMA031 V36) and a VL according to SEQ ID NO: 2 (VL BMA031 V36) and which otherwise has the amino acid sequence of the antigen binding polypeptide. In a preferred embodiment, the parental antigen binding polypeptide has the amino acid sequence of an antibody, e.g. BMA031 (V36), or is a functional fragment thereof, e.g. a Fab and is referred to as "parental antibody" in the context of the present invention.

The "parental antibody" does not comprise the substitutions as defined in context of the invention. An example for such a "parental antibody" is BMA031 or a further humanized variant of BMA031, e.g. BMA031 (V36) as disclosed herein below, or preferably a fragment thereof. The parental antibody is defined by its heavy and light chain variable domain, preferably, the parental antibody comprises a VH according to SEQ ID NO: 1 (BMA031 V36) and a VL according to SEQ ID NO: 2 (VL BMA031 V36). The term parental antibody is also used in context of the comparative molecule in the below defined embodiments and examples, e.g. determination of binding (e.g. EC50 or % gain in binding AUC), or determination of melting temperature (Tm).

In preferred embodiments, the parental antigen binding polypeptide comprises or consists of the VH and VL domains of BMA031(V36) as herein defined.

In a preferred embodiment, as it is the case in the example section, the functional features, such as "% gain in binding AUC", "binding EC50" and/or "Tm" further described herein below, are determined when the antigen binding polypeptide and the parental antigen binding polypeptide are both in the same format, for example a Fab fragment as described in example 1.

The comparison of the antigen binding polypeptide of the invention and the parental antigen binding polypeptide is carried out under similar, preferably identical experimental conditions, preferably in parallel, more preferably the antigen binding polypeptide of the invention and the parental antigen binding polypeptide are part of the same assay. Most preferably, the functional properties of the antigen binding polypeptide herein described are compared to the parental antigen binding polypeptide when both are present as a Fab or Fab fragment.

The term "T cell receptor" (TCR) refers in the context of the present invention to a heterodimeric cell surface protein of the immunoglobulin super-family, which is associated with invariant proteins of the CD3 complex involved in mediating signal transduction. TCRs exist in $\alpha/\beta$ and $\gamma/\delta$ forms, which are structurally similar but have quite distinct anatomical locations and also presumably different functions. The extracellular portion of native heterodimeric $\alpha\beta$ TCR and $\gamma\delta$ TCR each contain two polypeptides, each of which has a membrane-proximal constant domain, and a membrane-distal variable domain. Each of the constant and variable domains include an intra-chain disulfide bond. The variable domains contain the highly polymorphic loops analogous to the complementarity determining regions (CDRs) of antibodies. The term "TCR" refers in the context of the present invention also to fragments thereof, as well as single chain TCRs and fragments thereof, in particular variable alpha and beta domains of single domain TCRs, and chimeric, humanized, bispecific or multispecific TCRs. The use of TCR gene therapy overcomes a number of current hurdles. It allows equipping the subjects' (patients') own T-cells with desired specificities and generation of sufficient numbers of T-cells in a short period of time, avoiding their exhaustion. The TCR will be transduced into potent T-cells (e.g. central memory T-cells or T-cells with stem cell characteristics), which may ensure better persistence, preservation and function upon transfer. TCR-engineered T-cells will be infused into cancer patients rendered lymphopenic by chemotherapy or irradiation, allowing efficient engraftment but inhibiting immune suppression.

The term "fragments of a TCR" refers in the context of the present invention to a portion of a full-length or wildtype TCR, in particular the antigen binding site or variable region of such a TCR. Examples of TCR fragments include fragments of the $\alpha$, $\beta$, $\delta$ or $\gamma$ chain, such as $V_\alpha$-$C_\alpha$ or $V_\beta$-$C_\beta$ or portions thereof. These fragments may also further comprise the corresponding hinge region or single chain variable domains, such as $V_\alpha$, $V_\beta$, $V_\delta$, $V_\gamma$, single chain V$\alpha$/V$\beta$ fragments or bispecific and multispecific TCRs formed from TCR fragments. Fragments of a TCR exert identical functions compared to the naturally occurring full-length or wildtype TCR, i.e. fragments selectively and/or specifically bind to their target antigens, in particular antigenic peptides or target peptides in complex with major histocompatibility complex I or II (MHC I or MHC II).

The term "single chain TCR (scTCR)" refers in the context of the present invention to a protein or antigen binding polypeptide wherein the variable domains of the TCR, such as the $V_\alpha$ and $V_\beta$ or $V_\delta$ and $V_\gamma$ are located on one polypeptide chain. Typically, the variable domains are separated by a linker, wherein said linker typically comprises 10 to 30, such as 10 to 25 amino acids.

The term "wildtype alpha-beta heterodimeric TCRs" refers in the context of the present invention to a TCR having an alpha chain and a beta chain. Each alpha chain comprises variable, joining and constant regions, and the beta chain also usually contains a short diversity region between the variable and joining regions, but this diversity region is often considered as part of the joining region. The constant, or C, regions of TCR alpha and beta chains are referred to as TRAC and TRBC respectively (Lefranc, (2001), Curr Protoc Immunol Appendix 1: Appendix 10). Each variable region, herein referred to as alpha variable domain and beta variable domain, comprises three CDRs embedded in a framework sequence, one being the hypervariable region named CDR3. The alpha variable domain CDRs are herein referred to as CDRa1, CDRa2, CDRa3, and the beta variable domain CDRs are herein referred to as CDRb1, CDRb2, CDRb3. There are several types of alpha chain variable (Valpha) regions and several types of beta chain variable (Vbeta) regions distinguished by their framework, CDR1 and CDR2 sequences, and by a partly defined CDR3 sequence. The Valpha types are referred to in IMGT nomenclature by a unique TRAV number, Vbeta types are referred in IMGT nomenclature to by a unique TRBV number (Folch and Lefranc, (2000), Exp Clin Immunogenet 17(1): 42-54; Scaviner and Lefranc, (2000), Exp Clin Immunogenet 17(2): 83-96; LeFranc and LeFranc, (2001), "T cell Receptor Factsbook", Academic Press). For more information on immunoglobulin antibody and TCR genes see the international ImMunoGeneTics information System®, Lefranc M-P et al (Nucleic Acids Res. 2015 January; 43 (Database issue):D413-22). A conventional TCR antigen binding site, therefore, includes, usually, six CDRs, comprising the CDR set from each of an alpha and a beta chain variable region, wherein CDR1 and CDR3 sequences are relevant to the recognition and binding of the peptide antigen that is bound to the HLA protein and the CDR2 sequences are relevant to the recognition and binding of the HLA protein.

The term "antibody", also termed "immunoglobulin" refers in the context of the present invention to an antigen binding polypeptide comprising two heavy chains that are linked to each other by disulfide bonds and each heavy chain is linked to a light chain by a disulfide bond. There are two types of light chains, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody binding site or paratope and the antigenic determinant. Antibody binding sites are made up of residues that are primarily from the hypervariable or complementarity determining regions (CDRs). Occasionally, residues from non-hypervariable or FR influence the overall domain structure and hence the antigen binding site. CDRs refer to amino acid sequences that together define the binding affinity and specificity of the natural Fv region of a native immunoglobulin binding site. Examples of an antibody or immunoglobulin is an IgM, IgD, IgG, IgA or IgE. CDRs of antigen binding polypeptides of the present invention can be grafted into antibodies, bispecific antibodies, or multispecific antibodies. Knowing the amino acid sequence of the CDRs of for example an antibody, a TCR or an antigen binding polypeptide of the invention, one skilled in the art can determine the framework regions, such as the antibody framework regions or TCR framework regions. However, in cases where the CDRs are not indicated, the skilled person in the art can first determine the CDR amino acid sequences based on the IMGT definition for antibodies and then determine the amino acid sequences of the framework regions.

The antigen binding polypeptide may comprise an antibody or a fragment thereof comprising the herein provided substitutions. The term "antibody" refers in the context of the present invention also to antibodies and fragments thereof, as well as single domain antibodies and fragments thereof and multispecific antibodies and fragments thereof, in particular a variable heavy chain of a single domain antibody, chimeric, humanized, bispecific or multispecific antibodies. "Fragments of antibodies" comprise a portion of an intact antibody, in particular the antigen binding site or variable region of the antibody. The fragments of the herein provided antibodies comprise the herein provided substitution(s). Examples of antibody fragments include Fv, Fab, F(ab')2, Fab', dsFv, (dsFv)2, scFv, sc(Fv)2, diabodies, bispecific and multispecific antibodies formed from antibody fragments. A fragment of an antibody may also be a single domain antibody, such as a heavy chain variable region (VHH). Preferably, "fragments of a antibodies" comprise a portion of an intact antibody, in particular comprise the antigen binding site comprising at least variable domain CDRs which comprise the positively charged amino acids at respective CDR positions as defined herein below. Fragments of antigen binding polypeptides or antibodies exert essentially the same or the same functions compared to the antigen binding polypeptide or antibody from which they are derived from (e.g. a portion of the antigen binding polypeptide or antibody), i.e. fragments of antibodies specifically bind to their target. The fragments of the herein provided antigen binding polypeptide or fragments of antibodies comprised in the antigen binding polypeptides, such as functional variants defined herein below, have an improved or increased binding and/or Tm compared to the parental antigen binding polypeptide or parental antibody. It is particularly preferred that fragments as defined herein lead to an improved binding or decreased binding EC50 of at least 2-fold and/or to improved Tm of at least 1° C. or to a delta Tm of at least 1° C. as defined herein below and compared to the parental antibody.

The term "human framework region" refers in the context of the present invention to a framework region that is substantially identical (about 85%, or more, in particular 90%, 95%, 97%, 99%) or identical (100%) to the framework region of a naturally occurring antigen binding polypeptide, such as a naturally occurring human antibody or human TCR.

The term "humanized antibody" refers in the context of the present invention to an antibody which is completely or partially of non-human origin and which has been modified to replace certain amino acids, in particular in the framework regions of the heavy and light chains, in order to avoid or minimize an immune response in humans. The constant domains of a humanized antibody are mainly human heavy and light chain domains. Methods for humanization of antibody sequences are known in the art; (Almagro & Fransson (2008) Front Biosci. 13: 1619-1633). One commonly used method is CDR grafting, or antibody reshaping, which involves grafting of the CDR sequences of a donor antibody, generally a mouse antibody, into the framework scaffold of a human antibody of different specificity. Since CDR grafting may reduce the binding specificity and affinity, and thus, the biological activity, of a CDR grafted non-human antibody, back mutations may be introduced at selected positions of the CDR grafted antibody in order to retain the binding specificity and affinity of the parent antibody Amino acid residues that are part of a CDR will typically not be altered, although in certain cases it may be desirable to alter individual CDR amino acid residues, for example to remove a glycosylation site, a deamidation site, an isomerization site, or an undesired cysteine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, in particular by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ser. When such a deamidation site, in particular Asn-Gly, is present in a CDR sequence, it may therefore be desirable to remove the site, typically by conservative substitution to remove one of the implicated residues. Substitution in a CDR sequence to remove one of the implicated residues is also intended to be encompassed by the present invention.

The term "Fab" refers in the context of this invention to an antibody fragment having a molecular weight of about 50,000 Dalton and antigen binding activity, in which about a half of the N-terminal side of heavy chain and the entire light chain, among fragments obtained by treating IgG with a protease, e.g. papain, are bound together through a disulfide bond.

The term "bispecific molecule" refers in the context of this invention to the antigen binding polypeptide with at least two valences and binding specificities for two different antigens and, thus, comprises two antigen binding sites. The term "valence" refers to the number of binding sites of an antigen binding polypeptide, e.g. a bivalent antigen binding polypeptide relates to an antigen binding polypeptide that has two antigen-binding sites. The term valence refers to the number of binding sites, which may bind to the same or different target. A bivalent antigen binding polypeptide may be monospecific, i.e. may bind to one target, or bispecific, i.e. may bind to two different targets. Targets may be antigens including their respective epitopes, target peptides, off-target peptides such as similar peptides or the α/β TCR/CD3 complex.

For the term "bispecific" in the context of the present invention it is preferred that at least one specificity of the antigen binding sites is derived from an antibody, more particularly, that at least one antigen-binding site comprises antibody derived CDRs as disclosed herein. Accordingly, "bispecific" in the context of the present invention refers to an antigen binding polypeptide which combines at least one antigen binding site comprising CDRs as defined in context of the present invention, preferably antibody derived CDRs, and at least one further (second) antigen binding site, wherein said at least one further antigen binding site, may be derived from an antibody and thus, comprises antibody CDRs, or may be derived from a TCR, and, thus, comprises TCR CDRs. In a preferred embodiment, said further (second) antigen binding site is derived from a TCR and, thus, comprises TCR CDRs.

The term "format" refers in the context of the present invention to antigen binding polypeptides comprising a specific number and type of domains that are present in said antigen binding polypeptide and the spatial organization thereof. Many different formats, such as bispecific formats, are described in the art. Such formats include non-limiting examples of diabodies, Cross-Over-Dual-Variable-Domain (CODV) and/or Dual variable domain (DVD) polypeptides. The antigen binding polypeptide may be a diabody, a Cross-Over-Dual-Variable-Domain (CODV) and/or Dual variable domain (DVD) polypeptide that comprises the inventive amino acid residues at the positions defined in the claims.

The term "diabodies (Db)" refers in context of antibodies and in the context of the present invention typically to bivalent molecules composed of two chains, each comprising a VH and VL domain, either from the same or from different antibodies. The two chains typically have the configuration VHA-VLB and VHB-VLA (A and B representing two different specificities) or VLA-VHB and VLB-VHA.

In the context of the present invention, "diabodies (Db)" or the "diabody format" herein refers to bivalent molecules composed of two polypeptide chains, each comprising two variable domains connected by a linker ($L_{Db1}$ and $L_{Db2}$), wherein two of the domains are first and second domains as defined in the context of the present invention ($V_1$ and $V_2$) and the other two domains may be TCR derived or antibody derived variable domains ($V_A$, $V_B$). The $V_1$ and $V_2$ domains are located on two different polypeptides and the VA and VB domains are located on two different polypeptides and the domains dimerize in a head-to-tail orientation. Accordingly, the orientation may be $V_1$-$L_{Db1}$-$V_A$ and $V_B$-$L_{Db2}$-$V_2$, $V_2$-$L_{Db1}$-$V_A$, and $V_B$-$L_{Db2}$-$V_1$, $V_1$-$L_{Db1}$-$V_B$ and $V_A$-$L_{Db2}$-$V_2$ or $V_2$-$L_{Db1}$-$V_B$ and $V_A$-$L_{Db2}$-$V_1$. In order to allow the domains to dimerize head to-tail the linker, i.e. $L_{Db1}$ and $L_{Db1}$, can be identical or different and are short linkers. A short linker is a linker that is typically between 2 to 12, 3 to 13, such as 3, 4, 5, 6, 7, 8, 9 amino acids long, for example 4, 5 (Brinkmann U and Kontermann R. E., MAbs. 2017 February-March; 9(2): 182-212) or 8 amino acids long.

The "dual-variable-domain immunoglobulin (DVD-Ig™)" format was initially described in 2007 by Wu C. et al. (Nat Biotechnol. 2007 November; 25(11):1290-7). In this format, the target-binding variable domains of a second monoclonal antibody (B) are typically fused to a conventional antibody (A) (comprising the domains $V_{LA}$ and $V_{HA}$), wherein the light chain of the conventional antibody (A) thus comprises an additional light chain variable domain ($V_{LB}$) and the heavy chain of the conventional antibody (A) comprises an additional heavy chain variable domain ($V_{HB}$). The DVD-Ig™ as described in the art, is thus typically composed of two polypeptide chains, one heavy chain comprising $V_{HB}$-L-$V_{HA}$-$C_{H1}$-$C_{H2}$-$C_{H3}$ and one light chain comprising $V_{LB}$-L-$V_{LA}$-$C_L$. The domain pairs $V_{LA}$/$V_{HA}$ and $V_{LB}$/$V_{HB}$ are thus pairing in parallel.

In the context of the present invention, the "dual-variable-domain Ig format" refers to a polypeptide comprising two polypeptide chains, each comprising two variable domains connected by a linker ($L_1$, $L_3$), wherein two of the domains are first and second domains as defined in the context of the present invention ($V_1$ and $V_2$) and the other two domains are antibody derived heavy and light chain variable domains ($V_{HA}$ and $V_{HB}$). In the DVD-Ig format in the context of the present invention the polypeptide chains have, for example, the organization $V_1$-$L_1$-$V_{HA}$-$L_2$-$C_{H1}$-$C_{H2}$-$C_{H3}$ and $V_2$-$L_3$-$V_{LA}$-$L_4$-$C_L$ or $V_2$-$L_1$-$V_{HA}$-$L_2$-$C_{H1}$-$C_{H2}$-$C_{H3}$ and $V_1$-$L_3$-$V_{LA}$-$L_4$-$C_L$. The connecting linkers $L_1$ and $L_3$ are preferably between 5 to 20 amino acid residues long, such as 5 to 15 amino acid residues, and/or the connecting linkers $L_2$ and $L_4$ may be present or absent.

The "crossover dual-variable domain-Ig-like proteins" known in the art in the context of antibodies describes a format in which two $V_H$ and two $V_L$ domains are linked in a way that allows crossover pairing of the variable $V_H$-$V_L$ domains, which are arranged either (from N- to C-terminus) in the order $V_{HA}$-$V_{HB}$ and $V_{LB}$-$V_{LA}$, or in the order $V_{HB}$-$V_{HA}$ and $V_{LA}$-$V_{LB}$.

In the context of the present invention, the "crossover dual-variable domain-Ig-like protein" refers to a protein comprising two polypeptide chains, each comprising two variable domains connected by a linker ($L_1$, $L_2$, $L_3$ and $L_4$), wherein two of the domains are first and second domains as defined in the context of the present invention ($V_1$ and $V_2$) and the other two domains are antibody derived heavy and light chain variable domains ($V_{HA}$, $V_{HB}$). In the CDVD-Ig format in the context of the present invention the polypeptide chains have, for example the organization $V_1$-$L_1$-$V_{HA}$-$L_2$-$C_{H1}$-$C_{H2}$-$C_{H3}$ and $V_{LA}$-$L_3$-$V_2$-$L_4$-$C_L$, $V_2$-$L_1$-$V_{HA}$-$L_2$-$C_{H1}$-$C_{H2}$-$C_{H3}$ and $V_{LA}$-$L_3$-$V_1$-$L_4$-$C_L$, $V_{HA}$-$L_1$-$V_1$-$L_2$-$C_{H1}$-$C_{H2}$-$C_{H3}$ and $V_2$-$L_3$-$V_{LA}$-$L_{DVD3}$-$C_L$ or $V_{HA}$-$L_1$-$V_2$-$L_2$-$C_{H1}$-$C_{H2}$-$C_{H3}$ and $V_1$-$L_3$-$V_{LA}$-$L_4$-$C_L$. In this CDVD format, the linkers ($L_1$ to $L_4$) are typically of different length. For example, $L_1$ is 3 to 12 amino acid residues in length, $L_2$ is 3 to 14 amino acid residues in length, $L_3$ is 1 to 8 amino acid residues in length, and $L_4$ is 1 to 3 amino acid residues in length, or $L_1$ is 5 to 10 amino acid residues in length, $L_2$ is 5 to 8 amino acid residues in length, $L_3$ is 1 to 5 amino acid residues in length, and $L_4$ is 1 to 2 amino acid residues in length or $L_1$ is 7 amino acid residues in length, $L_2$ is 5 amino acid residues in length, $L_3$ is 1 amino acid residues in length, and $L_4$ is 2 amino acid residues in length.

The term "covalently linked" or "covalent link" refers in the context of the present invention for example to a disulfide bridge or disulfide bond or a peptide link or a covalent link via a linker or linker sequence, such as a polypeptide linker The term "linker" or "peptide linker" refers in the context of the present invention to "to an amino acid sequence which sterically separates two parts or moieties of a complex, e.g. two peptides, polypeptides or proteins. Typically, such linker comprises or consists of between one and 20 amino acids. Peptide linker provide flexibility among the two moieties that are linked together. Flexibility is generally increased if the amino acids are small. Accordingly, flexible peptide linkers comprise an increased content of small amino acids, in particular of glycine and/or alanine, and/or hydrophilic amino acids such as serine, threonine, asparagine and glutamines. In the context of the present invention, peptide linkers, e.g. one or more amino acid residues, inserted between two domains provide sufficient mobility for the domains, for example in single chain constructs, or between the variable domains of light and heavy chain variable domains, and allow correct folding to form the antigen binding site. In case of a bispecific antigen binding polypeptide, the linker allows forming the antigen binding site and the further antigen binding site, either in a cross over pairing (in a CODV format or in some of the diabody formats) or in a parallel pairing configuration (for example, in a DVD format) of the antigen binding polypeptides of the invention. Linker in context of the present invention are abbreviated as $L_1$, $L_2$, $L_3$, $L_4$ etc.

The term "dimerization domains" (also abbreviated as $D_1$ or $D_2$, respectively) in the context of the present invention preferably refers to heterodimerization domains that mediate heterodimerization of a first polypeptide chain with a second polypeptide chain, but not homodimerization of two first or two second polypeptide chains. In preferred embodiments, a pair of dimerization domains (e.g. $D_1$ and $D_2$) comprises immunoglobulin constant domains, such as antibody-derived $C_L$ and $C_{H1}$, or $C_L$-$F_c$ and $C_{H1}$-$F_c$, or TCR-derived $C_\alpha$ and $C_\beta$, or a pair of $C_{H3}$ domains or a pair of $F_c$, domains, wherein the $C_{H3}$ and $F_c$ domains preferably comprise introduced mutations that force heterodimerization, such as knob-into-hole mutations. In particular the dimerization domains relate to Fc domains as defined herein below.

The term "Fc domain" as used in the context of the present invention encompasses native Fc domains and Fc domain variants and sequences as further defined herein below. In context of Fc variants and native Fc molecules, the term "Fc domain" includes molecules in monomeric or multimeric form, whether digested from whole antibodies or produced by other means.

The term "native Fc" as used herein refers to a molecule comprising the sequence of a non-antigen-binding fragment resulting from digestion of an antibody or produced by other means, whether in monomeric or multimeric form, and may contain the hinge region. The original immunoglobulin source of the native Fc is, in particular, of human origin and can be any of the immunoglobulins, preferably IgG1 or IgG2, most preferably IgG1. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG. The term "native Fc" is generic to the monomeric, dimeric, and multimeric forms. It is preferred that the Fc domain comprises or further comprise the "RF" and/or "Knob-into-hole" mutation, preferably the "Knob-into-hole". The "RF mutation" typically refers to the amino acid substitutions of the amino acids HY into RF in the CH3 domain of Fc domains, such as the amino acid substitution H435R and Y436F in CH3 domain as described by Jendeberg, L. et al. (1997, J. Immunological Meth., 201: 25-34) and is described as advantageous for purification purposes as it abolishes binding to protein A. In case the bispecific antigen binding polypeptide comprises two FC-domains, the RF mutation may be in one or both, preferably in one Fc-domain. The "Knob-into-Hole" or also called "Knob-into-Hole" technology refers to amino acid substitutions T366S, L368A and Y407V (Hole) and T366W (Knob) both in the CH3-CH3 interface to promote heteromultimer formation. Those knob-into-hole mutation can be further stabilized by the introduction of additional cysteine amino acid substitutions Y349C and S354C. The "Knob-into-Hole" technology together with the stabilizing cysteine amino acid substitutions has been described in patents U.S. Pat. Nos. 5,731,168 and 8,216,805 incorporated herein by reference.

The term "amino acid" refers in the context of the present invention to any monomer unit that comprises a substituted or unsubstituted amino group, a substituted or unsubstituted carboxy group, and one or more side chains or groups, or analog of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labelled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these are to be interpreted as "any amino acid." The structures of these twenty natural amino acids are shown in, e.g., Stryer et al., Biochemistry, $5^{th}$ ed., Freeman and Company (2002). Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466). The term "amino acid" also includes unnatural amino acids, modified amino acids (e.g., having modified side chains and/or backbones), and amino acid analogs(see, e.g., Zhang et al. (2004) "Selective incorporation of 5-hydroxytryptophan into proteins in mammalian cells," Proc. Natl. Acad. Sci. U.S.A. 101(24):8882-8887; Anderson et al. (2004) "An expanded genetic code with a functional quadruplet codon" Proc. Natl. Acad. Sci. U.S.A. 101(20):7566-7571; Ikeda et al. (2003) "Synthesis of a novel histidine analogue and its efficient incorporation into a protein in vivo," Protein Eng. Des. Sel. 16(9):699-706; Chin et al. (2003) "An Expanded Eukaryotic Genetic Code," Science 301(5635):964-967; James et al. (2001) "Kinetic characterization of ribonuclease S mutants containing photoisomerizable phenylazophenylalanine residues," Protein Eng. Des. Sel. 14(12):983-991; Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25):14310-14315; Bacher et al. (2001) "Selection and Characterization of *Escherichia coli* Variants Capable of Growth on an Otherwise Toxic Tryptophan Analogue," J. Bacteriol. 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with {beta}-(thienopyrrolyl) alanines as alternative chromophores and pharmaceutically active amino acids," Protein Sci. 10(7): 1281-1292). Amino acids can be merged into peptides, polypeptides, or proteins.

Amino acids can be further categorized in polar and non polar amino acids. Polarity is defined as a separation of electric charge leading to a molecule or its chemical groups having an electric dipole moment with a negatively and a positively charged end. Polar molecules interact through dipole—dipole intermolecular forces and hydrogen bonds. Polarity underlies a number of physical properties including surface tension, solubility, and melting and boiling points. Polar amino acids comprise amino acids with hydrogen donor and/or acceptor atoms, except tryptophan. Indeed, tryptophan, despite its hydrogen donor atom, has been classified in the IMGT 'nonpolar' class, as it participates to the nonpolar core of the structural domains. The group of polar amino acids includes five charged (R, H, K, D, E) and five uncharged (N, Q, S, T, Y) amino acids. The group of nonpolar amino acids includes the uncharged amino acids, such as (A, C, G, I, L, M, F, P, W, V) amino acids. Polar amino acids are hydrophilic (Q, N) or neutral (S, T, Y), are usually on the outside of proteins, and are frequently engaged in hydrogen bonds. Nonpolar amino acids tend to cluster their side chains together in the inside of proteins and are frequently engaged in Van der Waals interactions.

The term "positively charged amino acid" refers in the context of the present invention to an amino acid wherein a side chain of the amino acid carries a positive charge. At pH 7, for example, lysine (K), arginine (R) are positively charged. Therefore, the positively charged amino acid is preferably R or K. H may also be charged at pH 7 under certain conditions. The term "Negatively charged" refers to an amino acid wherein a side chain of the amino acid carries a negative charge. At pH 7, for example, aspartic acid (D) and glutamic acid (E) are negatively charged. It is noted that the charge may depend on the pH of the solution an amino acid, peptide or protein is contained in and also on the temperature. In particular, the pH and temperature of the human body are of relevance if the antigen binding polypeptides of the present invention are applied as a medicament. Accordingly, the term "positively charged amino acid" refers to an amino acid that carries a positive charge under conditions found in the circulation and extracellular space of a subject, in particular the tumor tissue of a subject to which an antigen binding polypeptide is administered. Preferably the subject is a human. In this case, the amino acid carries a positive charge for example at the pH and temperature of the human body. In particular aspects, the positively charged amino acid is selected from the group consisting of arginine (R), histidine (H), and lysine (K), preferably wherein the positively charged amino acid is R or K. In the context of the present invention, the at least one amino acid of a respective position in a CDR or VH or VL as defined herein below and that is not positively charged is substituted with a positively charged amino acid. For example, a position carries serine (S) and thus, is a position with a not positively charged amino, and is substituted with a positively charged amino acid, for example R. Residue S, thus, constitutes the not positively charged amino acid. A residue of a certain CDR or of a certain VH or VL as defined herein below having a not positively charged amino acid may either have an uncharged or not charged amino acid or have a negatively charged amino acid residue. In this context it is preferred that, if Q naturally occurs at a certain position in HCDR2, it is preferably not substituted with a positively charged amino acid in the context of the invention.

The term "substituted" as used throughout the specification refers to the replacement of an amino acid in a parental antigen binding polypeptide with another amino acid, which is different from the amino acid that is replaced.

The term "peptide" refers in the context of the present invention to a short polymer of amino acids linked by peptide bonds. It has the same chemical (peptide) bonds as proteins but is commonly shorter in length. The shortest peptide is a dipeptide, consisting of two amino acids joined by a single peptide bond. There can also be a tripeptide, tetrapeptide, pentapeptide, etc. Typically, a peptide has a length of up to 8, 10, 12, 15, 18 or 20 amino acids. A peptide has an amino end and a carboxyl end, unless it is a cyclic peptide or chemically modified.

The term "amino acid sequence identity" refers in the context of the present invention to the percentage of sequence identity and is determined by comparing two optimally aligned sequences over a comparison window, wherein the portion of the sequence in the comparison window can comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" refers in the context of two or more polypeptides or nucleic acid sequences, refers to two or more sequences or subsequences that are the same, i.e. comprise the same sequence of amino acids or nucleic acids. Sequences are "substantially identical" to each other if they have a specified percentage of amino acid residues that are the same (e.g., at least 70%, at least 75%, at least 80, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over a specified region), when compared and aligned for maximum correspondence over a comparison window, or designated region as measured using one of the following sequence comparison algorithms or by manual alignment and visual inspection. These definitions also refer to the complement of a test sequence. Accordingly, the term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

The term "sequence comparison" refers in the context of the present invention to the process wherein one sequence acts as a reference sequence, to which test sequences are compared. When using a sequence comparison algorithm, test and reference sequences are inputted into a computer, if necessary subsequence coordinates are designated, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by its SEQ ID number, if not specifically indicated otherwise.

Methods of alignment of sequences for comparison are well known in the art. Optimal alignment of sequences for comparison can be conducted, for example, by the local homology algorithm of Smith and Waterman (Adv. Appl. Math. 2:482, 1970), by the homology alignment algorithm of Needleman and Wunsch (J. Mol. Biol. 48:443, 1970), by the search for similarity method of Pearson and Lipman (Proc. Natl. Acad. Sci. USA 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wisc.), or by manual alignment and visual inspection (see, e.g., Ausubel et al., Current Protocols in Molecular Biology (1995 supplement)). Algorithms suitable for determining percent sequence identity and sequence similarity are the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

Another measure of similarity provided by the BLAST algorithm is the smallest sum probability (P(N)), which provides an indication of the probability by which a match between amino acid sequences would occur by chance. For example, an amino acid is considered similar to a reference sequence if the smallest sum probability in a comparison of the test amino acid to the reference amino acid is less than about 0.2, typically less than about 0.01, and more typically less than about 0.001. Semi-conservative and especially conservative amino acid substitutions, wherein an amino acid is substituted with a chemically related amino acid are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are indicated in below Table 2.

TABLE 2

Amino acids and conservative and semi-conservative substitutions, respectively

| Amino acid | Conservative substitution | Semi-conservative substitution |
|---|---|---|
| A | G; S; T N; V; C | |
| C | A; V; L | M; I; F; G |
| D | E; N; Q | A; S; T; K; R; H |
| E | D; Q; N | A; S; T; K; R; |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V D; E; R; K; I | |
| V | A; L; I M; T; C; N | |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

The term "functional variant" or "variant" as used in the context of the present invention refers to an antigen binding polypeptide or a polypeptide of the invention having substantial or significant sequence identity or similarity to the given antigen binding polypeptide or polypeptide, wherein said functional variant retains the biological activity of the given antigen binding polypeptide or polypeptide. In the context the present invention, the antigen binding polypeptides comprising the inventive substitutions, in particular the respective positively charged amino acids and/or Y at position 90 as defined herein above and below, lead to improved or increased binding (e.g. binding $EC_{50}$) and/or to improved or increased Tm compared to the parental antigen binding polypeptide or reference antigen binding polypeptide. It is therefore, envisioned that functional variants of the antigen binding polypeptides of the invention have the same, or improved and increased, respectively, binding (e.g. binding $EC_{50}$) or Tm as the antigen binding polypeptide they are compared with. Furthermore, this is also envisioned for parts, regions, or fragments of the antigen binding polypeptide of the invention such as FR or VH or VL. Herein provided functional variants of, for example, FR, VH, VL or antigen binding polypeptides as defined herein may have an amino acid sequence that is at least 80%, 85%, 90%, 95%, 96%, 97%, 98% or 99% identical to the amino acid sequence of the given antigen binding polypeptide, for example the antigen binding polypeptide. In some embodiment, the functional fragment comprises the inventive substitutions. Preferably, the functional fragment has an improved or increased binding (e.g. binding $EC_{50}$) and/or Tm compared to the parental antigen binding polypeptide or a fragment thereof not comprising the inventive substitutions.

A "functional variant" as defined herein can, for example, comprise the amino acid sequence of the respective antigen binding polypeptide of the invention with at least one conservative amino acid substitution. Alternatively, or additionally, the functional variants can comprise the amino acid sequence of the respective antigen binding polypeptide of the invention with at least one non-conservative amino acid substitution. In this case, it is preferable that the non-conservative amino acid substitution does not interfere with or inhibit the biological activity of the functional variant. Preferably, the non-conservative amino acid substitution enhances the biological activity of the functional variant, such that the biological activity of the functional variant is increased as compared to the respective antigen binding polypeptide or fragment thereof.

The term "stability" refers in the context of the present invention to the thermal stability of proteins, polypeptides or antigen binding polypeptides. Proteins or polypeptides are typically characterized by inter alia thermal resistance or thermal stability, described by the parameter "melting temperature (Tm)". Temperature is a factor in order to provide functional and correctly folded proteins. The stability of proteins thus, vary under different temperature conditions applied. Above the native temperature of a protein, thermal energy will lead to unfolding and denaturation of said protein. If a protein is resistant to an irreversible change at high temperatures, it its described as thermostable or thermally stable. As mentioned above, thermal stability is defined by the descriptor melting temperature Tm.

The term "melting temperature (Tm)" refers in the context of the present invention to "thermal stability", the temperature at which the concentration of the protein in its folded state equals the concentration of the unfolded protein (Miotto et al., Insights on protein thermal stability: a graph representation of molecular interactions; bioRxiv preprint doi: https://doi.org/10.1101/354266; Jun. 22, 2018). In particular, the Tm is the temperature at which 50% of the protein is unfolded as demonstrated herein below in the examples. If polypeptides or proteins reach their Tm, the free energy change AG is equal to zero. At this point the polypeptide or protein molecules disappear into amorphous state and the proteins chains cannot refold themselves. A general rule of thumb is that an increase in Tm is associated with increases in the free energy of maximal stability delta G(T*). The Tm can be measured by using circular dichroism (CD)—a spectroscopic technique for following the unfolding and folding of proteins as a function of temperature or by differential scanning calorimetry (DSC), differential scanning fluorimetry (DSF) or biochemical assays. Generally, proteins or polypeptides with high T., values are more stable than those with lower Tm values. Increase in thermal stability leads to decreased denaturation of antigen binding polypeptides and, thus, to, for example, improved storage conditions of said polypeptides. Nano differential scanning fluorimetry (nano-DSF) as an exemplary method is disclosed herein below in the appended examples for determining the Tm using PBS (phosphate buffered saline) buffer at pH 7.4. Preferably, the Tm is determined by DSF, more preferably by nanoDSF. In particular, the Tm is determined by DSF in PBS pH 7.4 with a heating ramp rate of 1° C./min, wherein the antigen binding polypeptide has a concentration of 50 µg/ml. Absolute melting temperatures can be directly obtained. Delta Tm values of different analytes can be calculated. It is preferred that values that are compared with each other are comprised in the same experimental run.

The term "binding" refers in the context of the present invention to "binding affinity" or "binding area under the curve (AUC)" or "binding EC50 value" as further defined in detail below. In particular, "binding" refers to binding of the antigen binding polypeptide to the α/β TCR/CD3 complex as defined above, or preferably to binding of the antigen binding polypeptide to cells expressing the α/β TCR/CD3 complex, or more preferably T cells expressing the α/β TCR/CD3 complex. Binding of the antigen binding polypeptide can be determined by a flow cytometer assay as herein further disclosed below in the examples, e.g. by FACS, wherein the binding of the antigen binding polypeptide to α/β TCR/CD3-positive cell is determined, e.g. in comparison to a parental antigen binding polypeptide, in particular to an antigen binding polypeptide not comprising the inventive substitutions, e.g. BMA031 (V36). Preferably, binding of the antigen binding polypeptide to cells expressing the α/β TCR/CD3 complex is determined by flow cytometric binding analysis using α/β TCR/CD3-positive Jurkat cells (e.g. Clone E6-1 cells), and α/β TCR/CD3-negative Jurkat cells. In particular, the binding of the antigen binding polypeptide is determined by testing different concentrations, e.g. from 10 µg/ml to 10 ng/ml in half log steps of the antigen binding polypeptide. In further particular aspects, the binding to the cells and the washing steps are performed in a buffer comprising PBS, 2 mM ethylenediaminetetraacetic acid (EDTA), 5% fetal calf serum (FCS). In further particular aspects, the antigen negative cells (e.g. labelled with CFSE CellTrace) are mixed with the antigen positive cells in 1:1 ratio. In further particular aspects, the concentrations of the antigen binding polypeptide (e.g. 100

µl/well) is incubated with the cell mix (e.g. 100.000 cells/well) for e.g. 15 min on ice in said buffer, and the cells are washed to remove unbound antigen binding polypeptide. Preferably, a sorting/staining for live/dead cells is conducted. The staining of the cells bound to the antigen binding polypeptide can be determined in a flow cytometer (e.g. Intellicyt iQue Screener (Sartorius AG) or CytoFLEX (Beckmann Coulter, 2089495-01)) and the MFI (median fluorescence intensity) values can be compared.

The "binding affinity" or "affinity" in the context of the present invention may be expressed for example in half-maximal effective concentration ($EC_{50}$) or the equilibrium dissociation constant ($K_D$).

"half maximal effective concentration" also abbreviated as "$EC_{50}$" or "EC50" refers in the context of the present invention to "binding EC50" or to "functional EC50" and it is indicated, respectively throughout the application whichever term is used.

The term "binding EC50" in the context of the present invention can be described as the concentration of a ligand, for example an antigen binding polypeptide or protein at which half of the target, for example the α/β TCR/CD3 complex, is present in the bound state. The binding EC50 is a parameter for measuring the binding of the antigen binding polypeptide to target cells, preferably T cells expressing the α/β TCR/CD3 complex, i.e. the binding of the antigen binding polypeptides of the invention to their target. The binding EC50 value depends on the target concentration. EC50 and affinity are inversely related which means the lower the EC50 value, the higher is the binding affinity of the molecule. Low binding EC50 values are generally preferred. Binding EC50 values are, for example, determined by flow cytometric binding analysis as described in the examples herein below using a flow cytometer (for example Intellicyt iQue Screener (Sartorius AG) or CytoFLEX (Beckmann Coulter, 2089495-01). Typically, measurements are conducted under the following conditions: labelled cells (for example cells not expressing the target antigen α/β TCR/CD3 complex, labelled with CFSE CellTrace) are mixed with antigen positive cells in 1:1 ratio. In further particular aspects, the antigen binding polypeptide (e.g. concentration of 100 µl/well) is incubated with the cell mix (e.g. 100.000 cells/well) for e.g. 15 min on ice in said buffer, and the cells are washed to remove unbound antigen binding polypeptide Staining can be determined in a flow cytometer and MFI values of different samples can be compared. Preferably, the EC50 value of the MFI of the antigen binding polypeptides of the invention is calculated and presented as x-fold decrease over the EC50 value of the MFI of the parental antibody BMA031 (V36), also designated TPP-1374, not comprising the inventive amino acid substitutions. For example, TPP-1389 shows a fold decrease in EC50 of 31.8 which means that the EC50 is 31.8-fold decreased compared to the EC50 determined by the identical method for the parental antibody TPP-1374. The binding EC50 value of the antigen binding polypeptides of the present invention is, thus, preferably lower than the binding EC50 value of the parental antigen binding polypeptide, e.g. an antigen binding polypeptide not comprising the inventive substitutions (e.g. not comprising the substitution with the positively charged amino acid, and/or not comprising tyrosine at position 90). As used herein below, the x-fold decrease of the inventive antigen binding polypeptide is compared to a parental antigen binding polypeptide not comprising the inventive substitutions (e.g. not comprising the substitution with the positively charged amino acid, and/or not comprising tyrosine at position 90). Preferably, the x-fold decrease of the inventive antigen binding polypeptide is compared to the parental antibody BMA031 (V36) comprising a VH according to SEQ ID NO: 1 and a VL according to SEQ ID NO: 2.

The term "functional EC50" refers in the context of the present invention to the half maximal effective concentration of a substance and is, thus, a measure of the concentration of said substance which induces a response halfway between the baseline and maximum after a specified exposure time. It is commonly used as a measure of a drug's potency. The EC50 of a graded dose response curve therefore represents the concentration of a substance where 50% of its maximal effect is observed. The $EC_{50}$ of a quantal dose response curve represents the concentration of a compound where 50% of the population exhibit a response, after a specified exposure duration. In one example, the "functional "EC50 value" refers to the concentration of the antigen binding polypeptide of the invention which induces a response halfway between the baseline and maximum after a specified exposure time. EC50 values can be experimentally assessed by a variety of known methods, using for example an IFN-gamma release assay or a LDH release assay, as for example described herein in example 3.

The term "area under the curve (AUC)" refers in the context of the present invention to the "binding area under the curve (binding AUC)" and is interchangeably used herein.

As set out above, binding may also be expressed as AUC or binding AUC, which is calculated based on logarithmized concentrations of the antigen binding polypeptide and the MFI. The calculated EC50, or AUC, signify the binding strength of an antigen binding polypeptide, e.g. antibody, to its target, e.g. antigen, and vice versa, and, therefore, increased AUC values indicate increased or improved binding of the antigen binding polypeptide to its target or vice versa, e.g. to the α/β TCR/CD3 complex, or preferably to cells expressing the α/β TCR/CD3 complex, or more preferably to T cells expressing the α/β TCR/CD3 complex. Preferably, the AUC of the antigen binding polypeptides of the invention are indicated in "% gain in binding AUC" or "% gain in AUC" which means "% increased AUC". The terms "% gain in binding AUC" or "% gain in AUC" can be used herein interchangeably. The binding AUC of the antigen binding polypeptide is compared to the binding AUC of the parental antigen binding polypeptide, in particular not comprising the inventive substitutions (e.g. not comprising the substitution with the positively charged amino acid, and/or not comprising tyrosine at position 90. As used herein, "% gain in binding AUC" or "% increased AUC" of the inventive antigen binding polypeptide is compared to the parental antigen binding polypeptide, in particular not comprising the inventive substitutions (e.g. not comprising the substitution with the positively charged amino acid, and/or not comprising tyrosine at position 90). Preferably, the "% gain in binding AUC" or "% increased AUC" of the inventive antigen binding polypeptide is compared to the parental antibody BMA031(V36), also designated TPP-1374 in the below examples, under identical conditions (and preferably in the same experimental run) and which is set to zero % increase in AUC. For example, the antigen binding polypeptide TPP-1375 shows 87% gain in AUC (see Table 5 in the examples section), which indicates an increase of binding AUC of 87% compared to the parental antibody TPP-1374 used for comparison.

The term "synergistic or synergism" refers in the context of the present invention to synergistic effects that occur due to more than one different mutation in the CDRs or FR of the variable domain(s) of the antigen binding polypeptide. Synergistic effects are nonlinear cumulative effects which are larger than the simple sum of the effects caused by each single mutation alone. For example, the % gain in AUC of antigen binding polypeptide TPP-1360 carrying R at heavy chain position 31 is 144%, and for antigen binding polypeptide TPP-1387 carrying Y at position 90, is 14% (see Table 6 of the examples disclosed herein). As was surprisingly shown in the examples, the antigen binding polypeptides provide synergistic effects. For example, an antigen binding polypeptide comprising the substitution at position 31 by R and the substitution by Y at position 90 in the heavy chain, as shown in TPP-1388, shows 273% gain in AUC exemplifying the synergistic effect regarding the % gain in AUC; e.g. see Table 5 or 6.

The term "dissociation constant ($K_D$)" (measured in "mol/L", sometimes abbreviated as "M") in the context of the present invention refers to the dissociation equilibrium constant, a ratio of $k_{off}/k_{on}$, of the particular interaction between a binding moiety (e.g. an antigen binding polypeptide or fragment thereof) and a target molecule (e.g. an antigen or epitope thereof). $K_D$ and affinity are inversely related. The $K_D$ value relates to the concentration of the antigen binding polypeptide and the lower the $K_D$ value, the higher is the affinity of the antigen binding polypeptide. Affinity, i.e. the $K_D$ value, can be experimentally assessed by a variety of known methods, such as measuring association and dissociation rates with surface plasmon resonance (SPR) based assays (such as the BIAcore assay) or biolayer interferometry (BLI), enzyme-linked immunoabsorbent assay (ELISA), and competition assays (e.g. radio immuno assays (RIA)). Low-affinity antigen binding polypeptides generally bind antigens slowly and tend to dissociate readily, whereas high-affinity antibodies generally bind antigens faster and tend to remain bound. The $K_D$ is typically measured at 30° C., by BLI or SPR.

Typically, if the antigen binding polypeptide of the present invention comprises a second binding site, and that second binding site specifically binding to a given antigen comprises an affinity maturated TCR or a fragment thereof, or the antigen binding polypeptide is a soluble molecule in a bispecific format or fragment thereof, such as a TCER® molecule or a fragment thereof, the $K_D$ of the TCR or functional fragment thereof, in particular Vα or Vβ, is in the range of $9\times10^{-8}$ to $5\times10^{-13}$ M, $9\times10^{-9}$ to $1\times10^{-12}$ M, $8\times10^{-9}$ to $5\times10^{-12}$ M, $7\times10^{-9}$ to $1\times10^{-11}$ M, $6\times10^{-9}$ to $2\times10^{-11}$ M, $5\times10^{-9}$ to $5\times10^{-13}$ M, $4\times10^{-9}$ to $8\times10^{-11}$ M, $3\times10^{-9}$ to $1\times10^{-10}$ M. Molecules in the bispecific format referred to herein as "TCER®" molecules or "TCER®" typically comprise a first antigen binding site comprised in a first polypeptide chain that specifically binds to a surface molecule on a T cell and a second antigen binding site comprised in a second polypeptide chain that specifically binds to a MHC-peptide complex.

Typically, if the antigen binding polypeptide of the present invention comprises a second binding site, and that second binding site specifically binding to a given antigen comprises a TCR or a fragment thereof, the TCR or fragment thereof has a $K_d$ in the range of $3\times10^{-5}$ to $1\times10^{-7} s^{-1}$, $2\times10^{-5}$ to $5\times10^{-7} s^{-1}$, $1\times10^{-5}$ to $1\times10^{-6} s^{-1}$ or $5\times10^{-6}$ to $1\times10^{-6} s^{-1}$.

The term "TCER®", also termed "TCER® molecule" refers in the context of the present invention to a bispecific molecule which comprises one specificity that specifically binds to a surface molecule on a T cell and one specificity that specifically binds to an MHC-peptide complex. Thus, "TCER®" are bispecific TCRs which are soluble antigen binding polypeptides comprising a first antigen binding site and a second antigen binding site as defined herein, wherein the first antigen binding site comprises a VH and VL domain of an antigen binding polypeptide as defined in the context of the invention specifically binding to the α/β TCR/CD3 complex, and a further or second antigen binding site that is formed by the α variable domain (Vα) and a β variable domain (Vβ) of a TCR specifically binding to an MHC-peptide complex, for example a tumor-associated peptide-MHC complex.

The term "specifically binding" refers in the context of this invention to the binding of an antigen binding polypeptide or fragments thereof, e.g. an antibody or fragment thereof or a TCR or fragments thereof, to a specific binding site of its target when the target comprises specific and non-specific binding sites. However, sometimes binding of a polypeptide to closely related proteins is unavoidable, then the actual binding to the target may be specific but the antigen binding polypeptide is deemed to be non-specific in relation to the intended target binding. An antigen binding polypeptide of the invention is considered to specifically bind if it binds stronger or enhanced to its target than to one or more similar antigens. It is preferred that if the antigen binding polypeptide is an antibody that the antibody specifically binds to its target.

The term "cell surface protein" refers in the context of the present invention to proteins that are embedded in or span the layer of cell membranes of more complex organisms. These proteins are integral to the way in which a cell interacts with the environment around it, including other cells. Examples of cell surface proteins are antigen receptors such as antibodies or TCRs or TCR chains; antigen presenting molecules, such as MHC molecules or β-microglobulin; co-receptor molecules, such as CD4, CD8 or CD19, antigen receptor accessory molecules, such as CD3-γ, -δ and -ε chains, CD79a and CD79b; co-stimulatory or inhibitory molecules such as CD28, CD80 or CD86; receptors on natural killer cells; receptors on leukocytes, immunoglobulin-like cell adhesion molecules, such as ICAMs; NCAMs, CD2; cytokine receptors, such as IL-1 receptor or colony stimulating factor 1 receptor; growth factor receptors; receptor tyrosine kinases or phosphatases, Ig binding receptors, such as polymeric immunoglobulin receptor (PIGR) or Fc receptors. Further examples are surface marker molecules selected from the group consisting of CD3, CD4, CD25, CTLA4, GITR, NK1.1, SLAMF1, SLAMF6, TGFβ, Vα24, Jα18, IL-12R, IFNγR, CXCR3, IL-4R, IL33R, CCR4, IL-17RB, CRTH2; IL-23R, CCR6, IL-1R, CD161; CCR7 hi, CD44, CD62Lhi, TCR, CD3, IL-7R (CD127), IL-15R.

The term "MHC" refers in the context of the present invention to the abbreviation of the term "major histocompatibility complex". MHC's are a set of cell surface proteins, i.e. cell surface receptors that have an essential role in establishing acquired immunity against altered natural or foreign proteins in vertebrates, which in turn determines histocompatibility within a tissue. The main function of MHC molecules is to bind to antigens derived from altered proteins or pathogens and display them on the cell surface for recognition by appropriate T-cells. The human MHC is also called HLA (human leukocyte antigen) complex or HLA. The MHC gene family is divided into three subgroups: class I, class II, and class III. Complexes of peptide and MHC class I are recognized by CD8-positive T-cells bearing the appropriate TCR, whereas complexes of peptide and MHC class II molecules are recognized by CD4-positive-helper-T-cells bearing the appropriate TCR. Since both types of response, CD8- and CD4-dependent, contribute jointly and synergistically to the anti-tumor effect, the identification and characterization of tumor-associated antigens and corresponding TCRs is important in the development of cancer immunotherapies such as vaccines and cell therapies.

The term "MHC-I" refers in the context of the present invention to MHC class I molecules or MHC-I. The MHC I molecule consists of an alpha chain, also referred to as MHC I heavy chain and a beta chain, which constitutes a beta 2 microglobulin molecule. The alpha chain, comprises three alpha domains, i.e. alpha1 domain, alpha2 domain and alpha3 domain. Alpha1 and alpha2 domain mainly contribute to forming the peptide pocket to produce a peptide ligand MHC (pMHC) complex. MHC-I typically bind peptides that are derived from cytosolic antigenic proteins and which are degraded by the proteasome after ubiquitylation and subsequently transported through a specific transporter associated with antigen processing (TAP) from the cytosol to the endoplasmatic reticulum (ER). MCH I typically binds peptides of 8-12 amino acids in length.

The term "MHC-II" refers in the context of the present invention to MHC class II molecules or MHC-II. The MHC-II molecule consists of an alpha and a beta chain, wherein the alpha chain comprises two alpha domains, alpha1 domain, alpha2 domain and the beta chain comprises two beta domains, beta domain1 and beta domain2 MHC II typically fold in the ER in complex with a protein called invariant chain and are then transported to late endosomal compartments where the invariant chain is cleaved by cathepsin proteases and a short fragment remains bound to the peptide-binding groove of MHC II, termed class II-associated invariant chain peptide (CLIP). This placeholder peptide is then normally exchanged against higher affinity peptides, which are derived from proteolytically degraded proteins available in endocytic compartments. MHC-II typically binds peptides of 10-30 amino acids in length or peptides of 13-25 amino acids in length.

The term "HLA" refers in the context of the present invention to human MHC molecules which differ between different human beings in amino acid sequences.

The term "nucleic acid" refers in the context of the present invention to single or double-stranded oligo- or polymers of deoxyribonucleotide or ribonucleotide bases or both. Nucleotide monomers are composed of a nucleobase, a five-carbon sugar (such as but not limited to ribose or 2'-deoxyribose), and one to three phosphate groups. Typically, a nucleic acid is formed through phosphodiester bonds between the individual nucleotide monomers, In the context of the present invention, the term nucleic acid includes but is not limited to ribonucleic acid (RNA) and deoxyribonucleic acid (DNA) molecules but also includes synthetic forms of nucleic acids comprising other linkages (e.g., peptide nucleic acids as described in Nielsen et al. (Science 254:1497-1500, 1991). Typically, nucleic acids are single- or double-stranded molecules and are composed of naturally occurring nucleotides. The depiction of a single strand of a nucleic acid also defines (at least partially) the sequence of the complementary strand. The nucleic acid may be single or double stranded or may contain portions of both double and single stranded sequences. Exemplified, double-stranded nucleic acid molecules can have 3' or 5' overhangs and as such are not required or assumed to be completely double-stranded over their entire length. The nucleic acid may be obtained by biological, biochemical or chemical synthesis methods or any of the methods known in the art, including but not limited to methods of amplification, and reverse transcription of RNA. The term nucleic acid comprises chromosomes or chromosomal segments, vectors (e.g., expression vectors), expression cassettes, naked DNA or RNA polymer, primers, probes, cDNA, genomic DNA, recombinant DNA, cRNA, mRNA, tRNA, microRNA (miRNA) or small interfering RNA (siRNA). A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

The term "vector" refers in the context of the present invention to a polynucleotide that encodes a protein of interest or a mixture comprising polypeptide(s) and a polynucleotide that encodes a protein of interest, which is capable of being introduced or of introducing proteins and/or nucleic acids comprised therein into a cell. Examples of vectors include but are not limited to plasmids, cosmids, phages, viruses or artificial chromosomes. A vector is used to introduce a gene product of interest, such as e.g. foreign or heterologous DNA into a host cell. Vectors may contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Vectors may further encompass "expression control sequences" that regulate the expression of the gene of interest. Typically, expression control sequences are polypeptides or polynucleotides such as promoters, enhancers, silencers, insulators, or repressors. In a vector comprising more than one polynucleotide encoding for one or more gene products of interest, the expression may be controlled together or separately by one or more expression control sequences. More specifically, each polynucleotide comprised on the vector may be control by a separate expression control sequence or all polynucleotides comprised on the vector may be controlled by a single expression control sequence. Polynucleotides comprised on a single vector controlled by a single expression control sequence may form an open reading frame. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized. Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like. Any expression vector for animal cell can be used, as long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, e.g. pUC, pcDNA, pBR.

The term "transformation" refers in the context of the present invention to a naturally occurring process of gene transfer into a host cell which involves absorption of the genetic material, such as nucleic acids (DNA or RNA), by a cell through the cell membrane, so that the host cell will express the introduced gene or sequence to produce a desired gene product, typically a protein or enzyme encoded by the gene or sequence that is introduced into the host cell. Two types of transformation known as natural transformation and artificial or induced transformation, exist. The artificial or induced transformation is typically referred to as "transfection".

The term "transfection" refers in the context of the present invention to a mode of gene transfer involving creation of pores on the cell membrane of the host cell enabling the host cell to receive the foreign genetic material. Transfection refers to a transformation of eukaryotic cells, such as insect or mammalian cells. Chemical mediated transfection involves use of, for instance, calcium phosphate or cationic polymers or liposomes. Non-chemical mediated transfection methods are typically electroporation, sonoporation, impalefection, optical transfection or hydro dynamic delivery. Particle based transfection uses gene gun technique where a nanoparticle is used to transfer the nucleic acid to host cell or by another method called as magnetofection. Nucleofection and use of heat shock are the other evolved methods for successful transfection. A host cell that receives foreign nucleic acids via a transfection method has been "transfected".

The term "transduction" refers in the context of the present invention to the transfer of foreign nucleic acids, such as DNA or RNA, into a cell by a virus or viral vector. A host cell that receives and expresses foreign nucleic acids (DNA or RNA) by a virus or viral vector has been "transduced".

The term "pharmaceutical composition" or "therapeutic composition" refers in the context of the present invention to a compound or composition capable of inducing a desired therapeutic effect when properly administered to a subject.

The term "pharmaceutically" or "pharmaceutically acceptable" refers in the context of the present invention to molecular entities and compositions that do not lead to an adverse, allergic or other unwanted reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The term "pharmaceutically-acceptable carrier" in the context of the present invention may also be referred to as "pharmaceutically acceptable diluent" or "pharmaceutically acceptable vehicles" and may include solvents, bulking agents, stabilizing agents, dispersion media, coatings, antibacterial and antifungal agents, isotonic and absorption delaying agents, and the like which are physiologically compatible.

The term "therapeutic agent" refers in the context of the present invention to an agent that has a therapeutic effect.

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

As indicated above, the positions of the CDRs and FRs in the VH and VL may be determined by any of the above defined annotations, such as Chothia, Kabat, AbM or Contact.

A first aspect of the present invention relates to an antigen binding polypeptide comprising a heavy chain variable domain (VH) and a light chain variable domain (VL), wherein the CDRs and FRs are specified according to Chothia,
(1) the VH comprises
  (a) a heavy chain complementarity determining region 1 (HCDR1) comprising the amino acid sequence of SEQ ID NO:62,
  (b) a HCDR2 comprising the amino acid sequence of SEQ ID NO: 63,
  (c) a HCDR3, and
  (d) heavy chain framework regions (HFR) 1-4;
(2) the VL comprises
  (a) a light chain complementarity determining region 1 (LCDR1) comprising the amino acid sequence of SEQ ID NO: 54,
  (b) a LCDR2 comprising the amino acid sequence of SEQ ID NO: 55,
  (c) a LCDR3, and
  (d) light chain framework regions (LFR) 1-4;
  wherein
  (i) at least one amino acid of HCDR1 comprising the amino acid sequence of SEQ ID NO: 62 and/or at least one amino acid of HCDR2 comprising the amino acid sequence of SEQ ID NO: 63 that is not positively charged is substituted with a positively charged amino acid; and/or
  (ii) at least one amino acid of LCDR1 comprising the amino acid of SEQ ID NO:54 and/or at least one amino acid of LCDR2 comprising the amino acid sequence of SEQ ID NO: 55 that is not positively charged is substituted with a positively charged amino acid; and/or
  (iii) position 90 according to Chothia numbering in HFR3 is substituted with a tyrosine (Y) residue,
  and wherein the antigen binding polypeptide specifically binds to an α/β T cell receptor (TCR)/CD3 complex.

In further particular embodiments of this aspect, the antigen binding polypeptide comprises the positively charged amino acids:
  (i) at one or more of the following positions of the heavy chain: 30, 31, 53, and 54; and/or
  (ii) at one or more of the following positions of the light chain: 31 and 56,
  and wherein the positions are according to Chothia numbering.

In further particular embodiments of this aspect, the antigen binding polypeptide comprises
  (a) the positively charged amino acid in the heavy chain:
    (i) at position 30 is R, K or H;
    (ii) at position 31 is R, K or H;
    (iii) at position 53 is R, K or H; and/or
    (iv) at position 54 is R or K; and/or
  (b) the positively charged amino acid in the light chain
    (i) at position 31 is R or K; and/or
    (ii) at position 56 is R or K, wherein the positions are according to Chothia numbering.

Alternatively, the first aspect can also be specified on the basis of the Kabat annotation as follows:

An antigen binding polypeptide comprising a heavy chain variable domain (VH) and a light chain variable domain (VL), wherein
(1) the VH comprises
  (a) a heavy chain complementarity determining region 1 (HCDR1) comprising the amino acid sequence of SEQ ID NO: 52,
  (b) a HCDR2 comprising the amino acid sequence of YINPYNDVTKYX$_1$X$_2$KFX$_3$G (SEQ ID NO: 53), wherein
   X$_1$ is A or N;
   X$_2$ is E or Q; and/or
   X$_3$ is Q or K
  (c) a HCDR3, and
  (d) heavy chain framework regions (HFR) 1-4;
(2) the VL comprises
  (a) a light chain complementarity determining region 1 (LCDR1) comprising the amino acid sequence of SEQ ID NO: 54,
  (b) a LCDR2 comprising the amino acid sequence of SEQ ID NO: 55,
  (c) a LCDR3, and
  (d) light chain framework regions (LFR) 1-4;
wherein
(i) at least one amino acid of HCDR1 comprising the amino acid sequence of SEQ ID NO: 52 and/or at least one amino acid of HCDR2 comprising the amino acid sequence of SEQ ID NO: 53 that is not positively charged is substituted with a positively charged amino acid; and/or
(ii) at least one amino acid of LCDR1 comprising the amino acid of SEQ ID NO:54 and/or at least one amino acid of LCDR2 comprising the amino acid sequence of SEQ ID NO: 55 that is not positively charged is substituted with a positively charged amino acid; and/or
(iii) position 30 in HFR1 according to Kabat numbering is substituted with a positively charged amino acid, and/or
(iv) position 90 in HFR3 according to Kabat numbering is substituted with a tyrosine (Y) residue,
and wherein the antigen binding polypeptide specifically binds to an α/β T cell receptor (TCR)/CD3 complex.

In particular, and when explaining the following embodiments of the present invention, positions of amino acids within the variable light chain and the variable heavy chain are indicated according to Kabat numbering unless indicated otherwise.

It was observed in the context of the present invention that a mutation at position 90 in HFR3 to Y leads to an increase of the binding of the antigen binding polypeptide to the α/β TCR/CD3 complex and/or an increase of the thermostability (e.g. Tm ° C. or delta Tm ° C.) in comparison to the parental antigen binding polypeptide comprising none of the substitutions specified in (i) to (iv) and that these positive effects are more pronounced, if combined with one, two or all of the substitutions specified in (i) to (iii) above. An increased binding is described as a lowering of binding EC50 that is herein referred to as, e.g. "x-fold" decrease. Alternatively, an increase of the binding is also herein described as "% gain in binding AUC". Differences in Tm are described in "delta Tm ° C." as defined herein above.

Accordingly, in one embodiment of the antigen binding polypeptide position 90 in HFR3 is substituted with Y, and further at least one amino acid of HCDR1 comprising the amino acid sequence of SEQ ID NO: 52 that is not positively charged and/or least one amino acid of HCDR2 comprising the amino acid sequence of SEQ ID NO: 53 that is not positively charged is/are substituted with a positively charged amino acid.

In one embodiment of the antigen binding polypeptide of the first aspect of the invention position 30 in HFR1 is substituted with a positively charged amino acid. In one embodiment position 90 in HFR3 is substituted with Y.

In one embodiment, position 30 in HFR1 is substituted with a positively charged amino acid and position 90 in HFR3 is substituted with Y.

In one embodiment of the antigen binding polypeptide, position 90 of HFR3 is substituted with Y, position 30 of HFR1 is substituted with a positively charged amino acid; and further at least one amino acid of HCDR1 comprising the amino acid sequence of SEQ ID NO: 52 that is not positively charged and/or least one amino acid of HCDR2 comprising the amino acid sequence of SEQ ID NO: 53 that is not positively charged is/are substituted with a positively charged amino acid.

In one embodiment of the antigen binding polypeptide, position 30 of HFR1 is substituted with a positively charged amino acid; and further at least one amino acid of HCDR1 comprising the amino acid sequence of SEQ ID NO: 52 that is not positively charged and/or least one amino acid of HCDR2 comprising the amino acid sequence of SEQ ID NO: 53 that is not positively charged is/are substituted with a positively charged amino acid.

In one embodiment the antigen binding polypeptide comprises a LCDR1 according to SEQ ID NO: 54, wherein at least one amino acid that is not positively charged is substituted with a positively charged amino acid; and/or a LCDR2 according to SEQ ID NO: 55 wherein at least one amino acid that is not positively charged is substituted with a positively charged amino acid.

In one embodiment of the antigen binding polypeptide, position 30 of HFR1 is substituted with a positively charged amino acid and further at least one amino acid of LCDR1 comprising the amino acid sequence of SEQ ID NO: 54 that is not positively charged and/or least one amino acid of LCDR2 comprising the amino acid sequence of SEQ ID NO: 55 that is not positively charged is/are substituted with a positively charged amino acid.

In one embodiment of the antigen binding polypeptide, position 90 of HFR3 is substituted with Y, and further at least one amino acid of LCDR1 comprising the amino acid sequence of SEQ ID NO: 54 that is not positively charged and/or least one amino acid of LCDR2 comprising the amino acid sequence of SEQ ID NO: 55 that is not positively charged is/are substituted with a positively charged amino acid.

In one embodiment of the antigen binding polypeptide, position 30 of HFR1 is substituted with a positively charged amino acid; position 90 of HFR3 is substituted with Y, and further at least one amino acid of LCDR1 comprising the amino acid sequence of SEQ ID NO: 54 that is not positively charged and/or least one amino acid of LCDR2 comprising the amino acid sequence of SEQ ID NO: 55 that is not positively charged is/are substituted with a positively charged amino acid.

In one embodiment of the antigen binding polypeptide (iv) position 90 of HFR3 is substituted with Y, and (i) at least one amino acid of HCDR1 comprising the amino acid sequence of SEQ ID NO: 52 that is not positively charged and/or least one amino acid of HCDR2 comprising the amino acid sequence of SEQ ID NO: 53 that is not positively charged is substituted with a positively charged amino acid and (ii) at least one amino acid of LCDR1 comprising the amino acid sequence of SEQ ID NO: 54 that is not positively charged amino and/or least one amino acid of LCDR2 comprising the amino acid sequence of SEQ ID NO: 55 that is not positively charged is/are substituted with a positively charged amino acid.

In one embodiment of the antigen binding polypeptide (iv) position 90 of HFR3 is substituted with Y, and (iii) position 30 of HFR1 is substituted with a positively charged amino acid, and (i) at least one amino acid of HCDR1 comprising the amino acid sequence of SEQ ID NO: 52 that is not positively charged and/or least one amino acid of HCDR2 comprising the amino acid sequence of SEQ ID NO: 53 that is not positively charged is substituted with a positively charged amino acid and (ii) at least one amino acid of LCDR1 comprising the amino acid sequence of SEQ ID NO: 54 that is not positively charged and/or least one amino acid of LCDR2 comprising the amino acid sequence of SEQ ID NO: 55 that is not positively charged is/are substituted with a positively charged amino acid.

In one embodiment, the at least one amino acid of the antigen binding polypeptide is substituted with a positively charged amino acid in the HCDR1 and/or HCDR2 and/or LCDR1 and/or LCDR2 positions as defined herein above and below and not more than four positions in the CDRs are substituted with positively charged amino acids, preferably not more than three positions in the CDRs are substituted with positively charged amino acids.

In one embodiment, the at least one amino acid of the antigen binding polypeptide that is substituted in HCDR1 and/or HCDR2 and/or LCDR1 and/or LCDR2 with a positively charged amino acid is not more than 2, than 3, than 4 amino acids. In the following embodiments it is preferred that, if a positively charged amino acid is present at a certain position in HCDR1 of SEQ ID NO: 52, HCDR2 of SEQ ID NO: 53, LCDR1 of SEQ ID NO: 54, LCDR2 of SEQ ID NO: 55, HCDR3 of SEQ ID NO: 56 or LCDR3 of SEQ ID NO: 57, said amino acid is not substituted with a different positively charged amino acid in the context of the invention.

In one embodiment of the first aspect of the invention, the antigen binding polypeptide comprises a HCDR1 according to SEQ ID NO: 52, wherein at least one amino acid that is not positively charged is substituted with a positively charged amino acid. In particular, in one embodiment in case of SEQ ID NO: 52 comprising the amino acid sequence SYVMH, S is substituted with either H, K or R. In one embodiment in case of SEQ ID NO: 52 comprising the amino acid sequences SYVMH, Y is substituted with either H, K or R. In one embodiment in case of SEQ ID NO: 52 comprising the amino acid sequences SYVMH, V is substituted with either H, K or R. In one embodiment in case of SEQ ID NO: 52 comprising the amino acid sequences SYVMH, M is substituted with either H, K or R.

In one embodiment of the first aspect of the invention, the antigen binding polypeptide comprises a HCDR2 according to SEQ ID NO: 53, wherein at least one amino acid that is not positively charged is substituted with a positively charged amino acid. In particular, in one embodiment, HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that the N-terminal Y is substituted with either H, K or R. In particular, in one embodiment, HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that the second Y from the N-terminus is substituted with either H, K or R. In particular, in one embodiment, HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that the third Y from the N-terminus is substituted with either H, K or R. In particular, in one embodiment, HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that all three Y are substituted with either H, K or R.

In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that I is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that the N-terminal N is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that the second N-from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that the both N are substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that P is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that V is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that T is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that F is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is Q means that G is substituted with either H, K or R.

In one embodiment of the first aspect of the invention the antigen binding polypeptide comprises a HCDR2 according to SEQ ID NO: 53, wherein at least one amino acid that is not positively charged is substituted with a positively charged amino acid. In particular, in one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that the N-terminal Y is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that the second Y from N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that the third Y from N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that all three Y are substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that I is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that the N-terminal N is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that the second N from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that the both N are substituted with either H, K or R In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that P is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that V is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that T is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that F is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is E and X$_3$ is K means that G is substituted with either H, K or R.

In one embodiment of the first aspect of the invention the antigen binding polypeptide comprises a HCDR2 according to SEQ ID NO: 53, wherein at least one amino acid that is not positively charged is substituted with a positively charged amino acid. In particular, in one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that the N-terminal Y is substituted with either H, K or R. In particular, in one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that the second Y from the N-terminus is substituted with either H, K or R. In particular, in one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that the third Y from the N-terminus is substituted with either H, K or R. In particular, in one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that all three Y are substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that I is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that the N-terminal N is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that the second N from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that both N are substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that P is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that V is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that T is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that F is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is Q means that G is substituted with either H, K or R.

In one embodiment of the first aspect of the invention the antigen binding polypeptide comprises a HCDR2 according to SEQ ID NO: 53, wherein at least one amino acid that is not positively charged is substituted with a positively charged amino acid. In particular, in one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that N-terminal Y is substituted with either H, K or R. In particular, in one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that the second Y from N-terminus is substituted with either H, K or R. In particular, in one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that the third Y from N-terminus is substituted with either H, K or R. In particular, in one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that the all three Y are substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that I is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that the N-terminal N is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that the second N from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that both N are substituted with either H, K or R In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that P is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that V is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that T is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that F is substituted with either H, K or R. In one embodiment HCDR2 comprises SEQ ID NO: 53 comprising the amino acid sequence YINPYNDVTKYX$_1$X$_2$KFX$_3$G, wherein X$_1$ is A; X$_2$ is Q and X$_3$ is K means that G is substituted with either H, K or R.

In one embodiment, HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that the N-terminal Y is substituted with either H, K or R. In one embodiment, HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that the second Y from the N-terminus is substituted with either H, K or R. In one embodiment, HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that the third Y from the N-terminus is substituted with either H, K or R. In one embodiment, HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that all three Y are substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that I is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that the N-terminal N is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that the second N from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that both N are substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that P is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that V is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that T is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that F is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that G is substituted with either H, K or R.

In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that the N-terminal Y is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that the second Y from N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that the third Y from N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that all three Y are substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that I is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that the N-terminal N is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that the second N from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that both N are substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that P is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that V is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that T is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that F is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that G is substituted with either H, K or R.

In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that the N-terminal Y is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that the second Y from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that the third Y from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that all three Y are substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that I is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that the N-terminal N is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that the second N from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that both N are substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that P is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that V is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that T is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is Q means that F is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is Q and X$_3$ is K means that G is substituted with either H, K or R.

In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that the N-terminal Y is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that the second Y from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that the third Y from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that all three Y are substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that I is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that the N-terminal N is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that the second N from the N-terminus is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that both N are substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that P is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that V is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that T is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is Q means that F is substituted with either H, K or R. In one embodiment HCDR2 comprises SEQ ID NO: 53 comprising the amino acid sequence YINPYNDVTKYX$_1$X$_2$KFX$_3$G, wherein X$_1$ is N; X$_2$ is E and X$_3$ is K means that G is substituted with either H, K or R.

In one embodiment, the antigen binding polypeptide comprises a HCDR1 according to SEQ ID NO: 52, wherein at least one amino acid that is not positively charged is substituted with a positively charged amino acid, and a HCDR2 as set out above and further comprises a heavy chain framework regions (HFR) 1-4, wherein position 30 in HFR is substituted with a positively charged amino acid.

In one embodiment the antigen binding polypeptide comprises a HCDR1 according to SEQ ID NO: 52, wherein at least one amino acid that is not positively charged is substituted with a positively charged amino acid and a HCDR2 as set out above and further comprises a HCDR3 and HFR1-4.

In one embodiment the antigen binding polypeptide comprises a HCDR1 according to SEQ ID NO: 52, wherein at least one amino acid that is not positively charged is substituted with a positively charged amino acid and a HCDR2 as set out above and further comprises a HCDR3 and HFR1-4, wherein preferably position 90 is substituted with Y.

In one embodiment, the antigen binding polypeptide comprises a HCDR1 according to SEQ ID NO: 52, wherein at least one amino acid that is not positively charged is substituted with a positively charged amino acid and a HCDR2 as set out above and further comprises a HCDR3 and HFR1-4, wherein position 30 of HFR1 is substituted with a positively charged amino acid.

In one embodiment, the antigen binding polypeptide comprises a HCDR1 according to SEQ ID NO: 52, wherein at least one amino acid that is not positively charged is substituted with a positively charged amino acid and a HCDR2 as set out above and further comprises a HCDR3 and HFR1-4, wherein position 30 of HFR1 is substituted with a positively charged amino acid and position 90 in HFR3 is substituted with Y. Said HFR1-4 sequences may also comprise one or more further modifications such as substitutions, deletions or insertions compared to a FR sequence comprising none of said modifications. However, it is preferred that FR1-4 sequences are not modified at certain positions such as those in the Vernier zone, the VH/VL inter-chain interface or at positions determining the CDR canonical class. Preferably, HFR3 comprises a Y residue at position 90. Herein below, further positions in the FR are provided that should preferably not be modified in the context of the invention. It is also preferred that certain positions are comprised in FR and not comprised in CDRs regardless of the annotations used.

In one embodiment, the antigen binding polypeptide comprises a variable light chain (VL) comprising a light chain complementarity determining region 1 (LCDR1) comprising the amino acid sequence of SEQ ID NO: 54 (SATSSVSYMH), wherein least one amino acid of SEQ ID NO: 54 that is not positively charged is substituted with a positively charged amino acid. In particular, in one embodiment in case of SEQ ID NO: 54 comprising the amino acid sequence SATSSVSYMH, the N-terminal S is substituted with either H, K or R. In particular, in one embodiment in case of SEQ ID NO: 54 comprising the amino acid sequence SATSSVSYMH, the second S from the N-terminus is substituted with either H, K or R. In particular, in one embodiment in case of SEQ ID NO: 54 comprising the amino acid sequence SATSSVSYMH, the third S from the N-terminus is substituted with either H, K or R. In particular, in one embodiment in case of SEQ ID NO: 54 comprising the amino acid sequence SATSSVSYMH, the fourth S from the N-terminus is substituted with either H, K or R. In particular, in one embodiment in case of SEQ ID NO: 54 comprising the amino acid sequence SATSSVSYMH, all four S from the N-terminus are substituted with either H, K or R. In one embodiment in case of SEQ ID NO: 54 comprising the amino acid sequences SATSSVSYMH, A is substituted with either H, K or R. In one embodiment in case of SEQ ID NO: 54 comprising the amino acid sequences SATSSVSYMH, T is substituted with either H, K or R. In one embodiment in case of SEQ ID NO: 54 comprising the amino acid sequences SATSSVSYMH, V can be substituted with either H, K or R. In one embodiment in case of SEQ ID NO: 54 comprising the amino acid sequences SATSSVSYMH, Y is substituted with either H, K or R. In one embodiment in case of SEQ ID NO: 54 comprising the amino acid sequences SATSSVSYMH, M is substituted with either H, K or R.

In one embodiment, the antigen binding polypeptide comprises a variable light chain (VL) comprising a light chain complementarity determining region 2 (LCDR2) comprising the amino acid sequence of SEQ ID NO: 55 (DTSKLAS), wherein least one amino acid of SEQ ID NO: 55 that is not positively charged is substituted with a positively charged amino acid. In particular, in one embodiment in case of SEQ ID NO: 55 comprising the amino acid sequence DTSKLAS, T is substituted with either H, K or R. In one embodiment in case of SEQ ID NO: 55 comprising the amino acid sequences DTSKLAS, S is substituted with either H, K or R. In one embodiment in case of SEQ ID NO: 55 comprising the amino acid sequences DTSKLAS, L is substituted with either H, K or R. In one embodiment in case of SEQ ID NO: 55 comprising the amino acid sequences DTSKLAS, A is substituted with either H, K or R.

In one embodiment, the antigen binding polypeptide comprises a LCDR1 comprising the amino acid sequence of SEQ ID NO: 54 (SATSSVSYMH), wherein least one amino acid of SEQ ID NO: 54 that is not positively charged is substituted with a positively charged amino acid; and comprises a LCDR2 comprising the amino acid sequence of SEQ ID NO: 55 (DTSKLAS), wherein least one amino acid of SEQ ID NO: 55 that is not positively charged is substituted with a positively charged amino acid.

In particular, in one embodiment in case of SEQ ID NO: 54 comprising the amino acid sequence SATSSVSYMH, the N-terminal S is substituted with R, K or H and in case SEQ ID NO: 55 comprising the amino acid sequences DTSKLAS, L is substituted with R. In particular, in one embodiment in case of SEQ ID NO: 54 comprising the amino acid sequence SATSSVSYMH, the second S from the N-terminus is substituted with R, K or H and in case SEQ ID NO: 55 comprising the amino acid sequences DTSKLAS, L is substituted with R. In particular, in one embodiment in case of SEQ ID NO: 54 comprising the amino acid sequence SATSSVSYMH, the third S from the N-terminus is substituted with R, K or H and in case SEQ ID NO: 55 comprising the amino acid sequences DTSKLAS, L is substituted with R. In particular, in one embodiment in case of SEQ ID NO: 54 comprising the amino acid sequence SATSSVSYMH, the fourth S from the N-terminus is substituted with R, K or H and in case SEQ ID NO: 55 comprising the amino acid sequences DTSKLAS, L is substituted with R. In particular, in one embodiment in case of SEQ ID NO: 54 comprising the amino acid sequence SATSSVSYMH, the all four S are substituted with R, K or H and in case SEQ ID NO: 55 comprising the amino acid sequences DTSKLAS, L is substituted with R. In particular, in one embodiment in case of SEQ ID NO: 54 comprising the amino acid sequence SATSSVSYMH, the N-terminal S is substituted with K and in case SEQ ID NO: 55 comprising the amino acid sequences DTSKLAS, L can be substituted with R, K or H. In particular, in one embodiment in case of SEQ ID NO: 54 comprising the amino acid sequence SATSSVSYMH, the second S from the N-terminus is substituted with K and in case SEQ ID NO: 55 comprising the amino acid sequences DTSKLAS, L can be substituted with R, K or H. In particular, in one embodiment in case of SEQ ID NO: 54 comprising the amino acid sequence SATSSVSYMH, the third S from the N-terminus is substituted with K and in case SEQ ID NO: 55 comprising the amino acid sequences DTSKLAS, L can be substituted with R, K or H. In particular, in one embodiment in case of SEQ ID NO: 54 comprising the amino acid sequence SATSSVSYMH, the fourth S from the N-terminus is substituted with K and in case SEQ ID NO: 55 comprising the amino acid sequences DTSKLAS, L can be substituted with R, K or H. In particular, in one embodiment in case of SEQ ID NO: 54 comprising the amino acid sequence SATSSVSYMH, all four S are substituted with K and in case SEQ ID NO: 55 comprising the amino acid sequences DTSKLAS, L can be substituted with R, K or H.

In particular, in one embodiment in case of SEQ ID NO: 54 comprising the amino acid sequence SATSSVSYMH, the N-terminal S is substituted with H and in case SEQ ID NO: 55 comprising the amino acid sequences DTSKLAS, L can be substituted with R. In particular, in one embodiment in case of SEQ ID NO: 54 comprising the amino acid sequence SATSSVSYMH, the second S from the N-terminus is substituted with H and in case SEQ ID NO: 55 comprising the amino acid sequences DTSKLAS, L can be substituted with R. In particular, in one embodiment in case of SEQ ID NO: 54 comprising the amino acid sequence SATSSVSYMH, the third S from the N-terminus is substituted with H and in case SEQ ID NO: 55 comprising the amino acid sequences DTSKLAS, L can be substituted with R. In particular, in one embodiment in case of SEQ ID NO: 54 comprising the amino acid sequence SATSSVSYMH, the fourth S from the N-terminus is substituted with H and in case SEQ ID NO: 55 comprising the amino acid sequences DTSKLAS, L can be substituted with R. In particular, in one embodiment in case of SEQ ID NO: 54 comprising the amino acid sequence SATSSVSYMH, the all four S are substituted with H and in case SEQ ID NO: 55 comprising the amino acid sequences DTSKLAS, L can be substituted with R.

In particular, in one embodiment in case of SEQ ID NO: 54 comprising the amino acid sequence SATSSVSYMH, the N-terminal S is substituted with R, K or H and in case SEQ ID NO: 55 comprising the amino acid sequences DTSK-LAS, L is substituted with K. In particular, in one embodiment in case of SEQ ID NO: 54 comprising the amino acid sequence SATSSVSYMH, the second S from the N-terminus is substituted with R, K or H and in case SEQ ID NO: 55 comprising the amino acid sequences DTSKLAS, L is substituted with K. In particular, in one embodiment in case of SEQ ID NO: 54 comprising the amino acid sequence SATSSVSYMH, the third S from the N-terminus is substituted with R, K or H and in case SEQ ID NO: 55 comprising the amino acid sequences DTSKLAS, L is substituted with K. In particular, in one embodiment in case of SEQ ID NO: 54 comprising the amino acid sequence SATSSVSYMH, the fourth S from the N-terminus is substituted with R, K or H and in case SEQ ID NO: 55 comprising the amino acid sequences DTSKLAS, L is substituted with K. In particular, in one embodiment in case of SEQ ID NO: 54 comprising the amino acid sequence SATSSVSYMH, all four S from the N-terminus is substituted with R, K or H and in case SEQ ID NO: 55 comprising the amino acid sequences DTSK-LAS, L is substituted with K.

In particular, in one embodiment in case of SEQ ID NO: 54 comprising the amino acid sequence SATSSVSYMH, the N-terminal S is substituted with K and in case SEQ ID NO: 55 comprising the amino acid sequences DTSKLAS, L is substituted with K. In particular, in one embodiment in case of SEQ ID NO: 54 comprising the amino acid sequence SATSSVSYMH, the second S from the N-terminus is substituted with K and in case SEQ ID NO: 55 comprising the amino acid sequences DTSKLAS, L is substituted with K. In particular, in one embodiment in case of SEQ ID NO: 54 comprising the amino acid sequence SATSSVSYMH, the third S from the N-terminus is substituted with K and in case SEQ ID NO: 55 comprising the amino acid sequences DTSKLAS, L is substituted with K. In particular, in one embodiment in case of SEQ ID NO: 54 comprising the amino acid sequence SATSSVSYMH, the fourth S from the N-terminus is substituted with K and in case SEQ ID NO: 55 comprising the amino acid sequences DTSKLAS, L is substituted with K. In particular, in one embodiment in case of SEQ ID NO: 54 comprising the amino acid sequence SATSSVSYMH, all four S are is substituted with K and in case SEQ ID NO: 55 comprising the amino acid sequences DTSKLAS, L is substituted with K.

In particular, in one embodiment in case of SEQ ID NO: 54 comprising the amino acid sequence SATSSVSYMH, the N-terminal S is substituted with H and in case SEQ ID NO: 55 comprising the amino acid sequences DTSKLAS, L can be substituted with K. In particular, in one embodiment in case of SEQ ID NO: 54 comprising the amino acid sequence SATSSVSYMH, the second S from the N-terminus is substituted with H and in case SEQ ID NO: 55 comprising the amino acid sequences DTSKLAS, L can be substituted with K. In particular, in one embodiment in case of SEQ ID NO: 54 comprising the amino acid sequence SATSSVSYMH, the third S from the N-terminus is substituted with H and in case SEQ ID NO: 55 comprising the amino acid sequences DTSKLAS, L can be substituted with K. In particular, in one embodiment in case of SEQ ID NO: 54 comprising the amino acid sequence SATSSVSYMH, the fourth S from the N-terminus is substituted with H and in case SEQ ID NO: 55 comprising the amino acid sequences DTSKLAS, L can be substituted with K. In particular, in one embodiment in case of SEQ ID NO: 54 comprising the amino acid sequence SATSSVSYMH, all four S are substituted with H and in case SEQ ID NO: 55 comprising the amino acid sequences DTSKLAS, L can be substituted with K.

In particular, in one embodiment in case of SEQ ID NO: 54 comprising the amino acid sequence SATSSVSYMH, the N-terminal S is substituted with R, K or H and in case SEQ ID NO: 55 comprising the amino acid sequences DTSK-LAS, L is substituted with H. In particular, in one embodiment in case of SEQ ID NO: 54 comprising the amino acid sequence SATSSVSYMH, the second S from the N-terminus is substituted with R, K or H and in case SEQ ID NO: 55 comprising the amino acid sequences DTSKLAS, L is substituted with H. In particular, in one embodiment in case of SEQ ID NO: 54 comprising the amino acid sequence SATSSVSYMH, the third S from the N-terminus is substituted with R, K or H and in case SEQ ID NO: 55 comprising the amino acid sequences DTSKLAS, L is substituted with H. In particular, in one embodiment in case of SEQ ID NO: 54 comprising the amino acid sequence SATSSVSYMH, the fourth S from the N-terminus is substituted with R, K or H and in case SEQ ID NO: 55 comprising the amino acid sequences DTSKLAS, L is substituted with H. In particular, in one embodiment in case of SEQ ID NO: 54 comprising the amino acid sequence SATSSVSYMH, all four S are substituted with R, K or H and in case SEQ ID NO: 55 comprising the amino acid sequences DTSKLAS, L is substituted with H.

In particular, in one embodiment in case of SEQ ID NO: 54 comprising the amino acid sequence SATSSVSYMH, the N-terminal S is substituted with K and in case SEQ ID NO: 55 comprising the amino acid sequences DTSKLAS, L can be substituted with H. In particular, in one embodiment in case of SEQ ID NO: 54 comprising the amino acid sequence SATSSVSYMH, the second S from the N-terminus is substituted with K and in case SEQ ID NO: 55 comprising the amino acid sequences DTSKLAS, L can be substituted with H. In particular, in one embodiment in case of SEQ ID NO: 54 comprising the amino acid sequence SATSSVSYMH, the third S from the N-terminus is substituted with K and in case SEQ ID NO: 55 comprising the amino acid sequences DTSKLAS, L can be substituted with H. In particular, in one embodiment in case of SEQ ID NO: 54 comprising the amino acid sequence SATSSVSYMH, the fourth S from the N-terminus is substituted with K and in case SEQ ID NO: 55 comprising the amino acid sequences DTSKLAS, L can be substituted with H. In particular, in one embodiment in case of SEQ ID NO: 54 comprising the amino acid sequence SATSSVSYMH, all four S are substituted with K and in case SEQ ID NO: 55 comprising the amino acid sequences DTSKLAS, L can be substituted with H.

In particular, in one embodiment in case of SEQ ID NO: 54 comprising the amino acid sequence SATSSVSYMH, the N-terminal S is substituted with H and in case SEQ ID NO: 55 comprising the amino acid sequences DTSKLAS, L is substituted with H. In particular, in one embodiment in case of SEQ ID NO: 54 comprising the amino acid sequence SATSSVSYMH, the second S from the N-terminus is substituted with H and in case SEQ ID NO: 55 comprising the amino acid sequences DTSKLAS, L is substituted with H. In particular, in one embodiment in case of SEQ ID NO: 54 comprising the amino acid sequence SATSSVSYMH, the third S from the N-terminus is substituted with H and in case SEQ ID NO: 55 comprising the amino acid sequences DTSKLAS, L is substituted with H. In particular, in one embodiment in case of SEQ ID NO: 54 comprising the amino acid sequence SATSSVSYMH, the fourth S from the N-terminus is substituted with H and in case SEQ ID NO: 55 comprising the amino acid sequences DTSKLAS, L is substituted with H. In particular, in one embodiment in case of SEQ ID NO: 54 comprising the amino acid sequence SATSSVSYMH, all four S are substituted with H and in case SEQ ID NO: 55 comprising the amino acid sequences DTSKLAS, L is substituted with H.

In one embodiment, the antigen binding polypeptide comprises a LCDR1 comprising the amino acid sequence of SEQ ID NO: 54 (SATSSVSYMH), wherein least one amino acid of SEQ ID NO: 54 that is not positively charged is substituted with a positively charged amino acid; and/or comprises a LCDR2 comprising the amino acid sequence of SEQ ID NO: 55 (DTSKLAS), wherein least one amino acid of SEQ ID NO: 55 that is not positively charged is substituted with a positively charged amino acid as set out above; and further comprises at position 30 of HFR1 a positively charged amino acid. Preferably, the antigen binding polypeptide further comprises a HFR3. It is particularly preferred that the HFR3 comprises at position 90 Y.

In another embodiment the antigen binding polypeptide comprises a VH and a VL comprising a HCDR1, and/or a HCDR2 as defined above and/or a LCDR2 as defined above, wherein at least one amino acid of HCDR1 comprising the amino acid sequence of SEQ ID NO: 52 that is not positively charged and/or least one amino acid of HCDR2 comprising the amino acid sequence of SEQ ID NO: 53 that is not positively charged is/are substituted with a positively charged amino acid; and wherein at least one amino acid of LCDR1 comprising the amino acid sequence of SEQ ID NO: 54 that is not positively charged and/or least one amino acid of LCDR2 comprising the amino acid sequence of SEQ ID NO: 55 that is not positively charged is/are substituted with a positively charged amino acid. Preferably, the antigen binding polypeptide further comprises a HFR3. It is particularly preferred that the HFR3 comprises at position 90 Y. It is also preferred that the antigen binding polypeptide further comprises a HFR1 wherein position 30 of HFR1 is substituted with a positively charged amino acid.

In one embodiment the antigen binding polypeptide comprises a LCDR1 according to SEQ ID NO: 54, wherein at least one amino acid that is not positively charged is substituted with a positively charged amino acid and a LCDR2 as set out above and further comprises a light chain CDR 3 (LCDR3) and light chain framework regions (LFR) 1-4. In one embodiment, the antigen binding polypeptide comprises a LCDR1 according to SEQ ID NO: 54, wherein at least one amino acid that is not positively charged is substituted with a positively charged amino acid and a LCDR2 as set out above and further comprises a heavy chain CDR 3 (LCDR3) and heavy chain framework regions (LFR) 1-4. Said LFR1-4 sequences may also comprise one or more further modifications such as further substitutions, deletions or insertions compared to a FR sequence comprising none of said modifications. However, in some embodiments, in case of said further modifications, the FR sequences modified still comprise the inventive substitutions, for example tyrosine at position 90 of FR3 in the VH, and/or a positively charged amino acid at position 30 in the VH. It is further preferred that FR1-4 sequences are not modified at certain positions such as those in the Vernier zone, the VH/VL inter-chain interface or at positions determining the CDR canonical class. Herein below, further positions in the FR are provided that should preferably not be modified in the context of the invention. It is also preferred that certain positions are comprised in FR and not comprised in CDRs regardless of the annotations used.

Preferably, the antigen binding polypeptide specifically binds to an α/β TCR/CD3 complex, preferably the α/β TCR/CD3 complex is present on T cells, more preferably on T lymphocytes. The antigen binding polypeptides of the present invention compete with a reference antibody for binding to a T cell expressing the α/β TCR/CD3 complex. In certain embodiments, the antigen binding polypeptide binds to the same epitope as the reference antibody comprising a VH amino acid sequence according to SEQ ID NO: 1, and a VL amino acid sequence according to SEQ ID NO: 2. In certain embodiments, the antigen binding polypeptide competes with the reference antibody for binding to a T cell expressing the α/β TCR/CD3 complex with an antibody comprising a VH according to SEQ ID NO: 1 and a VL according to SEQ ID NO: 2. In a preferred embodiment the reference antibody comprises a constant domain, preferably a human IgG1 constant domain, and human kappa light chain region. In certain embodiments, the antigen binding polypeptide competes with the reference antibody for binding to a T cell expressing the α/β TCR/CD3 complex with an antibody comprising a heavy chain (HC) amino acid sequence according to SEQ ID NO: 60 and a light chain (LC) amino acid sequence according to SEQ ID NO: 6. Preferably, the antigen binding polypeptide competes with the reference antibody for binding to a cell expressing the α/β TCR/CD3 complex with an antibody comprising a heavy chain amino acid sequence according to SEQ ID NO: 60 and a light chain amino acid sequence according to SEQ ID NO: 6.

In one embodiment of the first aspect of the present invention the positively charged amino acid(s) comprised in the HCDRs and/or LCDRs of the antigen binding polypeptide are at position(s) 31, 53, and/or 54 of the heavy chain and/or at position(s) of 31 and/or 56 the light chain.

In one embodiment the positively charged amino acid comprised in the HCDR of the antigen binding polypeptide is at position 31 of the heavy chain. In one embodiment the positively charged amino acids comprised in the HCDRs of the antigen binding polypeptide are at positions 31 and 53 of the heavy chain. In one embodiment the positively charged amino acids comprised in the HCDRs of the antigen binding polypeptide are at positions 31 and 54 of the heavy chain. In one embodiment the positively charged amino acids comprised in the HCDRs of the antigen binding polypeptide are at positions 31, 53 and 54 of the heavy chain. In addition, the antigen binding polypeptide of any of these embodiments may further comprise Y at position 90 in the HFR3.

In one embodiment the positively charged amino acid comprised in the LCDR of the antigen binding polypeptide is at position 31 of the light chain. In one embodiment the positively charged amino acid comprised in the LCDR of the antigen binding polypeptide is at position 56 of the light chain. In one embodiment the positively charged amino acids comprised in the LCDRs of the antigen binding polypeptide are at positions of 31 and 56 of the light chain. In addition, the antigen binding polypeptide of any of these embodiments may further comprise Y at position 90 in HFR3.

In one embodiment the antigen binding polypeptide comprises the positively charged amino acids at position 31 of the heavy chain and at position 31 and/or 56 of the light chain. In one embodiment antigen binding polypeptide comprises the positively charged amino acids at position 53 of the heavy chain and at position 31 and/or 56 of the light chain. In one embodiment antigen binding polypeptide comprises the positively charged amino acids at position 54 of the heavy chain and at position 31 and/or 56 of the light chain. In one embodiment the antigen binding polypeptide comprises the positively charged amino acids at position 31 and 53 of heavy chain and at position 31 and/or 56 of the light chain. In one embodiment the antigen binding polypeptide comprises the positively charged amino acids at position 31 and 54 of heavy chain and at position 31 and/or 56 of the light chain. In one embodiment the antigen binding polypeptide comprises the positively charged amino acids at position 53 and 54 of heavy chain and at position 31 and/or 56 of the light chain. The antigen binding polypeptide of any of these embodiments may further comprise Y at position 90 in FR3 in the VH, and/or a positively charged amino acid at position 30 in the VH.

In one embodiment the positively charged amino acid in the heavy chain of the antigen binding polypeptide at position 30 is R, K or H. Preferably, the positively charged amino acid in the heavy chain of the antigen binding polypeptide at position 30 is R or K. Even more preferably, the positively charged amino acid in the heavy chain of the antigen binding polypeptide at position 30 is R. In one embodiment the positively charged amino acid in the heavy chain of the antigen binding polypeptide at positions 30 in HFR1 is R or K and at position 90 in HFR3 is Y.

In one embodiment of the first aspect of the present invention the positively charged amino acid in the heavy chain of the antigen binding polypeptide at position 31 is R, K or H. More preferably, the positively charged amino acid in the heavy chain of the antigen binding polypeptide at position 31 is R or K. Even more preferably, the positively charged amino acid in the heavy chain of the antigen binding polypeptide at position 31 is R. Even more preferably, the positively charged amino acid in the heavy chain of the antigen binding polypeptide at position 31 is R or K and at position 90 is Y or the positively charged amino acid in the heavy chain of the antigen binding polypeptide at position 31 is R and at position 90 in HFR3 is Y.

In one embodiment the positively charged amino acid in the heavy chain of the antigen binding polypeptide at position 53 is R, K or H. Preferably, the positively charged amino acid in the heavy chain of the antigen binding polypeptide at position 53 is K, R or H and at position 90 is Y in the heavy chain. Preferably, the positively charged amino acid in the heavy chain of the antigen binding polypeptide at position 53 is R or K. More preferably, the positively charged amino acid in the heavy chain of the antigen binding polypeptide at position 53 is R. It is particularly preferred that the positively charged amino acid in the heavy chain of the antigen binding polypeptide at position 53 is R and that at position 90 in the HFR3 is Y. It is further preferred that the positively charged amino acid in the heavy chain of the antigen binding polypeptide at position 53 is R or K and that serine is at position 30 of the heavy chain of the antigen binding polypeptide. It is particularly preferred that the positively charged amino acid in the heavy chain of the antigen binding polypeptide at position 53 is R and that serine is at position 30 of the heavy chain of the antigen binding polypeptide.

In one embodiment the positively charged amino acid in the heavy chain of the antigen binding polypeptide at position 54 is R or K. Preferably, the positively charged amino acid in the heavy chain of the antigen binding polypeptide at position 54 is K. It is particularly preferred that the positively charged amino acid in the heavy chain of the antigen binding polypeptide at position 54 is K and that at position 90 is Y or that the positively charged amino acid in the heavy chain of the antigen binding polypeptide at position 54 is R and that at position 90 in HFR3 is Y.

In one embodiment the positively charged amino acid in the light chain of the antigen binding polypeptide at position 31 is R or K. Preferably, the positively charged amino acid in the heavy chain of the antigen binding polypeptide at position 31 is R. It is particularly preferred that the positively charged amino acid in the light chain of the antigen binding polypeptide at position 31 is R and that at position 90 in HFR3 is Y or that the positively charged amino acid in the light chain of the antigen binding polypeptide at position 31 is K and that at position 90 in HFR3 is Y.

In one embodiment the positively charged amino acid in the light chain of the antigen binding polypeptide at position 56 is R or K. Preferably, the positively charged amino acid in the light chain of the antigen binding polypeptide at position 56 is R. It is particularly preferred that the positively charged amino acid in the light chain of the antigen binding polypeptide at position 56 is R and that at position 90 is Y or that the positively charged amino acid in the light chain of the antigen binding polypeptide at position 56 is K and at position 90 in HFR3 is Y.

The following positively charged amino acid combinations are preferred in the heavy chain: R31 and R53; R31 and K53; R31 and H53; R31 and R54; R31 and K54; K31 and R53; K31 and K53; K31 and H53; K31 and R54; K31 and K54; H31 and R53; H31 and K51; H31 and H51; H31 and R54; H31 and K54; R31, R53 and R54; R31, R53 and K54; R31, K53 and R54; R31, K53 and K54; R31, H53 and R54; R31, H53 and K54; K31, R53 and R54; K31, R53 and K54; K31, K53 and R54; K31, K53 and K54; K31, H53 and R54; K31, H53 and K54; H31, R53 and R54; H31, R53 and K54; H31, K53 and R54; H31, K53 and K54; H31, H53 and R54; H31, H53 and K54; R53 and R54; R53 and K54; K53 and R54; K53 and K54; H53 and R54; and H53 and K54. The antigen binding polypeptide of any of these embodiments may further comprise Y at position 90 in FR3 in the VH, and/or a positively charged amino acid at position 30 in the VH. It is even more preferred that the positively charged amino acid in the heavy chain of the antigen binding polypeptide at position 53 is R. It is even more preferred that the positively charged amino acid in the heavy chain of the antigen binding polypeptide at position 53 is R and the antigen binding polypeptide comprises Y at position 90 in FR3 in the VH.

The following positively charged amino acid combinations are preferred in the light chain: R31 and R56; R31 and K56; K31 and R56; and K31 and K56.

The following positively charged amino acid combinations are particularly preferred in the light chain together with a substitution at position 90 in the HFR3:
R31 and R56; and position 90 is Y;
R31 and K56; and position 90 is Y;
K31 and R56; and position 90 is Y;
K31 and K56 and position 90 is Y.

The following positively charged amino acid combinations in the heavy chain and in the light chain are particularly preferred: heavy chain 31R and light chain 56R; heavy chain 54K and light chain 56R; heavy chain 54K and light chain 31R; heavy chain 53R and light chain 56R; heavy chain 53R and light chain 31R and 56R; and heavy chain 31R, light chain 31R and light chain 56R.

The following positively charged amino acid combinations in the heavy chain and in the light chain are particularly preferred; with or without a substitution at position 90 in the heavy chain: heavy chain 31R and light chain 56R and heavy chain position 90 is Y; heavy chain 54K and light chain 56R and heavy chain position 90Y; heavy chain 54K and light chain 31R and 56R, and heavy chain position 90 Y; heavy chain 53R and light chain 56R; heavy chain 53R and light 56R and heavy chain position 90Y.

It was observed in the context of the present invention that substitutions with positively charged amino acids in the antigen binding polypeptide (e.g. at respective positions in HCDR1 and/or HCDR2 and/or LCDR1 and/or LCDR2 and/or at positions 30 of HFR1 as defined above) provide an increased binding to the α/β TCR/CD3 complex. Thus, a lowering of the binding EC50 in comparison to the parental antigen binding polypeptide comprising none of the inventive substitutions is provided. Lowering of binding EC50 is described in "x-fold" decrease in binding EC50 or in "% gain in binding AUC".

In context of the invention, the antigen binding polypeptide specifically binds to an α/β T cell receptor (TCR)/CD3 complex; and has an increased binding compared to a parental antigen binding polypeptide, wherein the antigen binding polypeptide has at least 2, 3, 4, 5, 6, 7, 8, 9, 10, 11, 12, 13, 14, 15, 16, 17, 18, 19, 20, 22, 24, 26, 28, 30-fold decrease in binding EC50 compared to a parental antigen binding polypeptide.

In one embodiment the antigen binding polypeptide has at least 2-fold decrease in binding EC50 compared to a parental antigen binding polypeptide.

In one embodiment the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid and wherein the antigen binding polypeptide shows at least 2-fold decrease in binding EC50 compared to a parental antigen binding polypeptide.

In one embodiment the antigen binding polypeptide comprises a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and wherein the antigen binding polypeptide shows at least 2-fold decrease in binding EC50 compared to a parental antigen binding polypeptide.

In one embodiment the antigen binding polypeptide comprises a HFR3 comprising a Y residue at position 90 and shows at least 2-fold decrease in EC50 compared to a parental antigen binding polypeptide.

In one embodiment of the antigen binding polypeptide comprises a HCDR1comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and comprises a HFR3 comprising Y at position 90; and wherein the antigen binding polypeptide shows at least 2-fold decrease in binding EC50 compared to a parental antigen binding polypeptide.

In one embodiment the antigen binding polypeptide comprises a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and comprises a HFR3 comprising Y at position 90; and wherein the antigen binding polypeptide shows at least 2-fold decrease in binding EC50 compared to a parental antigen binding polypeptide.

In one embodiment of the antigen binding polypeptide comprises a HCDR1comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and wherein the antigen binding polypeptide shows at least 2-fold decrease in binding EC50 compared to a parental antigen binding polypeptide.

In one embodiment of the antigen binding polypeptide comprises a HCDR1comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid; and comprises a HFR3 comprising Y at position 90; and wherein the antigen binding polypeptide shows at least 2-fold decrease in binding EC50 compared to a parental antigen binding polypeptide.

In one embodiment the antigen binding polypeptide comprises a positively charged amino acid in the heavy chain at position 30 and shows 2-fold decrease in EC50, compared to a parental antigen binding polypeptide. Preferably, the positively charged amino acid at position 30 in the heavy chain of the antigen binding polypeptide is R, K or H and the antigen binding polypeptide shows at least 2-fold decrease in EC50 compared to a parental antigen binding polypeptide, preferably the parental antibody. Even more preferably, the positively charged amino acid at position 30 in the heavy chain of the antigen binding polypeptide is R or K and the antigen binding polypeptide shows at least 2-fold decrease in EC50 compared to a parental antigen binding polypeptide.

In one embodiment the antigen binding polypeptides of the first aspect of the present invention preferably comprise one of the following mutations in the heavy chain: at position 30R at position 30K at position 31R at position 31K at position 53R, at position 54R; at position 54K and show at least 2-fold decrease in binding EC50, compared to a parental antigen binding polypeptide. In one embodiment the antigen binding polypeptides of the first aspect of the present invention preferably comprise one of the following mutations in the heavy chain: at position 31R; at position 31K; at position 53R, at position 54K, and show at least 4-fold decrease in binding EC50 compared to a parental antigen binding polypeptide.

In one embodiment the antigen binding polypeptides of the first aspect of the present invention preferably comprise one of the following mutations in the heavy chain: at position 31R; at position 53R, at position 54K, and show at least 5-fold decrease in binding EC50, compared to a parental antigen binding polypeptide. More preferably, antigen binding polypeptides comprise one a mutation in the heavy chain at position 54K and show at least 8-fold decrease in binding EC50 compared to a parental antigen binding polypeptide.

In one embodiment the antigen binding polypeptides preferably comprise a mutation in the light chain at position 56R or 56K and show at least 4-fold decrease in binding EC50, compared to a parental antigen binding polypeptide. More preferably, the antigen binding polypeptides preferably comprise a mutation in the light chain at position 56R and show at least 8-fold decrease in binding EC50 compared to a parental antigen binding polypeptide.

In one embodiment the antigen binding polypeptides preferably comprise a mutation in the heavy chain at position 90Y and show at least 3-fold decrease in binding EC50 compared to a parental antigen binding polypeptide. In one embodiment the antigen binding polypeptides preferably comprise one of the following preferred amino acid combinations in the heavy chain: at position 31R and at position 90Y; at position 53R and at position 90Y; at position 54K and at position 90Y; and at position 54R and at position 90Y and show at least 4-fold decrease in binding EC50, compared to a parental antigen binding polypeptide.

In one embodiment the antigen binding polypeptides preferably comprise one of the following preferred amino acid combinations in the heavy chain: at position 31R and at position 90Y; at position 53R and at position 90Y; and at position 54K and at position 90Y; and show at least 5-fold decrease in binding EC50 compared to a parental antigen binding polypeptide.

In one embodiment the antigen binding polypeptides preferably comprise one of the following preferred amino acid combinations in the heavy chain: at position 31R and at position 90Y; and at position 54K and at position 90Y; and show at least 7-fold decrease in binding EC50, compared to a parental antigen binding polypeptide.

In one embodiment the antigen binding polypeptides preferably comprise a mutation in the heavy chain at position 31R and at position 90Y; and show at least 8-fold decrease in binding EC50, compared to a parental antigen binding polypeptide, preferably the parental antibody.

In one embodiment the antigen binding polypeptides preferably comprise a mutation in the light chain at position 56R and further comprises a mutation at position 90Y and show at least 13-fold decrease in binding EC50, compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and in the heavy chain at position 53R and at position 90Y and in the light chain at position 56R and show at least 15-fold decrease e in binding EC50, compared to a parental antigen binding polypeptide. Preferably, the antigen binding polypeptides comprise the following amino acid combinations in the heavy chain and in the light chain: in the heavy chain at position 31R, at position 90Y and in the light chain at position 56R; and in the heavy chain at position 54K and at position 90Y and in the light chain at position 56R and show at least 20-fold decrease in binding EC50, compared to a parental antigen binding polypeptide. Even more preferably, the antigen binding polypeptides comprise the following preferred amino acid combinations in the heavy chain and in the light chain: in the heavy chain at position 31R, at position 90Y and in the light chain at position 56R and show at least 30-fold decrease in binding EC50, compared to a parental antigen binding polypeptide.

The inventors surprisingly demonstrated in the appended examples that the binding AUC of the antigen binding polypeptides of the invention is increased compared to the binding AUC of the parental antigen binding polypeptide, preferably to the binding AUC of the parental antibody, which is described in % gain in binding AUC. Thus, the antigen binding polypeptides provided herein have an increased binding AUC compared to the parental antigen binding polypeptide, preferably the antigen binding polypeptide, has at least about 10% gain in binding AUC; has at least about 15% gain in binding AUC; at least about 50% gain in binding AUC; at least about 140% gain in binding AUC; at least about 200% gain in binding AUC; at least about 250% gain in binding AUC; at least about 400% gain in binding AUC; at least about 500% gain in binding AUC; at least about 600% gain in binding AUC; at least about 700% gain in binding AUC or at least about 800% gain in binding AUC.

In one embodiment the inventive antigen binding polypeptide has at has at least about 10% gain in binding AUC compared to a parental antigen binding polypeptide.

In one embodiment the antigen binding polypeptide of the first aspect of the invention has at least about 10% gain in binding AUC, i.e. increased binding to a cell expressing the α/β TCR/CD3 complex compared to a parental antigen binding polypeptide. In one embodiment the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid and wherein the antigen binding polypeptide has at least about 15% gain in binding AUC, compared to a parental antigen binding polypeptide.

In one embodiment the antigen binding polypeptide comprises a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and wherein the antigen binding polypeptide has at least about 10% gain in binding AUC, compared to a parental antigen binding polypeptide.

In one embodiment the antigen binding polypeptide comprises at position 90 in HFR3 Y and has at least about 10% gain in binding AUC, compared to a parental antigen binding polypeptide.

In one embodiment of the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and comprises at position 90 in HFR3 Y and wherein the antigen binding polypeptide has at least about 10% gain in binding AUC compared to a parental antigen binding polypeptide.

In one embodiment the antigen binding polypeptide comprises a LCDR1 comprising the amino acid sequence of SEQ ID NO: 54 and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and comprises at position 90 in HFR3 Y and wherein the antigen binding polypeptide has at least about 10% gain in binding AUC compared to a parental antigen binding polypeptide.

In one embodiment of the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and wherein the antigen binding polypeptide has at least about 10% gain in binding AUC compared to a parental antigen binding polypeptide.

In one embodiment of the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid; and comprises position 90 in HFR3 Y and wherein the antigen binding polypeptide has at least about 10% gain in binding AUC compared to a parental antigen binding polypeptide.

In one embodiment the antigen binding polypeptides of the first aspect of the present invention preferably comprise one of the following substitutions in the heavy chain: at position 30R, at position 30K; at position 31R at position 31K; at position 53R, at position 54R; at position 54K and have at least about 15% gain in binding AUC compared to a parental antigen binding polypeptide.

In one embodiment the antigen binding polypeptides of the first aspect of the present invention preferably comprise one of the following mutations in the heavy chain: at position 30R, at position 30K; at position 31R at position 31K; at position 53R, at position 54K and have an at least about 50% gain in binding AUC compared to a parental antigen binding polypeptide.

In one embodiment the antigen binding polypeptide further comprises a positively charged amino acid in the heavy chain at position 30 in HFR1 and shows at least 80% gain in AUC. Preferably, the positively charged amino acid at position 30 in HFR1 of the antigen binding polypeptide is R, K or H and the antigen binding polypeptide shows at least 80% gain in AUC compared to a parental antigen binding polypeptide. Even more preferably, the positively charged amino acid at position 30 in HFR1 of the antigen binding polypeptide is R or K and the antigen binding polypeptide shows at least 80% gain in binding AUC compared to a parental antigen binding polypeptide.

In one embodiment the antigen binding polypeptides of the first aspect of the present invention preferably comprise one of the following mutations in the heavy chain: at position 30R, at position 30K; at position 31R at position 31K; at position 53R, at position 54K, and have an at least about 100% gain in binding AUC compared to a parental antigen binding polypeptide. Particularly preferred is the antigen binding polypeptides has a substitution in the heavy chain at position 31R and has about 140% gain in binding AUC compared to a parental antigen binding polypeptide.

In one embodiment the antigen binding polypeptides preferably comprise a mutation in the light chain at position 56R, and have an have an at least about 15% gain in binding AUC or more; at least about 20% gain in binding AUC; at least about 50% gain in; at least about 100%; or at least about 200% gain in binding AUC compared to a parental antigen binding polypeptide. More preferably, the antigen binding polypeptides preferably comprise a mutation in the light chain at position 56R, and has at least about 200% gain in binding AUC, compared to a parental antigen binding polypeptide.

In one embodiment the antigen binding polypeptides preferably comprise a mutation in the heavy chain at position 90Y and has at least about 10% gain in binding AUC, compared to a parental antigen binding polypeptide. In one embodiment the antigen binding polypeptides preferably comprise one of the following preferred amino acid combinations in the heavy chain: at position 31R and at position 90Y; at position 53R and at position 90Y; and at position 54K and at position 90Y; and have at least about 200% gain in binding AUC compared to a parental antigen binding polypeptide.

In one embodiment the antigen binding polypeptides preferably comprise one of the following preferred amino acid combinations in the heavy chain: at position 31R and at position 90Y; at position 53R and at position 90Y; and at position 54K and at position 90Y; and have at least about 250% gain in binding AUC compared to a parental antigen binding polypeptide.

In one embodiment the antigen binding polypeptides preferably comprise the amino acid combination in the heavy chain at position 54K and at position 90Y; and has at least about 300% gain in binding AUC, compared to a parental antigen binding polypeptide.

In one embodiment the antigen binding polypeptides preferably comprise a mutation in the light chain at position 56R and further comprises a mutation in the heavy chain at position 90Y and has at least about 10% gain in binding AUC; at least about 50% gain in binding AUC, about 100% gain in binding AUC; or about 200% gain in binding AUC, compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and in the heavy chain at position 54K and at position 90Y and in the light chain at position 56R and have at least about 200% gain in binding AUC, compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R or in the heavy chain at position 53R, at position 90Y and in the light chain at position 56R; and have at least about 250% gain in binding AUC, compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R or in the heavy chain at position 53R, at position 90Y and in the light chain at position 56R; and have at least about 300% gain in binding AUC, compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R or in the heavy chain at position 53R, at position 90Y and in the light chain at position 56R; and have at least about 400% gain in binding AUC, compared to a parental antigen binding polypeptide.

In one embodiment the antigen binding polypeptides comprise the following preferred amino acid combinations in the heavy chain and in the light chain: in the heavy chain at position 53R, at position 90Y and in the light chain at position 56R; and has at least about 500% gain in binding AUC; at least about 600% gain in binding AUC; at least about 700% gain in binding AUC; or at least about 800% gain in binding AUC, compared to a parental antigen binding polypeptide. It is particularly preferred that the antigen binding polypeptides comprise the following preferred amino acid combination in the heavy chain and in the light chain: in the heavy chain at position 53R, at position 90Y and in the light chain at position 56R has at least about 500% gain in binding AUC, compared to a parental antigen binding polypeptide.

The inventors surprisingly demonstrated in the appended examples that the Tm of the antigen binding polypeptides of the invention is increased compared to the Tm of the parental antigen binding polypeptide which is described in delta Tm in ° C. or in absolute temperature values in ° C. Thus, the antigen binding polypeptides provided herein have an increased Tm compared to the parental antigen binding polypeptide. Preferably the antigen binding polypeptide has a delta Tm of at least 1° C.; a delta Tm of at least 2° C., a delta Tm of at least 3° C., a delta Tm of at least 3.5° C. or a delta Tm of at least 4° C. compared to a parental antigen binding polypeptide.

The antigen binding polypeptide provided herein has an increased Tm compared to the parental antigen binding polypeptide, preferably compared to the parental antibody and has a Tm of at least 72.5° C., has a Tm of at least 72.8° C., has a Tm of at least 73.8° C., has a Tm of at least 74.8° C. or has a Tm of at least 75.3° C. More preferably the antigen binding polypeptide has a Tm of at least 73.0° C., even more preferably of at least 73.5° C., has a Tm of at least 74° C., has a Tm of at least 75° C. or has a Tm of at least 76° C.

In one embodiment the inventive antigen binding polypeptide has a delta Tm of at least 1° C. compared the parental antigen binding polypeptide, such as the parental antigen binding polypeptide comprising the VH and VL amino acid sequences as herein described in context of the parental antibody BMA031 (V36).

In one embodiment the herein provided antigen binding polypeptide has a delta Tm of at least 1° C. compared to the antigen binding polypeptide not comprising the inventive substitution or a Tm of at least 72.8° C.

In one embodiment the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid and wherein the antigen binding polypeptide has a delta Tm of at least 1° C., compared to a parental antigen binding polypeptide or has a Tm of at least 72.8° C.

In one embodiment the antigen binding polypeptide comprises a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and wherein the antigen binding polypeptide has a delta Tm of at least 1° C., compared to a parental antigen binding polypeptide, or has a Tm of at least 72.8° C.

In one embodiment the antigen binding polypeptide comprises a HFR3 comprising a Y residue at position 90 and has a delta Tm of at least 2° C., preferably of at least 2.5° C., more preferably of at least 3° C. compared to a parental antigen binding polypeptide.

In one embodiment of the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and comprises a HFR3 comprising Y at position 90; and wherein the antigen binding polypeptide has a delta Tm of at least 1° C., compared to a parental antigen binding polypeptide or has a Tm of at least 72.8° C.

In one embodiment the antigen binding polypeptide comprises a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and comprises a HFR3 comprising Y at position 90; and wherein the antigen binding polypeptide has a delta Tm of at least 1° C., compared to a parental antigen binding polypeptide or has a Tm of at least 72.8° C.

In one embodiment of the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and wherein the antigen binding polypeptide has a delta Tm of at least 1° C., compared to a parental antigen binding polypeptide or has a Tm of at least 72.8° C.

In one embodiment of the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid; and comprises a HFR3 comprising Y at position 90; and wherein the antigen binding polypeptide has a delta Tm of at least 1° C. compared to a parental antigen binding polypeptide or has a Tm of at least 72.8° C.

In one embodiment the antigen binding polypeptides preferably comprise a mutation in the heavy chain at position 90Y and have a delta Tm of at least 1.0° C., compared to a parental antigen binding polypeptide. In one embodiment the antigen binding polypeptides preferably comprise one of the following amino acid combinations in the heavy chain: at position 31R and at position 90Y; at position 53R and at position 90Y; and at position 54K and at position 90Y; and at position 54R and at position 90Y and have a delta Tm of at least 1.0° C., compared to a parental antigen binding polypeptide. Preferably, the antigen binding polypeptides comprise one of the following amino acid combinations in the heavy chain: at position 31R and at position 90Y; at position 53R and at position 90Y; and at position 54K and at position 90Y; and at position 54R and at position 90Y and have a delta Tm of at least 2.0° C., compared to a parental antigen binding polypeptide. Even more preferably, the antigen binding polypeptides preferably comprise one of the following amino acid combinations in the heavy chain: at position 31R and at position 90Y; at position 53R and at position 90Y; and at position 54K and at position 90Y; and at position 54R and at position 90Y and have a delta Tm of at least 3.0° C. compared to a parental antigen binding polypeptide.

In one embodiment the antigen binding polypeptides preferably comprise one of the following amino acid combinations in the heavy chain: at position 31R and at position 90Y; and at position 53R and at position 90Y; and have a delta Tm of at least 3.5° C. compared to a parental antigen binding polypeptide.

In one embodiment the antigen binding polypeptides preferably comprise a mutation in the heavy chain at position 53R and at position 90Y; and have a delta Tm of at least 4.0° C. compared to a parental antigen binding polypeptide.

In one embodiment the antigen binding polypeptides preferably comprise a mutation in the light chain at position 56R and further comprises a mutation at position 90Y and have a delta Tm of at least 3.0° C., compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and in the heavy chain at position 54K and at position 90Y and in the light chain at position 56R and have a delta Tm of at least 2.0° C. compared to a parental antigen binding polypeptide.

Preferably, the antigen binding polypeptides comprise the following amino acid combinations in the heavy chain and in the light chain: in the heavy chain at position 31R, at position 90Y and in the light chain at position 56R; and in the heavy chain at position 53R and at position 90Y and in the light chain at position 56R and have a delta Tm of at least 3.5° C. compared to a parental antigen binding polypeptide.

In one embodiment the antigen binding polypeptides preferably comprise a mutation in the heavy chain at position 90Y and have a Tm of at least 73.0° C., have a Tm of at least 74° C., have a Tm of at least 75° C. or have a Tm of at least 76° C.

In one embodiment the antigen binding polypeptides preferably comprise one of the following amino acid combinations in the heavy chain: at position 31R and at position 90Y; at position 53R and at position 90Y; and at position 54K and at position 90Y; and at position 54R and at position 90Y and have a Tm of at least 73.46° C. In one embodiment the antigen binding polypeptides preferably comprise one of the following amino acid combinations in the heavy chain: at position 31R and at position 90Y; at position 53R and at position 90Y; and at position 54K and at position 90Y; and at position 54R and at position 90Y and have a Tm of at least 74.46° C. In one embodiment the antigen binding polypeptides preferably comprise one of the following amino acid combinations in the heavy chain: at position 31R and at position 90Y; at position 53R and at position 90Y; and at position 54K and at position 90Y; and at position 54R and at position 90Y and have a Tm of at least 75.46° C.

In one embodiment, the antigen binding polypeptides comprise one of the following amino acid combinations in the heavy chain: at position 31R and at position 90Y; at position 53R and at position 90Y; and at position 54K and at position 90Y; and at position 54R and at position 90Y and have a Tm of at least 75.5° C. Even more preferably, the antigen binding polypeptides comprise one of the following amino acid combinations in the heavy chain: at position 31R and at position 90Y; at position 53R and at position 90Y; and at position 54K and at position 90Y; at position 54R and at position 90Y and have a Tm of at least 75.9° C.

In one embodiment the antigen binding polypeptides preferably comprise one of the following amino acid combinations in the heavy chain: at position 31R and at position 90Y; and at position 53R and at position 90Y; and have a Tm of at least 76.0° C.

In one embodiment the antigen binding polypeptides preferably comprise a mutation in the heavy chain at position 53R and at position 90Y; and have a Tm of at least 76.5° C.

In one embodiment the antigen binding polypeptides preferably comprise a mutation in the light chain at position 56R and further comprises a mutation in the heavy chain at position 90Y and have a Tm of at least 72.0° C., a Tm of at least 73.0° C., a Tm of at least 74.0° C., a Tm of at least 75.0° C.; or a Tm of at least 76.0° C. Preferably, the antigen binding polypeptide has a Tm of at least 75.0° C. Even more preferably, the antigen binding polypeptide has a Tm of at least 75.5° C.

In one embodiment the antigen binding polypeptides comprise the following preferred amino acid combinations in the heavy chain and in the light chain: at position 31R, at position 90Y and at position 56R; at position 53R, at position 90Y and at position 56R; and at position 54K and at position 90Y and at position 56R and have a Tm of at least 74.0° C. Preferably, the antigen binding polypeptides comprise the following preferred amino acid combinations in the heavy chain and in the light chain: at position 31R, at position 90Y and at position 56R; at position 53R, at position 90Y and at position 56R; and at position 54K and at position 90Y and at position 56R and have a Tm of at least 75.0° C.

In one embodiment the antigen binding polypeptides comprise the following amino acid combinations in the heavy chain and in the light chain: in the heavy chain at position 31R, at position 90Y and in the light chain at position 56R; and in the heavy chain at position 53R and at position 90Y and in the light chain at position 56R and have a Tm of at least 76.0° C.

In one embodiment the inventive antigen binding polypeptide has 10% gain in binding AUC and has a delta Tm of at least 1° C. compared to a parental antigen binding polypeptide.

In one embodiment the herein provided antigen binding polypeptide has at least about 10% gain in binding AUC and has a delta Tm of at least 1° C. compared to a parental antigen binding polypeptide.

In one embodiment the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid and wherein the antigen binding polypeptide has at least about 10% gain in binding AUC and has a delta Tm of at least 1° C., compared to a parental antigen binding polypeptide.

In one embodiment the antigen binding polypeptide comprises a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and wherein the antigen binding polypeptide has at least about 10% gain in binding AUC and has a delta Tm of at least 1° C., compared to a parental antigen binding polypeptide.

In one embodiment the antigen binding polypeptide comprises at position 90 in HFR3 Y and has at least about 10% gain in binding AUC compared to a parental antigen binding polypeptide.

In one embodiment of the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and comprises at position 90 in HFR3 Y; and wherein the antigen binding polypeptide has at least about 10% gain in binding AUC and has a delta Tm of at least 1° C. compared to a parental antigen binding polypeptide.

In one embodiment the antigen binding polypeptide comprises a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO:62 that is not positively charged is substituted with a positively charged amino acid and comprises at position 90 in HFR3 Y; and wherein the antigen binding polypeptide has at least about 10% gain in binding AUC and has a delta Tm of at least 1° C. compared to a parental antigen binding polypeptide In one embodiment of the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid and wherein the antigen binding polypeptide has at least about 10% gain in binding AUC and has a delta Tm of at least 1° C. compared to a parental antigen binding polypeptide.

In one embodiment of the antigen binding polypeptide comprises a HCDR1 comprising the amino acid sequence of SEQ ID NO: 52 and/or a HCDR2 comprising the amino acid sequence SEQ ID NO: 53, wherein at least one amino acid of HCDR1 comprising the amino acid sequence of SEQ ID NO: 52 and/or least one amino acid of HCDR2 comprising the amino acid sequence of SEQ ID NO: 53 that is not positively charged is substituted with a positively charged amino acid; and a LCDR1 comprising the amino acid sequence of SEQ ID NO: 54, and/or a LCDR2 comprising the amino acid sequence of SEQ ID NO: 55, wherein at least one amino acid of LCDR1 comprising the amino acid sequence of SEQ ID NO: 54 and/or at least one amino acid of LCDR2 comprising the amino acid sequence of SEQ ID NO: 55 that is not positively charged is substituted with a positively charged amino acid; and comprises position 90 in HFR3 Y; and wherein the antigen binding polypeptide has at least about 10% gain in binding AUC and has a delta Tm of at least 1° C. compared to a parental antigen binding polypeptide.

In one embodiment the antigen binding polypeptides preferably comprise a mutation in the heavy chain at position 90Y, have at least about 10% gain in binding AUC and have a delta Tm of at least 1° C. compared to a parental antigen binding polypeptide.

In one embodiment the antigen binding polypeptides preferably comprise one of the following preferred amino acid combinations in the heavy chain: at position 31R and at position 90Y; at position 53R and at position 90Y; and at position 54K and at position 90Y; and at position 54R and at position 90Y, have a delta Tm of at least 1.0° C. and have at least about 200% gain in binding AUC compared to a parental antigen binding polypeptide.

Preferably, the antigen binding polypeptides comprise one of the following amino acid combinations in the heavy chain: at position 31R and at position 90Y; at position 53R and at position 90Y; and at position 54K and at position 90Y; and at position 54R and at position 90Y, have a delta Tm of at least 2.0° C. and have at least about 200% gain in binding AUC compared to a parental antigen binding polypeptide.

In one embodiment the antigen binding polypeptides comprise one of the following amino preferred amino acid combinations in the heavy chain: at position 31R and at position 90Y; at position 53R and at position 90Y; and at position 54K and at position 90Y; have a delta Tm of at least 3.0° C. and have at least about 240% gain in binding AUC compared to a parental antigen binding polypeptide.

In one embodiment the antigen binding polypeptides preferably comprise a mutation in the heavy chain at position 54K and at position 90Y; has a delta Tm of at least 3.0° C. and has at least about 300% gain in binding AUC compared to a parental antigen binding polypeptide.

In one embodiment the antigen binding polypeptides preferably comprise one of the following amino acid combinations in the heavy chain: at position 31R and at position 90Y; and at position 53R and at position 90Y; have a delta Tm of at least 3.5° C. and have at least about 200% gain in binding AUC compared to a parental antigen binding polypeptide.

In one embodiment the antigen binding polypeptides preferably comprise one of the following amino acid combinations in the heavy chain: at position 31R and at position 90Y; and at position 53R and at position 90Y; have a delta Tm of at least 3.5° C. and have at least about 250% gain in binding AUC compared to a parental antigen binding polypeptide.

In one embodiment the antigen binding polypeptides preferably comprise a mutation in the heavy chain at position 53R and at position 90Y; have a delta Tm of at least 4.0° C. and have at least about 200% gain in binding AUC compared to a parental antigen binding polypeptide.

In one embodiment the antigen binding polypeptides preferably comprise a mutation in the heavy chain at position 53R and at position 90Y; have a delta Tm of at least 4.0° C. and have at least about 250% gain in binding AUC compared to a parental antigen binding polypeptide.

In one embodiment the antigen binding polypeptides preferably comprise a mutation in the light chain at position 56R and further comprises a mutation at position 90Y and have a delta Tm of at least 3.0° C., and have at least about 150% gain in binding AUC, compared to a parental antigen binding polypeptide.

In one embodiment the antigen binding polypeptides preferably comprise a mutation in the light chain at position 56R and further comprises a mutation at position 90Y and show have a delta Tm of at least 3.0° C., and have at least about 200% gain in binding AUC.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and in the light chain at position 54K and at position 90Y and in the heavy chain at position 56R, have a delta Tm of at least 2.0° C. and have at least about 200% gain in binding AUC, compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and in the heavy chain at position 54K and at position 90Y and in the light chain at position 56R, have a delta Tm of at least 2.0° C. and have at least about 300% gain in binding AUC, compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and in the heavy chain at position 54K and at position 90Y and in the light chain at position 56R, have a delta Tm of at least 2.0° C. and have at least about 400% gain in binding AUC, compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and in the heavy chain at position 54K and at position 90Y and in the light chain at position 56R, have a delta Tm of at least 2.0° C. and have at least about 500% gain in binding AUC, compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and in the heavy chain at position 54K and at position 90Y and in the light chain at position 56R, have a delta Tm of at least 2.0° C. and have at least about 600% gain in binding AUC compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and in the heavy chain at position 54K and at position 90Y and in the light chain at position 56R, have a delta Tm of at least 2.0° C. and have at least about 700% gain in binding AUC compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and in the heavy chain at position 54K and at position 90Y and in the light chain at position 56R, have a delta Tm of at least 2.0° C. and have at least about 800% gain in binding AUC compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; have a delta Tm of at least 3.0° C. and have at least about 200% gain in binding AUC compared to a parental antigen binding polypeptide.

In one embodiment the antigen binding polypeptides comprise the following preferred amino acid combinations in the heavy chain and in the light chain: at position in the heavy chain 31R, at position 90Y and in the light chain at position 56R; in the heavy chain at position 53R, at position 90Y and in the light chain at position 56R; have a delta Tm of at least 3.0° C. and have at least about 300% gain in binding AUC compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; have a delta Tm of at least 3.0° C. and have at least about 400% gain in binding AUC compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; have a delta Tm of at least 3.0° C. and have at least about 500% gain in binding AUC compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; have a delta Tm of at least 3.0° C. and have at least about 600% gain in binding AUC compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; have a delta Tm of at least 3.0° C. and have at least about 700% gain in binding AUC compared to a parental antigen binding polypeptide.

In one embodiment the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; have a delta Tm of at least 3.0° C. and have at least about 800% gain in binding AUC compared to a parental antigen binding polypeptide.

It could be surprisingly shown that certain substitutions of positions that carried non-positively charged amino acids with positively charged amino acids provide an improved binding (e.g. binding AUC (FIG. 5, upper panel)). Surprisingly, position 90Y was found to lead to a significant increase in Tm (FIG. 5, lower panel) Amino acid Y at position 90 may be seen as the building block for improved Tm since the substitution at position 90 by Y leads to an increase in Tm for all tested molecules (see FIG. 5, lower panel). Furthermore, the inventors surprisingly found that molecules carrying Y at position 90 together with the substitution of one or more positions with positively charged amino acids lead—additionally to the increase of Tm—to a significant increase/improvement in binding (e.g. binding AUC), i.e. these substitutions lead to synergistic effects.

In one embodiment, the antigen binding polypeptides comprise the following preferred amino acid combinations in the heavy chain: at position 31R and at position 90Y; at position 53R and at position 90Y; position 54R and at position 90 Y; and at position 54K and at position 90Y, and preferably said antigen binding polypeptides have a delta Tm of at least 3° C. degrees and have at least about 200% gain in binding AUC, compared to a parental antigen binding polypeptide. Preferably, the antigen binding polypeptides comprise the following amino acid combinations in the heavy chain: at position 31R and at position 90Y; at position 53R and at position 90Y; and preferably said antigen binding polypeptides have a delta Tm of at least 3° C. degrees and have at least about 270% gain in binding AUC, compared to a parental antigen binding polypeptide. Even more preferably, the antigen binding polypeptides comprise the following amino acid combinations in the heavy chain: at position 54K and at position 90Y, and said antigen binding polypeptides have a delta Tm of at least 3° C. degrees and have at least about 240% gain in binding AUC compared to a parental antigen binding polypeptide.

In one embodiment the antigen binding polypeptides comprise the following preferred amino acid combinations in the heavy chain and in the light chain: at position 31R, at position 90Y in VH and at position 56R in VL; at position 53R, at position 90Y in VH and at position 56R in VL; and at position 54K, at position 90Y in VH and at position 56R in VL, and have a delta Tm of at least 2.50° C. and have at least about 245% gain in binding AUC, compared to a parental antigen binding polypeptide. More preferably, the antigen binding polypeptides comprise the following preferred amino acid combinations in the heavy chain and in the light chain: at position 31R, at position 90Y in VH and at position 56R in VL; at position 53R, at position 90Y in VH and at position 56R in VL; and have a delta Tm of at least 3.50° C. and have at least about 400% gain in binding AUC, compared to a parental antigen binding polypeptide. It is particularly preferred that the antigen binding polypeptide comprises the following preferred amino acid combinations in the heavy chain and in the light chain: at position 53R, at position 90Y in VH and at position 56R in VL; and have a delta Tm of at least 3.50° C. and have at least about 800% gain in binding AUC, compared to a parental antigen binding polypeptide.

In one embodiment, the antigen binding polypeptides comprise the following preferred amino acid combinations in the heavy chain: at position 31R and at position 90Y; at position 53R and at position 90Y; position 54R and at position 90 Y; and at position 54K and at position 90Y and preferably have a Tm of at least 75° C. and have at least about 200% gain in binding AUC, compared to a parental antigen binding polypeptide. Preferably, the antigen binding polypeptides comprise the following amino acid combinations in the heavy chain: at position 31R and at position 90Y; at position 53R and at position 90Y; and preferably have a Tm of at least 76° C. and have at least about 270% gain in binding AUC, compared to a parental antigen binding polypeptide. Even more preferably, the antigen binding polypeptides comprise the following amino acid combinations in the heavy chain: at position 54K and at position 90Y and have a Tm of at least 75° C. and have at least about 240% gain in binding AUC, compared to a parental antigen binding polypeptide.

In one embodiment the antigen binding polypeptides comprise the following preferred amino acid combinations in the heavy chain and in the light chain: in the heavy chain at position 31R, at position 90Y in VH and in the light chain at position 56R; in the heavy chain at position 53R, at position 90Y and in the light chain at position 56R; and in the heavy chain at position 54K, at position 90Y and in the light chain at position 56R, and have a Tm of at least 75° C. and have at least about 245% gain in binding AUC, compared to a parental antigen binding polypeptide. More preferably, the antigen binding polypeptides comprise the following preferred amino acid combinations in the heavy chain and in the light chain: in the heavy chain at position 31R, at position 90Y and in the light chain at position 56R; in the heavy chain at position 53R, at position 90Y and in the light chain at position 56R; and have a Tm of at least 76° C. and have at least about 400% gain in binding AUC, compared to a parental antigen binding polypeptide. It is particularly preferred that the antigen binding polypeptide comprises the following preferred amino acid combinations in the heavy chain and in the light chain: in the heavy chain at position 53R, at position 90Y and in the heavy chain at position 56R; and have a Tm of at least 76° C. and have at least about 800% gain in binding AUC, compared to a parental antigen binding polypeptide.

In one embodiment of the first aspect of the present invention, the antigen binding polypeptide is an antibody or a fragment thereof. Preferably, the antigen binding polypeptide is a bispecific antibody or fragment thereof. More preferably, the antigen binding polypeptide is a bispecific antibody further comprising a TCR or a fragment thereof.

In one embodiment of the first aspect of the present invention the antigen binding polypeptide comprises a VH and a VL forming a first binding site as previously described and further comprises a second binding site. Preferably, said second binding site specifically binds to a cell surface protein. Preferred cell surface proteins are selected from the group consisting of glycoprotein, MHC class I proteins, MHC class II proteins; β-microglobulin, immunoglobulins such as IgA, IgD, IgE, IgG, IgM, TCRs, co-receptor molecules such as CD4 or CD8. In a preferred embodiment the cell surface protein is a surface protein of a cancer cell. Preferably, the second binding site of the antigen binding polypeptide specifically binds to a MHC-peptide complex. More preferably the MHC molecule is an MHC I molecule in complex with a peptide, wherein preferably the MHC I molecule is a human leukocyte antigen (HLA) molecule in complex with a peptide. Even more preferably, the second binding site of the antigen binding polypeptide specifically binds to a HLA peptide complex of a cancer cell, preferably wherein the HLA is HLA-A*02.

In one embodiment the second antigen binding site of the antigen binding polypeptide of the first aspect of the invention is, for example, comprised in or formed by an antibody, a TCR, a scaffold protein, or an antibody mimetica, such as designed ankyrin repeat proteins (DARPins), knottins, anticalins, fynomers or affibodies. Preferably, the second antigen binding site is comprised in a TCR or fragment thereof.

In one embodiment the second antigen binding site of the antigen binding polypeptide comprises at least the variable region of an α ($V_\alpha$) and/or β ($V_\beta$) chain of a TCR; or a γ ($V_\gamma$) and/or δ ($V_\delta$) chain of a TCR or the VL and/or the VH of a further antibody. Preferably, the second binding site of the antigen binding polypeptide comprises at least the $V_\alpha$ and/or $V_\beta$ or $V_\gamma$ and/or $V_\delta$ of a TCR. The $V_\alpha$ and $V_\beta$ or $V_\gamma$ and $V_\delta$ of the second antigen binding site can be on two separate polypeptide chains. The $V_\alpha$ and $V_\beta$ or $V_\gamma$ and $V_\delta$ of the second antigen binding site can be on the same polypeptide chain. Preferably, the Vα and $V_\beta$ or $V_\gamma$ and $V_\delta$ of the second antigen binding site are on two separate polypeptide chains. Preferably, the antigen binding polypeptide further comprises a constant domain.

In context of this invention, the $V_\alpha$ and the $V_\beta$ or the ($V_\gamma$ or the $V_\delta$) preferably bind to a tumor-associated antigen (TAA)/MHC complex. Vα and Vβ or Vγ or Vγ that may be comprised in the antigen binding polypeptide of the present invention are described in detail in, for example, WO2018172533, WO2018033291, WO2017158103, WO2018104438, WO2018104478, WO2019002444, WO2017158116, U.S. Pat. Nos. 10,800,845, 10,537,624, 10,538,573, 10,537,624, 10,590,194, 10,800,832, and 10,527,623, the contents of which are each hereby incorporated by references in their entireties.

Accordingly, in one embodiment, the Vα and Vβ or Vγ and Vδ comprise or consist of the amino acid sequence disclosed in WO2018172533, WO2018033291, WO2017158103, WO2018104438, WO2018104478, WO2019002444, WO2017158116 U.S. Pat. Nos. 10,800, 845, 10,537,624, 10,538,573, 10,537,624, 10,590,194, 10,800,832, and 10,527,623 and the Vα and Vβ or Vγ and Vδ described in the cited prior art bind to the TAA peptide, that is disclosed in the same patent applications as cited. The contents of which are each hereby incorporated by references in their entireties.

In an aspect, tumor associated antigen (TAA) peptides that are capable of use with the methods and embodiments described herein include, for example, those TAA peptides described in U.S. Publication 20160187351, U.S. Publication 20170165335, U.S. Publication 20170035807, U.S. Publication 20160280759, U.S. Publication 20160287687, U.S. Publication 20160346371, U.S. Publication 20160368965, U.S. Publication 20170022251, U.S. Publication 20170002055, U.S. Publication 20170029486, U.S. Publication 20170037089, U.S. Publication 20170136108, U.S. Publication 20170101473, U.S. Publication 20170096461, U.S. Publication 20170165337, U.S. Publication 20170189505, U.S. Publication 20170173132, U.S. Publication 20170296640, U.S. Publication 20170253633, U.S. Publication 20170260249, U.S. Publication 20180051080, U.S. Publication No. 20180164315, U.S. Publication 20180291082, U.S. Publication 20180291083, U.S. Publication 20190255110, U.S. Pat. Nos. 9,717,774, 9,895,415, U.S. Publication 20190247433, U.S. Publication 20190292520, U.S. Publication 20200085930, U.S. Pat. Nos. 10,336,809, 10,131,703, 10,081,664, 10,081,664, 10,093,715, 10,583,573, and US20200085930, the contents of each of these publications, sequences, and sequence listings described therein are herein incorporated by reference in their entireties.

In context of the invention, the VL and/or the VH of a further antibody preferably bind to a protein present on the surface of a tumor.

In one embodiment the VH and VL of the antigen binding polypeptide are of an antibody. In one embodiment the first antigen binding site comprises a VH and VL on two separate polypeptide chains. In one embodiment the first antigen binding site comprises a VH and VL on the same polypeptide chain. Preferably, the VH and VL comprised in the first antigen binding site are on two separate polypeptide chains unless the antigen binding polypeptide is a single chain polypeptide.

In one embodiment the at least one amino acid that is substituted with the positively charged amino acid of the antigen binding polypeptide is in SEQ ID NO: 52 (HCDR1). In one embodiment the at least one amino acid that is substituted with the positively charged amino acid of the antigen binding polypeptide is in SEQ ID NO: 52 (HCDR1) and SEQ ID NO: 53 (HCDR1 and HCDR2). In one embodiment the at least one amino acid that is substituted with the positively charged amino acid of the antigen binding polypeptide is in SEQ ID NO: 52 and SEQ ID NO:3 (HCDR1 and LCDR1). In one embodiment the at least one amino acid that is substituted with the positively charged amino acid of the antigen binding polypeptide is in SEQ ID NO: 52 and SEQ ID NO: 55 (HCDR1 and LCDR2). In one embodiment the at least one amino acid that is substituted with the positively charged amino acid of the antigen binding polypeptide is in SEQ ID NO: 52 and SEQ ID NO:3 and SEQ ID NO: 55 (HCDR1, LCDR1 and LCDR2). In one embodiment the at least one amino acid that is substituted with the positively charged amino acid of the antigen binding polypeptide is in SEQ ID NO: 52 and SEQ ID NO: 53 and SEQ ID NO: 54 (HCDR1, HCDR2 and LCDR1). In one embodiment the at least one amino acid that is substituted with the positively charged amino acid of the antigen binding polypeptide is in SEQ ID NO: 52 and SEQ ID NO: 53 and SEQ ID NO: 55 (HCDR1, HCDR2 and LCDR2). In one embodiment the at least one amino acid that is substituted with the positively charged amino acid of the antigen binding polypeptide is in SEQ ID NO: 52 and SEQ ID NO: 53 and SEQ ID NO: 54 and SEQ ID NO: 55 (HCDR1, HCDR2, LCDR1 and LCDR2). In one embodiment the at least one amino acid that is substituted with the positively charged amino acid of the antigen binding polypeptide is in SEQ ID NO: 53 and SEQ ID NO: 54 (HCDR2 and LCDR1). In one embodiment the at least one amino acid that is substituted with the positively charged amino acid of the antigen binding polypeptide is in in SEQ ID NO: 53 and SEQ ID NO: 55 (HCDR2 and LCDR2). In one embodiment the at least one amino acid that is substituted with the positively charged amino acid of the antigen binding polypeptide is in SEQ ID NO: 53 and SEQ ID NO: 54 and SEQ ID NO: 55 (HCDR2 and LCDR1 and LCDR2). In one embodiment the at least one amino acid that is substituted with the positively charged amino acid of the antigen binding polypeptide is in SEQ ID NO: 54. In one embodiment the at least one amino acid that is substituted with the positively charged amino acid of the antigen binding polypeptide is in SEQ ID NO: 54 and SEQ ID NO: 53 (LCDR1 and HCDR2). In one embodiment the at least one amino acid that is substituted with the positively charged amino acid of the antigen binding polypeptide in SEQ ID NO: 54 and SEQ ID NO: 55 (LCDR1 and LCDR2). In one embodiment the at least one amino acid that is substituted with the positively charged amino acid of the antigen binding polypeptide is in SEQ ID NO: 55 (LCDR2). Preferably, the at least one amino acid that is substituted with the positively charged amino acid of the antigen binding polypeptide is in SEQ ID NO: 55 (LCDR2), SEQ ID NO: 53 (HCDR2) or SEQ ID NO: 52 (HCDR1). More preferably, the at least one amino acid that is substituted with the positively charged amino acid of the antigen binding polypeptide is in SEQ ID NO: 52 (HCDR1) and SEQ ID NO: 55 (LCDR2). It is particularly preferred that the at least one amino acid that is substituted with the positively charged amino acid of the antigen binding polypeptide is in SEQ ID NO: 53 (HCDR2) and SEQ ID NO: 55 (LCDR2).

In one embodiment the antigen binding polypeptide comprises serine (S) or asparagine (N) at position 30 in the HFR1 of the antigen binding polypeptide. It is further preferred that the positively charged amino acid in the heavy chain of the antigen binding polypeptide at position 53 is R or K and that serine is at position 30 in HFR1 of the antigen binding polypeptide. It is further also preferred that the positively charged amino acid in the heavy chain of the antigen binding polypeptide at position 53 is R and that serine is at position 30 in HFR1 of the antigen binding polypeptide.

In one embodiment the antigen binding polypeptide comprises serine (S) or asparagine (N) at position 30 in HFR1 of the antigen binding polypeptide.

In one embodiment threonine (T) at position 30 in HFR1 of the antigen binding polypeptide is substituted with asparagine (N) or serine (S). In one embodiment S at position 31 in HFR1 of the antigen binding polypeptide is substituted with asparagine (N). In one embodiment valine (V) at position 56 in the heavy chain of the antigen binding polypeptide is substituted with isoleucine (I). In one embodiment glutamic acid (E) at position 100a in the heavy chain of the antigen binding polypeptide is substituted with aspartic acid (D).

In one embodiment threonine (T) at position 30 in the heavy chain of the antigen binding polypeptide is substituted with asparagine (N) or serine (S). In one embodiment S at position 31 in the heavy chain of the antigen binding polypeptide is substituted with asparagine (N). In one embodiment valine (V) at position 56 in the heavy chain of the antigen binding polypeptide is substituted with isoleucine (I). In one embodiment glutamic acid (E) at position 100a in the heavy chain of the antigen binding polypeptide is substituted with aspartic acid (D). In one embodiment S at position 31 in the light chain of the antigen binding polypeptide is substituted with N. In one embodiment S at position 93 in the light chain is substituted with N. In one embodiment S at position 31 and position 93 in the light chain are both substituted with N. In one embodiment T at position 30 in the heavy chain of the antigen binding polypeptide is substituted with N or S, S at position 31 in the heavy chain of the antigen binding polypeptide is substituted with N, V at position 56 in the heavy chain of the antigen binding polypeptide is substituted with I, E at position 100a in the heavy chain of the antigen binding polypeptide is substituted with D, and S at position 31 in the light chain of the antigen binding polypeptide is substituted with N. In one embodiment T at position 30 in the heavy chain of the antigen binding polypeptide is substituted with N or S, S at position 31 in the heavy chain of the antigen binding polypeptide is substituted with N, V at position 56 in the heavy chain of the antigen binding polypeptide is substituted with I, E at position 100a in the heavy chain of the antigen binding polypeptide is substituted with D, and S at position 93 in the light chain of the antigen binding polypeptide is substituted with N. In one embodiment T at position 30 in the heavy chain of the antigen binding polypeptide is substituted with N or S, S at position 31 in the heavy chain of the antigen binding polypeptide is substituted with N, V at position 56 in the heavy chain of the antigen binding polypeptide is substituted with I, E at position 100a in the heavy chain of the antigen binding polypeptide is substituted with D, and S at position 31 and 93 in the light chain of the antigen binding polypeptide is substituted with N.

In one embodiment the antigen binding polypeptide comprises further modifications in the heavy chain CDR3 (HCDR3). In one embodiment said modification is a substitution with a negatively charged amino acid, such as E or D. Preferably, amino acid at position 100 of HCDR3 is substituted. Particularly preferred is that position 100a is substituted with E or D. In one embodiment the antigen binding polypeptide comprises further modifications in the light chain CDR3 (LCDR3). In one embodiment, said modification is a substitution with a polar amino acid selected from the group consisting of R, H, K, D, E, N, Q, S, T, Y. Preferably, amino acid position 93 of LCDR3 is substituted. Particularly preferred is that position 93 is N or S. In one embodiment the antigen binding polypeptide comprises further modifications in the heavy chain HCDR3 and in the LCDR3. In one embodiment the antigen binding polypeptide comprises a substitution with a negatively charged amino acid in HCDR3 and a substitution with a polar amino acid in LCDR3. Preferably, position 100a in HCDR3 is substituted with a negatively charged amino acid and position 93 in LCDR3 is substituted with a polar amino acid. Even more preferably, position 100a in HCDR3 is substituted with E and position 93 in LCDR3 and is substituted with a polar amino acid S; position 100a in HCDR3 is substituted with E and position 93 in LCDR3 and is substituted with a polar amino acid N; position 100a in HCDR3 is substituted with D and position 93 in LCDR3 and is substituted with a polar amino acid S; position 100a in HCDR3 is substituted with D and position 93 in LCDR3 is substituted with a polar amino acid N.

In one embodiment the HCDR3 of the antigen binding polypeptide has the sequence GSYYDYX$_1$GFVY (SEQ ID NO: 56), wherein X$_1$ is D or E. Preferably, X$_1$ is E (GSYYDYEGFVY SEQ ID NO: 64). In one embodiment the LCDR3 of the antigen binding polypeptide has the sequence QQWSX$_1$X$_2$X$_3$LT (SEQ ID NO: 57), wherein X$_1$ is S or N, X$_2$ is an amino acid selected from the group consisting of Q, D, H, S, Y, A and N; and X$_3$ is P or A. Preferably, the LCDR3 of the antigen binding polypeptide has the sequence QQWSSX$_2$X$_3$LT (SEQ ID NO: 65). Preferably, the LCDR3 of the antigen binding polypeptide has the sequence QQWSX$_1$NX$_3$LT (SEQ ID NO:66), wherein X$_2$ is N. Preferably, the LCDR3 of the antigen binding polypeptide has the sequence QQWSX$_1$X$_2$PLT (SEQ ID NO: 67). In one embodiment the LCDR3 of the antigen binding polypeptide has the sequence QQWSSQPLT (SEQ ID NO: 68). In one embodiment the LCDR3 of the antigen binding polypeptide has the sequence QQWSSDPLT (SEQ ID NO: 69). In one embodiment the LCDR3 of the antigen binding polypeptide has the sequence QQWSSHPLT (SEQ ID NO: 70). In one embodiment the LCDR3 of the antigen binding polypeptide has the sequence QQWSSSPLT (SEQ ID NO: 71). In one embodiment the LCDR3 of the antigen binding polypeptide has the sequence QQWSSYPLT (SEQ ID NO: 72). In one embodiment the LCDR3 of the antigen binding polypeptide has the sequence QQWSSAPLT (SEQ ID NO: 73). In a particularly preferred embodiment the LCDR3 of the antigen binding polypeptide has the sequence QQWSSNPLT (SEQ ID NO: 74).

In one embodiment the LCDR3 of the antigen binding polypeptide has the sequence QQWSSQALT (SEQ ID NO: 75). In one embodiment the LCDR3 of the antigen binding polypeptide has the sequence QQWSSDALT (SEQ ID NO: 76). In one embodiment the LCDR3 of the antigen binding polypeptide has the sequence QQWSSHALT (SEQ ID NO: 77). In one embodiment the LCDR3 of the antigen binding polypeptide has the sequence QQWSSSALT (SEQ ID NO: 78). In one embodiment the LCDR3 of the antigen binding polypeptide has the sequence QQWSSYALT (SEQ ID NO: 79). In one embodiment the LCDR3 of the antigen binding polypeptide has the sequence QQWSSAALT (SEQ ID NO: 80). In one embodiment the LCDR3 of the antigen binding polypeptide has the sequence QQWSSNALT (SEQ ID NO: 81).

In one embodiment the LCDR3 of the antigen binding polypeptide has the sequence QQWSNQPLT (SEQ ID NO: 82). In one embodiment the LCDR3 of the antigen binding polypeptide has the sequence QQWSNDPLT (SEQ ID NO: 83). In one embodiment the LCDR3 of the antigen binding polypeptide has the sequence QQWSNHPLT (SEQ ID NO: 84). In one embodiment the LCDR3 of the antigen binding polypeptide has the sequence QQWSNSPLT (SEQ ID NO: 85). In one embodiment the LCDR3 of the antigen binding polypeptide has the sequence QQWSNYPLT (SEQ ID NO: 86). In one embodiment the LCDR3 of the antigen binding polypeptide has the sequence QQWSNAPLT (SEQ ID NO: 87). In one embodiment the LCDR3 of the antigen binding polypeptide has the sequence QQWSNNPLT (SEQ ID NO: 88).

In one embodiment the LCDR3 of the antigen binding polypeptide has the sequence QQWSNQALT (SEQ ID NO: 89). In one embodiment the LCDR3 of the antigen binding polypeptide has the sequence QQWSNDALT (SEQ ID NO: 90). In one embodiment the LCDR3 of the antigen binding polypeptide has the sequence QQWSNHALT (SEQ ID NO: 91). In one embodiment the LCDR3 of the antigen binding polypeptide has the sequence QQWSNSALT (SEQ ID NO: 92). In one embodiment the LCDR3 of the antigen binding polypeptide has the sequence QQWSNYALT (SEQ ID NO: 93). In one embodiment the LCDR3 of the antigen binding polypeptide has the sequence QQWSNAALT (SEQ ID NO: 94). In one embodiment the LCDR3 of the antigen binding polypeptide has the sequence QQWSNNALT (SEQ ID NO: 95). Preferably, the LCDR3 of the antigen binding polypeptide has the sequence QQWSX$_1$NPLT (SEQ ID NO: 96), wherein X$_a$ is S or N. Even more preferably, X$_1$ is S.

In one embodiment the antigen binding polypeptide comprises or consists of a HFR1, HFR2 and HFR3 as comprised in the VH set forth in SEQ ID NO: 1 (BMA031 V36_VH), SEQ ID NO: 97 (GL1_BM_VH28_HV), SEQ ID NO: 98 (GL1_BM_VH31_HV), SEQ ID NO: 99 (HEBE1_H10_HV), SEQ ID NO: 100 (HEBE1_H66_HV), and SEQ ID NO: 101 (HEBE1_H71_HV). Preferably, the HFR1, HFR2 and HFR3 are comprised in the VH set forth in SEQ ID NO: 1 (BMA031 V36_VH). In preferred embodiments of the antigen binding polypeptide of the invention, in which position 30 in HFR1 and/or position 90 in HFR3 is substituted, this substitution is maintained although the remaining amino acids of the framework regions comprise or consist of the HFR1, HFR2 and HFR2 as set forth above.

In one embodiment the antigen binding polypeptide comprises or consists of LFR1, LFR2 and LFR3 as comprised in the VL set forth in SEQ ID NO: 2 (BMA031 V36_VL) or SEQ ID NO: 102 (GL1BMVK43_VL). Preferably the LFR1, LFR2, LFR3 and LFR4 are comprised in the VL set forth in SEQ ID NO: 2 (BMA031 V36_VL).

In one embodiment the antigen binding polypeptide comprises or consists of a HFR1, HFR2 and HFR3 as comprised in the VH set forth in SEQ ID NO: 1 (BMA031 V36_VH), SEQ ID NO: 97 (GL1_BM_VH28_HV), SEQ ID NO: 98 (GL1_BM_VH31_HV), SEQ ID NO: 99 (HEBE1_H10_HV), SEQ ID NO: 100 (HEBE1_H66_HV), and SEQ ID NO: 101 (HEBE1_H71_HV) and comprises or consists of LFR1, LFR2 and LFR3 as comprised in the VL set forth in SEQ ID NO: 2 (BMA031 V36_VL). In one embodiment the antigen binding polypeptide comprises or consists of a HFR1, HFR2 and HFR3 as comprised in the VH set forth in SEQ ID NO: 1 (BMA031 V36_VH), SEQ ID NO: 97 (GL1_BM_VH28_HV), SEQ ID NO: 98 (GL1_BM_VH31_HV), SEQ ID NO: 99 (HEBE1_H10_HV), SEQ ID NO: 100 (HEBE1_H66_HV), and SEQ ID NO: 101 (HEBE1_H71_HV) and comprises or consists of LFR1, LFR2 and LFR3 as comprised in the VL set forth in SEQ ID NO: 102 (GL1BMVK43_VL). Preferably, the antigen binding polypeptide comprises of a HFR1, HFR2 and HFR3 as comprised in the VH set forth in SEQ ID NO: 1 (BMA031 V36_VH) and comprises or consists of the LFR1, LFR2 and LFR3 as comprised in the VL set forth in SEQ ID NO: 2 (BMA031 V36_VL). In preferred embodiments of the antigen binding polypeptide of the invention, in which position 30 in HFR1 and/or position 90 is substituted, this substitution is maintained although the remaining amino acids of the framework regions comprise or consist of the HFR1, HFR2 and HFR2 as set forth above.

In one embodiment the antigen binding polypeptide further comprises or consists of a HFR4 as comprised in the VH set forth in SEQ ID NO: 1 (BMA031 V36_VH); or a LFR4 as comprised in the VL set forth in SEQ ID NO: 2 (BMA031 V36_VL). In a preferred embodiment the antigen binding polypeptide comprises or consists of a HFR1, HFR2, HFR3 and HFR4 as comprised in the VH set forth in SEQ ID NO: 1 (BMA031 V36_VH) and comprises or consists of the LFR1, LFR2, LFR3 and LFR4 as comprised in the VL set forth in SEQ ID NO: 2 (BMA031 V36_VL). In preferred embodiments of the antigen binding polypeptide of the invention, in which position 30 in HFR1 and/or position 90 is substituted, this substitution is maintained although the remaining amino acids of the framework regions comprise or consist of the HFR1, HFR2 and HFR2 as set forth above.

In further embodiments as described in more detail in the following the antigen binding polypeptides of the invention comprise of heavy chain framework regions (HFR) and/or light chain framework regions (LFR) or functional variants thereof as defined herein above. As defined above, the antigen binding polypeptide comprising the HFR or LFR sequences having a certain degree of sequence identity may also exert similar or higher functional properties, such as increased or improved binding $EC_{50}$ or Tm. In particular, the antigen binding polypeptide comprising the functional variants of HFR or LFR have an improved or increased binding EC50 of at least 2-fold and/or have an improved or increased Tm of at least 1° C. or a delta Tm of at least 1° C. as defined herein above. In one embodiment the antigen binding polypeptide comprises the HFR1 as set forth in SEQ ID NO 103 or a human HFR1 sequence having at least about 60% sequence identity with the HFR1 as set forth in SEQ ID NO: 103, the HFR2 as set forth in SEQ ID NO 104 or a human HFR2 sequence having at least about 75% sequence identity with SEQ ID NO: 104, the HFR3 as set forth in SEQ ID NO 105 or a human HFR3 sequence having at least about 55% sequence identity with SEQ ID NO: 105 and the HFR4 sequence as set forth in SEQ ID NO: 106 or a human HFR4 sequence having at least 90% sequence identity with SEQ ID NO: 106. In each of these cases the preferred amino acid substitutions in the HFRs outlined above are maintained, in particular at position 30 and/or 90. For instance, HFR1 of SEQ ID NO: 1 (BMA031 V36_VH) has a sequence identity of 63.33% to HFR1 of SEQ ID NO: 100 (HEBE1_H66_HV), or HFR2 of SEQ ID NO: 1 (BMA031 V36_VH) has a sequence identity of 78.6% to HFR2 of SEQ ID NO: 99 (HEBE1_H10_HV). Therefore, the framework regions as provided herein above and below are envisaged to be comprised in the antigen binding polypeptides herein provided.

In a preferred embodiment, the antigen binding polypeptide comprises the HFR1, HFR2, HFR3, and HFR4 according to SEQ ID NO: 103 to SEQ ID NO: 106 or a human HFR1, HFR2, HFR3, and HFR4 sequence having in each case at least 90% sequence with SEQ ID NO: 103 to SEQ ID NO: 106, respectively. In embodiments, wherein the antigen binding polypeptide comprises 90Y in the heavy chain, the herein above and below provided framework region of the antigen binding polypeptide comprises HFRs of the sequence identity defined and further comprises 90Y in the heavy chain.

In one embodiment the antigen binding polypeptide comprises a LFR1 as set forth in SEQ ID NO 107 or a human LFR1 sequence having at least about 50% sequence identity with SEQ ID NO: 107, the LFR2 as set forth in SEQ ID NO 108 or a human LFR2 sequence having at least about 80% sequence identity with SEQ ID NO: 108, the LFR3 sequence as set forth in SEQ ID NO: 109 or a human LFR3 sequence having at least about 80% sequence identity with SEQ ID NO: 109, and the LFR4 sequence as set forth in SEQ ID NO: 110 or a human LFR4 sequence having at least about 80% sequence identity with SEQ ID NO: 110. In a preferred embodiment, the antigen binding polypeptide comprises the LFR1, LFR2, LFR 3, and LFR4 according to SEQ ID NO: 107 to SEQ ID NO: 110 or a human LFR1, LFR2, LFR3 and LFR4 sequence having in each case at least 90% sequence with SEQ ID NO:107 to SEQ ID NO: 110, respectively.

It is preferred that HFR1-4 and LFR1-4 sequences having at least 50, 60, 70, 80, 90 or 95% sequence identity to the respectively indicated amino acid sequences according to SEQ ID NO: 103 to 110 are not modified at certain positions, for example positions of the Vernier zone, positions that contribute to the VH/VL inter-chain interface or at positions determining the CDR canonical class. In embodiments, wherein the antigen binding polypeptide comprises Y90 in the heavy chain, the antigen binding polypeptide comprising the herein above and below provided framework regions comprise the 90Y in the heavy chain. In embodiments, wherein the antigen binding polypeptide comprises a positively charged amino acid at position 30 in the heavy chain, the antigen binding polypeptide comprising the herein above and below provided framework regions comprise the positively charged amino acid at position 30 in the heavy chain. In all of the following embodiments the sequences of the HCDRs according to (i) of the first aspect of the invention and the sequences of the LCDRs according to (ii) are maintained.

In particular aspects, positions that are not modified in the VL are position 6, position 23, position 38, position 44, position 59, position 61, position 62, position 64, position 66, position 82, position 86, position 87, position 88, position 98, position 99, and/or position 101.

In particular aspects, positions that are not modified in the VH, are position 6, position 14, position 22, position 36, position 37, position 39, position 45, position 46, position 69, position 71, position 78, position 86, position 91, position 92, position 103, position 104 and position 106.

In one embodiment the antigen binding polypeptide comprises a VH domain having at least 80% sequence identity with SEQ ID NO: 1 and wherein the VH domain having at least 80% sequence identity comprises the amino acids 14P, 46E, 86D, 104G and 106G and comprises the inventive substitution(s), in particular the HCDR1, and/or HCDR2 as specified in (i) of the first aspect of the invention and/or the substitutions as specified in (iii) and/or (iv).

In one embodiment, preferably the antigen binding polypeptide comprises a VL domain having at least 80% sequence identity with SEQ ID NO: 2 and wherein the VL domain having at least 80% sequence identity to SEQ ID NO: 2 comprises the amino acids 59P, 61R, 62F, 82D, 99G, and 101G and comprises the inventive substitution(s), in particular the LCDR1, and/or LCDR2 as specified in (ii) of the first aspect of the invention.

In one embodiment the antigen binding polypeptide comprises a VH domain having at least 80% sequence identity with SEQ ID NO: 1 and wherein the VH domain having at least 80% sequence identity comprises the amino acids 14P, 46E, 86D, 104G and 106G and comprises the inventive substitution(s), in particular the HCDR1, and/or HCDR2 as specified in (i) of the first aspect of the invention and/or the substitutions as specified in (iii) and/or (iv); and a VL domain according to SEQ ID NO: 2 or a sequence having at least about 80% sequence identity with SEQ ID NO: 2 and wherein the VL domain having at least 80% sequence identity comprises the amino acids 59P, 61R, 62F, 82D, 8 99G and 101G and comprises the inventive substitution(s), in particular the LCDR1, and/or LCDR2 as specified in (ii) of the first aspect of the invention.

In one embodiment, preferably the antigen binding polypeptide comprises a VH domain having at least 80% sequence identity with SEQ ID NO: 1 and wherein the VH domain having at least 80% sequence identity comprises the amino acid: 6Q and 36W, and comprises the inventive substitution(s), in particular the HCDR1, and/or HCDR2 as specified in (i) of the first aspect of the invention and/or the substitutions as specified in (iii) and/or (iv).

In one embodiment, preferably the antigen binding polypeptide comprises a VL domain having at least 80% sequence identity with SEQ ID NO: 2 and wherein the VL domain having at least 80% sequence identity comprises the amino acids 6Q and 86Y, and the antigen binding polypeptide and comprises the inventive substitution(s), in particular the LCDR1, and/or LCDR2 as specified in (ii) of the first aspect of the invention.

In one embodiment, preferably the antigen binding polypeptide comprises a VH domain having at least 80% sequence identity with SEQ ID NO: 1 and wherein the VH domain having at least 80% sequence identity comprises the amino acid 6Q and 36W and the antigen binding polypeptide comprises the inventive substitution(s), in particular the HCDR1, and/or HCDR2 as specified in (i) of the first aspect of the invention and/or the substitutions as specified in (iii) and/or (iv).; and a VL domain having at least 80% sequence identity with SEQ ID NO: 2 and wherein the VL domain having at least 80% sequence identity comprises the amino acids 6Q and 86Y, and the antigen binding polypeptide comprises the inventive substitution(s), in particular the LCDR1, and/or LCDR2 as specified in (ii) of the first aspect of the invention.

In one embodiment, preferably the antigen binding polypeptide comprises a VH domain having at least 80% sequence identity with SEQ ID NO: 1 and wherein the VH domain having at least 80% sequence identity comprises the amino acids: 22C, 37V, 39Q, 45L, 69L, 71S, 78A, 91Y, 92C and 103W and the antigen binding polypeptide comprises the inventive substitution(s), in particular the HCDR1, and/or HCDR2 as specified in (i) of the first aspect of the invention and/or the substitutions as specified in (iii) and/or (iv).

In one embodiment, preferably the antigen binding polypeptide comprises a VL domain having at least 80% sequence identity with SEQ ID NO: 2 and wherein the VL domain having at least 80% sequence identity comprises the amino acids: C23, 38Q, 44P, 64G, 66G, 87Y, 88C and 98F and the antigen binding polypeptide comprises the inventive substitution(s), in particular the LCDR1, and/or LCDR2 as specified in (ii) of the first aspect of the invention.

In one embodiment, preferably the antigen binding polypeptide comprises a VH domain having at least 80% sequence identity with SEQ ID NO: 1 and wherein the VH domain having at least 80% sequence identity comprises the amino acids: 22C, 37V, 39Q, 45L, 69L, 71S, 78A, 91Y, 92C and 103W and the antigen binding polypeptide comprises the inventive substitution(s), in particular the HCDR1, and/or HCDR2 as specified in (i) of the first aspect of the invention and/or the substitutions as specified in (iii) and/or (iv); and a VL domain having at least 80% sequence identity with SEQ ID NO: 2 and wherein the VL domain having at least 80% sequence identity comprises the amino acids: 23C, 38Q, 44P, 64G, 66G, 87Y, 88C and 98F, and the antigen binding polypeptide comprises the inventive substitution(s), in particular the LCDR1, and/or LCDR2 as specified in (ii) of the first aspect of the invention.

In one embodiment, preferably the antigen binding polypeptide comprises a VH domain having at least 80% sequence identity with SEQ ID NO: 1 and wherein the VH domain having at least 80% sequence identity comprises the amino acids: 6Q, 14P, 22C, 36W, 37V, 39Q, 45L, 46E, 69L, 71S, 78A, 86D, 91Y, 92C, 103W, 104G, and 106G and the antigen binding polypeptide comprises the inventive substitution(s), in particular the HCDR1, and/or HCDR2 as specified in (i) of the first aspect of the invention and/or the substitutions as specified in (iii) and/or (iv).

In one embodiment, preferably the antigen binding polypeptide comprises a VL domain having at least 80% sequence identity with SEQ ID NO: 2 and wherein the VL domain having at least 80% sequence identity comprises the amino acids: 6Q, 23C, 38Q, 44P, 59P, 61R, 62F, 64G, 66G, 82D, 86Y, 88C, 98F, 99G, and 101G, and the antigen binding polypeptide comprises the inventive substitution(s), in particular the LCDR1, and/or LCDR2 as specified in (ii) of the first aspect of the invention.

In one embodiment, preferably the antigen binding polypeptide comprises a VH domain having at least 80% sequence identity with SEQ ID NO: 1 and wherein the VH domain having at least 80% sequence identity comprises the amino acids: 6Q, 14P, 22C, 36W, 37V, 39Q, 45L, 46E, 69L, 71S, 78A, 86D, 91Y, 92C, 103W, 104G, and 106G and the antigen binding polypeptide comprises the inventive substitution(s), in particular the HCDR1, and/or HCDR2 as specified in (i) of the first aspect of the invention and/or the substitutions as specified in (iii) and/or (iv).; and a VL domain having at least 80% sequence identity with SEQ ID NO: 2 and wherein the VL domain having at least 80% sequence identity comprises the amino acids: 6Q, 23C, 38Q, 44P, 59P, 61R, 62F, 64G, 66G, 82D, 86Y, 88C, 98F, 99G and 101G, and the antigen binding polypeptide comprises the inventive substitution(s), in particular the LCDR1, and/or LCDR2 as specified in (ii) of the first aspect of the invention In one embodiment the antigen binding polypeptide comprises a VH comprising the amino acid sequence selected from the group consisting of SEQ ID NO: 7 (VH H90Y); SEQ ID NO: 9 (VH_T30N_S31R), SEQ ID NO: 10 (VH_T30S_S31R_Y53R_E100aD), SEQ ID NO: 11 (VH S31R), SEQ ID NO: 12 (VH_T30S_Y53R), SEQ ID NO: 14 (VH N54K H90Y), SEQ ID NO: 15 (VH_T30N_S31N_Y53R), SEQ ID NO: 16 (VH_T30N_S31R_V56I), SEQ ID NO: 17 (VH_S31R_N54K_E100aD), SEQ ID NO: 19 (VH_T30R), SEQ ID NO: 20 (VH T30K); SEQ ID NO: 21 (VH S31K); SEQ ID NO: 22 (VH_Y53R), SEQ ID NO: 23 (VH_Y53K), SEQ ID NO: 24 (VH_N54R), SEQ ID NO: 25 (VH N54K), SEQ ID NO: 29 (VH_Y53H), SEQ ID NO: 30 (VH_S31H), SEQ ID NO: 31 (VH S31R H90Y), SEQ ID NO: 32 (VH Y53R H90Y), SEQ ID NO: 33 (VH N54R H90Y), and SEQ ID NO: 34 (VH_E61Q_H90Y) or a VH variant thereof comprising an amino acid sequence at least 85%, at least 90% or at least 95% identical to the amino acid sequence selected from the group consisting of SEQ ID NO: 7, 9, 10, 11, 12, 14, 15, 16, 17, 19, 20, 21, 22, 23, 24, 25, 29, 30, 31, 32, 33, and 34, respectively, wherein the VH variant retains the respective, inventive substitution(s) in comparison to the VH with a sequence according to SEQ ID NO: 1, and preferably comprise the HCDR1 to 3 of the sequences according to SEQ ID NO: 7, 9, 10, 11, 12, 14, 15, 16, 17, 19, 20, 21, 22, 23, 24, 25, 29, 30, 31, 32, 33, and 34, respectively. As used herein "retains the respective substitution(s)" means that the inventive substitution(s) as provided herein are maintained. Thus, in particular aspects, the antigen binding polypeptide that is identical with the provided % to the given SEQ ID NO retains the inventive substitution(s), e.g. (i) at one or more of the following positions of the heavy chain: 30, 31, 53, and 54; and/or (ii) at one or more of the following positions of the light chain: 31 and 56, and/or at position 90 of the heavy chain. In preferred aspects, the antigen binding polypeptide comprises a VH comprising the amino acid sequence selected from the group consisting of SEQ ID NO: 7, 9, 10, 11, 12, 14, 15, 16, 17, 19, 20, 21, 22, 23, 24, 25, 29, 30, 31, 32, 33, and 34. In particular aspects, the antigen binding polypeptide comprises a VH comprising the amino acid sequence of SEQ ID NO: 11 (VH S31R), or SEQ ID NO: 22 (VH_Y53R). In further preferred aspects, the antigen binding polypeptide may also be a functional fragment of the above provided VHs, wherein the functional fragment comprises the inventive substitution(s).

In one embodiment the antigen binding polypeptide comprises a VL comprising the amino acid sequence selected from the group consisting of SEQ ID NO: 8 (VL S31R S56R), SEQ ID NO: 13 (VL S31N S56R S93N), SEQ ID NO: 18 (VL S56R), SEQ ID NO: 26 (VL_S31R), SEQ ID NO: 27 (VL_S31K), and SEQ ID NO: 28 (VL_S56K) or a VL variant thereof comprising an amino acid sequence at least 85%, at least 90% or at least 95% identical to the amino acid sequence selected from the group consisting of SEQ ID NO: 8, 13, 18, 26, 27, and 28, respectively, wherein the VL variant retains the respective, inventive substitution(s) in comparison to the VL with a sequence according to SEQ ID NO: 2, and preferably comprise the LCDR1 to 3 of said sequences according to SEQ ID NOs: 8, 13, 18, 26, 27, and 28, respectively. As used herein "retains the respective substitution(s)" means that the inventive substitution(s) as provided herein are maintained. Thus, in particular aspects, the antigen binding polypeptide that is identical with the provided % to the given SEQ ID NO retains the inventive substitution(s), e.g. (i) at one or more of the following positions of the heavy chain: 30, 31, 53, and 54; and/or (ii) at one or more of the following positions of the light chain: 31 and 56, and/or at position 90 of the heavy chain. In preferred aspects, the antigen binding polypeptide comprises a VL comprising the amino acid sequence selected from the group consisting of SEQ ID NOs: 8, 13, 18, 26, 27, and 28. In further preferred aspects, the antigen binding polypeptide may also be functional fragment of the above provided VLs, wherein the functional fragment comprises the inventive substitution(s).

In the following, particular combinations of the herein provided VH and VL are set out. It is herein understood that the above provided VHs and VLs may be combined respectively.

In one embodiment the antigen binding polypeptide comprises a VH and VL comprising a sequence selected from the group consisting of: SEQ ID NO 7 and SEQ ID NO 8, SEQ ID NO 9 and SEQ ID NO 2, SEQ ID NO 10 and SEQ ID NO 2, SEQ ID NO 11 and SEQ ID NO 2, SEQ ID NO 12 and SEQ ID NO 2, SEQ ID NO 11 and SEQ ID NO 13, SEQ ID NO 14 and SEQ ID NO 2, SEQ ID NO 15 and SEQ ID NO 2, SEQ ID NO 16 and SEQ ID NO 2, SEQ ID NO 17 and SEQ ID NO 2, SEQ ID NO 1 and SEQ ID NO 18, SEQ ID NO 11 and SEQ ID NO 18, SEQ ID NO 11 and SEQ ID NO 8, SEQ ID NO 12 and SEQ ID NO 18, SEQ ID NO 12 and SEQ ID NO 8, SEQ ID NO 14 and SEQ ID NO 18, SEQ ID NO 14 and SEQ ID NO 8, SEQ ID NO 19 and SEQ ID NO 2, SEQ ID NO 20 and SEQ ID NO 2, SEQ ID NO 21 and SEQ ID NO 2, SEQ ID NO 22 and SEQ ID NO 2, SEQ ID NO 23 and SEQ ID NO 2, SEQ ID NO 24 and SEQ ID NO 2, SEQ ID NO 25 and SEQ ID NO 2, SEQ ID NO 1 and SEQ ID NO 26, SEQ ID NO 1 and SEQ ID NO 27, SEQ ID NO 1 and SEQ ID NO 28, SEQ ID NO 29 and SEQ ID NO 2, SEQ ID NO 30 and SEQ ID NO 2, SEQ ID NO 7 and SEQ ID NO 2, SEQ ID NO 31 and SEQ ID NO 2, SEQ ID NO 31 and SEQ ID NO 18, SEQ ID NO 32 and SEQ ID NO 2, SEQ ID NO 33 and SEQ ID NO 2, SEQ ID NO 32 and SEQ ID NO 18, SEQ ID NO 7 and SEQ ID NO 18.

In further preferred aspects, the antigen binding polypeptide may also be functional fragment(s) of the above provided VLs and VHs, wherein the functional fragment(s) comprises the inventive substitution(s).

Preferably, the antigen binding polypeptide comprises a VH and VL according to SEQ ID NO 11 and SEQ ID NO 2, SEQ ID NO 22 and SEQ ID NO 2, SEQ ID NO 14 and SEQ ID NO 2, SEQ ID NO 31 and SEQ ID NO 2, SEQ ID NO 32 and SEQ ID NO 2, SEQ ID NO: 32 and SEQ ID NO: 18 (VH_Y53R_H90Y and VL_S56R); SEQ ID NO: 14 and SEQ ID NO: 18 (VH_N54K_H90Y and VL_S56R) SEQ ID NO: 31 and SEQ ID NO: 18 (VH_S31R_H90Y and VL_S56R); or SEQ ID NO: 7 and SEQ ID NO: 2 (VH_H90Y and BMA031 (V36)_VL).

More preferably, the antigen binding polypeptide comprises a VH and VL according to SEQ ID NO 11 and SEQ ID NO 2, SEQ ID NO 22 and SEQ ID NO 2, SEQ ID NO: 32 and SEQ ID NO: 2; SEQ ID NO 14 and SEQ ID NO 2, or SEQ ID NO 31 and SEQ ID NO 2.

As disclosed herein above and below, the invention preferably relates to the antigen binding polypeptide, wherein the VH comprises the amino acid sequence of SEQ ID NO: 32 (VH Y53R H90Y) or a VH variant thereof comprising an amino acid sequence at least 85%, at least 90% or at least 95% identical to the amino acid sequence of SEQ ID NO: 32, wherein the VH variant retains the respective substitutions (Y53 and H90Y or corresponding amino acid substitutions) in comparison to the VH with a sequence according to SEQ ID NO: 1 and wherein the VL comprises the VL of an antibody binding to the α/β TCR/CD3 complex (as defined herein), in particular wherein the VL comprises the amino acid sequence of SEQ ID NO: 2.

In further preferred aspects, the antigen binding polypeptide may also be functional fragments of the above defined VHs and VLs, wherein the functional fragments comprise the inventive substitution(s). In one embodiment the antigen binding polypeptide comprises further modifications, e.g. further substitution(s) of amino acid(s) within the same category of amino acids in the CDRs. Further modifications may be the substitution of a polar uncharged amino acid with another polar uncharged amino acid; the substitution of a negatively charged amino acid with another negatively charged amino acid; and/or the substitution of a hydrophobic amino acid with another hydrophobic amino acid. Further modifications may also be the substitution of a polar uncharged amino acid with another polar uncharged amino acid; the substitution of a negatively charged amino acid with another negatively charged amino acid; and the substitution of a hydrophobic amino acid with another hydrophobic amino acid.

In one embodiment position 31 in the heavy chain and position 56 in the light chain are substituted with the positively charged amino acid, preferably wherein position 31 in the heavy chain is substituted with R and position 56 in the light chain is substituted with R.

In one embodiment position 31 in the heavy chain according to SEQ ID NO: 1 and position 56 in the light chain are substituted with the positively charged amino acid and position 90 in the heavy chain is Y, preferably position 31 in the heavy chain is substituted with R, and position 56 in the light chain is substituted with R, and position 90 in the heavy chain is Y.

In one embodiment position 31 in the heavy chain is substituted with the positively charged amino acid and position 90 in the heavy chain is Y, preferably position 31 in the heavy chain is substituted with R, and position 90 in the heavy chain is Y.

In one embodiment position 53 in the heavy chain and position 56 in the light chain are substituted with the positively charged amino acid, preferably position 53 in the heavy chain is substituted with R and position 56 in the light chain is substituted with R.

In one embodiment position 53 in the heavy chain and position 56 in the light chain are substituted with the positively charged amino acid and position 90 in the heavy chain is Y, preferably position 53 in the heavy chain is substituted with R, position 90 in the heavy chain is Y and position 56 in the light chain is substituted with R.

In one embodiment position 54 in the heavy chain is substituted with the positively charged amino acid and position 90 in the heavy chain is Y, preferably position 54 in the heavy chain is substituted with R and position 90 in the heavy chain is Y.

In one embodiment position 90 in the heavy chain is Y and position 56 in the light chain is substituted with a positively charged amino acid, preferably position 90 in the heavy chain is Y and position 56 in the light chain is substituted with R.

In one embodiment position 56 in the light chain is substituted with a positively charged amino acid, preferably 56 in the light chain is substituted with R.

In one embodiment position 54 in the heavy chain and position 56 in the light chain are substituted with the positively charged amino acid, and wherein position 90 in the heavy chain is substituted with a hydrophobic amino acid, preferably position 54 in the heavy chain is substituted with K, position 56 in the light chain is substituted with R, and position 90 in the heavy chain is substituted with Y.

In one embodiment position 54 in the heavy chain and positions 31 and 56 in the light chain are substituted with the positively charged amino acid, and wherein position 90 in the heavy chain is substituted with a hydrophobic amino acid, preferably position 54 in the heavy chain is substituted with K, positions 31 and 56 in the light chain are substituted with R, and position 90 in the heavy chain is substituted with Y.

In one embodiment positions 31 and 53 in the heavy chain are substituted with the positively charged amino acid, preferably positions 31 and 53 in the heavy chain are substituted with R.

In one embodiment position 53 in the heavy chain and positions 31 and 56 in the light chain are substituted with the positively charged amino acid, preferably wherein position 53 in the heavy chain is substituted with R, positions 31 and 56 in the light chain are substituted with R.

In one embodiment position 31 in the heavy chain is substituted with the positively charged amino acid, preferably position 31 in the heavy chain is substituted with R.

In one embodiment position 31 in the heavy chain is substituted with the positively charged amino acid, preferably position 31 in the heavy chain is substituted with K.

In one embodiment position 30 in the heavy chain is substituted with the positively charged amino acid, preferably position 30 in the heavy chain is substituted with K.

In one embodiment position 56 in the light chain is substituted with the positively charged amino acid, preferably position 56 in the light chain is substituted with R.

In one embodiment position 56 in the light chain is substituted with the positively charged amino acid, preferably position 56 in the light chain is substituted with K.

In one embodiment position 54 in the heavy chain is substituted with the positively charged amino acid, preferably position 54 in the heavy chain is substituted with K.

In one embodiment position 54 in the heavy chain is substituted with the positively charged amino acid, and position 90 in the heavy chain is substituted with a hydrophobic amino acid, preferably position 54 in the heavy chain is substituted with K and position 90 in the heavy chain is substituted with Y.

In one embodiment positions 31 and 54 in the heavy chain are substituted with the positively charged amino acid, preferably wherein position 31 in the heavy chain is substituted with R and position 54 in the heavy chain is substituted with K.

In one embodiment position 53 in the heavy chain is substituted with the positively charged amino acid, preferably wherein position 53 in the heavy chain is substituted with R.

In one embodiment position 53 in the heavy chain is substituted with the positively charged amino acid and position 90 is Y, preferably wherein position 53 in the heavy chain is substituted with R and position 90 is Y.

In one embodiment position 31 in the heavy chain is substituted with the positively charged amino acid, preferably position 31 in the heavy chain is substituted with R.

In one embodiment position 31 in the heavy chain and positions 31 and 56 in the light chain are substituted with the positively charged amino acid, preferably wherein position 31 in the heavy chain is substituted with R, and positions 31 and 56 in the light chain are substituted with R.

In one embodiment position 53 in the heavy chain is substituted with the positively charged amino acid, preferably wherein position 53 in the heavy chain is substituted with R.

In one embodiment position positions 31 and 56 in the light chain are substituted with the positively charged amino acid, and wherein position 90 in the heavy chain is substituted with a hydrophobic amino acid, preferably wherein positions 31 and 56 in the light chain are substituted with R, and position 90 in the heavy chain is substituted with Y.

In one embodiment the VH and VL or Vα and Vβ are covalently or non-covalently linked together. Preferably, VH and VL or Vα and Vβ are covalently linked by a disulfide bond.

In one embodiment the antigen binding polypeptide further comprises one or more further antigen binding site. For example, if the antigen binding polypeptide comprise a first and a second binding site and further comprises a further binding site the antigen binding polypeptide may be trispecific molecule or trivalent etc. In one embodiment the antigen binding polypeptide may further comprise a transmembrane region. In one embodiment the antigen binding polypeptide may further comprise a transmembrane region optionally including a cytoplasmic signaling region. In one embodiment the antigen binding polypeptide may further comprise a a diagnostic agent. In one embodiment the antigen binding polypeptide may further comprise a therapeutic agent. In an embodiment the antigen binding polypeptide of the invention can be administered concurrently with, before, or after a variety of drugs and treatments widely employed in cancer treatment such as, for example, chemotherapeutic agents, non-chemotherapeutic, anti-neoplastic agents, and/or radiation, preferably chemotherapeutic agents. In one embodiment, such a therapeutic agent may be a growth inhibitory agent, such as a cytotoxic agent or a radioactive isotope.

In one embodiment the antigen binding polypeptides of the invention may be used in a bispecific format, in particular in bispecific TCER® molecules. It was surprisingly shown that bispecific molecules comprising an antigen binding polypeptide comprising a first binding site as defined above that is substituted with at least one positively charged amino acids at the respective positions in HCDR1 and/or HCDR2 and/or LCDR1 and/or LCDR2 and further comprising a second binding site which comprises, for example a TCR or fragments thereof, show improved effector functions in the bispecific format. As demonstrated in the Examples herein below, such bispecific molecules comprising a first and a second binding site as defined herein above show increased potency in T cell mediated killing of tumor cells (see Example 3 described below). It was thus, surprisingly shown that the antigen binding polypeptides described according to the first aspect of the invention above are also functional and show improvement in the bispecific format. It was also surprisingly shown, that the antigen binding polypeptides according to the first aspect of the invention as described above exert increased potency in T cell mediated tumor killing of peptide-HLA positive tumor cells and additionally, almost no cytotoxicity towards peptide-HLA negative tumor cell lines was detectable in the bispecific TCER® scaffold compared to the parental antigen binding polypeptide comprising the VHs of BMA031 (V36) in the TCER® format. The potency of said bispecific TCER® molecules is assessed by measurement of released LDH and EC50 values (functional EC50 as defined herein above). For example, the functional EC50 of the antigen binding polypeptide against Hs695T cells and U2OS cells is decreased compared to the parental antigen binding polypeptide comprising the VH and VL of BMA031 (V36) in the TCER® format.

In one embodiment the antigen binding polypeptide comprises a first and a second polypeptide chain that form the first and the second antigen binding site, wherein the first polypeptide chain has a structure represented by the formula:

$$V_1\text{-}L_1\text{-}V_2\text{-}L_2\text{-}D_1 \qquad [I]$$

wherein
$V_1$ is a first variable domain;
$V_2$ is a second variable domain;
$L_1$ and $L_2$ are linkers; $L_2$ is present or absent;
$D_1$ is a dimerization domain and is present or absent;
and wherein the second polypeptide chain has a structure represented by the formula:

$$V_3\text{-}L_3\text{-}V_4\text{-}L_4\text{-}D_2 \qquad [II]$$

wherein
$V_3$ is a third variable domain;
$V_4$ is a fourth variable domain;
$L_3$ and $L_4$ are linkers; $L_4$ is present or absent; and
$D_2$ is a dimerization domain and is present or absent;
wherein $D_1$ and $D_2$ specifically bind to each other, and wherein
one of $V_1$, $V_2$, $V_3$, $V_4$ is a $V_H$ as defined in context of the invention,
one of $V_1$, $V_2$, $V_3$, $V_4$ is a $V_L$ as defined in context of the invention, and
one of $V_1$, $V_2$, $V_3$, $V_4$ is a Vα or Vγ of a TCR, and
one of $V_1$, $V_2$, $V_3$, $V_4$ is a Vβ or Vδ of said TCR.

In one embodiment, $V_H$ and $V_L$ form the first binding site and Vα and Vβ or Vγ and Vδ form the second binding site.

In one embodiment, $V_1$ or $V_2$ is a $V_L$ as defined in context of the invention and $V_3$ or $V_4$ is a $V_H$ as defined in context of the invention, and $V_3$ or $V_4$ is a Vα or Vγ and $V_1$ or $V_2$ is a Vβ or Vδ of a TCR.

In one embodiment $V_1$ or $V_2$ is a $V_H$ as defined in context of the invention and $V_3$ or $V_4$ is a $V_L$ as defined in context of the invention, and $V_3$ or $V_4$ is a Vβ or Vδ and $V_1$ or $V_2$ is a Vα or Vγ of a TCR.

In one embodiment $V_1$ or $V_2$ is a $V_L$ as defined in context of the invention and $V_3$ or $V_4$ is a $V_H$ as defined in context of the invention, and $V_3$ or $V_4$ is a Vβ or Vδ and $V_1$ or $V_2$ is a Vα or Vγ of a TCR. In one embodiment $V_1$ or $V_2$ is a $V_H$ is as defined in context of the invention and $V_3$ or $V_4$ is a $V_L$ as defined in context of the invention, and $V_3$ or $V_4$ is a Vα or Vγ and $V_1$ or $V_2$ is a Vβ or Vδ of a TCR.

In one embodiment the antigen binding polypeptide comprises $V_1$ to $V_4$ as follows: $V_1$ is a $V_H$, $V_2$ is a Vβ or Vδ, $V_3$ is a Vα or Vγ, and $V_4$ is a $V_L$.

In one embodiment the antigen binding polypeptide comprises $V_1$ to $V_4$ as follows: $V_1$ is a Vβ or Vδ; $V_2$ is a $V_H$; $V_3$ is a $V_L$; and $V_4$ is a Vα or Vγ.

In one embodiment the antigen binding polypeptide comprises $V_1$ to $V_4$ as follows: $V_1$ is a Vβ or Vδ, $V_2$ is a $V_L$, $V_3$ is a $V_H$, and $V_4$ is a Vα or Vγ.

In one embodiment the antigen binding polypeptide comprises $V_1$ to $V_4$ as follows: $V_1$ is a $V_L$, $V_2$ is a Vβ or Vδ, $V_3$ is a Vα or Vγ, and $V_4$ is a $V_H$.

In one embodiment the antigen binding polypeptide comprises $V_1$ to $V_4$ as follows: $V_1$ is a $V_H$, $V_2$ is a $V_\beta$ or $V_\delta$, $V_3$ is a $V_L$, and $V_4$ is a $V_\alpha$ or $V_\gamma$.

In one embodiment the antigen binding polypeptide comprises $V_1$ to $V_4$ as follows: $V_1$ is a $V_\beta$ or $V_\delta$, $V_2$ is a $V_H$; $V_3$ is a $V_\alpha$ or $V_\gamma$, and $V_4$ is a $V_L$.

In one embodiment the antigen binding polypeptide comprises $V_1$ to $V_4$ as follows: $V_1$ is a $V_L$, $V_2$ is a $V_\beta$ or $V_\delta$; $V_3$ is a $V_H$, and $V_4$ is a $V_\alpha$ or $V_\gamma$.

In one embodiment the antigen binding polypeptide comprises $V_1$ to $V_4$ as follows: $V_1$ is a $V_\beta$ or $V_\delta$, $V_2$ is a $V_L$; $V_3$ is a $V_\alpha$ or $V_\gamma$, and $V_4$ is a $V_H$.

In one embodiment the antigen binding polypeptide comprises $V_1$ to $V_4$ as follows: $V_1$ is a $V_H$, $V_2$ is a $V_L$, and $V_3$ is a $V_\alpha$ or $V_\gamma$; $V_4$ is a $V_\beta$ or $V_\delta$.

In one embodiment the antigen binding polypeptide comprises $V_1$ to $V_4$ as follows: $V_1$ is a $V_L$; $V_2$ is a $V_H$; $V_3$ is a $V_\alpha$ or $V_\gamma$; and $V_4$ is a $V_\beta$ or $V_\delta$.

In one embodiment the antigen binding polypeptide comprises $V_1$ to $V_4$ as follows: $V_1$ is a $V_H$; $V_2$ is a $V_L$; $V_3$ is a $V_\beta$ or $V_\delta$; and $V_4$ is a $V_\alpha$ or $V_\gamma$.

In one embodiment the antigen binding polypeptide comprises $V_1$ to $V_4$ as follows: $V_1$ is a $V_L$; $V_2$ is a $V_H$; $V_3$ is a $V_\beta$ or $V_\delta$ and $V_4$ is a $V_\alpha$ or $V_\gamma$.

With respect to formula I and II, it is preferred that $V_H$ and $V_L$ are located on different polypeptide chains and $V\alpha$ or $V\gamma$ and $V\beta$ or $V\delta$ are located on different polypeptide chains, and that the dimerization domains D1, and D2, are heterodimerization domains. It is particularly preferred that in the antigen binding polypeptide $V_1$ is a $V_H$, $V_2$ is a $V_\beta$, $V_3$ is a $V_\alpha$, and $V_4$ is a $V_L$. In one embodiment, D1 and D2 of the antigen binding polypeptide are Fc domains, preferably a pair of Fc domains and preferably are different and comprise a mutation that forces heterodimerization, preferably a "knob-into-hole" mutation.

$L_1$, $L_2$, $L_3$, $L_4$ if present, can be 2-25, 2-20, or 3-18 amino acids long. In some embodiments, a linker, such as $L_1$, $L_2$, $L_3$, $L_4$ can be a peptide of a length of no more than 14, 13, 12, 11, 10, 9, 8, 7, 6, or 5 amino acids. In other embodiments, a linker, such as $L_1$, $L_2$, $L_3$, $L_4$ can be 5-25, 5-15, 4-11, 10-20, or 20-30 amino acids long.

In one embodiment L1 and/or L3 have a length of 5-15 amino acids, preferably 5-10 amino acids, more preferably 8 amino acids. In a preferred embodiment, L2 and L4 are absent and L1 and L3 are present and have a length of 5-10, preferably 8 amino acids. In one embodiment the antigen binding polypeptide according to the first aspect of the invention as described herein above may be used in any format as defined herein above, for example in a bispecific format, or a COVD format. Preferably, the antigen binding polypeptide is a bispecific molecule. Even more preferably, the antigen binding polypeptide is a bispecific TCER® molecule.

In one embodiment, the V1 being VH or VL and V2 being VH or VL, respectively, form the first binding site and comprise a VH and a VL such as comprised in the antigen binding polypeptide as defined in detail above and having at least one positively charged amino acid at the respective positions as defined above.

In one embodiment the bispecific molecules disclosed herein comprise the TCER® format as described herein and show increased cytotoxicity calculated as functional $EC_{50}$ as described herein above and preferably having a functional EC50 of less than 1000 pM, of less than 900 pM; of less than 800 pM; of less than 700 pM of less than 600 pM and in particular of less than 500 pM. Preferably, the bispecific molecule is a bispecific TCER® molecules as defined herein above and below and has a functional EC50 of less than 1000 pM, of less than 900 pM; of less than 800 pM; of less than 700 pM of less than 600 pM and in particular of less than 500 pM.

In a preferred embodiment, the antigen binding polypeptide refers to a bispecific antigen binding polypeptide and comprises a first and a second polypeptide chain that form the first and the second antigen binding site, wherein the first and the second polypeptide chain have a structure represented by the formula (I) and (II) as defined above and wherein the first polypeptide chain comprises a first binding site that specifically binds to the α/β TCR/CD3 complex and comprises a first variable domain (V1) and a second variable domain (V2) and wherein the first variable domain is a heavy chain variable domain (VH) and the second variable domain is a light chain variable domain (VL) as defined herein above; and wherein the second polypeptide chain comprises a second antigen binding site that comprises a third variable domain (V3) and a fourth variable domain (V4) and wherein the third variable domain comprises a variable alpha domain (Vα) and a variable beta domain (Vβ).

In a preferred embodiment the antigen binding polypeptide comprising the first polypeptide chain comprising a VH and a VL forming the first antigen binding site, and wherein the VH and VL comprise the HCDR and LCDRs having at least one positively charged amino acid as defined above in the context of the present invention and comprises a Vα and a Vβ forming the second binding site, and wherein the Vα and a Vβ comprise the VαCDR1-3 and Vβ CDR1-3 of a TCR. In a further preferred embodiment, the antigen binding polypeptide further comprises in the VH and VL forming the first antigen binding site in the VH HFR1-4 and in the VL LFR1-4 as defined herein above and in the Vα and the Vβ forming the second binding site FR1-4 of the Vα and FR1-4 of the Vβ.

In a preferred embodiment the antigen binding polypeptide comprising the first polypeptide chain comprising a VH and a VL forming the first antigen binding site, and wherein the VH and VL comprise the HCDR and LCDRs having at least one positively charged amino acid as defined above and tyrosine at position 90 in the VH and comprises a Vα and a Vβ forming the second binding site, and wherein the Vα and a Vβ comprise the VαCDR1-3 and Vβ CDR1-3 of a TCR. In a further preferred embodiment, the antigen binding polypeptide further comprises in the VH and VL forming the first antigen binding site in the VH HFR1-4 and in the VL LFR1-4 as defined herein above and in the Vα and the Vβ forming the second binding site FR1-4 of the Vα and FR1-4 of the Vβ.

In one embodiment, the antigen binding polypeptide comprising the first polypeptide chain of formula [I] further comprises at its C-terminus a linker (L2) and a dimerization domain (D1) or a portion thereof and/or comprising the second polypeptide chain of formula [II] further comprises at its C-terminus a linker (L4) and a dimerization domain (D2) or a portion thereof wherein D1 and D2 specifically bind to each other. Dimerization domains are defined herein above in the section 'definition'. Preferably, linker $L_1$ and $L_3$ have a length of 10-25 amino acids or 5-10 amino acids, more preferably 8 amino acids.In one embodiment, the first polypeptide chain of formula [I] further comprises at its C-terminus a linker (L2) and a Fc1 domain or a portion thereof and/or the second polypeptide chain of formula [II] further comprises at its C-terminus a linker (L4) and a Fc2 domain or a portion thereof. Fc-domain is as defined herein above in the section 'definition' and specifically bind to each other. Fc1 and Fc2 are different and specifically bind to each other and their sequences are, for example, as indicated herein below.

In one embodiment, the Fc-domain is a human IgG Fc domain, preferably derived from human IgG1, IgG2, IgG3 or IgG4, preferably IgG1 or IgG2, more preferably IgG1. In particular, when the bispecific antigen binding polypeptide comprises two Fc domains, i.e. in the TCER® format described herein above (such as Fc1 and Fc2), the two Fc domains may be of the same immunoglobulin isotype or isotype subclass or of different immunoglobulin isotype or isotype subclass, preferably of the same. Accordingly, in some embodiments Fc1 and Fc2, are of the IgG1 subclass, or of the IgG2 subclass, or of the IgG3 subclass, or of the IgG4 subclass, preferably of the IgG1 subclass, or of the IgG2 subclass, more preferably of the IgG1 subclass.

In some embodiments, the Fc domain comprises or further comprise the "RF" and/or "Knob-into-hole" mutation, preferably the "Knob-into-hole". It is preferred that Fc1 comprises or consists of SEQ ID NO: 124 (hole) and Fc2 comprises or consists of SEQ ID NO: 125 (knob).

In one embodiment the antigen binding polypeptide comprises a first polypeptide chain comprising formula [I] $V_1$-$L_1$-$V_2$-$L_2$-$D_1$ comprising or consisting of SEQ ID NO: 39; and comprising the second polypeptide chain comprising of formula I [II] $V_3$-$L_3$-$V_4$-$L_4$-$D_2$ comprising or consisting of SEQ ID NO: 35. In one embodiment the antigen binding polypeptide comprises a first polypeptide chain comprising formula [I] $V_1$-$L_1$-$V_2$-$L_2$-$D_1$ comprising or consisting of SEQ ID NO: 39; and comprising the second polypeptide chain comprising of formula I [II] $V_3$-$L_3$-$V_4$-$L_4$-$D_2$ comprising or consisting of SEQ ID NO: 38.

In one embodiment the antigen binding polypeptide comprises a first polypeptide chain comprising formula [I] $V_1$-$L_1$-$V_2$-$L_2$-$D_1$ comprising or consisting of SEQ ID NO: 39; and comprising the second polypeptide chain comprising of formula I [II] $V_3$-$L_3$-$V_4$-$L_4$-$D_2$ comprising or consisting of SEQ ID NO: 36. In this embodiment, the parental antigen binding polypeptide may comprise of a first polypeptide chain comprising or consisting of SEQ ID NO: 39; and may comprise of a second polypeptide chain comprising or consisting of SEQ ID NO: 37.

A second aspect of the invention further relates to an isolated nucleic acid or set of nucleic acids comprising a sequence coding for an antigen binding polypeptide of the first aspect of the invention, or a nucleic acid vector comprising said nucleic acid or set of nucleic acids. A set of nucleic acids may be used, if the antigen binding polypeptide of the invention comprises two or more polypeptide chains. Alternatively, two or more polypeptide chains may be encoded by one polycistronic nucleic acid sequence or may be encoded as a single polypeptide comprising cleavage sites that allow separation of the initial single polypeptide into two or more polypeptide chains.

In one embodiment an isolated nucleic acid comprises or consists of a sequence encoding for an antigen binding polypeptide of the invention. In one embodiment a nucleic acid vector comprises said nucleic acid comprising or consisting of a sequence encoding for an antigen binding polypeptide of the invention. Typically, said nucleic acid is a DNA or RNA molecule, which may be included in any suitable vector, such as a plasmid, cosmid, episome, artificial chromosome, phage or a viral vector.

A third aspect of the invention relates to a recombinant host cell comprising an antigen binding polypeptide of the first aspect of the invention, or a nucleic acid or a set of nucleic acids or a vector of the second aspect of the invention. Typically, such a host cell is transformed, transduced or transfected with a nucleic acid and/or a vector according to the second aspect of the invention. Host cells that receive and subsequently express foreign nucleic acids or vectors consisting of DNA or RNA by the process of transformation or transduction have been "transformed" or "transduced".

In one embodiment, cells may be transduced using the methods described in US20190216852, the content of which is hereby incorporated by reference in its entirety. In one embodiment the nucleic acids or set of nucleic acids according to the third aspect of the present invention may be used to produce a recombinant antigen binding polypeptide of the invention in a suitable expression system.

In one embodiment the host cell comprises the antigen binding polypeptide of the first aspect of the invention. Preferably, the host cell of the invention comprises a nucleic acid, or a vector as described above. The host cell can be a eukaryotic cell, e.g., mammalian cell (e.g. a human cell), yeast, plant, animal, fungi, or algae, or can be a prokaryotic cell, e.g., bacteria or protozoa. For purposes of producing an antigen binding polypeptide, such as an antigen binding polypeptide comprising a TCR or recombinant TCR or a bispecific antigen binding polypeptide, the host cell is preferably a mammalian cell, such as lymphocyte, preferably a T lymphocyte or T lymphocyte progenitor cell. Example of preferred host cells are CD4 or CD8 positive T cell. A preferred host cell for recombinant expression is a Chinese Hamster Ovary (CHO) cell. Suitable host cells for screening assays may be yeast cells.

In one embodiment, the host cell comprises the antigen binding polypeptide according to the first aspect of the invention, or the nucleic acid or set of nucleic acids, or the vector of the invention, wherein said host cell preferably is a lymphocyte, such as a T lymphocyte or T lymphocyte progenitor cell, preferably a CD4 or CD8 positive T cell. For the purpose of expression of the antigen binding polypeptides of the invention the expression vector may be either of a type in which a gene encoding the first antigen binding polypeptide, such as an antibody heavy chain or an alpha chain, and a gene encoding a second polypeptide, such as an antibody light chain or a beta chain, exists on separate vectors or of a type in which both genes exist on the same vector (tandem type).

A fourth aspect of the invention relates to a pharmaceutical composition comprising the antigen binding polypeptide of the first aspect of the invention, the nucleic acid or set of nucleic acids or vector of the second aspect of the invention or the host cell of the third aspect of the invention and a pharmaceutically acceptable carrier, diluent, stabilizer, and/or excipient.

In one embodiment the pharmaceutical composition comprises a therapeutically effective amount of an antigen binding polypeptide, the nucleic acid or set of nucleic acids or vector or the host cell of the invention. In one embodiment the pharmaceutical composition of the fourth aspect of the present invention contains a therapeutically effective amount of the active ingredient, preferably the antigen-binding polypeptide of the first aspect of the present invention, the nucleic acid or vector of the second aspect of the invention or the host cell of the third aspect of the invention, preferably in purified form, together with a suitable amount of carrier and/or excipient so as to provide the form for proper administration to the patient. In a further embodiment, the pharmaceutical composition comprises the antigen-binding polypeptide, or the nucleic acid or vector encoding the antigen binding polypeptide or the host cell expressing the antigen binding polypeptide and a pharmaceutically active composition. The formulation should suit the mode of administration. For intravenous administration, it is preferred that the carrier is an aqueous carrier. In one embodiment such an aqueous carrier is capable of imparting improved properties when combined with an antigen binding polypeptide of the invention, for example, improved solubility, efficacy, and/or improved immunotherapy.

In one embodiment the pharmaceutical composition may further comprise a therapeutic agent or pharmacologically active substance such as but not limited to adjuvants and/or additional active ingredients, in a pharmaceutically or physiologically acceptable formulation selected to be suitably administered according to the selected mode of administration.

In one embodiment the pharmaceutical compositions can take the form of solutions, suspensions, emulsion, tablets, pills, capsules, powders, sustained-release formulations and the like. For preparing pharmaceutical compositions of the present invention, pharmaceutically acceptable carriers can be either solid or liquid and are preferably liquid. Liquid form compositions include solutions, suspensions, and emulsions, for example, water, saline solutions, aqueous dextrose, glycerol solutions or water/propylene glycol solutions. For parenteral injections (e.g. intravenous, intraarterial, intraosseous infusion, intramuscular, subcutaneous, intraperitoneal, intradermal, and intrathecal injections), liquid preparations can be formulated in solution in, e.g. aqueous polyethylene glycol solution. A saline solution is a preferred carrier when the pharmaceutical composition is administered intravenously.

In one embodiment, the pharmaceutical composition is in a unit dosage form. In such form the composition may be subdivided into unit doses containing appropriate quantities of the active component. The unit dosage form can be a packaged composition, the package containing discrete quantities of the composition, such as packaged tablets, capsules, and powders in vials or ampoules. Also, the unit dosage form can be a capsule, an injection vial, a tablet, a cachet, or a lozenge itself, or it can be the appropriate number of any of these in packaged form. The pharmaceutical composition, if desired, can also contain minor amounts of wetting or emulsifying agents, or pH buffering agents.

The form of the pharmaceutical compositions, the route of administration, the dosage and the regimen naturally depend upon the condition to be treated, the severity of the illness, the age, weight, and gender of the patient, the desired duration of the treatment etc. This pharmaceutical composition may be in any suitable form depending on the desired method of administering it to a patient).

In one embodiment the pharmaceutical compositions of the fourth aspect of the invention contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts) or dry, especially freeze-dried compositions which upon addition, depending on the case, of sterilized water or physiological saline, permit the constitution of injectable solutions.

To prepare pharmaceutical compositions, an effective amount of the antigen binding polypeptide of the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the preparation of sterile injectable solutions or dispersions. In all cases, the form must be sterile and must be fluid to the extent that easy syringeability exists. It must be stable under the conditions of manufacture and storage and must be preserved against the contaminating action of microorganisms, such as bacteria and fungi. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In one embodiment the antigen binding polypeptide of the invention can be formulated into a pharmaceutical composition in a neutral or salt form using pharmaceutically acceptable salts.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

A fifth aspect of the invention relates to the antigen binding polypeptide of the first aspect of the invention, the nucleic acid or vector of the second aspect of the invention or the host cell of the third aspect of the invention or the pharmaceutical composition of the fourth aspect of the invention for use in medicine.

In one embodiment said antigen binding polypeptide, said nucleic acid or vector, said host cell or said pharmaceutical composition is for use in medicine.

A sixth aspect of the invention relates to the antigen binding polypeptide of the first aspect of the invention, the nucleic acid or vector of the second aspect of the invention or the host cell of the third aspect of the invention or the pharmaceutical composition of the fourth aspect of the invention for use in the diagnosis, prevention, and/or treatment of a proliferative disease, preferably cancer, or a tumor or tumorous disease and/or disorder.

In one embodiment said antigen binding polypeptide, said nucleic acid or vector, said host cell or said pharmaceutical composition is for use in the diagnosis, prevention, and/or treatment of a proliferative disease. Preferably, the proliferative disease to be diagnosed, prevented and/or treated is cancer.

In one embodiment the antigen binding polypeptide of the first aspect of the invention, the nucleic acid or vector of the second aspect of the invention or the host cell of the third aspect of the invention or the pharmaceutical composition of the fourth aspect of the invention is for use in inhibiting tumor growth or treating cancer.

In one embodiment, the present disclosure may include methods of treating a patient who has cancer that presents a peptide consisting of an amino acid sequence described herein or incorporated by reference herein in a complex with an MHC protein, comprising administering to the patient a composition comprising an antigen binding protein described herein.

In one embodiment, the present disclosure may include methods of eliciting an immune response in a patient who has cancer that presents a peptide consisting of an amino acid sequence of described herein in a complex with an MHC protein, comprising administering to the patient a composition comprising an antigen binding protein described herein.

A seventh aspect of the invention relates to a method for improving the stability and/or the binding of the antigen binding polypeptide, wherein the herein provided substitutions are introduced into the antigen binding polypeptide. In particular, the method comprises introducing positively charged amino acids into the HCDRs and/or the LCDRs and/or introducing tyrosine at position 90 in the heavy chain according to Kabat numbering. In particular, the method comprises:
 (i) substituting at least one amino acid of HCDR1 comprising the amino acid sequence of SEQ ID NO: 52 and/or at least one amino acid of HCDR2 comprising the amino acid sequence of SEQ ID NO: 53 that is not positively charged with a positively charged amino acid; and/or
 (ii) substituting at least one amino acid of LCDR1 comprising the amino acid of SEQ ID NO: 54 and/or at least one amino acid of LCDR2 comprising the amino acid sequence of SEQ ID NO: 55 that is not positively charged with a positively charged amino acid; and/or
 (iii) substituting position 30 in HFR1 according to Kabat numbering with a positively charged amino acid, and/or
 (iv) substituting position 90 in HFR3 according to Kabat numbering with a tyrosine (Y),
 wherein
 (1) the binding of the antigen binding polypeptide to an α/β T cell receptor (TCR)/CD3 complex is increased compared to the parental antigen binding polypeptide;
 (2) the binding of the antigen binding polypeptide to an α/β T cell receptor (TCR)/CD3 complex is maintained or increased and the stability of the antigen binding polypeptide is increased compared to the parental antigen binding polypeptide; or
 (3) the stability of the antigen binding polypeptide is increased compared to the parental antigen binding polypeptide.

In particular, the position(s) of the antigen binding polypeptide is/are substituted as herein provided above and below as well as shown in the appended examples. Preferably, the method comprises the substitution by the positively charged amino acid
 in the heavy chain:
 (i) at position 30,
 (ii) at position 31;
 (iii) at position 53;
 (iv) at position 54; and/or
 in the light chain:
 (i) at position 31; and/or
 (ii) at position 56.

In particular, the method comprises the substitution of histidine at position 90 by tyrosine in the heavy chain. The substitution of histidine at position 90 by tyrosine in the heavy chain may be combined with further substitutions in the heavy chain and/or light chain as herein provided below and above.

In one embodiment the method provides antigen binding polypeptides that have an increased binding, preferably measured by assessing binding as herein described above and below, compared to the parental antigen binding polypeptide not comprising the inventive substitutions, e.g. SEQ ID NO: 1 (BMA031 (V36) VH) and SEQ ID NO: 2 (BMA031 (V36) VL). The effects herein disclosed above in the context of the antigen binding polypeptides do also apply for the herein provided method. In one embodiment the method according to the seventh aspect of the invention leads to antigen binding polypeptides with increased Tm compared to the parental antigen binding polypeptide, e.g. comprising a VH/VL according to SEQ ID NO: 1 (BMA031 (V36) VH) and SEQ ID NO: 2 (BMA031 (V36) VL). Preferably, the Tm of the antigen binding polypeptides is increased by at least 1° C.-3° C. compared to the parental antigen binding polypeptide, preferably the parental antibody, e.g. comprising a VH/VL according to SEQ ID NO: 1 (BMA031 (V36) VH) and SEQ ID NO: 2 (BMA031 (V36) VL). As was unexpectedly demonstrated in the examples, the substitution of the histidine at position 90 by tyrosine increased the stability in comparison to the parental antigen binding polypeptide not comprising said substitution at position 90 by tyrosine, e.g. the antigen binding polypeptide comprising a VH/VL according to SEQ ID NO: 1 (BMA031 (V36) VH) and SEQ ID NO: 2 (BMA031 (V36) VL). In particular, the substitution of the histidine at position 90 by tyrosine increases the stability by at least about 1° C., preferably by at least about 2° C., more preferably by at least about 2.5° C. or even more preferably by at least about 3° C. in comparison to the parental antigen binding polypeptide not comprising said substitution at position 90 by tyrosine.

In one embodiment the method leads to the production of antigen binding polypeptides that provide increased binding compared to the parental antigen binding polypeptide, e.g. comprising a VH/VL according to SEQ ID NO: 1 (BMA031 (V36) VH) and SEQ ID NO: 2 (BMA031 (V36) VL); and an increased Tm compared to the parental antigen binding polypeptide, preferably the parental antibody, e.g. comprising a VH/VL according to SEQ ID NO: 1 (BMA031 (V36) VH) and SEQ ID NO: 2 (BMA031 (V36) VL).

In one embodiment the method comprises antigen binding polypeptides, wherein at least one of the following positions of the heavy chain 30, 31, 53, and 54 is substituted with a positively charged amino acid.

In one embodiment the method comprises antigen binding polypeptides, wherein at least one of the following positions of the light chain 31, 56, and 93 is substituted with a positively charged amino acid.

In one embodiment the method comprises antigen binding polypeptides, wherein at least one of the following positions of the heavy chain 30, 31, 53, and 54 is substituted with a positively charged amino acid and at least one of the following positions of the light chain 31, and 56, is substituted with a positively charged amino acid.

In one embodiment this/these substitution(s) increase(s) the stability and/or the binding of the antigen binding polypeptide compared to the parental antigen binding polypeptide that does not comprise the substitutions.

An eighth aspect of the invention relates to a method for detecting, determining and/or enriching cells, such as T cells, expressing the α/β TCR/CD3 complex, comprising a step of contacting cells with the antigen binding polypeptide of the first aspect of the invention. The method may further comprises enriching T cells expressing the α/β TCR/CD3 complex, e.g. enriching the T cells that are bound to the antigen binding polypeptide. The method for detecting or determining the cells expressing the α/β TCR/CD3 complex may further comprise detecting and/or determining the antigen binding polypeptide bound to the cells. The method may further comprise a purification step wherein cells that are bound to the antigen binding polypeptide of the first aspect of the invention are purified. The invention further relates to the use of the herein provided antigen binding polypeptide in detecting, determining and/or enriching cells, such as T cells, expressing the α/β TCR/CD3 complex.

A further aspect relates to a method of activating T cells, wherein the method comprises contacting T cells with the antigen binding polypeptide of the first aspect of the invention.

A further aspect of the invention relates to a method of producing the antigen binding polypeptide of the first aspect of the invention.

In one embodiment the method of producing the antigen binding polypeptide comprises the following steps:
a. providing a suitable host cell,
b. providing a genetic construct comprising a coding sequence encoding the antigen binding polypeptide according to the first aspect of the invention,
c. introducing said genetic construct into said suitable host cell according to the third aspect of the invention, and
d. expressing said genetic construct by said suitable host cell,
e. optionally, isolating the antigen binding polypeptide.

The genetic construct is preferably a nucleic acid or a vector according to the second aspect of the invention. In one embodiment the method further comprises the isolation and purification of the antigen binding polypeptide from the suitable host cell and, optionally, reconstitution of the antigen binding polypeptide in a T cell. In one embodiment the genetic construct is an expression construct comprising a promoter sequence operably linked to said coding sequence. The genetic construct is introduced into the host cell using methods known in the art, for example transformation, transduction or transfection. An antigen binding polypeptide of the invention may be produced by any technique known in the art, such as, without limitation, any chemical, biological, genetic or enzymatic technique, either alone or in combination.

A further aspect of the invention relates to a kit comprising the antigen binding polypeptide of any one of the previous claims.

In accordance with the above, the invention preferably relates to the following items:

1. An antigen binding polypeptide comprising a heavy chain variable domain (VH) and a light chain variable domain (VL), wherein
   (1) the VH comprises
      (a) a heavy chain complementarity determining region 1 (HCDR1) comprising the amino acid sequence of SEQ ID NO: 52,
      (b) a HCDR2 comprising the amino acid sequence of YINPYNDVTKYX$_1$X$_2$KFX$_3$G (SEQ ID NO: 53), wherein
         X$_1$ is A or N;
         X$_2$ is E or Q; and/or
         X$_3$ is Q or K
      (c) a HCDR3, and
      (d) heavy chain framework regions (HFR) 1-4;
   (2) the VL comprises
      (a) a light chain complementarity determining region 1 (LCDR1) comprising the amino acid sequence of SEQ ID NO: 54,
      (b) a LCDR2 comprising the amino acid sequence of SEQ ID NO: 55,
      (c) a LCDR3, and
      (d) light chain framework regions (LFR) 1-4;
   wherein
      (i) at least one amino acid of HCDR1 comprising the amino acid sequence of SEQ ID NO: 52 and/or at least one amino acid of HCDR2 comprising the amino acid sequence of SEQ ID NO: 53 that is not positively charged is substituted with a positively charged amino acid; and/or
      (ii) at least one amino acid of LCDR1 comprising the amino acid of SEQ ID NO: 54 and/or at least one amino acid of LCDR2 comprising the amino acid sequence of SEQ ID NO: 55 that is not positively charged is substituted with a positively charged amino acid; and/or
      (iii) position 30 in HFR1 according to Kabat numbering is substituted with a positively charged amino acid, and/or
      (iv) position 90 in HFR3 according to Kabat numbering is substituted with a tyrosine (Y) residue,
   and wherein the antigen binding polypeptide specifically binds to an α/β T cell receptor (TCR)/CD3 complex.

2. The antigen binding polypeptide according to item 1, wherein the positively charged amino acids are:
   (i) at one or more of the following positions of the heavy chain: 31, 53, and 54; and/or
   (ii) at one or more of the following positions of the light chain: 31 and 56, and wherein the positions are according to Kabat numbering.

3. The antigen binding polypeptide according to item 1 or 2, wherein
   (a) the positively charged amino acid in the heavy chain:
      (i) at position 30 is R, K or H;
      (ii) at position 31 is R, K or H;
      (iii) at position 53 is R, K or H; and/or
      (iv) at position 54 is R or K; and/or
   (b) the positively charged amino acid in the light chain
      (i) at position 31 is R or K; and/or
      (ii) at position 56 is R or K.

4. The antigen binding polypeptide according to any one of items 1 to 3, wherein the VH and VL form a first binding site, and wherein the antigen binding polypeptide comprises a second antigen binding site, preferably specifically binding to a cell surface protein, preferably a cell surface protein of a cancer cell, more preferably specifically binding to a major histocompatibility (MHC) peptide complex, preferably MHC I, preferably specifically binding to a human leukocyte antigen (HLA) peptide complex, and most preferably specifically binding to a human leukocyte antigen (HLA) peptide complex of a cancer cell.

5. The antigen binding polypeptide according to item 4, wherein the second antigen binding site comprises at least the variable region of:
   (i) an α (V$_α$) and/or β (V$_β$) chain of a TCR; or
   (ii) a γ (V$_γ$) and/or δ (V$_δ$) chain of a TCR, or
   (iii) a light chain different from the VL as defined in item 1 and/or heavy chain different from the VH as defined in item 1.

6. The antigen binding polypeptide according to item 5, wherein the second antigen binding site comprises the Vα and Vβ or Vγ and Vδ on two separate polypeptide chains or the same polypeptide chain.

7. The antigen binding polypeptide according to any of items 1 to 5, wherein the VL and VH are the VL and the VH of an antibody.

8. The antigen binding polypeptide according to any of items 1 to 7, wherein the first antigen binding site comprises a VH and VL on two separate polypeptide chains or the same polypeptide chain.

9. The antigen binding polypeptide according to any one of items 1-8, wherein the at least one amino acid that is substituted with the positively charged amino acid is:
   (1) in SEQ ID NO: 52;
   (2) in SEQ ID NO: 52 and SEQ ID NO: 53;
   (3) in SEQ ID NO: 52 and SEQ ID NO: 54;
   (4) in SEQ ID NO: 52 and SEQ ID NO:55;
   (5) in SEQ ID NO: 52 and SEQ ID NO: 54 and SEQ ID NO: 55;
   (6) in SEQ ID NO: 52 and SEQ ID NO: 53 and SEQ ID NO: 54;
   (7) in SEQ ID NO: 52 and SEQ ID NO: 53 and SEQ ID NO: 55;
   (8) in SEQ ID NO: 52 and SEQ ID NO: 53 and SEQ ID NO: 54 and SEQ ID NO: 55;
   (9) in SEQ ID NO: 53;
   (10) in SEQ ID NO: 53 and SEQ ID NO: 54;
   (11) in SEQ ID NO: 53 and SEQ ID NO: 55;
   (12) SEQ ID NO: 53 and SEQ ID NO: 54 and SEQ ID NO: 55;
   (13) in SEQ ID NO: 54 (LCDR1);
   (14) in SEQ ID NO: 54 and SEQ ID NO: 55; or
   (15) in SEQ ID NO: 55.

10. The antigen binding polypeptide according to any one of items 1-9, wherein the positively charged amino acid is selected from the group consisting of arginine (R), histidine (H), and lysine (K), preferably wherein the positively charged amino acid is R or K.

11. The antigen binding polypeptide according to any one of items 1-10, comprising serine (S) or asparagine (N) at position 30 in the heavy chain, wherein the positions are according to Kabat numbering.

12. The antigen binding polypeptide according to any one of items 1 to 11, wherein the antigen binding polypeptide comprises further modifications in
   (i) the heavy chain CDR3 (HCDR3), preferably a substitution with a negatively charged amino acid, preferably at position 100a, more preferably glutamate (E); and/or
   (ii) the light chain CDR3 (LCDR3), preferably a substitution with a polar amino acid, preferably at position 93, more preferably asparagine (N),
   wherein the position is according to Kabat numbering.

13. The antigen binding polypeptide according to item 12, wherein the
   (i) HCDR3 has the sequence GSYYDYX$_1$GFVY (SEQ ID NO: 56), wherein X$_1$ is D or E, preferably E; and/or
   (ii) LCDR3 has the sequence QQWSX$_1$X$_2$X$_3$LT (SEQ ID NO: 57), wherein X$_1$ is S or N; X$_2$ is an amino acid selected from the group consisting of Q, D, H, S, Y, and A; and X$_3$ is P or A; preferably wherein the LCDR3 has the sequence QQWSX$_1$NPLT (SEQ ID NO: 96), wherein X$_1$ is S or N, preferably S.

14. The antigen binding polypeptide according to any one of items 1-13, comprising a
   (i) HFR1, HFR2 and HFR3 as comprised in the VH set forth in SEQ ID NO: 1 (BMA031 V36_VH), SEQ ID NO: 97 (GL1_BM_VH28_HV), SEQ ID NO: 98 (GL1_BM_VH31_HV), SEQ ID NO: 99 (HEBE1_H10_HV), SEQ ID NO: 100 (HEBE1_H66_HV), and SEQ ID NO: 101 (HEBE1_H71_HV), preferably wherein the HFR1, HFR2 and HFR3 are comprised in the VH set forth in SEQ ID NO: 1 (BMA031 V36_VH); and/or
   (ii) LFR1, LFR2 and LFR3 as comprised in the VL set forth in SEQ ID NO: 2 (BMA031 V36_VL) or SEQ ID NO: 102 (GL1BMVK43_VL), preferably wherein the LFR1, LFR2 and LFR3 are comprised in the VL set forth in SEQ ID NO: 2 (BMA031 V36_VL); and optionally wherein the antigen binding polypeptide further comprises a HFR4 as comprised in the VH set forth in SEQ ID NO: 1 (BMA031 V36_VH); or a LFR4 as comprised in the VL set forth in SEQ ID NO: 2 (BMA031 V36_VL).

15. The antigen binding polypeptide according to any one of items 1 to 14, comprising the:
   (i) HFR1 as set forth in SEQ ID NO 1 or a human HFR1 sequence having at least about 60% sequence identity with the HFR1 as set forth in SEQ ID NO: 1, optionally comprising a substitution at position 30 according to the Kabat annotation;
   (ii) HFR2 as set forth in to SEQ ID NO 1 or a human HFR2 sequence having at least about 75% sequence identity with SEQ ID NO: 1; and
   (iii) HFR3 as set forth in to SEQ ID NO 10 or a human HFR3 sequence having at least about 55% sequence identity with SEQ ID NO: 1, optionally comprising a substitution at position 90 according to the Kabat annotation.

16. The antigen binding polypeptide according to any one of items 1 to 15, wherein the VL domain comprises a:
   (i) LFR1 as set forth in to SEQ ID NO 2 or a human LFR1 sequence having at least about 50% sequence identity with SEQ ID NO: 2;
   (ii) LFR2 as set forth in to SEQ ID NO 2 or a human LFR2 sequence having at least about 80% sequence identity with SEQ ID NO: 2; and
   (iii) LFR3 as set forth in to SEQ ID NO 2 or a human LFR3 sequence having at least about 80% sequence identity with SEQ ID NO: 2.

17. The antigen binding polypeptide according to any one of item 1 to 16, further comprising a
   (i) HFR4 as set forth in SEQ ID NO 1 or a human HFR4 sequence having at least about 90% sequence identity with SEQ ID NO: 1; and/or
   (ii) LFR4 as set forth in SEQ ID NO 1 or a human LFR4 sequence having at least about 90% sequence identity with SEQ ID NO: 1.

18. The antigen binding polypeptide according to any one of items 1 to 17, wherein the VH comprises the amino acid sequence selected from the group consisting of SEQ ID NO: 7 (VH H90Y); SEQ ID NO: 9 (VH_T30N_S31R), SEQ ID NO: 10 (VH_T30S_S31R_Y53R_E100aD), SEQ ID NO: 11 (VH_S31R), SEQ ID NO: 12 (VH_T30S_Y53R), SEQ ID NO: 14 (VH_N54K_H90Y), SEQ ID NO: 15 (VH_T30N_S31N_Y53R), SEQ ID NO: 16 (VH_T30N_S31R_V56I), SEQ ID NO: 17 (VH_S31R_N54K_E100aD), SEQ ID NO: 19 (VH_T30R), SEQ ID NO: 20 (VH T30K); SEQ ID NO: 21 (VH S31K); SEQ ID NO: 22 (VH_Y53R), SEQ ID NO: 23 (VH_Y53K), SEQ ID NO: 24 (VH_N54R), SEQ ID NO: 25 (VH N54K), SEQ ID NO: 29 (VH_Y53H), SEQ ID NO: 30 (VH_S31H), SEQ ID NO: 31 (VH S31R H90Y), SEQ ID NO: 32 (VH Y53R H90Y), SEQ ID NO: 33 (VH N54R H90Y), and SEQ ID NO: 34 (VH_E61Q_H90Y), or a VH variant thereof comprising an amino acid sequence at least 85%, at least 90% or at least 95% identical to the amino acid sequence selected from the group consisting of SEQ ID NO: 7, 9, 10, 11, 12, 14, 15, 16, 17, 19, 20, 21, 22, 23, 24, 25, 29, 30, 31, 32, 33, and 34, respectively, wherein the VH variant retains the respective substitution(s) in comparison to the VH with a sequence according to SEQ ID NO: 1.

19. The antigen binding polypeptide according to any one of items 1 to 18, wherein the VL comprises the amino acid sequence selected from the group consisting SEQ ID NO: 8 (VL S31R S56R), SEQ ID NO: 13 (VL S31N S56R S93N), SEQ ID NO: 18 (VL S56R), SEQ ID NO: 26 (VL_S31R), SEQ ID NO: 27 (VL_S31K), and SEQ ID NO: 28 (VL_S56K) or a VL variant thereof comprising an amino acid sequence at least 85%, at least 90% or at least 95% identical to the amino acid sequence selected from the group consisting of SEQ ID NO: 8, 13, 18, 26, 27, and 28, respectively wherein the VL variant retains the respective substitution(s) in comparison to the VL with a sequence according to SEQ ID NO: 2.

20. The antigen binding polypeptide according to any one of items 1 to 19, wherein the VH and VL comprise a sequence selected from the group consisting of:

SEQ ID NO: 7 and SEQ ID NO: 8, SEQ ID NO: 9 and SEQ ID NO: 2, SEQ ID NO: 10 and SEQ ID NO: 2, SEQ ID NO: 11 and SEQ ID NO: 2, SEQ ID NO: 12 and SEQ ID NO: 2, SEQ ID NO: 11 and SEQ ID NO: 13, SEQ ID NO: 14 and SEQ ID NO: 2, SEQ ID NO: 15 and SEQ ID NO: 2, SEQ ID NO: 16 and SEQ ID NO: 2, SEQ ID NO: 17 and SEQ ID NO: 2, SEQ ID NO: 1 and SEQ ID NO: 18, SEQ ID NO: 11 and SEQ ID NO: 18, SEQ ID NO: 11 and SEQ ID NO: 8, SEQ ID NO: 12 and SEQ ID NO: 18, SEQ ID NO: 12 and SEQ ID NO: 8, SEQ ID NO: 14 and SEQ ID NO: 18, SEQ ID NO: 14 and SEQ ID NO: 8, SEQ ID NO: 19 and SEQ ID NO: 2, SEQ ID NO: 20 and SEQ ID NO: 2, SEQ ID NO: 21 and SEQ ID NO: 2, SEQ ID NO: 22 and SEQ ID NO: 2, SEQ ID NO: 23 and SEQ ID NO: 2, SEQ ID NO: 24 and SEQ ID NO: 2, SEQ ID NO: 25 and SEQ ID NO: 2, SEQ ID NO: 1 and SEQ ID NO: 26, SEQ ID NO: 1 and SEQ ID NO: 27, SEQ ID NO: 1 and SEQ ID NO: 28, SEQ ID NO: 29 and SEQ ID NO: 2, SEQ ID NO:: 30 and SEQ ID NO: 2, SEQ ID NO: 7 and SEQ ID NO: 2, SEQ ID NO: 31 and SEQ ID NO: 2, SEQ ID NO: 31 and SEQ ID NO: 18, SEQ ID NO: 32 and SEQ ID NO: 2, SEQ ID NO: 33 and SEQ ID NO: 2, SEQ ID NO: 32 and SEQ ID NO: 18, and SEQ ID NO: 7 and SEQ ID NO: 18.

21. The antigen binding polypeptide according to any one of items 1-20, wherein
    a) threonine (T) at position 30 in the heavy chain is substituted with asparagine (N) or serine (S);
    b) S at position 31 in the heavy chain is substituted with asparagine (N);
    c) valine (V) at position 56 in the heavy chain is substituted with isoleucine (I);
    d) glutamic acid (E) at position 100a in the heavy chain is substituted with aspartic acid (D); and/or
    e) S at position 31 and/or position 93 in the light chain is/are substituted with asparagine (N).

22. The antigen binding polypeptide according to any one of items 1 to 21, wherein the VH and VL or Vα and Vβ are covalently or non-covalently linked together.

23. The antigen binding polypeptide according to any of items 1 to 22, further comprising one or more of the following:
    (i) a further antigen binding site;
    (ii) a transmembrane region, optionally including a cytoplasmic signaling region;
    (iii) a diagnostic agent; and/or
    (iv) a therapeutic agent.

24. The antigen binding polypeptide according to any one of items 1 to 23, comprising a first and a second polypeptide chain that form the first and the second antigen binding site, wherein the first polypeptide chain has a structure represented by the formula:

$$V_1\text{-}L_1\text{-}V_2\text{-}L_2\text{-}D_1 \qquad [I]$$

wherein $V_1$ is a first variable domain;

$V_2$ is a second variable domain;

$L_1$ and $L_2$ are linkers; $L_2$ is present or absent;

$D_1$ is a dimerization domain and is present or absent;

and wherein the second polypeptide chain has a structure represented by the formula:

$$V_3\text{-}L_3\text{-}V_4\text{-}L_4\text{-}D_2 \qquad [II]$$

wherein $V_3$ is a third variable domain;

$V_4$ is a fourth variable domain;

$L_3$ and $L_4$ are linkers; $L_4$ is present or absent; and $D_2$ is a dimerization domain and is present or absent;

wherein $D_1$ and $D_2$ specifically bind to each other, and wherein $V_1$ or $V_2$ is a $V_H$ of item 1 and $V_3$ or $V_4$ is a $V_L$ of item 1, and $V_3$ or $V_4$ is a Vα or Vγ and $V_1$ or $V_2$ is a Vβ or Vδ of item 5;

or $V_1$ or $V_2$ is a $V_L$ of item 1 and $V_3$ or $V_4$ is a $V_H$ of item 1, and $V_3$ or $V_4$ is a Vα or Vγ and $V_1$ or $V_2$ is a Vβ or Vδ of item 5;

or $V_1$ or $V_2$ is a $V_H$ of item 1 and $V_3$ or $V_4$ is a $V_L$ of item 1, and $V_3$ or $V_4$ is a Vβ or Vδ and $V_1$ or $V_2$ is a Vα or Vγ of item 5;

or $V_1$ or $V_2$ is a $V_L$ of item 1 and $V_3$ or $V_4$ is a $V_H$ of item 1, and $V_3$ or $V_4$ is a Vβ or Vδ and $V_1$ or $V_2$ is a Vα or Vγ of item 5.

25. The antigen binding polypeptide according to item 24, wherein
    (1) $V_1$ is a $V_H$,
        $V_2$ is a Vβ or Vδ,
        $V_3$ is a Vα or Vγ, and
        $V_4$ is a $V_L$;
    (2) $V_1$ is a Vβ or Vδ;
        $V_2$ is a $V_H$;
        $V_3$ is a $V_L$; and
        $V_4$ is a Vα or Vγ;
    (3) $V_1$ is a Vβ or Vδ,
        $V_2$ is a $V_L$,
        $V_3$ is a $V_H$, and
        $V_4$ is a Vα or Vγ;
    (4) $V_1$ is a $V_L$,
        V2 is a Vβ or Vδ,
        $V_3$ is a Vα or Vγ, and $V_4$ is a $V_H$;
(5) $V_1$ is a $V_H$,
$V_2$ is a $V_\beta$ or $V_\delta$,
$V_3$ is a $V_L$, and
$V_4$ is a $V_\alpha$ or $V_\gamma$;
(6) $V_1$ is a $V_\beta$ or $V_\delta$,
$V_2$ is a $V_H$;
$V_3$ is a $V_\alpha$ or $V_\gamma$, and
$V_4$ is a $V_L$;
(7) $V_1$ is a $V_L$,
$V_2$ is a $V_\beta$ or $V_\delta$;
$V_3$ is a $V_H$, and
$V_4$ is a $V_\alpha$ or $V_\gamma$;
(8) $V_1$ is a $V_\beta$ or $V_\delta$,
$V_2$ is a $V_L$;
$V_3$ is a $V_\alpha$ or $V_\gamma$, and
$V_4$ is a $V_H$;
(9) $V_1$ is a $V_H$,
$V_2$ is a $V_L$, and
$V_3$ is a $V_\alpha$ or $V_\gamma$;
$V_4$ is a $V_\beta$ or $V_\delta$;
(10) $V_1$ is a $V_L$;
$V_2$ is a $V_H$;
$V_3$ is a $V_\alpha$ or $V_\gamma$; and
$V_4$ is a $V_\beta$ or $V_\delta$;
(11) $V_1$ is a $V_H$;
$V_2$ is a $V_L$;
$V_3$ is a $V_\beta$ or $V_\delta$; and
$V_4$ is a $V_\alpha$ or $V_\gamma$;
(12) $V_1$ is a $V_L$;
$V_2$ is a $V_H$;
$V_3$ is a $V_\beta$ or $V_\delta$; and
$V_4$ is a $V_\alpha$ or $V_\gamma$.

26. The antigen binding polypeptide according to item 24 or 25, wherein
(i) D1 and D2 are Fc domains;
(ii) L1 has a length of 1-30 amino acids and/or
(iii) L2 if present has a length of 1-30 amino acids; and/or
(iv) L3 has length of 1-30 amino acids; and/or
(v) L4 is present has a length of 1-30 amino acids.

27. The antigen binding polypeptide according to any one of items 24-26, wherein the antigen binding polypeptide
(i) has a first polypeptide chain according to SEQ ID NO: 39 and has a second polypeptide chain according to SEQ ID NO: 38; or
(ii) has a first polypeptide chain according to SEQ ID NO: 39 and has a second polypeptide chain according to SEQ ID NO: 35

28. A nucleic acid or set of nucleic acids coding for an antigen binding polypeptide according to any one of items 1 to 26, or a nucleic acid vector comprising said nucleic acid or set of nucleic acids.

29. A recombinant host cell comprising an antigen binding polypeptide according to any one of items 1 to 27, or a nucleic acid or set of nucleic acids or a vector according to item 28, wherein said host cell is
(i) a lymphocyte, preferably a T lymphocyte or T lymphocyte progenitor cell, for example a CD4 or CD8 positive T cell; or
(ii) a cell for recombinant expression, such as a Chinese Hamster Ovary (CHO) cell or a yeast cell.

30. A pharmaceutical composition comprising the antigen polypeptide according to any one of items 1 to 27, the nucleic acid or set of nucleic acids or vector according to item 28, or the host cell according to item 29, and a pharmaceutically acceptable carrier, diluent stabilizer, and/or excipient.

31. A method of producing the antigen binding polypeptide according to any one of items 1 to 27, comprising
(i) providing a suitable host cell,
(ii) providing a genetic construct comprising a coding sequence encoding the antigen binding polypeptide according to any one of items 1 to 22,
(iii) introducing said genetic construct into said suitable host cell, and
(iv) expressing said genetic construct by said suitable host cell.

32. The method according to item 31, further comprising the isolation and purification of the antigen binding polypeptide from the suitable host cell and, optionally, reconstitution of the antigen binding polypeptide in a T cell.

33. The antigen binding polypeptide according to any one of items 1 to 27, the nucleic acid or set of nucleic acids or vector according to item 28, the host cell according to item 29 or the pharmaceutical composition according to item 30, for use in medicine.

34. The antigen binding polypeptide according to any one of items 1 to 27, the nucleic acid or set of nucleic acids or vector according to item 28, the host cell according to item 29 or the pharmaceutical composition according to item 30 for use in the diagnosis, prevention, and/or treatment of a proliferative disease, preferably cancer.

35. A method for improving or maintaining the binding and/or improving the stability the antigen binding polypeptide comprising a heavy chain variable domain (VH) and a light chain variable domain (VL), wherein
(1) the VH comprises
(a) a heavy chain complementarity determining region 1 (HCDR1) comprising the amino acid sequence of SEQ ID NO: 52,
(b) a HCDR2 comprising the amino acid sequence of YINPYNDVTKYX$_1$X$_2$KFX$_3$G (SEQ ID NO: 53), wherein
X$_1$ is A or N;
X$_2$ is E or Q; and/or
X$_3$ is Q or K
(c) a HCDR3, and
(d) heavy chain framework regions (HFR) 1-4;
(2) the VL comprises
(a) a light chain complementarity determining region 1 (LCDR1) comprising the amino acid sequence of SEQ ID NO: 54,
(b) a LCDR2 comprising the amino acid sequence of SEQ ID NO: 55,
(c) a LCDR3, and
(d) light chain frameworks (LCR) 1-4;
wherein
(i) at least one amino acid of HCDR1 comprising the amino acid sequence of SEQ ID NO: 52 and/or at least one amino acid of HCDR2 comprising the amino acid sequence of SEQ ID NO: 53 that is not positively charged is substituted with a positively charged amino acid; and/or
(ii) at least one amino acid of LCDR1 comprising the amino acid of SEQ ID NO: 54 and/or at least one amino acid of LCDR2 comprising the amino acid sequence of SEQ ID NO: 55 that is not positively charged is substituted with a positively charged amino acid; and/or
(iii) position 30 in HFR1 according to Kabat numbering is substituted with a positively charged amino acid, and/or
(iv) position 90 in HFR3 according to Kabat numbering is substituted with a tyrosine (Y) residue, wherein
(1) the binding of the antigen binding polypeptide to an α/β T cell receptor (TCR)/CD3 complex is increased compared to the parental antigen binding polypeptide;
(2) the binding of the antigen binding polypeptide to an α/β T cell receptor (TCR)/CD3 complex is maintained or increased and the stability of the antigen binding polypeptide is increased compared to the parental antigen binding polypeptide; or
(3) the stability of the antigen binding polypeptide is increased compared to the parental antigen binding polypeptide.

36. The method of item 35, wherein
(i) at least one of the following positions of the heavy chain 31, 53, and 54 is substituted with a positively charged amino acid; and/or
(ii) at least one of the following positions of the light chain 31, and 56, is substituted with a positively charged amino acid, and wherein the positions are according to Kabat numbering.

37. The method of item 35, wherein the substitution(s) increase(s) the stability and/or the binding of the antigen binding polypeptide compared to a parental antigen binding polypeptide that does not comprise the substitutions with the positively charged amino acid at positions 30, 31, 53, and/or 54 in the heavy chain, the substitutions with the positively charged amino acid at positions 31 and/or 56, in the light chain, and/or the substitution of tyrosine (Y) at position 90 in the heavy chain.

38. The method of any one of the previous items, wherein the substitution at position 90 in HFR3 with a tyrosine (Y) residue according to Kabat numbering increases the stability compared to the parental antigen binding polypeptide.

39. A method for detecting, determining or enriching T cells expressing the α/β TCR/CD3 complex, comprising the step of contacting cells with the antigen binding polypeptide according to any one of items 1-27.

40. A kit comprising the antigen binding polypeptide according to any one of items 1-27.

The term "about" refers in the context of this invention and when used in reference to a particular recited numerical value, to a value and means that the value may vary from the recited value by no more than 5%, no more than 4.5%, 4.0%, 3.5%, 3.0%, 2.5%, 2.0%, 1.5%, 1.0%, or 0.5%. For example, as used herein, the expression "about 100" includes 95 and 105 and all values in between (e.g. 95.0, 95.5, 96.0, 96.5, 97.0, 97.5, 98.0, 98.5, 99.0, 99.5, 100.5, 101.0, 101.5, 102.0, 102.5, 103.0, 103.5, 104.0, 104.5 and 105.0).

Throughout the instant application, the term "and/or" is a grammatical conjunction that is to be interpreted as encompassing that one or more of the cases it connects may occur. For example, the wording "such native sequence proteins can be prepared using standard recombinant and/or synthetic methods" indicates that native sequence proteins can be prepared using standard recombinant and synthetic methods or native sequence proteins can be prepared using standard recombinant methods or native sequence proteins can be prepared using synthetic methods.

Furthermore, throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

Furthermore the indefinite article "a" or "an" does not exclude a plurality. The mere fact that certain measures are recited in mutually different dependent claims does not indicate that a combination of these measures cannot be used to advantage The following examples are merely illustrative of the present invention and should not be construed to limit the scope of the invention as indicated by the appended claims in any way.

EXAMPLES

Example 1

In order to provide antigen binding polypeptides that have an increased stability and/or an increased binding affinity, the variable chains of the antibody BMA031 (V36) (TPP-1374, Fab fragment) were converted into an scFv (SEQ ID NO: 44) and the corresponding DNA was synthesized. Mutations in the CDRs were introduced by overlap extension PCR, using degenerate primers at positions 28 to 31, 33, 50, 52, 53, 54, 56, 58 and 96 to 100b of the variable heavy chain and/or positions 27, 29, 49, 50, 53, 55, 56, 91 to 94 and 96 of the variable light chain. The resulting DNA strings were ligated to a phagemid vector, based on pHAL and transformed into E.coli TG1 for the generation of scFv-bearing phages, essentially as described in Unkauf et al. 2018. The resulting phage particles were used for a selection strategy including a negative selection step first with an α/β TCR/CD3 negative Jurkat T cells (J.RT3T3.5), followed by positive selection with an α/β TCR/CD3 positive Jurkat T cell line (Jurkat, Clone E6-1) over 2 selection rounds, essentially as described in Wenzel et al. 2020. The α/β TCR/CD3 negative Jurkat T cells J.RT3T3.5 is derived from Jurkat cells via irradiation and lost the presentation of its α/β TCR/CD3 complex, while retaining expression of other surface proteins at indistinguishable levels (Weiss and Stobo 1984). Upon transfer of the TCR beta chain and consequently also expression of the TCR/CD3 complex on the surface, the J.RT3T3.5 cell line regains its functionality (Ohashi et al. 1985). Thus, this cell line was considered a good tool for the negative-selection of an α/β TCR/CD3 complex binder. Final clones were transduced into E.coli XL1 for flow cytometric analysis of soluble scFv molecules. All clones were analyzed for binding to both Jurkat cell lines and the 11 unique binding-improved clones (SEQ ID NOs 45 to 55) with retained specificity (binding to Jurkat, Clone E6-1, but not J.RT3T3.5, FIG. 1) were converted into the Fab format (herein also referred to as Fab fragment) for further investigation of binding properties as well as stability assessment. The Fab fragment comprised the respective VL-CL and VH-CH1 connected via a disulfide bridge. The amino acid sequence of CH1 is shown in SEQ ID NO: 3. The amino acid sequence of CL is shown in SEQ ID NO: 4. An exemplary Fab fragment of the parental antigen binding polypeptide (TPP1374—Fab fragment of BMA031(V36)) is shown in SEQ ID NOs: 5 and 6. The antigen binding polypeptides tested below in the Fab format also comprised the CL and CH1 as shown in SEQ ID NOs: 5 and 6. Furthermore, an additional His-tag was added to the C-terminus of the CH1 for purification and detection of the Fab fragments. In other words, the substitutions tested were introduced into the exemplary parental antibody. In addition to the inserted CDR mutations (including position 30 in the VH according to Kabat), an unplanned framework mutation, namely H90Y in the heavy chain framework 3 (HFR3), was also selected from the scFv-phage libraries. The numbering of the amino acids residues is according to Kabat numbering unless otherwise indicated. The selected variable domains were shuffled and cloned into a pCSE-based Fab expression vector and transfected into HEK293 cells for transient soluble protein expression (TPP-1357 to TPP-1373), always accompanied by the exemplary parental antibody (TPP-1374), essentially as described in Jäger et al. 2013. Proteins were purified from cell culture supernatant via immobilized metal affinity chromatography, essentially as described in Siegemund et al. 2014. Binding properties were investigated via flow cytometric binding analysis using the above described α/β TCR/CD3-positive (and γ/δ negative) and -negative Jurkat cell lines and applying a titration series of the purified Fab fragments (concentrations from 10 µg/ml to 10 ng/ml in half log steps). Briefly, all cytometry steps were performed in FACS buffer (PBS, 2 mM EDTA, 5% FCS). Antigen negative J.RT3T3.5 cells were labelled with CFSE CellTrace (ThermoFisher, C34554) according to the manual and mixed with antigen positive Jurkat, Clone E6-1 cells in 1:1 ratio. After that, the cells were washed once in FACS buffer via centrifugation at 300 rcf. A dilution series of the antibody Fab of interest (100 µl/well and the concentration as indicated above) was subsequently incubated with the cell mix (100.000 cells/well) for 15 min on ice in FACS buffer. Unbound antibody was washed away by one washing step with FACS buffer. For detection of the binding, an anti-HIS-tag Alexa647-labeled antibody (Biolegend, 652513) was used in a 1:2000 dilution (50 µl/well) for 15 min on ice (in the dark) in FACS buffer. The unbound secondary staining antibody was removed by three washing steps with FACS buffer via centrifugation at 300 rcf. After washing, cells were resuspended in FACS buffer containing 1× propidiumiodide (Roth, CN74.1) (40 µl/well) for live/dead staining Finally, the staining of the cells was determined in a flow cytometer (Intellicyt iQue Screener (Sartorius AG) or CytoFLEX (Beckmann Coulter, 2089495-01)) and the MFI (median fluorescence intensity) values were compared. For living cells (propidiumiodide negative staining) that are antigen positive (CFSE CellTrace negative staining), binding area under the curve (binding AUC) was calculated using MFI and logarithmized concentration values. All of the selected variants demonstrate increased binding AUC values compared to the exemplary parental antibody TPP-1374 (FIG. 2). At the same time target specificity was addressed by performing the same assay on TCR/CD3 negative Jurkat cells. All Fab fragments did not show binding (FIG. 3). Stability of the Fab fragments was examined by nanoDSF using the Prometheus NT.48 system, calculating melting points of the Fab fragments upon when 50% of the protein is unfolded (Table 3). All measurements were performed in PBS pH7.4 at a Fab concentration of 50 µg/ml and a heating ramp rate of 1° C./min. Evaluation of melting temperature was performed via PR.StabilityAnalysis (v. PR.StabilityAnalysis_x64_1.1.0.11077). Delta Tm values were only calculated for variants that had been run within one experiment. With 71.8° C. the parental BMA031 (V36) Fab fragment already showed high stability and apart from TPP-1366 all other proteins could retain their stability above a melting temperature of 70 C. Various substitutions further improved the stability in comparison to the BMA031 (V36) Fab fragment; see Table 3. Surprisingly, the mutation H90Y (according to Kabat numbering) in the heavy chain provided a tremendous gain in temperature stability with a shift well above 75° C. (see Table 3).

TABLE 3

Melting temperature of maturated Fab molecules. The melting temperature of the purified Fab fragments was addressed by nanoDSF. TPP-1374 served as reference molecule.

| Molecule | Mutations | Tm [° C.] |
|---|---|---|
| TPP-1357 | VH_H90Y_VL_S31R_S56R | 76.8 |
| TPP-1358 | VH_T30N_S31R_VL_wt | 71.4 |
| TPP-1359 | VH_T30S_S31R_Y53R_E100aD_VL_wt | 70.1 |
| TPP-1361 | VH_T30S_Y53R_VL_wt | 71.9 |
| TPP-1362 | VH_S31R_VL_LS31N_S56R_S93N | 71.6 |
| TPP-1364 | VH_T30N_S31N_Y53R_VL_wt | 71.9 |
| TPP-1365 | VH_T30N_S31R_V56I_VL_wt | 70.7 |
| TPP-1366 | VH_S31R_N54K_E100aD_VL_wt | 67.6 |
| TPP-1368 | VH_S31R_VL_S56R | 72.1 |
| TPP-1369 | VH_S31R_VL_S31R_S56R | 72.9 |
| TPP-1370 | VH_T30S_Y53R_VL_S56R | 71.7 |
| TPP-1371 | VH_T30S_Y53R_VL_S31R_S56R | 72.5 |
| TPP-1373 | VH_N54K_H90Y_VL_S31R_S56R | 76.6 |
| TPP-1374 | VH_wt_VL_wt | 71.8 |

Example 2

Combinations of the substitutions selected in Example 1 were introduced in the exemplary parental antibody (TPP-1374). Several positions within the CDRs 1 and 2 of the heavy chain and the light chain were substituted with positively charged amino acids (basic amino acids). In a first experiment, only one basic amino acid per chain was applied. In addition, the framework mutation H90Y was introduced into selected variants. The Fab fragments TPP-1360, TPP-1363, TPP-1372, TPP-1374 to TPP-1384 and TPP-1387 to TPP-1393 were produced, purified and analyzed as depicted in example 1 for binding AUC and melting temperature. Furthermore, binding EC50 was investigated by fitting the MFI with a non-linear 4-point curve fitting; see FIG. 6. Replacement at position 30 of the heavy chain with basic amino acids (e.g. R or K) resulted in improvement of binding EC50 to target bearing Jurkat, Clone E6-1 cells, in comparison to the reference BMA031 (V36) Fab (TPP-1374) (Table 4, Table 7, FIG. 5). Substitution of serine in position 31 in the heavy chain with arginine or lysine improved binding EC50 in all variants tested in comparison to parental BMA031 (V36) Fab (Table 4, Table 6, Table 4, FIG. 5). All the variants tested with an exchanged asparagine residue at position 54 of the heavy chain yielded improved binding properties compared to the BMA031 (V36) Fab (Table 4, Table 6, Table 7, FIG. 5). The replacement of tyrosine by the arginine substitution at position 53 in the heavy chain improved binding AUC compared to BMA031 (V36) Fab (Table 4 and 6).

In the light chain, the replacement by a positive charge at position 56 strengthened binding (Table 4, Table 7, FIG. 5). The replacement of serine at position 31 in the light chain by a positive charge provided a decreased binding and simultaneously increased the stability (Table 4, FIG. 5).

Unexpectedly, introduction of H90Y in the heavy chain increased the melting temperature by more than 3° C. to a minimal level of 75° C. (except VH_N54K_H90Y_VL_S56R (TPP-1372) increased the melting temperature by 2.8° C.). The exemplary Fab fragments VH_H90Y VL_S31R_S56R and VH_N54K_H90Y_VL_S31R_S56R even increased the melting temperature by more than 4° C. (compare Table 4 to Table 5, Table 6, FIG. 5).

Furthermore, combination of H90Y with the arginine substitution of positions 31, 53 and 54 of the heavy chain (TPP-1388, TPP-1390 and TPP-1391) yields synergistic effects regarding the binding AUC. This synergistic effect in binding AUC was also found for the additional combination of molecules VH_S31R and VH_Y53R with arginine at position 56 of the light chain (TPP-1389 and TPP-1392), resulting in the highest binding AUC values (Table 6, FIG. 5). The tremendous effect on binding of the combination of these single mutations can also be depicted by improved binding curves and EC50 values (Table 7, FIG. 6).

Specificity of the Fab fragments was again addressed by flow cytometric analysis of J.RT3T3.5 cells as in example 1. None of the examined proteins demonstrated any cross-reactivity to this TCR/CD3 negative cell line, while binding to the target cell line was present for all variants (FIG. 4).

TABLE 4

Characteristics of maturated Fab molecules (CDR mutations only). Binding of the purified Fab fragments towards α/β TCR/CD3 positive Jurkat cells (Clone E6-1) was investigated in a titration series ranging from 10 μg/ml to 10 ng/ml. Area under the curve was calculated for MFI values and the corresponding logarithmized concentrations. Percent gain in binding AUC as well as difference in melting temperature compared to VH_wt_VL_wt (TPP-1374) is shown.

| Molecule | Mutations | % gain in binding AUC | delta Tm [° C.] | Tm [° C.] |
|---|---|---|---|---|
| TPP-1375 | VH_T30R_VL_wt | 87 | −1.6 | 70.9 |
| TPP-1376 | VH_T30K_VL_wt | 83 | −1.8 | 70.7 |
| TPP-1360 | VH_S31R_VL_wt | 144 | 0.0 | 72.4 |
| TPP-1377 | VH_S31K_VL_wt | 56 | 0.8 | 73.3 |
| TPP-1378 | VH_Y53R_VL_wt | 79 | n.d. | n.d. |
| TPP-1379 | VH_Y53K_VL_wt | 1 | 1.0 | 73.5 |
| TPP-1380 | VH_N54R_VL_wt | 18 | −3.3 | 69.2 |
| TPP-1381 | VH_N54K_VL_wt | 98 | −3.0 | 69.5 |
| TPP-1382 | VH_wt_VL_S31R | −66 | 1.2 | 73.7 |
| TPP-1383 | VH_wt_VL_S31K | −73 | 1.0 | 73.4 |
| TPP-1367 | VH_wt_VL_S56R | 220 | −0.6 | 71.9 |
| TPP-1384 | VH_wt_VL_S56K | 203 | −0.1 | 72.3 |
| TPP-1374 | VH_wt_VL_wt | 0 | 0.0 | 72.5 |

TABLE 5

Characteristics of maturated Fab molecules (variants including heavy chain framework mutation H90Y). Binding of the purified Fab fragments towards α/β TCR/CD3 positive Jurkat cells (Clone E6-1) was investigated in a titration series ranging from 10 μg/ml to 10 ng/ml. Area under the curve was calculated for MFI values and the corresponding logarithmized concentrations. Percent gain in binding AUC as well as difference in melting temperature compared to VH_wt_VL_wt (TPP-1374) is shown.

| Molecule | Mutations | % gain in binding AUC | delta Tm [° C.] | Tm [° C.] |
|---|---|---|---|---|
| TPP-1389 | VH_S31R_H90Y_VL_S56R | 423 | 3.6 | 76.0 |
| TPP-1388 | VH_S31R_H90Y_VL_wt | 273 | 3.9 | 76.4 |
| TPP-1392 | VH_Y53R_H90Y_VL_S56R | 813 | 3.6 | 76.1 |
| TPP-1390 | VH_Y53R_H90Y_VL_wt | 270 | 4.4 | 76.9 |
| TPP-1391 | VH_N54R_H90Y_VL_wt | 245 | 3.3 | 75.8 |
| TPP-1372 | VH_N54K_H90Y_VL_S56R | 246 | 2.8 | 75.3 |
| TPP-1363 | VH_N54K_H90Y_VL_wt | 380 | 3.4 | 75.9 |
| TPP-1393 | VH_H90Y_VL_S56R | 226 | 3.2 | 75.7 |
| TPP-1387 | VH_H90Y_VL_wt | 14 | 3.9 | 76.4 |

TABLE 6

Characteristics of maturated Fab molecules (direct comparison of particular mutations). Binding of the purified Fab fragments towards α/β TCR/CD3 positive Jurkat cells (Clone E6-1) was investigated in a titration series ranging from 10 μg/ml to 10 ng/ml. Area under the curve was calculated for MFI values and the corresponding logarithmized concentrations. Percent gain in binding AUC as well as difference in melting temperature compared to VH_wt_VL_wt (TPP-1374) is shown.

| Molecule | Mutations | % gain in binding AUC | delta Tm [° C.] | Tm [° C.] |
|---|---|---|---|---|
| TPP-1360 | VH_S31R_VL_wt | 144 | 0.0 | 72.4 |
| TPP-1388 | VH_S31R_H90Y_VL_wt | 273 | 3.9 | 76.4 |
| TPP-1389 | VH_S31R_H90Y_VL_S56R | 423 | 3.6 | 76.0 |
| TPP-1378 | VH_Y53R_VL_wt | 79 | n.d. | n.d. |
| TPP-1390 | VH_Y53R_H90Y_VL_wt | 270 | 4.4 | 76.9 |
| TPP-1392 | VH_Y53R_H90Y_VL_S56R | 813 | 3.6 | 76.1 |
| TPP-1380 | VH_N54R_VL_wt | 18 | −3.3 | 69.2 |
| TPP-1391 | VH_N54R_H90Y_VL_wt | 245 | 3.3 | 75.8 |
| TPP-1367 | VH_wt_VL_S56R | 220 | −0.6 | 71.9 |
| TPP-1393 | VH_H90Y_VL_S56R | 226 | 3.2 | 75.7 |
| TPP-1374 | VH_wt_VL_wt | 0 | 0.0 | 72.5 |
| TPP-1387 | VH_H90Y_VL_wt | 14 | 3.9 | 76.4 |

TABLE 7

Binding EC50 of maturated Fab molecules. Binding of the purified Fab fragments towards α/β TCR/CD3 positive Jurkat cells (Clone E6-1) was investigated in a titration series ranging from 10 μg/ml to 10 ng/ml. EC50 of median fluorescence intensity (MFI) was calculated and fold decrease compared to VH_wt_VL_wt (TPP-1374) is shown.

| Molecule | Mutations | fold decrease in EC50 |
|---|---|---|
| TPP-1389 | VH_S31R_H90Y_VL_S56R | 31.8 |
| TPP-1372 | VH_N54K_H90Y_VL_S56R | 21.5 |
| TPP-1392 | VH_Y53R_H90Y_VL_S56R | 16.6 |
| TPP-1393 | VH_H90Y_VL_S56R | 13.9 |
| TPP-1367 | VH_wt_VL_S56R | 8.8 |
| TPP-1381 | VH_N54K_VL_wt | 8.2 |
| TPP-1388 | VH_S31R_H90Y_VL_wt | 8.1 |
| TPP-1363 | VH_N54K_H90Y_VL_wt | 7.3 |
| TPP-1360 | VH_S31R_VL_wt | 5.7 |
| TPP-1390 | VH_Y53R_H90Y_VL_wt | 5.5 |
| TPP-1391 | VH_N54R_H90Y_VL_wt | 4.7 |
| TPP-1384 | VH_wt_VL_S56K | 4.1 |
| TPP-1377 | VH_S31K_VL_wt | 4.1 |

TABLE 7-continued

Binding EC50 of maturated Fab molecules. Binding
of the purified Fab fragments towards α/β TCR/CD3
positive Jurkat cells (Clone E6-1) was investigated in a
titration series ranging from 10 µg/ml to 10 ng/ml.
EC50 of median fluorescence intensity (MFI) was
calculated and fold decrease compared to
VH_wt_VL_wt (TPP-1374) is shown.

| Molecule | Mutations | fold decrease in EC50 |
|---|---|---|
| TPP-1387 | VH_H90Y_VL_wt | 3.2 |
| TPP-1380 | VH_N54R_VL_wt | 2.9 |
| TPP-1376 | VH_T30K_VL_wt | 2.8 |
| TPP-1375 | VH_T30R_VL_wt | 2.1 |

Example 3: Selected TCER Variants (TPP-226 (PPB-1156), TPP-894 (PPB-1155), TPP-879 (PPB-1152))

In order to investigate whether the observed beneficial effects of the modified BMA031 molecules also improve the properties of bispecific antigen binding polypeptides, TCER® molecules were constructed comprising the herein provided modified BMA031 molecules. Therefore, DNA-sequences coding for VH and VL, derived from the optimized variants of BMA031(V36) and Valpha and Vbeta as well as sequences coding for linkers were obtained by gene synthesis. Vectors for the expression of recombinant proteins were designed as mono-cistronic, controlled by HCMV-derived promoter elements, pUC19-derivatives. Plasmid DNA was amplified in E.coli according to standard culture methods and subsequently purified using commercial-available kits (Macherey & Nagel). Purified plasmid DNA was used for transient transfection of CHO cells. Transfected CHO-cells were cultured for 10-11 days at 32° C. to 37° C. Conditioned cell supernatant was cleared by filtration (0.22 µm) utilizing Sartoclear Dynamics® Lab Filter Aid (Sartorius). Bispecific molecules were purified using an Akta Pure 25 L FPLC system (GE Lifesciences) equipped to perform affinity and size-exclusion chromatography in line. Affinity chromatography was performed on protein L columns (GE Lifesciences) following standard affinity chromatographic protocols. Size exclusion chromatography was performed directly after elution (pH 2.8) from the affinity column to obtain highly pure monomeric protein using Superdex 200 pg 16/600 columns (GE Lifesciences) following standard protocols. Protein concentrations were determined on a NanoDrop system (Thermo Scientific) using calculated extinction coefficients according to predicted protein sequences. Concentration was adjusted, if needed, by using Vivaspin devices (Sartorius). Finally, purified molecules were stored in phosphate-buffered saline at concentrations of about 1 mg/mL at temperatures of 2-8° C. Quality of purified bispecific molecules was controlled by HPLC-SEC on MabPac SEC-1 columns (5 µm, 4×300 mm) running in 50 mM sodium-phosphate pH 6.8 containing 300 mM NaCl within a Vanquish uHPLC-System. Potency of improved BMA031-variants was assessed in LDH-release assays. Therefore, tumor cell lines presenting various levels of target pHLA on their cell surface as well as a target pHLA-negative tumor cell line were used as targets for PBMC derived from healthy HLA-A*02-positive donors (E:T=10:1) in presence of raising concentrations of TCER molecules. TCER-induced cytolysis was quantified after 48 hours by measurement of released LDH. EC50 values of dose-response curves were calculated utilizing non-linear 4-point curve fitting. The results of two independent assays using PBMC of two independent donors are shown in FIG. 7 and FIG. 8, respectively. The calculated EC50 values of the respective non-linear curve fits are summarized within Table 8. These results demonstrate that the usage of modified BMA031 molecules (TPP-879, TPP-894) within the TCER® scaffold results in increased potency of T cell mediated killing of target pHLA-positive tumor cell lines in comparison to TPP-226 comprising VH according to SEQ ID NO: 1 and VL according to SEQ ID NO: 2 of BMA031 (V36). These results also show no or only marginal increase of T cell mediated cytotoxicity towards target pHLA-negative tumor cell line T98G induced by the optimized recruiting domains.

TABLE 8

Summary of EC50 values of T cell mediated cytotoxicity induced by TCER molecule

| | Hs695T EC50 [pM] | | U2OS EC50 [pM] | | T98G EC50 [pM] | |
|---|---|---|---|---|---|---|
| | PBMC-donor | | | | | |
| Molecule | HBC-1005 | HBC-1039 | HBC-1005 | HBC-1039 | HBC-1005 | HBC-1039 |
| TPP-226 | 340 | 3204 | 999 | 9099 | 42211 | 1255220 |
| TPP-879 | 60 | 489 | 168 | 535 | 108513 | 612709 |
| TPP-894 | 100 | 636 | 193 | 920 | 16480 | 349590 |

Exemplary references are herein provided, wherein these references are herein incorporated in their entireties.

Jäger V, Büssow K, Wagner A, Weber S, Hust M, Frenzel A, Schirrmann T. High level transient production of recombinant antibodies and antibody fusion proteins in HEK293 cells. BMC Biotechnol. 2013 Jun. 26; 13:52. doi: 10.1186/1472-6750-13-52. PMID: 23802841

Ohashi P S, Mak T W, Van den Elsen P, Yanagi Y, Yoshikai Y, Calman A F, Terhorst C, Stobo J D, Weiss A. Reconstitution of an active surface T3/T-cell antigen receptor by DNA transfer. Nature. 1985 Aug. 15-21; 316(6029):606-9. doi: 10.1038/316606a0. PMID: 4033759.

Siegemund M, Richter F, Seifert O, Unverdorben F, Kontermann R E. Expression and purification of recombinant antibody formats and antibody fusion proteins. Methods Mol Biol. 2014; 1131:273-95. doi: 10.1007/978-1-62703-992-5_18. PMID: 24515473.

Unkauf T, Hust M, Frenzel A. Antibody Affinity and Stability Maturation by Error-Prone PCR. Methods Mol Biol. 2018; 1701:393-407. doi: 10.1007/978-1-4939-7447-4_22. PMID: 29116518.

Weiss A, Stobo J D. Requirement for the coexpression of T3 and the T cell antigen receptor on a malignant human T cell line. J Exp Med. 1984 Nov. 1; 160(5):1284-99. doi: 10.1084/jem.160.5.1284. PMID: 6208306; PMCID: PMC2187507.

Wenzel E V, Roth K D R, Russo G, Fühner V, Helmsing S, Frenzel A, Hust M. Antibody Phage Display: Antibody Selection in Solution Using Biotinylated Antigens. Methods Mol Biol. 2020; 2070:143-155. doi: 10.1007/978-1-4939-9853-1_8. PMID: 31625094.

| SEQ ID NO: | Description: | | Sequence: |
|---|---|---|---|
| 1 | VH | TPP-1374, TPP-1367, TPP-1382, TPP-1383, TPP-1384, TPP-667, TPP-226 | EVQLVQSGAEVKKPGASVKVSCKASGYKFTSYVMHWVR QAPGQGLEWMGYINPYNDVTKYAEKFQGRVTLTSDTSTS TAYMELSSLRSEDTAVHYCARGSYYDYEGFVYWGQGTLV TVSS |
| 2 | VL | TPP-1374, TPP-1358, TPP-1359, TPP-1360, TPP-1361, TPP-1363, TPP-1364, TPP-1365, TPP-1366, TPP-1375, TPP-1376, TPP-1377, TPP-1378, TPP-1379, TPP-1380, TPP-1381, TPP-1385, TPP-1386, TPP-1387, TPP-1388, TPP-1390, TPP-1391, TPP-666, TPP-669, TPP-879, TPP-894, TPP-226, TPP-876, TPP-891, TPP-1292, TPP-1293, PP-1294, TPP-1295 | QIQMTQSPSSLSASVGDRVTITCSATSSVSYMHWYQQKPG KAPKRWIYDTSKLASGVPSRFSGSGSGTDYTLTISSLQPED AATYYCQQWSSNPLTFGGGTKVEIK |
| 3 | CH1 (all Fabs) | | ASTKGPSVFPLAPSSKSTSGGTAALGCLVKDYFPEPVTVS WNSGALTSGVHTFPAVLQSSGLYSLSSVVTVPSSSLGTQTY ICNVNHKPSNTKVDKKVEPKSCGSGHHHHHH |
| 4 | CL (all Fabs) | | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC |
| 5 | heavy | TPP-1374 | EVQLVQSGAEVKKPGASVKVSCKASGYKFTSYVMHWVR QAPGQGLEWMGYINPYNDVTKYAEKFQGRVTLTSDTSTS TAYMELSSLRSEDTAVHYCARGSYYDYEGFVYWGQGTLV TVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKKVEPKSCGSGHHHHHH |
| 6 | light | TPP-1374 | QIQMTQSPSSLSASVGDRVTITCSATSSVSYMHWYQQKPG KAPKRWIYDTSKLASGVPSRFSGSGSGTDYTLTISSLQPED AATYYCQQWSSNPLTFGGGTKVEIKRTVAAPSVFIFPPSDE QLKSGTASVVCLLNNFYPREAKVQWKVDNALQSGNSQES VTEQDSKDSTYSLSSTLTLSKADYEKHKVYACEVTHQGLS SPVTKSFNRGEC |
| 7 | VH | TPP-1357, TPP-1387, TPP-1393 | EVQLVQSGAEVKKPGASVKVSCKASGYKFTSYVMHWVR QAPGQGLEWMGYINPYNDVTKYAEKFQGRVTLTSDTSTS TAYMELSSLRSEDTAVYYCARGSYYDYEGFVYWGQGTLV TVSS |
| 8 | VL | TPP-1357, TPP-1369, TPP-1371, TPP-1373 | QIQMTQSPSSLSASVGDRVTITCSATSSVRYMHWYQQKPG KAPKRWIYDTSKLARGVPSRFSGSGSGTDYTLTISSLQPED AATYYCQQWSSNPLTFGGGTKVEIK |
| 9 | VH | TPP-1358 | EVQLVQSGAEVKKPGASVKVSCKASGYKFNRYVMHWVR QAPGQGLEWMGYINPYNDVTKYAEKFQGRVTLTSDTSTS TAYMELSSLRSEDTAVHYCARGSYYDYEGFVYWGQGTLV TVSS |

-continued

| SEQ ID NO: | Description | | Sequence: |
|---|---|---|---|
| 10 | VH | TPP-1359 | EVQLVQSGAEVKKPGASVKVSCKASGYKFSRYVMHWVR QAPGQGLEWMGYINPRNDVTKYAEKFQGRVTLTSDTSTS TAYMELSSLRSEDTAVHYCARGSYYDYDGFVYWGQGTL VTVSS |
| 11 | VH | TPP-1360, TPP-1362, TPP-1368, TPP-1369, TPP-666, TPP-668, TPP-879, TPP-876 | EVQLVQSGAEVKKPGASVKVSCKASGYKFTRYVMHWVR QAPGQGLEWMGYINPYNDVTKYAEKFQGRVTLTSDTSTS TAYMELSSLRSEDTAVHYCARGSYYDYEGFVYWGQGTLV TVSS |
| 12 | VH | TPP-1361, TPP-1370, TPP-1371 | EVQLVQSGAEVKKPGASVKVSCKASGYKFSSYVMHWVR QAPGQGLEWMGYINPRNDVTKYAEKFQGRVTLTSDTSTS TAYMELSSLRSEDTAVHYCARGSYYDYEGFVYWGQGTLV TVSS |
| 13 | VL | TPP-1362 | QIQMTQSPSSLSASVGDRVTITCSATSSVNYMHWYQQKPG KAPKRWIYDTSKLARGVPSRFSGSGSGTDYTLTISSLQPED AATYYCQQWSNNPLTFGGGTKVEIK |
| 14 | VH | TPP-1363, TPP-1372, TPP-1373 | EVQLVQSGAEVKKPGASVKVSCKASGYKFTSYVMHWVR QAPGQGLEWMGYINPYKDVTKYAEKFQGRVTLTSDTSTS TAYMELSSLRSEDTAVYYCARGSYYDYEGFVYWGQGTLV TVSS |
| 15 | VH | TPP-1364 | EVQLVQSGAEVKKPGASVKVSCKASGYKFNNYVMHWVR QAPGQGLEWMGYINPRNDVTKYAEKFQGRVTLTSDTSTS TAYMELSSLRSEDTAVHYCARGSYYDYEGFVYWGQGTLV TVSS |
| 16 | VH | TPP-1365 | EVQLVQSGAEVKKPGASVKVSCKASGYKFNRYVMHWVR QAPGQGLEWMGYINPYNDITKYAEKFQGRVTLTSDTSTST AYMELSSLRSEDTAVHYCARGSYYDYEGFVYWGQGTLVT VSS |
| 17 | VH | TPP-1366 | EVQLVQSGAEVKKPGASVKVSCKASGYKFTRYVMHWVR QAPGQGLEWMGYINPYKDVTKYAEKFQGRVTLTSDTSTS TAYMELSSLRSEDTAVHYCARGSYYDYDGFVYWGQGTL VTVSS |
| 18 | VL | TPP-1367, TPP-1368, TPP-1370, TPP-1372, TPP-1389, TPP-1392, TPP-1393, TPP-667, TPP-668, TPP-670 | QIQMTQSPSSLSASVGDRVTITCSATSSVSYMHWYQQKPG KAPKRWIYDTSKLARGVPSRFSGSGSGTDYTLTISSLQPED AATYYCQQWSSNPLTFGGGTKVEIK |
| 19 | VH | TPP-1375 | EVQLVQSGAEVKKPGASVKVSCKASGYKFRSYVMHWVR QAPGQGLEWMGYINPYNDVTKYAEKFQGRVTLTSDTSTS TAYMELSSLRSEDTAVHYCARGSYYDYEGFVYWGQGTLV TVSS |
| 20 | VH | TPP-1376 | EVQLVQSGAEVKKPGASVKVSCKASGYKFSYVMHWVR QAPGQGLEWMGYINPYNDVTKYAEKFQGRVTLTSDTSTS TAYMELSSLRSEDTAVHYCARGSYYDYEGFVYWGQGTLV TVSS |
| 21 | VH | TPP-1377 | EVQLVQSGAEVKKPGASVKVSCKASGYKFTKYVMHWVR QAPGQGLEWMGYINPYNDVTKYAEKFQGRVTLTSDTSTS TAYMELSSLRSEDTAVHYCARGSYYDYEGFVYWGQGTLV TVSS |
| 22 | VH | TPP-1378, TPP-669, TPP-670, TPP-894, TPP-891 | EVQLVQSGAEVKKPGASVKVSCKASGYKFTSYVMHWVR QAPGQGLEWMGYINPRNDVTKYAEKFQGRVTLTSDTSTS TAYMELSSLRSEDTAVHYCARGSYYDYEGFVYWGQGTLV TVSS |
| 23 | VH | TPP-1379 | EVQLVQSGAEVKKPGASVKVSCKASGYKFTSYVMHWVR QAPGQGLEWMGYINPKNDVTKYAEKFQGRVTLTSDTSTS TAYMELSSLRSEDTAVHYCARGSYYDYEGFVYWGQGTLV TVSS |

-continued

| SEQ ID NO: | Description: | | Sequence: |
|---|---|---|---|
| 24 | VH | TPP-1380 | EVQLVQSGAEVKKPGASVKVSCKASGYKFTSYVMHWVR QAPGQGLEWMGYINPYRDVTKYAEKFQGRVTLTSDTSTS TAYMELSSLRSEDTAVHYCARGSYYDYEGFVYWGQGTLV TVSS |
| 25 | VH | TPP-1381 | EVQLVQSGAEVKKPGASVKVSCKASGYKFTSYVMHWVR QAPGQGLEWMGYINPYKDVTKYAEKFQGRVTLTSDTSTS TAYMELSSLRSEDTAVHYCARGSYYDYEGFVYWGQGTLV TVSS |
| 26 | VL | TPP-1382 | QIQMTQSPSSLSASVGDRVTITCSATSSVRYMHWYQQKPG KAPKRWIYDTSKLASGVPSRFSGSGSGTDYTLTISSLQPED AATYYCQQWSSNPLTFGGGTKVEIK |
| 27 | VL | TPP-1383 | QIQMTQSPSSLSASVGDRVTITCSATSSVKYMHWYQQKPG KAPKRWIYDTSKLASGVPSRFSGSGSGTDYTLTISSLQPED AATYYCQQWSSNPLTFGGGTKVEIK |
| 28 | VL | TPP-1384 | QIQMTQSPSSLSASVGDRVTITCSATSSVSYMHWYQQKPG KAPKRWIYDTSKLAKGVPSRFSGSGSGTDYTLTISSLQPED AATYYCQQWSSNPLTFGGGTKVEIK |
| 29 | VH | TPP-1385 | EVQLVQSGAEVKKPGASVKVSCKASGYKFTSYVMHWVR QAPGQGLEWMGYINPHNDVTKYAEKFQGRVTLTSDTSTS TAYMELSSLRSEDTAVHYCARGSYYDYEGFVYWGQGTLV TVSS |
| 30 | VH | TPP-1386 | EVQLVQSGAEVKKPGASVKVSCKASGYKFTHYVMHWVR QAPGQGLEWMGYINPYNDVTKYAEKFQGRVTLTSDTSTS TAYMELSSLRSEDTAVHYCARGSYYDYEGFVYWGQGTLV TVSS |
| 31 | VH | TPP-1388, TPP-1389, TPP-1292 | EVQLVQSGAEVKKPGASVKVSCKASGYKFTRYVMHWVR QAPGQGLEWMGYINPYNDVTKYAEKFQGRVTLTSDTSTS TAYMELSSLRSEDTAVYYCARGSYYDYEGFVYWGQGTLV TVSS |
| 32 | VH | TPP-1390, TPP-1392, TPP-1293, TPP-1294, TPP-1295 | EVQLVQSGAEVKKPGASVKVSCKASGYKFTSYVMHWVR QAPGQGLEWMGYINPRNDVTKYAEKFQGRVTLTSDTSTS TAYMELSSLRSEDTAVYYCARGSYYDYEGFVYWGQGTLV TVSS |
| 33 | VH | TPP-1391 | EVQLVQSGAEVKKPGASVKVSCKASGYKFTSYVMHWVR QAPGQGLEWMGYINPYRDVTKYAEKFQGRVTLTSDTSTS TAYMELSSLRSEDTAVYYCARGSYYDYEGFVYWGQGTLV TVSS |
| 34 | VH | TPP-1394 | EVQLVQSGAEVKKPGASVKVSCKASGYKFTSYVMHWVR QAPGQGLEWMGYINPYNDVTKYAQKFQGRVTLTSDTSTS TAYMELSSLRSEDTAVYYCARGSYYDYDGFVYWGQGTL VTVSS |
| 35 | TCER chain2 | TPP-666, TPP-879 | ILNVEQSPQSLHVQEGDSTKFTCSFPVKEFQDLHWYRKET AKSPEFLFYFGPYGKEKKKGRISATLNTKEGYSYLYITDSQ PEDSATYLCALYNNYDMRFGAGTRLTVKPGGGSGGGGEV QLVQSGAEVKKPGASVKVSCKASGYKFTRYVMHWVRQA PGQGLEWMGYINPYNDVTKYAEKFQGRVTLTSDTSTSTA YMELSSLRSEDTAVHYCARGSYYDYEGFVYWGQGTLVTV SSEPKSSDKTHTCPPCPAPPVAGPSVFLFPPKPKDTLMISRT PEVTCVVVDVSHEDPEVKFNWYVDGVEVHNAKTKPREEQ YQSTYRVVSVLTVLHQDWLNGKEYKCKVSNKALPASIEK TISKAKGQPREPQVCTLPPSRDELTKNQVSLSCAVKGFYPS DIAVEWESNGQPENNYKTTPPVLDSDGSFFLVSKLTVDKS RWQQGNVFSCSVMHEALHNHYTQKSLSLSP |
| 36 | TCER chain 2 | TPP-1294, TPP-1295 | ILNVEQSPQSLHVQEGDSTKFTCSFPVKEFQDLHWYRKET AKSPEFLFYFGPYGKEKKKGRISATLNTKEGYSYLYITDSQ PEDSATYLCALYNNYDMRFGAGTRLTVKPGGGSGGGGEV QLVQSGAEVKKPGASVKVSCKASGYKFTSYVMHWVRQA PGQGLEWMGYINPRNDVTKYAEKFQGRVTLTSDTSTSTA YMELSSLRSEDTAVYYCARGSYYDYEGFVYWGQGTLVTV SSEPKSSDKTHTCPPCPAPPVAGPSVFLFPPKPKDTLMISRT PEVTCVVVDVSHEDPEVKFNWYVDGVEVHNAKTKPREEQ YQSTYRVVSVLTVLHQDWLNGKEYKCKVSNKALPASIEK TISKAKGQPREPQVCTLPPSRDELTKNQVSLSCAVKGFYPS |

| SEQ ID NO: Description: | | Sequence: |
|---|---|---|
| | | DIAVEWESNGQPENNYKTTPPVLDSDGSFFLVSKLTVDKS<br>RWQQGNVFSCSVMHEALHNHYTQKSLSLSP |
| 37 TCER chain2 | TPP-667, TPP-226 | ILNVEQSPQSLHVQEGDSTKFTCSFPVKEFQDLHWYRKET<br>AKSPEFLFYFGPYGKEKKKGRISATLNTKEGYSYLYITDSQ<br>PEDSATYLCALYNNYDMRFGAGTRLTVKPGGGSGGGGEV<br>QLVQSGAEVKKPGASVKVSCKASGYKFTSYVMHWVRQA<br>PGQGLEWMGYINPYNDVTKYAEKFQGRVTLTSDTSTSTA<br>YMELSSLRSEDTAVHYCARGSYYDYEGFVYWGQGTLVTV<br>SSEPKSSDKTHTCPPCPAPPVAGPSVFLFPPKPKDTLMISRT<br>PEVTCVVVDVSHEDPEVKFNWYVDGVEVHNAKTKPREEQ<br>YQSTYRVVSVLTVLHQDWLNGKEYKCKVSNKALPASIEK<br>TISKAKGQPREPQVCTLPPSRDELTKNQVSLSCAVKGFYPS<br>DIAVEWESNGQPENNYKTTPPVLDSDGSFFLVSKLTVDKS<br>RWQQGNVFSCSVMHEALHNHYTQKSLSLSP |
| 38 TCER chain2 | TPP-669, TPP-894 | ILNVEQSPQSLHVQEGDSTKFTCSFPVKEFQDLHWYRKET<br>AKSPEFLFYFGPYGKEKKKGRISATLNTKEGYSYLYITDSQ<br>PEDSATYLCALYNNYDMRFGAGTRLTVKPGGGSGGGGEV<br>QLVQSGAEVKKPGASVKVSCKASGYKFTSYVMHWVRQA<br>PGQGLEWMGYINPRNDVTKYAEKFQGRVTLTSDTSTSTA<br>YMELSSLRSEDTAVHYCARGSYYDYEGFVYWGQGTLVTV<br>SSEPKSSDKTHTCPPCPAPPVAGPSVFLFPPKPKDTLMISRT<br>PEVTCVVVDVSHEDPEVKFNWYVDGVEVHNAKTKPREEQ<br>YQSTYRVVSVLTVLHQDWLNGKEYKCKVSNKALPASIEK<br>TISKAKGQPREPQVCTLPPSRDELTKNQVSLSCAVKGFYPS<br>DIAVEWESNGQPENNYKTTPPVLDSDGSFFLVSKLTVDKS<br>RWQQGNVFSCSVMHEALHNHYTQKSLSLSP |
| 39 TCER chain 1 | TPP-226, TPP-879, TPP-894, TPP-1295 | QIQMTQSPSSLSASVGDRVTITCSATSSVSYMHWYQQKPG<br>KAPKRWIYDTSKLASGVPSRFSGSGSGTDYTLTISSLQPED<br>AATYYCQQWSSNPLTFGGGTKVEIKGGGSGGGGGVIQSPR<br>HEVTEMGQEVTLRCKPISGHNSLFWYRETPMQGLELLIYF<br>QNTAVIDDSGMPEDRFSAKMPNASFSTLKIQPSEPRDSAVY<br>FCASSPGATDKQYFGPGTRLTVLEPKSSDKTHTCPPCPAPP<br>VAGPSVFLFPPKPKDTLMISRTPEVTCVVVDVSHEDPEVKF<br>NWYVDGVEVHNAKTKPREEQYQSTYRVVSVLTVLHQDW<br>LNGKEYKCKVSNKALPASIEKTISKAKGQPREPQVYTLPPC<br>RDELTKNQVSLWCLVKGFYPSDIAVEWESNGQPENNYKT<br>TPPVLDSDGSFFLYSKLTVDKSRWQQGNVFSCSVMHEALH<br>NHYTQKSLSLSP |
| 40 scFv | | EVQLVQSGAEVKKPGASVKVSCKASGYKFTSYVMHWVR<br>QAPGQGLEWMGYINPYNDVTKYAEKFQGRVTLTSDTSTS<br>TAYMELSSLRSEDTAVHYCARGSYYDYEGFVYWGQGTLV<br>TVSSGGGSEGGGSEGGGSEGGGQIQMTQSPSSLSASVGDR<br>VTITCSATSSVSYMHWYQQKPGKAPKRWIYDTSKLASGVP<br>SRFSGSGSGTDYTLTISSLQPEDAATYYCQQWSSNPLTFGG<br>GTKVEIK |
| 41 scFv | | EVQLVQSGAEVKKPGASVKVSCKASGYKFTSYVMHWVR<br>QAPGQGLEWMGYINPYNDVTKYAEKFQGRVTLTSDTSTS<br>TAYMELSSLRSEDTAVYYCARGSYYDYEGFVYWGQGTLV<br>TVSSGGGSEGGGSEGGGSEGGGQIQMTQSPSSLSASVGDR<br>VTITCSATSSVRYMHWYQQKPGKAPKRWIYDTSKLARGV<br>PSRFSGSGSGTDYTLTISSLQPEDAATYYCQQWSSNPLTFG<br>GGTKVEIK |
| 42 scFv | | EVQLVQSGAEVKKPGASVKVSCKASGYKFNRYVMHWVR<br>QAPGQGLEWMGYINPYNDVTKYAEKFQGRVTLTSDTSTS<br>TAYMELSSLRSEDTAVHYCARGSYYDYEGFVYWGQGTLV<br>TVSSGGGSEGGGSEGGGSEGGGQIQMTQSPSSLSASVGDR<br>VTITCSATSSVSYMHWYQQKPGKAPKRWIYDTSKLASGVP<br>SRFSGSGSGTDYTLTISSLQPEDAATYYCQQWSSNPLTFGG<br>GTKVEIK |
| 43 scFv | | EVQLVQSGAEVKKPGASVKVSCKASGYKFSRYVMHWVR<br>QAPGQGLEWMGYINPRNDVTKYAEKFQGRVTLTSDTSTS<br>TAYMELSSLRSEDTAVHYCARGSYYDYDGFVYWGQGTL<br>VTVSSGGGSEGGGSEGGGSEGGGQIQMTQSPSSLSASVGD<br>RVTITCSATSSVSYMHWYQQKPGKAPKRWIYDTSKLASG<br>VPSRFSGSGSGTDYTLTISSLQPEDAATYYCQQWSSNPLTF<br>GGGTKVEIK |

| SEQ ID NO: Description: | Sequence: |
|---|---|
| 44 scFv | EVQLVQSGAEVKKPGASVKVSCKASGYKFTRYVMHWVRQAPGQGLEWMGYINPYNDVTKYAEKFQGRVTLTSDTSTSTAYMELSSLRSEDTAVHYCARGSYYDYEGFVYWGQGTLVTVSSGGGSEGGGSEGGGSEGGGQIQMTQSPSSLSASVGDRVTITCSATSSVSYMHWYQQKPGKAPKRWIYDTSKLASGVPSRFSGSGSGTDYTLTISSLQPEDAATYYCQQWSSNPLTFGGGTKVEIK |
| 45 scFv | EVQLVQSGAEVKKPGASVKVSCKASGYKFSSYVMHWVRQAPGQGLEWMGYINPRNDVTKYAEKFQGRVTLTSDTSTSTAYMELSSLRSEDTAVHYCARGSYYDYEGFVYWGQGTLVTVSSGGGSEGGGSEGGGSEGGGQIQMTQSPSSLSASVGDRVTITCSATSSVSYMHWYQQKPGKAPKRWIYDTSKLASGVPSRFSGSGSGTDYTLTISSLQPEDAATYYCQQWSSNPLTFGGGTKVEIK |
| 46 scFv | EVQLVQSGAEVKKPGASVKVSCKASGYKFTRYVMHWVRQAPGQGLEWMGYINPYNDVTKYAEKFQGRVTLTSDTSTSTAYMELSSLRSEDTAVHYCARGSYYDYEGFVYWGQGTLVTVSSGGGSEGGGSEGGGSEGGGQIQMTQSPSSLSASVGDRVTITCSATSSVNYMHWYQQKPGKAPKRWIYDTSKLARGVPSRFSGSGSGTDYTLTISSLQPEDAATYYCQQWSNNPLTFGGGTKVEIK |
| 47 scFv | EVQLVQSGAEVKKPGASVKVSCKASGYKFTSYVMHWVRQAPGQGLEWMGYINPYKDVTKYAEKFQGRVTLTSDTSTSTAYMELSSLRSEDTAVYYCARGSYYDYEGFVYWGQGTLVTVSSGGGSEGGGSEGGGSEGGGQIQMTQSPSSLSASVGDRVTITCSATSSVSYMHWYQQKPGKAPKRWIYDTSKLASGVPSRFSGSGSGTDYTLTISSLQPEDAATYYCQQWSSNPLTFGGGTKVEIK |
| 48 scFv | EVQLVQSGAEVKKPGASVKVSCKASGYKFNNYVMHWVRQAPGQGLEWMGYINPRNDVTKYAEKFQGRVTLTSDTSTSTAYMELSSLRSEDTAVHYCARGSYYDYEGFVYWGQGTLVTVSSGGGSEGGGSEGGGSEGGGQIQMTQSPSSLSASVGDRVTITCSATSSVSYMHWYQQKPGKAPKRWIYDTSKLASGVPSRFSGSGSGTDYTLTISSLQPEDAATYYCQQWSSNPLTFGGGTKVEIK |
| 49 scFv | EVQLVQSGAEVKKPGASVKVSCKASGYKFNRYVMHWVRQAPGQGLEWMGYINPYNDITKYAEKFQGRVTLTSDTSTAYMELSSLRSEDTAVHYCARGSYYDYEGFVYWGQGTLVTVSSGGGSEGGGSEGGGSEGGGQIQMTQSPSSLSASVGDRVTITCSATSSVSYMHWYQQKPGKAPKRWIYDTSKLASGVPSRFSGSGSGTDYTLTISSLQPEDAATYYCQQWSSNPLTFGGGTKVEIK |
| 50 scFv | EVQLVQSGAEVKKPGASVKVSCKASGYKFTRYVMHWVRQAPGQGLEWMGYINPYKDVTKYAEKFQGRVTLTSDTSTSTAYMELSSLRSEDTAVHYCARGSYYDYDGFVYWGQGTLVTVSSGGGSEGGGSEGGGSEGGGQIQMTQSPSSLSASVGDRVTITCSATSSVSYMHWYQQKPGKAPKRWIYDTSKLASGVPSRFSGSGSGTDYTLTISSLQPEDAATYYCQQWSSNPLTFGGGTKVEIK |
| 51 scFv | EVQLVQSGAEVKKPGASVKVSCKASGYKFTSYVMHWVRQAPGQGLEWMGYINPYNDVTKYAEKFQGRVTLTSDTSTSTAYMELSSLRSEDTAVHYCARGSYYDYEGFVYWGQGTLVTVSSGGGSEGGGSEGGGSEGGGQIQMTQSPSSLSASVGDRVTITCSATSSVSYMHWYQQKPGKAPKRWIYDTSKLARGVPSRFSGSGSGTDYTLTISSLQPEDAATYYCQQWSSNPLTFGGGTKVEIK |
| 52 HCDR1 Kabat | SYVMH |
| 53 HCDR2 Kabat | YINPYNDVTKYX$_1$X$_2$KFX$_3$G, X1 is A or N; X2 is E or Q; and/or X3 is Q or K |
| 54 LCDR1 | SATSSVSYMH |
| 55 LCDR2 | DTSKLAS |

| SEQ ID NO: | Description: | | Sequence: |
|---|---|---|---|
| 56 | HCDR3 Kabat | | GSYYDYX₁GFVY, wherein X1 is D or E |
| 57 | LCDR3 Kabat | | QQWSX₁X₂X₃LT, wherein X1 is S or N, X₂ is an amino acid selected from the group consisting of Q, D, H, S, Y, A and N; and X3 is P or A |
| 58 | VH BMA03 | VH Humanized BMA031 Shearman et al. | EVQLQQSGPELVKPGASVKMSCKASGYKFTSYVMHWVK QKPGQGLEWIGYINPYNDVTKYNEKFKGKATLTSDKSSST AYMELSSLTSEDSAVHYCARGSYYDYDGFVYWGQGTLVT VSA |
| 59 | VL BMA031 | VL Humanized BMA031 Shearman et al. | QIVLTQSPAIMSASPGEKVTMTCSATSSVSYMHWYQQKSG TSPKRWIYDTSKLASGVPARFSGSGSGTSYSLTISSMEAED AATYYCQQWSSNPLTFGAGTKLELK |
| 60 | HC BMA031 (V36) | | EVQLVQSGAEVKKPGASVKVSCKASGYKFTSYVMHWVR QAPGQGLEWMGYINPYNDVTKYAEKFQGRVTLTSDTSTS TAYMELSSLRSEDTAVHYCARGSYYDYEGFVYWGQGTLV TVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKKVEPKSCDKTHTCPPCPAPELL GGPSVFLFPPKPKDTLMISRTPEVTCVVVDVSHEDPEVKFN WYVDGVEVHNAKTKPREEQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 61 | huIgGI Fc | huIgGI (G1m17, 1), including hinge | EPKSCDKTHTCPPCPAPELLGGPSVFLFPPKPKDTLMISRTP EVTCVVVDVSHEDPEVKFNWYVDGVEVHNAKTKPREEQ YNSTYRVVSVLTVLHQDWLNGKEYKCKVSNKALPAPIEK TISKAKGQPREPQVYTLPPSRDELTKNQVSLTCLVKGFYPS DIAVEWESNGQPENNYKTTPPVLDSDGSFFLYSKLTVDKS RWQQGNVFSCSVMHEALHNHYTQKSLSLSPGK |
| 62 | HCDRI Chothia | | GYKFTSY |
| 63 | HCDR2 Chothia | | NPYNDV |
| 64 | HCDR3 | | GSYYDYEGFVY |
| 65 | LCDR3 | | QQWSSX₂X₃LT, wherein X2 is an amino acid selected from the group consisting of Q, D, H, S, Y, A and N; and X3 is P or A |
| 66 | LCDR3 | | QQWSX₁NX₃LT, wherein X1 is S or N; and X3 is P or A |
| 67 | LCDR3 | | QQWSX₁X₂PLT, wherein X1 is S or N, and X2 is an amino acid selected from the group consisting of Q, D, H, S, Y, A and N. |
| 68 | LCDR3 | | QQWSSQPLT |
| 69 | LCDR3 | | QQWSSDPLT |
| 70 | LCDR3 | | QQWSSHPLT |
| 71 | LCDR3 | | QQWSSSPLT |
| 72 | LCDR3 | | QQWSSYPLT |
| 73 | LCDR3 | | QQWSSAPLT |
| 74 | LCDR3 | | QQWSSNPLT |
| 75 | LCDR3 | | QQWSSQALT |
| 76 | LCDR3 | | QQWSSDALT |
| 77 | LCDR3 | | QQWSSHALT |
| 78 | LCDR3 | | QQWSSSALT |
| 79 | LCDR3 | | QQWSSYALT |

| SEQ ID NO: | Description: | Sequence: |
|---|---|---|
| 80 | LCDR3 | QQWSSAALT |
| 81 | LCDR3 | QQWSSNALT |
| 82 | LCDR3 | QQWSNQPLT |
| 83 | LCDR3 | QQWNSDPLT |
| 84 | LCDR3 | QQWNSHPLT |
| 85 | LCDR3 | QQWNSSPLT |
| 86 | LCDR3 | QQWNSYPLT |
| 87 | LCDR3 | QQWNSAPLT |
| 88 | LCDR3 | QQWNSNPLT |
| 89 | LCDR3 | QQWSNQALT |
| 90 | LCDR3 | QQWNSDALT |
| 91 | LCDR3 | QQWNSHALT |
| 92 | LCDR3 | QQWNSSALT |
| 93 | LCDR3 | QQWNSYALT |
| 94 | LCDR3 | QQWNSAALT |
| 95 | LCDR3 | QQWNSNALT |
| 96 | LCDR3 | QQWSX$_1$NPLT, wherein X1 is S or N |
| 97 | GL1_BM_VH28_HV | QVQLVQSGAEVKKPGASVKVSCKASGYKFTSYVMHWVKQAPGQGLEWIGYINPYNDVTKYNEKFKGRVTITRDTSASTAYMELSSLRSEDTAVYYCARGSYYDYDGFVYWGQGTLVTVSS |
| 98 | GL1_BM_VH31_HV | QVQLVQSGAEVKKPGASVKVSCKASGYKFTSYVMHWVRQAPGQGLEWIGYINPYNDVTKYNEKFKGRVTITRDTSASTAYMELSSLRSEDTAVYYCARGSYYDYDGFVYWGQGTLVTVSS |
| 99 | HEBE1_H10_HV | EVQLQQSGPELVKPGASVKMSCKASGYKFTSYVMHWVKQAPGKGLEWIGYINPYNDVTKYNEKFKGKATLSRDNSKNTLYLQMNSLRAEDTAVHYCARGSYYDYDGFVYWGQGTLVTVSS |
| 100 | HEBE1_H66_HV | EVQLLQSGGGLVQPGGSLRLSCAASGYKFTSYVMHWVRQAPGKGLEWVGYINPYNDVTKYNEKFKGRFTLSRDNSKNTLYLQMNSLRAEDTAVYYCARGSYYDYDGFVYWGQGTLVTVSS |
| 101 | HEBE1_H71_HV | EVQLLESGGGLVQPGGSVRLSCAASGYKFTSYVMHWVRQAPGKGLEWVGYINPYNDVTKYNEKFKGRFTLSRDNSKNTLYLQMNSLRAEDTAVYYCARGSYYDYDGFVYWGQGTLVTVSS |
| 102 | GL1BMVK43_VL | EIVLTQSPATLSLSPGERATLSCSATSSVSYMHWYQQKPGQAPRRLIYDTSKLASGVPARFSGSGSGTSYTLTISSLEPEDFAVYYCQQWSSNPLTFGGGTKVEIK |
| 103 | HFR1 | EVQLVQSGAEVKKPGASVKVSCKASGYKFT |
| 104 | HFR2 | WVRQAPGQGLEWMG |
| 105 | HFR3 | RVTLTSDTSTSTAYMELSSLRSEDTAVYYCAR |
| 106 | HFR4 | WGQGTLVTVSS |
| 107 | LFR1 | QIQMTQSPSSLSASVGDRVTITC |
| 108 | LFR2 | WYQQKPGKAPKRWIY |

| SEQ ID NO: | Description: | Sequence: |
|---|---|---|
| 109 | LFR3 | GVPSRFSGSGSGTDYTLTISSLQPEDAATYYC |
| 110 | LFR4 | FGGGTKVEIK |
| 111 | IgG Fc | EPKSSDKTHTCPPCPAPPVAGPSVFLFPPKPKDTLMISRTPE VTCVVVDVSHEDPEVKFNWYVDGVEVHNAKTKPREEQY QSTYRVVSVLTVLHQDWLNGKEYKCKVSNKALPASIEKTI SKAKGQPREPQVCTLPPSRDELTKNQVSLSCAVKGFYPSDI AVEWESNGQPENNYKTTPPVLDSDGSFFLVSKLTVDKSR WQQGNVFSCSVMHEALHNHYTQKSLSLSP |
| 112 | IgG Fc | EPKSSDKTHTCPPCPAPPVAGPSVFLFPPKPKDTLMISRTPE VTCVVVDVSHEDPEVKFNWYVDGVEVHNAKTKPREEQY QSTYRVVSVLTVLHQDWLNGKEYKCKVSNKALPASIEKTI SKAKGQPREPQVYTLPPCRDELTKNQVSLWCLVKGFYPSD IAVEWESNGQPENNYKTTPPVLDSDGSFFLYSKLTVDKSR WQQGNVFSCSVMHEALHNHYTQKSLSLSP |

The invention claimed is:

1. An antigen binding polypeptide comprising a heavy chain variable domain (VH) and a light chain variable domain (VL), wherein
   (1) the VH comprises
      (a) a heavy chain complementarity determining region 1 (HCDR1) comprising the amino acid sequence of SEQ ID NO: 52,
      (b) a HCDR2 comprising the amino acid sequence of YINPYNDVTKYX$_1$X$_2$KFX$_3$G (SEQ ID NO: 53), wherein
         X$_1$ is A;
         X$_2$ is E; and
         X$_3$ is Q;

wherein the tyrosine (Y) at position 53 of the HCDR2 is substituted with an arginine (R), wherein the 2$^{nd}$ tyrosine (Y) from the N-terminus of SEQ ID NO: 53 is substituted with an arginine (R), and wherein the 2$^{nd}$ tyrosine (Y) is at position 53 of the HCDR2 according to Kabat numbering,
      (c) a HCDR3 comprising the amino acid sequence of SEQ ID NO: 64, and
      (d) heavy chain framework regions (HFR)1-4;
   (2) the VL comprises
      (a) a light chain complementarity determining region 1 (LCDR1) comprising the amino acid sequence of SEQ ID NO: 54, (b) a LCDR2 comprising the amino acid sequence of SEQ ID NO: 55,
(c) a LCDR3 comprising the amino acid sequence of SEQ ID NO: 74, and
(d) light chain framework regions (LFR)1-4;
wherein
(i) position 30 in HFR1 according to Kabat numbering is a threonine (T) or is substituted with a positively charged amino acid, and/or
(ii) position 90 in HFR3 according to Kabat numbering is substituted with a tyrosine Y residue,
and wherein the antigen binding polypeptide specifically binds to an α/β T cell receptor (TCR)/CD3 complex.

2. The antigen binding polypeptide according to claim 1, wherein
the positively charged amino acid in the heavy chain at position 30 is R, K or H.

3. The antigen binding polypeptide according to claim 1, wherein the VH and VL form a first binding site, and wherein the antigen binding polypeptide comprises a second antigen binding site.

4. The antigen binding polypeptide according to claim 1, wherein threonine (T) at position 30 in the heavy chain is substituted with asparagine (N) or serine (S).

5. A nucleic acid or set of nucleic acids coding for an antigen binding polypeptide according to claim 1 or a nucleic acid vector comprising said nucleic acid.

6. A recombinant host cell comprising the vector according to claim 5, wherein said host cell is
(i) a lymphocyte, optionally a T lymphocyte or T lymphocyte progenitor cell, or a CD4 or CD8 positive T cell; or
(ii) a cell for recombinant expression, such as a Chinese Hamster Ovary (CHO) cell or a yeast cell.

7. A pharmaceutical composition comprising the antigen polypeptide according to claim 1, a pharmaceutically acceptable carrier, diluent stabilizer, and/or excipient.

8. A method of producing the antigen binding polypeptide according to claim 1, comprising
(i) providing a suitable host cell,
(ii) providing a genetic construct comprising a coding sequence encoding the antigen binding polypeptide,
(iii) introducing said genetic construct into said suitable host cell, and
(iv) expressing said genetic construct by said suitable host cell.

9. A method for improving or maintaining the binding and/or improving the stability of an antigen binding polypeptide comprising a heavy chain variable domain (VH) and a light chain variable domain (VL), wherein
(1) the VH comprises
(a) a heavy chain complementarity determining region 1 (HCDR1) comprising the amino acid sequence of SEQ ID NO: 52 (SYVMH),
(b) a HCDR2 comprising the amino acid sequence of YINPYNDVTKYX$_1$X$_2$KFX$_3$G (SEQ ID NO: 53),
wherein X$_1$ is A;
X$_2$ is E; and
X$_3$ is Q;
wherein the tyrosine (Y) at position 53 of the HCDR2 is substituted with an arginine (R), wherein the 2$^{nd}$ tyrosine (Y) from the N-terminus of SEQ ID NO: 53 is substituted with an arginine (R), and wherein the 2$^{nd}$ tyrosine (Y) is at position 53 of the HCDR2 according to Kabat numbering,
(c) a HCDR3 comprising the amino acid sequence of SEQ ID NO: 64, and
(d) heavy chain framework regions (HFR)1-4;
(2) the VL comprises
(a) a light chain complementarity determining region 1 (LCDR1) comprising the amino acid sequence of SEQ ID NO: 54 (SATSSVSYMH),
(b) a LCDR2 comprising the amino acid sequence of SEQ ID NO: 55 (DTSKLAS),
(c) a LCDR3 comprising the amino acid sequence of SEQ ID NO: 74, and
(d) light chain frameworks (LCR)1-4;
wherein
(i) position 30 in HFR1 according to Kabat numbering is a threonine (T) or is substituted with a positively charged amino acid, and/or
(ii) position 90 in HFR3 according to Kabat numbering is substituted with a tyrosine (Y) residue,
wherein
(1) the binding of the antigen binding polypeptide to an α/β T cell receptor (TCR)/CD3 complex is increased compared to the parental antigen binding polypeptide;
(2) the binding of the antigen binding polypeptide to an α/β T cell receptor (TCR)/CD3 complex is maintained or increased and the stability of the antigen binding polypeptide is increased compared to the parental antigen binding polypeptide; or
(3) the stability of the antigen binding polypeptide is increased compared to the parental antigen binding polypeptide.

10. A method for detecting, determining or enriching T cells expressing the α/β TCR/CD3 complex, comprising the step of contacting cells with the antigen binding polypeptide according to claim 1.

11. A method of treating a patient who has cancer, comprising administering to the patient the composition of claim 7.

12. The antigen binding polypeptide according to claim 2, wherein the positively charged amino acid in the heavy chain at position 30 is R.

13. The antigen binding polypeptide according to claim 2, wherein the positively charged amino acid in the heavy chain at position 30 is K.

14. The antigen binding polypeptide according to claim 2, wherein the positively charged amino acid in the heavy chain at position 30 is H.

15. The antigen binding polypeptide according to claim 1, wherein the VH comprises SEQ ID NO: 32 and the VL comprises SEQ ID NO: 2.

* * * * *

SEQUENCE LISTING

<160> NUMBER OF SEQ ID NOS: 112

<210> SEQ ID NO 1
<211> LENGTH: 120
<212> TYPE: PRT
<213> ORGANISM: Artificial Sequence
<220> FEATURE:
<223> OTHER INFORMATION: variable heavy chain of BMA031 (V36)

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
            85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
        115                 120

<210> SEQ ID NO 2
<211> LENGTH: 106
<212> TYPE: PRT
<213> ORGANISM: Artificial Sequence
<220> FEATURE:
<223> OTHER INFORMATION: variable light chain of BMA031 (V36)

<400> SEQUENCE: 2

Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Met
            20                  25                  30

His Trp Tyr Gln Gln Lys Pro Gly Lys Ala Pro Lys Arg Trp Ile Tyr
            35                  40                  45

Asp Thr Ser Lys Leu Ala Ser Gly Val Pro Ser Arg Phe Ser Gly Ser
 50                  55                  60

Gly Ser Gly Thr Asp Tyr Thr Leu Thr Ile Ser Ser Leu Gln Pro Glu
 65                  70                  75                  80

Asp Ala Ala Thr Tyr Tyr Cys Gln Gln Trp Ser Ser Asn Pro Leu Thr
                     85                  90                  95

Phe Gly Gly Gly Thr Lys Val Glu Ile Lys
                100                 105

<210> SEQ ID NO 3
<211> LENGTH: 112
<212> TYPE: PRT
<213> ORGANISM: Artificial Sequence
<220> FEATURE:
<223> OTHER INFORMATION: CH1 of BMA031 (V36) including His tag

<400> SEQUENCE: 3

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Lys Val Glu Pro Lys Ser Cys Gly Ser Gly His His His His His His
                100                 105                 110

<210> SEQ ID NO 4
<211> LENGTH: 107
<212> TYPE: PRT
<213> ORGANISM: Artificial Sequence
<220> FEATURE:
<223> OTHER INFORMATION: human kappa light chain constant domain

<400> SEQUENCE: 4

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                     85                  90                  95

Pro Val Thr Lys Ser Phe Asn Arg Gly Glu Cys
                100                 105

<210> SEQ ID NO 5

```
<211> LENGTH: 232
<212> TYPE: PRT
<213> ORGANISM: Artificial Sequence
<220> FEATURE:
<223> OTHER INFORMATION: Fab heavy chain BMA031 (V36)

<400> SEQUENCE: 5

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Ser Gly His His His His His His
225                 230

<210> SEQ ID NO 6
<211> LENGTH: 213
<212> TYPE: PRT
<213> ORGANISM: Artificial Sequence
<220> FEATURE:
<223> OTHER INFORMATION: Fab light chain BMA031 (V36)

<400> SEQUENCE: 6

Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Ala Ala Thr Tyr Tyr Cys Gln Gln Trp Ser Ser Asn Pro Leu Thr
```

```
                        85                  90                  95
Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 7
<211> LENGTH: 120
<212> TYPE: PRT
<213> ORGANISM: Artificial Sequence
<220> FEATURE:
<223> OTHER INFORMATION: VH_H90Y

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Asp Tyr Glu Gly Phe Val Tyr Trp Gly Gln
                100                 105                 110

Gly Thr Leu Val Thr Val Ser Ser
            115                 120

<210> SEQ ID NO 8
<211> LENGTH: 106
<212> TYPE: PRT
<213> ORGANISM: Artificial Sequence
<220> FEATURE:
<223> OTHER INFORMATION: VL_S31R_S56R

<400> SEQUENCE: 8

Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Arg Tyr Met
            20                  25                  30

His Trp Tyr Gln Gln Lys Pro Gly Lys Ala Pro Lys Arg Trp Ile Tyr
        35                  40                  45
```

```
Asp Thr Ser Lys Leu Ala Arg Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
                100                 105
```

<210> SEQ ID NO 9
<211> LENGTH: 120
<212> TYPE: PRT
<213> ORGANISM: Artificial Sequence
<220> FEATURE:
<223> OTHER INFORMATION: VH_T30N_S31R

<400> SEQUENCE: 9

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Asn Arg Tyr
                20                  25                  30

Val Met His Trp Val Arg Gln Ala Pro Gly Gln Gly Leu Glu Trp Met
            35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
                100                 105                 110

Gly Thr Leu Val Thr Val Ser Ser
            115                 120
```

<210> SEQ ID NO 10
<211> LENGTH: 120
<212> TYPE: PRT
<213> ORGANISM: Artificial Sequence
<220> FEATURE:
<223> OTHER INFORMATION: VH_T30S_S31R_Y53R_E100aD

<400> SEQUENCE: 10

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Ser Arg Tyr
                20                  25                  30

Val Met His Trp Val Arg Gln Ala Pro Gly Gln Gly Leu Glu Trp Met
            35                  40                  45

Gly Tyr Ile Asn Pro Arg Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120
```

```
<210> SEQ ID NO 11
<211> LENGTH: 120
<212> TYPE: PRT
<213> ORGANISM: Artificial Sequence
<220> FEATURE:
<223> OTHER INFORMATION: VH_S31R

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Arg Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: VH_T30S_Y53R

<400> SEQUENCE: 12

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Ser Ser Tyr
            20                  25                  30

Val Met His Trp Val Arg Gln Ala Pro Gly Gln Gly Leu Glu Trp Met
        35                  40                  45

Gly Tyr Ile Asn Pro Arg Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
        115                 120

<210> SEQ ID NO 13
<211> LENGTH: 106
<212> TYPE: PRT
<213> ORGANISM: Artificial Sequence
<220> FEATURE:
<223> OTHER INFORMATION: VL_S31N_S56R_S93N

<400> SEQUENCE: 13
```

```
Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Asn Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Arg Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Ala Ala Thr Tyr Tyr Cys Gln Gln Trp Ser Asn Asn Pro Leu Thr
                85                  90                  95

Phe Gly Gly Gly Thr Lys Val Glu Ile Lys
            100                 105
```

<210> SEQ ID NO 14
<211> LENGTH: 120
<212> TYPE: PRT
<213> ORGANISM: Artificial Sequence
<220> FEATURE:
<223> OTHER INFORMATION: VH_N54K_H90Y

<400> SEQUENCE: 14

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Lys Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
        115                 120
```

<210> SEQ ID NO 15
<211> LENGTH: 120
<212> TYPE: PRT
<213> ORGANISM: Artificial Sequence
<220> FEATURE:
<223> OTHER INFORMATION: VH_T30N_S31N_Y53R

<400> SEQUENCE: 15

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Asn Asn Tyr
            20                  25                  30

Val Met His Trp Val Arg Gln Ala Pro Gly Gln Gly Leu Glu Trp Met
        35                  40                  45

Gly Tyr Ile Asn Pro Arg Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80
```

```
Met Glu Leu Ser Ser Leu Arg Ser Glu Asp Thr Ala Val His Tyr Cys
            85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
            115                 120

<210> SEQ ID NO 16
<211> LENGTH: 120
<212> TYPE: PRT
<213> ORGANISM: Artificial Sequence
<220> FEATURE:
<223> OTHER INFORMATION: VH_T30N_S31R_V56I

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Asn Arg Tyr
            20                  25                  30

Val Met His Trp Val Arg Gln Ala Pro Gly Gln Gly Leu Glu Trp Met
            35                  40                  45

Gly Tyr Ile Asn Pro Tyr Asn Asp Ile Thr Lys Tyr Ala Glu Lys Phe
        50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
            85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
            115                 120

<210> SEQ ID NO 17
<211> LENGTH: 120
<212> TYPE: PRT
<213> ORGANISM: Artificial Sequence
<220> FEATURE:
<223> OTHER INFORMATION: VH_S31R_N54K_E100aD

<400> SEQUENCE: 17

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Arg Tyr
            20                  25                  30

Val Met His Trp Val Arg Gln Ala Pro Gly Gln Gly Leu Glu Trp Met
            35                  40                  45

Gly Tyr Ile Asn Pro Tyr Lys Asp Val Thr Lys Tyr Ala Glu Lys Phe
        50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
            85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
            115                 120
```

```
<210> SEQ ID NO 18
<211> LENGTH: 106
<212> TYPE: PRT
<213> ORGANISM: Artificial Sequence
<220> FEATURE:
<223> OTHER INFORMATION: VL_S56R

<400> SEQUENCE: 18

Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Arg Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Ala Ala Thr Tyr Tyr Cys Gln Gln Trp Ser Asn Pro Leu Thr
                85                  90                  95

Phe Gly Gly Gly Thr Lys Val Glu Ile Lys
            100                 105

<210> SEQ ID NO 19
<211> LENGTH: 120
<212> TYPE: PRT
<213> ORGANISM: Artificial Sequence
<220> FEATURE:
<223> OTHER INFORMATION: VH_T30R

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Arg Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
        115                 120

<210> SEQ ID NO 20
<211> LENGTH: 120
<212> TYPE: PRT
<213> ORGANISM: Artificial Sequence
<220> FEATURE:
<223> OTHER INFORMATION: VH_T30K

<400> SEQUENCE: 20

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Lys Ser Tyr
            20                  25                  30
```

```
Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
 65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
            115                 120

<210> SEQ ID NO 21
<211> LENGTH: 120
<212> TYPE: PRT
<213> ORGANISM: Artificial Sequence
<220> FEATURE:
<223> OTHER INFORMATION: VH_S31K

<400> SEQUENCE: 21

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Lys Phe Thr Lys Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
 65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
            115                 120

<210> SEQ ID NO 22
<211> LENGTH: 120
<212> TYPE: PRT
<213> ORGANISM: Artificial Sequence
<220> FEATURE:
<223> OTHER INFORMATION: VH_Y53R

<400> SEQUENCE: 22

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Arg Asn Asp Val Thr Lys Tyr Ala Glu Lys Phe
    50                  55                  60

Gln Gly Arg Val Thr Leu Thr Ser Asp Thr Ser Thr Ser Thr Ala Tyr
 65                  70                  75                  80

Met Glu Leu Ser Ser Leu Arg Ser Glu Asp Thr Ala Val His Tyr Cys
```

```
                85                  90                  95
Ala Arg Gly Ser Tyr Tyr Asp Tyr Glu Gly Phe Val Tyr Trp Gly Gln
            100                 105                 110

Gly Thr Leu Val Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: VH_Y53K

<400> SEQUENCE: 23

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Lys Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
        115                 120

<210> SEQ ID NO 24
<211> LENGTH: 120
<212> TYPE: PRT
<213> ORGANISM: Artificial Sequence
<220> FEATURE:
<223> OTHER INFORMATION: VH_N54R

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Arg Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
        115                 120

<210> SEQ ID NO 25
<211> LENGTH: 120
```

```
<212> TYPE: PRT
<213> ORGANISM: Artificial Sequence
<220> FEATURE:
<223> OTHER INFORMATION: VH_N54K

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Lys Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
        115                 120

<210> SEQ ID NO 26
<211> LENGTH: 106
<212> TYPE: PRT
<213> ORGANISM: Artificial Sequence
<220> FEATURE:
<223> OTHER INFORMATION: VL_S31R

<400> SEQUENCE: 26

Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Arg Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 27
<211> LENGTH: 106
<212> TYPE: PRT
<213> ORGANISM: Artificial Sequence
<220> FEATURE:
<223> OTHER INFORMATION: VL_S31K

<400> SEQUENCE: 27

Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Lys Tyr Met
            20                  25                  30

His Trp Tyr Gln Gln Lys Pro Gly Lys Ala Pro Lys Arg Trp Ile Tyr
```

```
                35                  40                  45
Asp Thr Ser Lys Leu Ala Ser Gly Val Pro Ser Arg Phe Ser Gly Ser
             50                  55                  60

Gly Ser Gly Thr Asp Tyr Thr Leu Thr Ile Ser Ser Leu Gln Pro Glu
 65                  70                  75                  80

Asp Ala Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105
```

<210> SEQ ID NO 28
<211> LENGTH: 106
<212> TYPE: PRT
<213> ORGANISM: Artificial Sequence
<220> FEATURE:
<223> OTHER INFORMATION: VL_S56K

<400> SEQUENCE: 28

```
Gln Ile Gln Met Thr Gln Ser Pro Ser Ser Leu Ser Ala Ser Val Gly
 1               5                  10                  15

Asp Arg Val Thr Ile Thr Cys Ser Ala Thr Ser Ser Val Ser Tyr Met
             20                  25                  30

His Trp Tyr Gln Gln Lys Pro Gly Lys Ala Pro Lys Arg Trp Ile Tyr
             35                  40                  45

Asp Thr Ser Lys Leu Ala Lys Gly Val Pro Ser Arg Phe Ser Gly Ser
             50                  55                  60

Gly Ser Gly Thr Asp Tyr Thr Leu Thr Ile Ser Ser Leu Gln Pro Glu
 65                  70                  75                  80

Asp Ala Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105
```

<210> SEQ ID NO 29
<211> LENGTH: 120
<212> TYPE: PRT
<213> ORGANISM: Artificial Sequence
<220> FEATURE:
<223> OTHER INFORMATION: VH_Y53H

<400> SEQUENCE: 29

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Lys Phe Thr Ser Tyr
             20                  25                  30

Val Met His Trp Val Arg Gln Ala Pro Gly Gln Gly Leu Glu Trp Met
             35                  40                  45

Gly Tyr Ile Asn Pro His Asn Asp Val Thr Lys Tyr Ala Glu Lys Phe
 50                  55                  60

Gln Gly Arg Val Thr Leu Thr Ser Asp Thr Ser Thr Ser Thr Ala Tyr
 65                  70                  75                  80

Met Glu Leu Ser Ser Leu Arg Ser Glu Asp Thr Ala Val His Tyr Cys
                 85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
            115                 120
```

<210> SEQ ID NO 30
<211> LENGTH: 120
<212> TYPE: PRT
<213> ORGANISM: Artificial Sequence
<220> FEATURE:
<223> OTHER INFORMATION: VH_S31H

<400> SEQUENCE: 30

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr His Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
        115                 120
```

<210> SEQ ID NO 31
<211> LENGTH: 120
<212> TYPE: PRT
<213> ORGANISM: Artificial Sequence
<220> FEATURE:
<223> OTHER INFORMATION: VH_S31R_H90Y

<400> SEQUENCE: 31

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Arg Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
        115                 120
```

<210> SEQ ID NO 32
<211> LENGTH: 120
<212> TYPE: PRT
<213> ORGANISM: Artificial Sequence
<220> FEATURE:
<223> OTHER INFORMATION: VH_Y53R_H90Y

<400> SEQUENCE: 32

```
Glu Val Gln Leu Val Gln Ser Gly Ala Glu Val Lys Lys Pro Gly Ala
```

```
  1               5                  10                 15
Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
            35                  40                  45

Gly Tyr Ile Asn Pro Arg Asn Asp Val Thr Lys Tyr Ala Glu Lys Phe
            50                  55                  60

Gln Gly Arg Val Thr Leu Thr Ser Asp Thr Ser Thr Ser Thr Ala Tyr
 65                  70                  75                  80

Met Glu Leu Ser Ser Leu Arg Ser Glu Asp Thr Ala Val Tyr Tyr Cys
            85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
            115                 120
```

<210> SEQ ID NO 33
<211> LENGTH: 120
<212> TYPE: PRT
<213> ORGANISM: Artificial Sequence
<220> FEATURE:
<223> OTHER INFORMATION: VH_N54R_H90Y

<400> SEQUENCE: 33

```
Glu Val Gln Leu Val Gln Ser Gly Ala Glu Val Lys Lys Pro Gly Ala
 1               5                  10                 15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
            35                  40                  45

Gly Tyr Ile Asn Pro Tyr Arg Asp Val Thr Lys Tyr Ala Glu Lys Phe
            50                  55                  60

Gln Gly Arg Val Thr Leu Thr Ser Asp Thr Ser Thr Ser Thr Ala Tyr
 65                  70                  75                  80

Met Glu Leu Ser Ser Leu Arg Ser Glu Asp Thr Ala Val Tyr Tyr Cys
            85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser
            115                 120
```

<210> SEQ ID NO 34
<211> LENGTH: 120
<212> TYPE: PRT
<213> ORGANISM: Artificial Sequence
<220> FEATURE:
<223> OTHER INFORMATION: VH_E61Q_H90Y

<400> SEQUENCE: 34

```
Glu Val Gln Leu Val Gln Ser Gly Ala Glu Val Lys Lys Pro Gly Ala
 1               5                  10                 15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
            35                  40                  45

Gly Tyr Ile Asn Pro Tyr Asp Val Thr Lys Tyr Ala Gln Lys Phe
            50                  55                  60
```

-continued

```
Gln Gly Arg Val Thr Leu Thr Ser Asp Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 35
<211> LENGTH: 467
<212> TYPE: PRT
<213> ORGANISM: Artificial Sequence
<220> FEATURE:
<223> OTHER INFORMATION: TCER chain 2 VH_S31R

<400> SEQUENCE: 35

Ile Leu Asn Val Glu Gln Ser Pro Gln Ser Leu His Val Gln Glu Gly
1               5                   10                  15

Asp Ser Thr Lys Phe Thr Cys Ser Phe Pro Val Lys Glu Phe Gln Asp
            20                  25                  30

Leu His Trp Tyr Arg Lys Glu Thr Ala Lys Ser Pro Glu Phe Leu Phe
        35                  40                  45

Tyr Phe Gly Pro Tyr Gly Lys Glu Lys Lys Lys Gly Arg Ile Ser Ala
 50                  55                  60

Thr Leu Asn Thr Lys Glu Gly Tyr Ser Tyr Leu Tyr Ile Thr Asp Ser
 65                  70                  75                  80

Gln Pro Glu Asp Ser Ala Thr Tyr Leu Cys Ala Leu Tyr Asn Asn Tyr
             85                  90                  95

Asp Met Arg Phe Gly Ala Gly Thr Arg Leu Thr Val Lys Pro Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Lys Phe Thr Arg Tyr Val Met His Trp Val Arg Gln Ala Pro Gly
145                 150                 155                 160

Gln Gly Leu Glu Trp Met Gly Tyr Ile Asn Pro Tyr Asn Asp Val Thr
            165                 170                 175

Lys Tyr Ala Glu Lys Phe Gln Gly Arg Val Thr Leu Thr Ser Asp Thr
            180                 185                 190

Ser Thr Ser Thr Ala Tyr Met Glu Leu Ser Ser Leu Arg Ser Glu Asp
        195                 200                 205

Thr Ala Val His Tyr Cys Ala Arg Gly Ser Tyr Tyr Asp Tyr Glu Gly
    210                 215                 220

Phe Val Tyr Trp Gly Gln Gly Thr Leu Val Thr Val Ser Ser Glu Pro
225                 230                 235                 240

Lys Ser Ser Asp Lys Thr His Thr Cys Pro Pro Cys Pro Ala Pro Pro
            245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300
```

Glu Val His Asn Ala Lys Thr Lys Pro Arg Glu Gln Tyr Gln Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Ser Ile Glu Lys Thr Ile Ser Lys Ala Lys Gly Gln Pro Arg Glu Pro
            355                 360                 365

Gln Val Cys Thr Leu Pro Pro Ser Arg Asp Glu Leu Thr Lys Asn Gln
    370                 375                 380

Val Ser Leu Ser Cys Ala Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Val Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro
465

<210> SEQ ID NO 36
<211> LENGTH: 467
<212> TYPE: PRT
<213> ORGANISM: Artificial Sequence
<220> FEATURE:
<223> OTHER INFORMATION: TCER chain 2 VH_Y53R_H90Y

<400> SEQUENCE: 36

Ile Leu Asn Val Glu Gln Ser Pro Gln Ser Leu His Val Gln Glu Gly
1               5                   10                  15

Asp Ser Thr Lys Phe Thr Cys Ser Phe Pro Val Lys Glu Phe Gln Asp
            20                  25                  30

Leu His Trp Tyr Arg Lys Glu Thr Ala Lys Ser Pro Glu Phe Leu Phe
        35                  40                  45

Tyr Phe Gly Pro Tyr Gly Lys Glu Lys Lys Lys Gly Arg Ile Ser Ala
    50                  55                  60

Thr Leu Asn Thr Lys Glu Gly Tyr Ser Tyr Leu Tyr Ile Thr Asp Ser
65                  70                  75                  80

Gln Pro Glu Asp Ser Ala Thr Tyr Leu Cys Ala Leu Tyr Asn Asn Tyr
                85                  90                  95

Asp Met Arg Phe Gly Ala Gly Thr Arg Leu Thr Val Lys Pro Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
            130                 135                 140

Tyr Lys Phe Thr Ser Tyr Val Met His Trp Val Arg Gln Ala Pro Gly
145                 150                 155                 160

Gln Gly Leu Glu Trp Met Gly Tyr Ile Asn Pro Arg Asn Asp Val Thr
                165                 170                 175

Lys Tyr Ala Glu Lys Phe Gln Gly Arg Val Thr Leu Thr Ser Asp Thr
            180                 185                 190

```
Ser Thr Ser Thr Ala Tyr Met Glu Leu Ser Ser Leu Arg Ser Glu Asp
            195                 200                 205

Thr Ala Val Tyr Tyr Cys Ala Arg Gly Ser Tyr Tyr Asp Tyr Glu Gly
    210                 215                 220

Phe Val Tyr Trp Gly Gln Gly Thr Leu Val Thr Val Ser Ser Glu Pro
225                 230                 235                 240

Lys Ser Ser Asp Lys Thr His Thr Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Gln Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Ser Ile Glu Lys Thr Ile Ser Lys Ala Lys Gly Gln Pro Arg Glu Pro
            355                 360                 365

Gln Val Cys Thr Leu Pro Pro Ser Arg Asp Glu Leu Thr Lys Asn Gln
    370                 375                 380

Val Ser Leu Ser Cys Ala Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Val Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro
465

<210> SEQ ID NO 37
<211> LENGTH: 467
<212> TYPE: PRT
<213> ORGANISM: Artificial Sequence
<220> FEATURE:
<223> OTHER INFORMATION: TCER Chain 2 VH_wt

<400> SEQUENCE: 37

Ile Leu Asn Val Glu Gln Ser Pro Gln Ser Leu His Val Gln Glu Gly
1               5                   10                  15

Asp Ser Thr Lys Phe Thr Cys Ser Phe Pro Val Lys Glu Phe Gln Asp
            20                  25                  30

Leu His Trp Tyr Arg Lys Glu Thr Ala Lys Ser Pro Glu Phe Leu Phe
            35                  40                  45

Tyr Phe Gly Pro Tyr Gly Lys Glu Lys Lys Gly Arg Ile Ser Ala
    50                  55                  60

Thr Leu Asn Thr Lys Glu Gly Tyr Ser Tyr Leu Tyr Ile Thr Asp Ser
65                  70                  75                  80
```

```
Gln Pro Glu Asp Ser Ala Thr Tyr Leu Cys Ala Leu Tyr Asn Asn Tyr
                85                  90                  95

Asp Met Arg Phe Gly Ala Gly Thr Arg Leu Thr Val Lys Pro Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Lys Phe Thr Ser Tyr Val Met His Trp Val Arg Gln Ala Pro Gly
145                 150                 155                 160

Gln Gly Leu Glu Trp Met Gly Tyr Ile Asn Pro Tyr Asn Asp Val Thr
                165                 170                 175

Lys Tyr Ala Glu Lys Phe Gln Gly Arg Val Thr Leu Thr Ser Asp Thr
            180                 185                 190

Ser Thr Ser Thr Ala Tyr Met Glu Leu Ser Ser Leu Arg Ser Glu Asp
        195                 200                 205

Thr Ala Val His Tyr Cys Ala Arg Gly Ser Tyr Tyr Asp Tyr Glu Gly
    210                 215                 220

Phe Val Tyr Trp Gly Gln Gly Thr Leu Val Thr Val Ser Ser Glu Pro
225                 230                 235                 240

Lys Ser Ser Asp Lys Thr His Thr Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Gln Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Ser Ile Glu Lys Thr Ile Ser Lys Ala Lys Gly Gln Pro Arg Glu Pro
        355                 360                 365

Gln Val Cys Thr Leu Pro Pro Ser Arg Asp Glu Leu Thr Lys Asn Gln
    370                 375                 380

Val Ser Leu Ser Cys Ala Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Val Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro
465

<210> SEQ ID NO 38
<211> LENGTH: 467
<212> TYPE: PRT
```

<213> ORGANISM: Artificial Sequence
<220> FEATURE:
<223> OTHER INFORMATION: TCER chain 2 VH_Y53R

<400> SEQUENCE: 38

```
Ile Leu Asn Val Glu Gln Ser Pro Gln Ser Leu His Val Gln Glu Gly
1               5                   10                  15

Asp Ser Thr Lys Phe Thr Cys Ser Phe Pro Val Lys Glu Phe Gln Asp
            20                  25                  30

Leu His Trp Tyr Arg Lys Glu Thr Ala Lys Ser Pro Glu Phe Leu Phe
        35                  40                  45

Tyr Phe Gly Pro Tyr Gly Lys Glu Lys Lys Gly Arg Ile Ser Ala
    50                  55                  60

Thr Leu Asn Thr Lys Glu Gly Tyr Ser Tyr Leu Tyr Ile Thr Asp Ser
65                  70                  75                  80

Gln Pro Glu Asp Ser Ala Thr Tyr Leu Cys Ala Leu Tyr Asn Asn Tyr
                85                  90                  95

Asp Met Arg Phe Gly Ala Gly Thr Arg Leu Thr Val Lys Pro Gly Gly
            100                 105                 110

Gly Ser Gly Gly Gly Gly Glu Val Gln Leu Val Gln Ser Gly Ala Glu
        115                 120                 125

Val Lys Lys Pro Gly Ala Ser Val Lys Val Ser Cys Lys Ala Ser Gly
130                 135                 140

Tyr Lys Phe Thr Ser Tyr Val Met His Trp Val Arg Gln Ala Pro Gly
145                 150                 155                 160

Gln Gly Leu Glu Trp Met Gly Tyr Ile Asn Pro Arg Asn Asp Val Thr
                165                 170                 175

Lys Tyr Ala Glu Lys Phe Gln Gly Arg Val Thr Leu Thr Ser Asp Thr
            180                 185                 190

Ser Thr Ser Thr Ala Tyr Met Glu Leu Ser Ser Leu Arg Ser Glu Asp
        195                 200                 205

Thr Ala Val His Tyr Cys Ala Arg Gly Ser Tyr Tyr Asp Tyr Glu Gly
    210                 215                 220

Phe Val Tyr Trp Gly Gln Gly Thr Leu Val Thr Val Ser Ser Glu Pro
225                 230                 235                 240

Lys Ser Ser Asp Lys Thr His Thr Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Gln Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Ser Ile Glu Lys Thr Ile Ser Lys Ala Lys Gly Gln Pro Arg Glu Pro
        355                 360                 365

Gln Val Cys Thr Leu Pro Pro Ser Arg Asp Glu Leu Thr Lys Asn Gln
    370                 375                 380

Val Ser Leu Ser Cys Ala Val Lys Gly Phe Tyr Pro Ser Asp Ile Ala
```

```
385                 390                 395                 400
Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Val Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro
465

<210> SEQ ID NO 39
<211> LENGTH: 454
<212> TYPE: PRT
<213> ORGANISM: Artificial Sequence
<220> FEATURE:
<223> OTHER INFORMATION: TCER chain 1 VL_wt

<400> SEQUENCE: 39

Gln Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys Gly Gly Gly Ser Gly Gly
            100                 105                 110

Gly Gly Gly Val Ile Gln Ser Pro Arg His Glu Val Thr Glu Met Gly
        115                 120                 125

Gln Glu Val Thr Leu Arg Cys Lys Pro Ile Ser Gly His Asn Ser Leu
    130                 135                 140

Phe Trp Tyr Arg Glu Thr Pro Met Gln Gly Leu Glu Leu Leu Ile Tyr
145                 150                 155                 160

Phe Gln Asn Thr Ala Val Ile Asp Asp Ser Gly Met Pro Glu Asp Arg
                165                 170                 175

Phe Ser Ala Lys Met Pro Asn Ala Ser Phe Ser Thr Leu Lys Ile Gln
            180                 185                 190

Pro Ser Glu Pro Arg Asp Ser Ala Val Tyr Phe Cys Ala Ser Ser Pro
        195                 200                 205

Gly Ala Thr Asp Lys Gln Tyr Phe Gly Pro Gly Thr Arg Leu Thr Val
    210                 215                 220

Leu Glu Pro Lys Ser Ser Asp Lys Thr His Thr Cys Pro Pro Cys Pro
225                 230                 235                 240

Ala Pro Pro Val Ala Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
```

```
                  275                 280                 285
Asp Gly Val Glu Val His Asn Ala Lys Thr Lys Pro Arg Glu Gln
    290                 295                 300
Tyr Gln Ser Thr Tyr Arg Val Ser Val Leu Thr Val Leu His Gln
305                 310                 315                 320
Asp Trp Leu Asn Gly Lys Glu Tyr Lys Cys Lys Val Ser Asn Lys Ala
                    325                 330                 335
Leu Pro Ala Ser Ile Glu Lys Thr Ile Ser Lys Ala Lys Gly Gln Pro
                340                 345                 350
Arg Glu Pro Gln Val Tyr Thr Leu Pro Pro Cys Arg Asp Glu Leu Thr
                355                 360                 365
Lys Asn Gln Val Ser Leu Trp Cys Leu Val Lys Gly Phe Tyr Pro Ser
370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
                420                 425                 430
Ser Cys Ser Val Met His Glu Ala Leu His Asn His Tyr Thr Gln Lys
                435                 440                 445
Ser Leu Ser Leu Ser Pro
    450

<210> SEQ ID NO 40
<211> LENGTH: 244
<212> TYPE: PRT
<213> ORGANISM: Artificial Sequence
<220> FEATURE:
<223> OTHER INFORMATION: scFv BMA031(V36)

<400> SEQUENCE: 40

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Lys Phe Thr Ser Tyr
                20                  25                  30
Val Met His Trp Val Arg Gln Ala Pro Gly Gln Gly Leu Glu Trp Met
            35                  40                  45
Gly Tyr Ile Asn Pro Tyr Asn Asp Val Thr Lys Tyr Ala Glu Lys Phe
        50                  55                  60
Gln Gly Arg Val Thr Leu Thr Ser Asp Thr Ser Thr Ser Thr Ala Tyr
65                  70                  75                  80
Met Glu Leu Ser Ser Leu Arg Ser Glu Asp Thr Ala Val His Tyr Cys
                85                  90                  95
Ala Arg Gly Ser Tyr Tyr Asp Tyr Glu Gly Phe Val Tyr Trp Gly Gln
                100                 105                 110
Gly Thr Leu Val Thr Val Ser Ser Gly Gly Ser Glu Gly Gly Gly
            115                 120                 125
Ser Glu Gly Gly Gly Ser Glu Gly Gly Gln Ile Gln Met Thr Gln
            130                 135                 140
Ser Pro Ser Ser Leu Ser Ala Ser Val Gly Asp Arg Val Thr Ile Thr
145                 150                 155                 160
Cys Ser Ala Thr Ser Ser Val Ser Tyr Met His Trp Tyr Gln Gln Lys
                165                 170                 175
Pro Gly Lys Ala Pro Lys Arg Trp Ile Tyr Asp Thr Ser Lys Leu Ala
```

```
                180                 185                 190
Ser Gly Val Pro Ser Arg Phe Ser Gly Ser Gly Ser Gly Thr Asp Tyr
            195                 200                 205

Thr Leu Thr Ile Ser Ser Leu Gln Pro Glu Asp Ala Ala Thr Tyr Tyr
            210                 215                 220

Cys Gln Gln Trp Ser Ser Asn Pro Leu Thr Phe Gly Gly Gly Thr Lys
225                 230                 235                 240

Val Glu Ile Lys

<210> SEQ ID NO 41
<211> LENGTH: 244
<212> TYPE: PRT
<213> ORGANISM: Artificial Sequence
<220> FEATURE:
<223> OTHER INFORMATION: scFv-YU561-A01

<400> SEQUENCE: 41

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser Gly Gly Gly Ser Glu Gly Gly Gly
        115                 120                 125

Ser Glu Gly Gly Gly Ser Glu Gly Gly Gly Gln Ile Gln Met Thr Gln
    130                 135                 140

Ser Pro Ser Ser Leu Ser Ala Ser Val Gly Asp Arg Val Thr Ile Thr
145                 150                 155                 160

Cys Ser Ala Thr Ser Ser Val Arg Tyr Met His Trp Tyr Gln Gln Lys
                165                 170                 175

Pro Gly Lys Ala Pro Lys Arg Trp Ile Tyr Asp Thr Ser Lys Leu Ala
            180                 185                 190

Arg Gly Val Pro Ser Arg Phe Ser Gly Ser Gly Ser Gly Thr Asp Tyr
        195                 200                 205

Thr Leu Thr Ile Ser Ser Leu Gln Pro Glu Asp Ala Ala Thr Tyr Tyr
    210                 215                 220

Cys Gln Gln Trp Ser Ser Asn Pro Leu Thr Phe Gly Gly Gly Thr Lys
225                 230                 235                 240

Val Glu Ile Lys

<210> SEQ ID NO 42
<211> LENGTH: 244
<212> TYPE: PRT
<213> ORGANISM: Artificial Sequence
<220> FEATURE:
<223> OTHER INFORMATION: scFv-YU561-C03

<400> SEQUENCE: 42
```

Glu Val Gln Leu Val Gln Ser Gly Ala Glu Val Lys Pro Gly Ala
1               5                   10                  15

Ser Val Lys Val Ser Cys Lys Ala Ser Gly Tyr Lys Phe Asn Arg Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser Gly Gly Gly Ser Glu Gly Gly Gly
        115                 120                 125

Ser Glu Gly Gly Gly Ser Glu Gly Gly Gln Ile Gln Met Thr Gln
130                 135                 140

Ser Pro Ser Ser Leu Ser Ala Ser Val Gly Asp Arg Val Thr Ile Thr
145                 150                 155                 160

Cys Ser Ala Thr Ser Ser Val Ser Tyr Met His Trp Tyr Gln Gln Lys
            165                 170                 175

Pro Gly Lys Ala Pro Lys Arg Trp Ile Tyr Asp Thr Ser Lys Leu Ala
            180                 185                 190

Ser Gly Val Pro Ser Arg Phe Ser Gly Ser Gly Ser Gly Thr Asp Tyr
            195                 200                 205

Thr Leu Thr Ile Ser Ser Leu Gln Pro Glu Asp Ala Ala Thr Tyr Tyr
        210                 215                 220

Cys Gln Gln Trp Ser Ser Asn Pro Leu Thr Phe Gly Gly Gly Thr Lys
225                 230                 235                 240

Val Glu Ile Lys

<210> SEQ ID NO 43
<211> LENGTH: 244
<212> TYPE: PRT
<213> ORGANISM: Artificial Sequence
<220> FEATURE:
<223> OTHER INFORMATION: scFv-YU561-F02

<400> SEQUENCE: 43

Glu Val Gln Leu Val Gln Ser Gly Ala Glu Val Lys Pro Gly Ala
1               5                   10                  15

Ser Val Lys Val Ser Cys Lys Ala Ser Gly Tyr Lys Phe Ser Arg Tyr
            20                  25                  30

Val Met His Trp Val Arg Gln Ala Pro Gly Gln Gly Leu Glu Trp Met
        35                  40                  45

Gly Tyr Ile Asn Pro Arg Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Asp Gly Phe Val Tyr Trp Gly Gln
            100                 105                 110

```
Gly Thr Leu Val Thr Val Ser Gly Gly Ser Glu Gly Gly
            115                 120                 125

Ser Glu Gly Gly Gly Ser Glu Gly Gly Gln Ile Gln Met Thr Gln
            130                 135                 140

Ser Pro Ser Ser Leu Ser Ala Ser Val Gly Asp Arg Val Thr Ile Thr
145                 150                 155                 160

Cys Ser Ala Thr Ser Ser Val Ser Tyr Met His Trp Tyr Gln Gln Lys
                165                 170                 175

Pro Gly Lys Ala Pro Lys Arg Trp Ile Tyr Asp Thr Ser Lys Leu Ala
            180                 185                 190

Ser Gly Val Pro Ser Arg Phe Ser Gly Ser Gly Ser Gly Thr Asp Tyr
            195                 200                 205

Thr Leu Thr Ile Ser Ser Leu Gln Pro Glu Asp Ala Ala Thr Tyr Tyr
210                 215                 220

Cys Gln Gln Trp Ser Ser Asn Pro Leu Thr Phe Gly Gly Gly Thr Lys
225                 230                 235                 240

Val Glu Ile Lys
```

<210> SEQ ID NO 44
<211> LENGTH: 244
<212> TYPE: PRT
<213> ORGANISM: Artificial Sequence
<220> FEATURE:
<223> OTHER INFORMATION: scFv-YU561-A02

<400> SEQUENCE: 44

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Arg Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Gly Gly Ser Glu Gly Gly
            115                 120                 125

Ser Glu Gly Gly Gly Ser Glu Gly Gly Gln Ile Gln Met Thr Gln
            130                 135                 140

Ser Pro Ser Ser Leu Ser Ala Ser Val Gly Asp Arg Val Thr Ile Thr
145                 150                 155                 160

Cys Ser Ala Thr Ser Ser Val Ser Tyr Met His Trp Tyr Gln Gln Lys
                165                 170                 175

Pro Gly Lys Ala Pro Lys Arg Trp Ile Tyr Asp Thr Ser Lys Leu Ala
            180                 185                 190

Ser Gly Val Pro Ser Arg Phe Ser Gly Ser Gly Ser Gly Thr Asp Tyr
            195                 200                 205

Thr Leu Thr Ile Ser Ser Leu Gln Pro Glu Asp Ala Ala Thr Tyr Tyr
210                 215                 220

Cys Gln Gln Trp Ser Ser Asn Pro Leu Thr Phe Gly Gly Gly Thr Lys
```

225              230              235              240

Val Glu Ile Lys

<210> SEQ ID NO 45
<211> LENGTH: 244
<212> TYPE: PRT
<213> ORGANISM: Artificial Sequence
<220> FEATURE:
<223> OTHER INFORMATION: scFv-YU561-D01

<400> SEQUENCE: 45

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Ser Ser Tyr
                20                  25                  30

Val Met His Trp Val Arg Gln Ala Pro Gly Gln Gly Leu Glu Trp Met
            35                  40                  45

Gly Tyr Ile Asn Pro Arg Asn Asp Val Thr Lys Tyr Ala Glu Lys Phe
        50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser Gly Gly Gly Ser Glu Gly Gly Gly
        115                 120                 125

Ser Glu Gly Gly Gly Ser Glu Gly Gly Gln Ile Gln Met Thr Gln
130                 135                 140

Ser Pro Ser Ser Leu Ser Ala Ser Val Gly Asp Arg Val Thr Ile Thr
145                 150                 155                 160

Cys Ser Ala Thr Ser Ser Val Ser Tyr Met His Trp Tyr Gln Gln Lys
                165                 170                 175

Pro Gly Lys Ala Pro Lys Arg Trp Ile Tyr Asp Thr Ser Lys Leu Ala
            180                 185                 190

Ser Gly Val Pro Ser Arg Phe Ser Gly Ser Gly Ser Gly Thr Asp Tyr
        195                 200                 205

Thr Leu Thr Ile Ser Ser Leu Gln Pro Glu Asp Ala Ala Thr Tyr Tyr
    210                 215                 220

Cys Gln Gln Trp Ser Ser Asn Pro Leu Thr Phe Gly Gly Gly Thr Lys
225                 230                 235                 240

Val Glu Ile Lys

<210> SEQ ID NO 46
<211> LENGTH: 244
<212> TYPE: PRT
<213> ORGANISM: Artificial Sequence
<220> FEATURE:
<223> OTHER INFORMATION: scFv-YU561-D02

<400> SEQUENCE: 46

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Arg Tyr
                20                  25                  30

Val Met His Trp Val Arg Gln Ala Pro Gly Gln Gly Leu Glu Trp Met
            35                  40                  45

Gly Tyr Ile Asn Pro Tyr Asn Asp Val Thr Lys Tyr Ala Glu Lys Phe
        50                  55                  60

Gln Gly Arg Val Thr Leu Thr Ser Asp Thr Ser Thr Ser Thr Ala Tyr
 65                  70                  75                  80

Met Glu Leu Ser Ser Leu Arg Ser Glu Asp Thr Ala Val His Tyr Cys
                 85                  90                  95

Ala Arg Gly Ser Tyr Tyr Asp Tyr Glu Gly Phe Val Tyr Trp Gly Gln
                100                 105                 110

Gly Thr Leu Val Thr Val Ser Ser Gly Gly Ser Glu Gly Gly Gly
                115                 120                 125

Ser Glu Gly Gly Gly Ser Glu Gly Gly Gln Ile Gln Met Thr Gln
        130                 135                 140

Ser Pro Ser Ser Leu Ser Ala Ser Val Gly Asp Arg Val Thr Ile Thr
145                 150                 155                 160

Cys Ser Ala Thr Ser Ser Val Asn Tyr Met His Trp Tyr Gln Gln Lys
                165                 170                 175

Pro Gly Lys Ala Pro Lys Arg Trp Ile Tyr Asp Thr Ser Lys Leu Ala
                180                 185                 190

Arg Gly Val Pro Ser Arg Phe Ser Gly Ser Gly Ser Gly Thr Asp Tyr
                195                 200                 205

Thr Leu Thr Ile Ser Ser Leu Gln Pro Glu Asp Ala Ala Thr Tyr Tyr
                210                 215                 220

Cys Gln Gln Trp Ser Asn Asn Pro Leu Thr Phe Gly Gly Gly Thr Lys
225                 230                 235                 240

Val Glu Ile Lys

<210> SEQ ID NO 47
<211> LENGTH: 244
<212> TYPE: PRT
<213> ORGANISM: Artificial Sequence
<220> FEATURE:
<223> OTHER INFORMATION: scFv-YU561-B01

<400> SEQUENCE: 47

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Lys Phe Thr Ser Tyr
                 20                  25                  30

Val Met His Trp Val Arg Gln Ala Pro Gly Gln Gly Leu Glu Trp Met
            35                  40                  45

Gly Tyr Ile Asn Pro Tyr Lys Asp Val Thr Lys Tyr Ala Glu Lys Phe
        50                  55                  60

Gln Gly Arg Val Thr Leu Thr Ser Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Glu Gly Phe Val Tyr Trp Gly Gln
                100                 105                 110

Gly Thr Leu Val Thr Val Ser Ser Gly Gly Ser Glu Gly Gly Gly
                115                 120                 125

Ser Glu Gly Gly Gly Ser Glu Gly Gly Gln Ile Gln Met Thr Gln
        130                 135                 140

Ser Pro Ser Ser Leu Ser Ala Ser Val Gly Asp Arg Val Thr Ile Thr
145                 150                 155                 160

```
Cys Ser Ala Thr Ser Ser Val Ser Tyr Met His Trp Tyr Gln Gln Lys
                165                 170                 175

Pro Gly Lys Ala Pro Lys Arg Trp Ile Tyr Asp Thr Ser Lys Leu Ala
            180                 185                 190

Ser Gly Val Pro Ser Arg Phe Ser Gly Ser Gly Ser Gly Thr Asp Tyr
        195                 200                 205

Thr Leu Thr Ile Ser Ser Leu Gln Pro Glu Asp Ala Ala Thr Tyr Tyr
    210                 215                 220

Cys Gln Gln Trp Ser Ser Asn Pro Leu Thr Phe Gly Gly Gly Thr Lys
225                 230                 235                 240

Val Glu Ile Lys

<210> SEQ ID NO 48
<211> LENGTH: 244
<212> TYPE: PRT
<213> ORGANISM: Artificial Sequence
<220> FEATURE:
<223> OTHER INFORMATION: scFv-YU561-D03

<400> SEQUENCE: 48

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Asn Asn Tyr
            20                  25                  30

Val Met His Trp Val Arg Gln Ala Pro Gly Gln Gly Leu Glu Trp Met
        35                  40                  45

Gly Tyr Ile Asn Pro Arg Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser Gly Gly Gly Ser Glu Gly Gly Gly
        115                 120                 125

Ser Glu Gly Gly Gly Ser Glu Gly Gly Gln Ile Gln Met Thr Gln
130                 135                 140

Ser Pro Ser Ser Leu Ser Ala Ser Val Gly Asp Arg Val Thr Ile Thr
145                 150                 155                 160

Cys Ser Ala Thr Ser Ser Val Ser Tyr Met His Trp Tyr Gln Gln Lys
                165                 170                 175

Pro Gly Lys Ala Pro Lys Arg Trp Ile Tyr Asp Thr Ser Lys Leu Ala
            180                 185                 190

Ser Gly Val Pro Ser Arg Phe Ser Gly Ser Gly Ser Gly Thr Asp Tyr
        195                 200                 205

Thr Leu Thr Ile Ser Ser Leu Gln Pro Glu Asp Ala Ala Thr Tyr Tyr
    210                 215                 220

Cys Gln Gln Trp Ser Ser Asn Pro Leu Thr Phe Gly Gly Gly Thr Lys
225                 230                 235                 240

Val Glu Ile Lys

<210> SEQ ID NO 49
<211> LENGTH: 244
<212> TYPE: PRT
<213> ORGANISM: Artificial Sequence
```

<220> FEATURE:
<223> OTHER INFORMATION: scFv-YU561-E01

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Asn Arg Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Ile Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser Gly Gly Gly Ser Glu Gly Gly Gly
        115                 120                 125

Ser Glu Gly Gly Gly Ser Glu Gly Gly Gly Gln Ile Gln Met Thr Gln
    130                 135                 140

Ser Pro Ser Ser Leu Ser Ala Ser Val Gly Asp Arg Val Thr Ile Thr
145                 150                 155                 160

Cys Ser Ala Thr Ser Ser Val Ser Tyr Met His Trp Tyr Gln Gln Lys
                165                 170                 175

Pro Gly Lys Ala Pro Lys Arg Trp Ile Tyr Asp Thr Ser Lys Leu Ala
            180                 185                 190

Ser Gly Val Pro Ser Arg Phe Ser Gly Ser Gly Ser Gly Thr Asp Tyr
        195                 200                 205

Thr Leu Thr Ile Ser Ser Leu Gln Pro Glu Asp Ala Ala Thr Tyr Tyr
    210                 215                 220

Cys Gln Gln Trp Ser Ser Asn Pro Leu Thr Phe Gly Gly Gly Thr Lys
225                 230                 235                 240

Val Glu Ile Lys

<210> SEQ ID NO 50
<211> LENGTH: 244
<212> TYPE: PRT
<213> ORGANISM: Artificial Sequence
<220> FEATURE:
<223> OTHER INFORMATION: scFv-YU561-C01

<400> SEQUENCE: 50

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Arg Tyr
            20                  25                  30

Val Met His Trp Val Arg Gln Ala Pro Gly Gln Gly Leu Glu Trp Met
        35                  40                  45

Gly Tyr Ile Asn Pro Tyr Lys Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser Gly Gly Gly Ser Glu Gly Gly Gly
            115                 120                 125

Ser Glu Gly Gly Gly Ser Glu Gly Gly Gln Ile Gln Met Thr Gln
130                 135                 140

Ser Pro Ser Ser Leu Ser Ala Ser Val Gly Asp Arg Val Thr Ile Thr
145                 150                 155                 160

Cys Ser Ala Thr Ser Ser Val Ser Tyr Met His Trp Tyr Gln Gln Lys
            165                 170                 175

Pro Gly Lys Ala Pro Lys Arg Trp Ile Tyr Asp Thr Ser Lys Leu Ala
            180                 185                 190

Ser Gly Val Pro Ser Arg Phe Ser Gly Ser Gly Ser Gly Thr Asp Tyr
            195                 200                 205

Thr Leu Thr Ile Ser Ser Leu Gln Pro Glu Asp Ala Ala Thr Tyr Tyr
            210                 215                 220

Cys Gln Gln Trp Ser Ser Asn Pro Leu Thr Phe Gly Gly Gly Thr Lys
225                 230                 235                 240

Val Glu Ile Lys

<210> SEQ ID NO 51
<211> LENGTH: 244
<212> TYPE: PRT
<213> ORGANISM: Artificial Sequence
<220> FEATURE:
<223> OTHER INFORMATION: scFv-YU561-C02

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser Gly Gly Gly Ser Glu Gly Gly Gly
            115                 120                 125

Ser Glu Gly Gly Gly Ser Glu Gly Gly Gln Ile Gln Met Thr Gln
130                 135                 140

Ser Pro Ser Ser Leu Ser Ala Ser Val Gly Asp Arg Val Thr Ile Thr
145                 150                 155                 160

Cys Ser Ala Thr Ser Ser Val Ser Tyr Met His Trp Tyr Gln Gln Lys
            165                 170                 175

Pro Gly Lys Ala Pro Lys Arg Trp Ile Tyr Asp Thr Ser Lys Leu Ala
            180                 185                 190

Arg Gly Val Pro Ser Arg Phe Ser Gly Ser Gly Ser Gly Thr Asp Tyr
            195                 200                 205

```
Thr Leu Thr Ile Ser Ser Leu Gln Pro Glu Asp Ala Ala Thr Tyr Tyr
    210                 215                 220

Cys Gln Gln Trp Ser Ser Asn Pro Leu Thr Phe Gly Gly Gly Thr Lys
225                 230                 235                 240

Val Glu Ile Lys

<210> SEQ ID NO 52
<211> LENGTH: 5
<212> TYPE: PRT
<213> ORGANISM: Artificial Sequence
<220> FEATURE:
<223> OTHER INFORMATION: HCR1 Kabat

<400> SEQUENCE: 52

Ser Tyr Val Met His
1               5

<210> SEQ ID NO 53
<211> LENGTH: 17
<212> TYPE: PRT
<213> ORGANISM: Artificial Sequence
<220> FEATURE:
<223> OTHER INFORMATION: HCDR2 Kabat
<220> FEATURE:
<221> NAME/KEY: MISC_FEATURE
<222> LOCATION: (12)..(12)
<223> OTHER INFORMATION: Xaa at position 12 is A or N
<220> FEATURE:
<221> NAME/KEY: MISC_FEATURE
<222> LOCATION: (13)..(13)
<223> OTHER INFORMATION: Xaa at position 13 is E or Q
<220> FEATURE:
<221> NAME/KEY: MISC_FEATURE
<222> LOCATION: (16)..(16)
<223> OTHER INFORMATION: Xaa at position 16 is Q or K

<400> SEQUENCE: 53

Tyr Ile Asn Pro Tyr Asn Asp Val Thr Lys Tyr Xaa Xaa Lys Phe Xaa
1               5                   10                  15

Gly

<210> SEQ ID NO 54
<211> LENGTH: 10
<212> TYPE: PRT
<213> ORGANISM: Artificial Sequence
<220> FEATURE:
<223> OTHER INFORMATION: LCDR1

<400> SEQUENCE: 54

Ser Ala Thr Ser Ser Val Ser Tyr Met His
1               5                   10

<210> SEQ ID NO 55
<211> LENGTH: 7
<212> TYPE: PRT
<213> ORGANISM: Artificial Sequence
<220> FEATURE:
<223> OTHER INFORMATION: LCDR2

<400> SEQUENCE: 55

Asp Thr Ser Lys Leu Ala Ser
1               5

<210> SEQ ID NO 56
<211> LENGTH: 11
<212> TYPE: PRT
<213> ORGANISM: Artificial Sequence
```

```
<220> FEATURE:
<223> OTHER INFORMATION: HCDR3 Kabat
<220> FEATURE:
<221> NAME/KEY: MISC_FEATURE
<222> LOCATION: (7)..(7)
<223> OTHER INFORMATION: Xaa at position 7 is D or E

<400> SEQUENCE: 56

Gly Ser Tyr Tyr Asp Tyr Xaa Gly Phe Val Tyr
1               5                   10

<210> SEQ ID NO 57
<211> LENGTH: 9
<212> TYPE: PRT
<213> ORGANISM: Artificial Sequence
<220> FEATURE:
<223> OTHER INFORMATION: LCDR3 Kabat
<220> FEATURE:
<221> NAME/KEY: MISC_FEATURE
<222> LOCATION: (5)..(5)
<223> OTHER INFORMATION: Xaa at position 5 is S or N
<220> FEATURE:
<221> NAME/KEY: MISC_FEATURE
<222> LOCATION: (6)..(6)
<223> OTHER INFORMATION: Xaa at position 6 is selected from the group
      consisting of Q, D, H, S, Y, A and N
<220> FEATURE:
<221> NAME/KEY: MISC_FEATURE
<222> LOCATION: (7)..(7)
<223> OTHER INFORMATION: Xaa at position 7 is P or A

<400> SEQUENCE: 57

Gln Gln Trp Ser Xaa Xaa Xaa Leu Thr
1               5

<210> SEQ ID NO 58
<211> LENGTH: 120
<212> TYPE: PRT
<213> ORGANISM: Artificial Sequence
<220> FEATURE:
<223> OTHER INFORMATION: VH humanized BMA031 Shearman

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Lys Phe Thr Ser Tyr
                20                  25                  30

Val Met His Trp Val Lys Gln Ala Pro Gly Gln Gly Leu Glu Trp Ile
            35                  40                  45

Gly Tyr Ile Asn Pro Tyr Asn Asp Val Thr Lys Tyr Asn Glu Lys Phe
    50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120

<210> SEQ ID NO 59
<211> LENGTH: 106
<212> TYPE: PRT
<213> ORGANISM: Artificial Sequence
<220> FEATURE:
<223> OTHER INFORMATION: VL humanized BMA031 Shearman
```

<400> SEQUENCE: 59

```
Asp Ile Gln Met Thr Gln Ser Pro Ser Thr Leu Ser Ala Ser Val Gly
1               5                   10                  15

Asp Arg Val Thr Met Thr Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ala Arg Phe Ile Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105
```

<210> SEQ ID NO 60
<211> LENGTH: 450
<212> TYPE: PRT
<213> ORGANISM: Artificial Sequence
<220> FEATURE:
<223> OTHER INFORMATION: HC BMA031 (V36): huIgG1 (constant domains allotype G1m17,1)

<400> SEQUENCE: 60

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Val Thr Lys Tyr Ala Glu Lys Phe
    50                  55                  60

Gln Gly Arg Val Thr Leu Thr Ser Asp Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Glu Gly Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 61
<211> LENGTH: 232
<212> TYPE: PRT
<213> ORGANISM: Artificial Sequence
<220> FEATURE:
<223> OTHER INFORMATION: huIgG1 (G1m17,1) CH1 and CH2 including hinge

<400> SEQUENCE: 61

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140
```

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 62
<211> LENGTH: 7
<212> TYPE: PRT
<213> ORGANISM: Artificial Sequence
<220> FEATURE:
<223> OTHER INFORMATION: HCDR1 Chothia

<400> SEQUENCE: 62

Gly Tyr Lys Phe Thr Ser Tyr
1               5

<210> SEQ ID NO 63
<211> LENGTH: 6
<212> TYPE: PRT
<213> ORGANISM: Artificial Sequence
<220> FEATURE:
<223> OTHER INFORMATION: HCDR2 Chothia

<400> SEQUENCE: 63

Asn Pro Tyr Asn Asp Val
1               5

<210> SEQ ID NO 64
<211> LENGTH: 11
<212> TYPE: PRT
<213> ORGANISM: Artificial Sequence
<220> FEATURE:
<223> OTHER INFORMATION: HCDR3 Kabat

<400> SEQUENCE: 64

Gly Ser Tyr Tyr Asp Tyr Glu Gly Phe Val Tyr
1               5                   10

<210> SEQ ID NO 65
<211> LENGTH: 9
<212> TYPE: PRT
<213> ORGANISM: Artificial Sequence
<220> FEATURE:
<223> OTHER INFORMATION: LCDR3 Kabat
<220> FEATURE:
<221> NAME/KEY: MISC_FEATURE
<222> LOCATION: (6)..(6)
<223> OTHER INFORMATION: Xaa at position 6 is an amino acid selected
      from the group consisting of Q, D, H, S, Y, A and N
<220> FEATURE:
<221> NAME/KEY: MISC_FEATURE
<222> LOCATION: (7)..(7)
<223> OTHER INFORMATION: Xaa at position 7 is P or A

<400> SEQUENCE: 65

Gln Gln Trp Ser Ser Xaa Xaa Leu Thr
1               5
```

```
<210> SEQ ID NO 66
<211> LENGTH: 9
<212> TYPE: PRT
<213> ORGANISM: Artificial Sequence
<220> FEATURE:
<223> OTHER INFORMATION: LCDR3 Kabat
<220> FEATURE:
<221> NAME/KEY: MISC_FEATURE
<222> LOCATION: (5)..(5)
<223> OTHER INFORMATION: Xaa at position 5 is S or N
<220> FEATURE:
<221> NAME/KEY: MISC_FEATURE
<222> LOCATION: (7)..(7)
<223> OTHER INFORMATION: Xaa at position 7 is P or A

<400> SEQUENCE: 66

Gln Gln Trp Ser Xaa Asn Xaa Leu Thr
1               5

<210> SEQ ID NO 67
<211> LENGTH: 9
<212> TYPE: PRT
<213> ORGANISM: Artificial Sequence
<220> FEATURE:
<223> OTHER INFORMATION: LCDR3 Kabat
<220> FEATURE:
<221> NAME/KEY: MISC_FEATURE
<222> LOCATION: (5)..(5)
<223> OTHER INFORMATION: Xaa at position 5 is S or N
<220> FEATURE:
<221> NAME/KEY: MISC_FEATURE
<222> LOCATION: (6)..(6)
<223> OTHER INFORMATION: Xaa at position 6  is an amino acid selected
      from the group consisting of Q, D, H, S, Y, A and N

<400> SEQUENCE: 67

Gln Gln Trp Ser Xaa Xaa Pro Leu Thr
1               5

<210> SEQ ID NO 68
<211> LENGTH: 9
<212> TYPE: PRT
<213> ORGANISM: Artificial Sequence
<220> FEATURE:
<223> OTHER INFORMATION: LCDR3

<400> SEQUENCE: 68

Gln Gln Trp Ser Ser Gln Pro Leu Thr
1               5

<210> SEQ ID NO 69
<211> LENGTH: 9
<212> TYPE: PRT
<213> ORGANISM: Artificial Sequence
<220> FEATURE:
<223> OTHER INFORMATION: LCDR3

<400> SEQUENCE: 69

Gln Gln Trp Ser Ser Asp Pro Leu Thr
1               5

<210> SEQ ID NO 70
<211> LENGTH: 9
<212> TYPE: PRT
<213> ORGANISM: Artificial Sequence
<220> FEATURE:
<223> OTHER INFORMATION: LCDR3

<400> SEQUENCE: 70
```

Gln Gln Trp Ser Ser His Pro Leu Thr
1               5

<210> SEQ ID NO 71
<211> LENGTH: 9
<212> TYPE: PRT
<213> ORGANISM: Artificial Sequence
<220> FEATURE:
<223> OTHER INFORMATION: LCDR3

<400> SEQUENCE: 71

Gln Gln Trp Ser Ser Ser Pro Leu Thr
1               5

<210> SEQ ID NO 72
<211> LENGTH: 9
<212> TYPE: PRT
<213> ORGANISM: Artificial Sequence
<220> FEATURE:
<223> OTHER INFORMATION: LCDR3

<400> SEQUENCE: 72

Gln Gln Trp Ser Ser Tyr Pro Leu Thr
1               5

<210> SEQ ID NO 73
<211> LENGTH: 9
<212> TYPE: PRT
<213> ORGANISM: Artificial Sequence
<220> FEATURE:
<223> OTHER INFORMATION: LCDR3

<400> SEQUENCE: 73

Gln Gln Trp Ser Ser Ala Pro Leu Thr
1               5

<210> SEQ ID NO 74
<211> LENGTH: 9
<212> TYPE: PRT
<213> ORGANISM: Artificial Sequence
<220> FEATURE:
<223> OTHER INFORMATION: LCDR3

<400> SEQUENCE: 74

Gln Gln Trp Ser Ser Asn Pro Leu Thr
1               5

<210> SEQ ID NO 75
<211> LENGTH: 9
<212> TYPE: PRT
<213> ORGANISM: Artificial Sequence
<220> FEATURE:
<223> OTHER INFORMATION: LCDR3

<400> SEQUENCE: 75

Gln Gln Trp Ser Ser Gln Ala Leu Thr
1               5

<210> SEQ ID NO 76
<211> LENGTH: 9
<212> TYPE: PRT
<213> ORGANISM: Artificial Sequence
<220> FEATURE:
<223> OTHER INFORMATION: LCDR3

<400> SEQUENCE: 76

```
Gln Gln Trp Ser Ser Asp Ala Leu Thr
1               5

<210> SEQ ID NO 77
<211> LENGTH: 9
<212> TYPE: PRT
<213> ORGANISM: Artificial Sequence
<220> FEATURE:
<223> OTHER INFORMATION: LCDR3

<400> SEQUENCE: 77

Gln Gln Trp Ser Ser His Ala Leu Thr
1               5

<210> SEQ ID NO 78
<211> LENGTH: 9
<212> TYPE: PRT
<213> ORGANISM: Artificial Sequence
<220> FEATURE:
<223> OTHER INFORMATION: LCDR3

<400> SEQUENCE: 78

Gln Gln Trp Ser Ser Ser Ala Leu Thr
1               5

<210> SEQ ID NO 79
<211> LENGTH: 9
<212> TYPE: PRT
<213> ORGANISM: Artificial Sequence
<220> FEATURE:
<223> OTHER INFORMATION: LCDR3

<400> SEQUENCE: 79

Gln Gln Trp Ser Ser Tyr Ala Leu Thr
1               5

<210> SEQ ID NO 80
<211> LENGTH: 9
<212> TYPE: PRT
<213> ORGANISM: Artificial Sequence
<220> FEATURE:
<223> OTHER INFORMATION: LCDR3

<400> SEQUENCE: 80

Gln Gln Trp Ser Ser Ala Ala Leu Thr
1               5

<210> SEQ ID NO 81
<211> LENGTH: 9
<212> TYPE: PRT
<213> ORGANISM: Artificial Sequence
<220> FEATURE:
<223> OTHER INFORMATION: LCDR3

<400> SEQUENCE: 81

Gln Gln Trp Ser Ser Asn Ala Leu Thr
1               5

<210> SEQ ID NO 82
<211> LENGTH: 9
<212> TYPE: PRT
<213> ORGANISM: Artificial Sequence
<220> FEATURE:
<223> OTHER INFORMATION: LCDR3

<400> SEQUENCE: 82

Gln Gln Trp Ser Asn Gln Pro Leu Thr
```

```
1               5

<210> SEQ ID NO 83
<211> LENGTH: 9
<212> TYPE: PRT
<213> ORGANISM: Artificial Sequence
<220> FEATURE:
<223> OTHER INFORMATION: LCDR3

<400> SEQUENCE: 83

Gln Gln Trp Asn Ser Asp Pro Leu Thr
1               5

<210> SEQ ID NO 84
<211> LENGTH: 9
<212> TYPE: PRT
<213> ORGANISM: Artificial Sequence
<220> FEATURE:
<223> OTHER INFORMATION: LCDR3

<400> SEQUENCE: 84

Gln Gln Trp Asn Ser His Pro Leu Thr
1               5

<210> SEQ ID NO 85
<211> LENGTH: 9
<212> TYPE: PRT
<213> ORGANISM: Artificial Sequence
<220> FEATURE:
<223> OTHER INFORMATION: QQWNSSPLT

<400> SEQUENCE: 85

Gln Gln Trp Asn Ser Ser Pro Leu Thr
1               5

<210> SEQ ID NO 86
<211> LENGTH: 9
<212> TYPE: PRT
<213> ORGANISM: Artificial Sequence
<220> FEATURE:
<223> OTHER INFORMATION: LCDR3

<400> SEQUENCE: 86

Gln Gln Trp Asn Ser Tyr Pro Leu Thr
1               5

<210> SEQ ID NO 87
<211> LENGTH: 9
<212> TYPE: PRT
<213> ORGANISM: Artificial Sequence
<220> FEATURE:
<223> OTHER INFORMATION: LCDR3

<400> SEQUENCE: 87

Gln Gln Trp Asn Ser Ala Pro Leu Thr
1               5

<210> SEQ ID NO 88
<211> LENGTH: 9
<212> TYPE: PRT
<213> ORGANISM: Artificial Sequence
<220> FEATURE:
<223> OTHER INFORMATION: LCDR3

<400> SEQUENCE: 88

Gln Gln Trp Asn Ser Asn Pro Leu Thr
1               5
```

```
<210> SEQ ID NO 89
<211> LENGTH: 9
<212> TYPE: PRT
<213> ORGANISM: Artificial Sequence
<220> FEATURE:
<223> OTHER INFORMATION: LCDR3

<400> SEQUENCE: 89

Gln Gln Trp Ser Asn Gln Ala Leu Thr
1               5

<210> SEQ ID NO 90
<211> LENGTH: 9
<212> TYPE: PRT
<213> ORGANISM: Artificial Sequence
<220> FEATURE:
<223> OTHER INFORMATION: LCDR3

<400> SEQUENCE: 90

Gln Gln Trp Asn Ser Asp Ala Leu Thr
1               5

<210> SEQ ID NO 91
<211> LENGTH: 9
<212> TYPE: PRT
<213> ORGANISM: Artificial Sequence
<220> FEATURE:
<223> OTHER INFORMATION: LCDR3

<400> SEQUENCE: 91

Gln Gln Trp Asn Ser His Ala Leu Thr
1               5

<210> SEQ ID NO 92
<211> LENGTH: 9
<212> TYPE: PRT
<213> ORGANISM: Artificial Sequence
<220> FEATURE:
<223> OTHER INFORMATION: LCDR3

<400> SEQUENCE: 92

Gln Gln Trp Asn Ser Ser Ala Leu Thr
1               5

<210> SEQ ID NO 93
<211> LENGTH: 9
<212> TYPE: PRT
<213> ORGANISM: Artificial Sequence
<220> FEATURE:
<223> OTHER INFORMATION: LCDR3

<400> SEQUENCE: 93

Gln Gln Trp Asn Ser Tyr Ala Leu Thr
1               5

<210> SEQ ID NO 94
<211> LENGTH: 9
<212> TYPE: PRT
<213> ORGANISM: Artificial Sequence
<220> FEATURE:
<223> OTHER INFORMATION: LCDR3

<400> SEQUENCE: 94

Gln Gln Trp Asn Ser Ala Ala Leu Thr
1               5
```

<210> SEQ ID NO 95
<211> LENGTH: 9
<212> TYPE: PRT
<213> ORGANISM: Artificial Sequence
<220> FEATURE:
<223> OTHER INFORMATION: LCDR3

<400> SEQUENCE: 95

Gln Gln Trp Asn Ser Asn Ala Leu Thr
1               5

<210> SEQ ID NO 96
<211> LENGTH: 9
<212> TYPE: PRT
<213> ORGANISM: Artificial Sequence
<220> FEATURE:
<223> OTHER INFORMATION: LCDR3
<220> FEATURE:
<221> NAME/KEY: MISC_FEATURE
<222> LOCATION: (5)..(5)
<223> OTHER INFORMATION: Xaa at position 5 is S or N

<400> SEQUENCE: 96

Gln Gln Trp Ser Xaa Asn Pro Leu Thr
1               5

<210> SEQ ID NO 97
<211> LENGTH: 120
<212> TYPE: PRT
<213> ORGANISM: Artificial Sequence
<220> FEATURE:
<223> OTHER INFORMATION: GL1_BM_VH28_HV

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
                20                  25                  30

Val Met His Trp Val Lys Gln Ala Pro Gly Gln Gly Leu Glu Trp Ile
            35                  40                  45

Gly Tyr Ile Asn Pro Tyr Asn Asp Val Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 98
<211> LENGTH: 120
<212> TYPE: PRT
<213> ORGANISM: Artificial Sequence
<220> FEATURE:
<223> OTHER INFORMATION: GL1_BM_VH31_HV

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
                20                  25                  30

Val Met His Trp Val Arg Gln Ala Pro Gly Gln Gly Leu Glu Trp Ile
            35                  40                  45

Gly Tyr Ile Asn Pro Tyr Asn Asp Val Thr Lys Tyr Asn Glu Lys Phe
        50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
                115                 120

<210> SEQ ID NO 99
<211> LENGTH: 120
<212> TYPE: PRT
<213> ORGANISM: Artificial Sequence
<220> FEATURE:
<223> OTHER INFORMATION: HEBE1_H10_HV

<400> SEQUENCE: 99

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Lys Phe Thr Ser Tyr
                20                  25                  30

Val Met His Trp Val Lys Gln Ala Pro Gly Lys Gly Leu Glu Trp Ile
            35                  40                  45

Gly Tyr Ile Asn Pro Tyr Asn Asp Val Thr Lys Tyr Asn Glu Lys Phe
        50                  55                  60

Lys Gly Lys Ala Thr Leu Ser Arg Asp Asn Ser Lys Asn Thr Leu Tyr
65                  70                  75                  80

Leu Gln Met Asn Ser Leu Arg Ala Glu Asp Thr Ala Val His Tyr Cys
                85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
                115                 120

<210> SEQ ID NO 100
<211> LENGTH: 120
<212> TYPE: PRT
<213> ORGANISM: Artificial Sequence
<220> FEATURE:
<223> OTHER INFORMATION: HEBE1_H66_HV

<400> SEQUENCE: 100

Glu Val Gln Leu Leu Gln Ser Gly Gly Gly Leu Val Gln Pro Gly Gly
1               5                   10                  15

Ser Leu Arg Leu Ser Cys Ala Ala Ser Gly Tyr Lys Phe Thr Ser Tyr
                20                  25                  30

Val Met His Trp Val Arg Gln Ala Pro Gly Lys Gly Leu Glu Trp Val
            35                  40                  45

Gly Tyr Ile Asn Pro Tyr Asn Asp Val Thr Lys Tyr Asn Glu Lys Phe
        50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
        115                 120

<210> SEQ ID NO 101
<211> LENGTH: 120
<212> TYPE: PRT
<213> ORGANISM: Artificial Sequence
<220> FEATURE:
<223> OTHER INFORMATION: HEBE1_H71_HV

<400> SEQUENCE: 101

Glu Val Gln Leu Leu Glu Ser Gly Gly Gly Leu Val Gln Pro Gly Gly
1               5                   10                  15

Ser Val Arg Leu Ser Cys Ala Ala Ser Gly Tyr Lys Phe Thr Ser Tyr
                20                  25                  30

Val Met His Trp Val Arg Gln Ala Pro Gly Lys Gly Leu Glu Trp Val
            35                  40                  45

Gly Tyr Ile Asn Pro Tyr Asn Asp Val Thr Lys Tyr Asn Glu Lys Phe
        50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
        115                 120

<210> SEQ ID NO 102
<211> LENGTH: 106
<212> TYPE: PRT
<213> ORGANISM: Artificial Sequence
<220> FEATURE:
<223> OTHER INFORMATION: GL1BMVK43_VL

<400> SEQUENCE: 102

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Tyr Gln Gln Lys Pro Gly Gln Ala Pro Arg Arg Leu Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 103
<211> LENGTH: 30
<212> TYPE: PRT
<213> ORGANISM: Artificial Sequence
<220> FEATURE:
```

<223> OTHER INFORMATION: HFR1

<400> SEQUENCE: 103

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Lys Phe Thr
            20                  25                  30

<210> SEQ ID NO 104
<211> LENGTH: 14
<212> TYPE: PRT
<213> ORGANISM: Artificial Sequence
<220> FEATURE:
<223> OTHER INFORMATION: HFR2

<400> SEQUENCE: 104

Trp Val Arg Gln Ala Pro Gly Gln Gly Leu Glu Trp Met Gly
1               5                   10

<210> SEQ ID NO 105
<211> LENGTH: 32
<212> TYPE: PRT
<213> ORGANISM: Artificial Sequence
<220> FEATURE:
<223> OTHER INFORMATION: HFR3

<400> SEQUENCE: 105

Arg Val Thr Leu Thr Ser Asp Thr Ser Thr Ser Thr Ala Tyr Met Glu
1               5                   10                  15
Leu Ser Ser Leu Arg Ser Glu Asp Thr Ala Val His Tyr Cys Ala Arg
            20                  25                  30

<210> SEQ ID NO 106
<211> LENGTH: 11
<212> TYPE: PRT
<213> ORGANISM: Artificial Sequence
<220> FEATURE:
<223> OTHER INFORMATION: HFR4

<400> SEQUENCE: 106

Trp Gly Gln Gly Thr Leu Val Thr Val Ser Ser
1               5                   10

<210> SEQ ID NO 107
<211> LENGTH: 23
<212> TYPE: PRT
<213> ORGANISM: Artificial Sequence
<220> FEATURE:
<223> OTHER INFORMATION: LFR1

<400> SEQUENCE: 107

Gln Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 108
<211> LENGTH: 15
<212> TYPE: PRT
<213> ORGANISM: Artificial Sequence
<220> FEATURE:
<223> OTHER INFORMATION: LFR2

<400> SEQUENCE: 108

Trp Tyr Gln Gln Lys Pro Gly Lys Ala Pro Lys Arg Trp Ile Tyr

-continued

```
1               5               10              15
```

<210> SEQ ID NO 109
<211> LENGTH: 32
<212> TYPE: PRT
<213> ORGANISM: Artificial Sequence
<220> FEATURE:
<223> OTHER INFORMATION: LFR3

<400> SEQUENCE: 109

```
Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Ala Ala Thr Tyr Tyr Cys
            20                  25                  30
```

<210> SEQ ID NO 110
<211> LENGTH: 10
<212> TYPE: PRT
<213> ORGANISM: Artificial Sequence
<220> FEATURE:
<223> OTHER INFORMATION: LFR4

<400> SEQUENCE: 110

```
Phe Gly Gly Gly Thr Lys Val Glu Ile Lys
1               5                   10
```

<210> SEQ ID NO 111
<211> LENGTH: 229
<212> TYPE: PRT
<213> ORGANISM: Artificial Sequence
<220> FEATURE:
<223> OTHER INFORMATION: Fc hole mutant

<400> SEQUENCE: 111

```
Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Gln Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Ser Ile Glu Lys Thr Ile Ser Lys Ala Lys Gly Gln Pro Arg
        115                 120                 125

Glu Pro Gln Val Cys Thr Leu Pro Pro Ser Arg Asp Glu Leu Thr Lys
    130                 135                 140

Asn Gln Val Ser Leu Ser Cys Ala Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Val Ser
            180                 185                 190

Lys Leu Thr Val Asp Lys Ser Arg Trp Gln Gln Gly Asn Val Phe Ser
        195                 200                 205
```

```
Cys Ser Val Met His Glu Ala Leu His Asn His Tyr Thr Gln Lys Ser
    210                 215                 220

Leu Ser Leu Ser Pro
225

<210> SEQ ID NO 112
<211> LENGTH: 229
<212> TYPE: PRT
<213> ORGANISM: Artificial Sequence
<220> FEATURE:
<223> OTHER INFORMATION: Fc knob mutant

<400> SEQUENCE: 112

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Gln Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Ser Ile Glu Lys Thr Ile Ser Lys Ala Lys Gly Gln Pro Arg
            115                 120                 125

Glu Pro Gln Val Tyr Thr Leu Pro Pro Cys Arg Asp Glu Leu Thr Lys
        130                 135                 140

Asn Gln Val Ser Leu Trp Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro
225
```